United States Patent
Adiwijaya et al.

(10) Patent No.: US 11,318,131 B2
(45) Date of Patent: May 3, 2022

(54) NANOLIPOSOMAL IRINOTECAN FOR USE IN TREATING SMALL CELL LUNG CANCER

(71) Applicant: Ipsen Biopharm Ltd., Wrexham (GB)

(72) Inventors: Bambang Adiwijaya, Belmont, MA (US); Jonathan Basil Fitzgerald, Arlington, MA (US); Helen Lee, Cambridge, MA (US)

(73) Assignee: Ipsen Biopharm Ltd.

( * ) Notice: Subject to any disclaimer, the term of this patent is extended or adjusted under 35 U.S.C. 154(b) by 0 days.

(21) Appl. No.: 16/302,050

(22) PCT Filed: May 17, 2017

(86) PCT No.: PCT/IB2017/000681
§ 371 (c)(1),
(2) Date: Nov. 15, 2018

(87) PCT Pub. No.: WO2017/199093
PCT Pub. Date: Nov. 23, 2017

(65) Prior Publication Data
US 2019/0167661 A1 Jun. 6, 2019

Related U.S. Application Data

(60) Provisional application No. 62/337,961, filed on May 18, 2015, provisional application No. 62/345,178, (Continued)

(51) Int. Cl.
*A61K 31/4745* (2006.01)
*A61K 9/127* (2006.01)
(Continued)

(52) U.S. Cl.
CPC ........ *A61K 31/4745* (2013.01); *A61K 9/0019* (2013.01); *A61K 9/127* (2013.01);
(Continued)

(58) Field of Classification Search
CPC .............. A61K 31/4745; A61K 9/0019; A61K 31/573; A61K 9/127; A61K 33/243; A61K 45/06; A61K 2300/00; A61P 35/00
See application file for complete search history.

(56) References Cited

U.S. PATENT DOCUMENTS 4,604,463 A 8/1986 Miyasaka et al.
5,013,556 A 5/1991 Woodle et al.
(Continued)

FOREIGN PATENT DOCUMENTS

CA 2412790 A1 1/2002
CN 1829741 A 9/2006
(Continued)

OTHER PUBLICATIONS

Daniel CF Chan, Evaluating the pharmacodynamics and pharmacokinetic effects of MM-398, a nanoliposomal irinotecan (nal-IRI) in subcutaneous xenograft tumor models of human squamous cell carcinoma and small cell lung cancers (Year: 2014).*
(Continued)

*Primary Examiner* — Gollamudi S Kishore
(74) *Attorney, Agent, or Firm* — McNeill Baur PLLC

(57) ABSTRACT

Novel therapies for the treatment of small cell lung cancer (SCLC) include the administration of an antineoplastic therapy consisting of liposomal irinotecan administered once every two weeks, optionally including the administration of other non-antineoplastic agents to the patient such as the administration of a corticosteroid and an anti-emetic to the patient prior to the administration of the irinotecan liposome.

30 Claims, 40 Drawing Sheets

Related U.S. Application Data filed on Jun. 3, 2016, provisional application No. 62/362,735, filed on Jul. 15, 2016, provisional application No. 62/370,449, filed on Aug. 3, 2016, provisional application No. 62/394,870, filed on Sep. 15, 2016, provisional application No. 62/414,050, filed on Oct. 28, 2016, provisional application No. 62/415,821, filed on Nov. 1, 2016, provisional application No. 62/422,807, filed on Nov. 16, 2016, provisional application No. 62/433,925, filed on Dec. 14, 2016, provisional application No. 62/455,823, filed on Feb. 7, 2017, provisional application No. 62/474,661, filed on Mar. 22, 2017.

(51) Int. Cl.
*A61P 35/00* (2006.01)
*A61K 9/00* (2006.01)
*A61K 31/573* (2006.01)
*A61K 33/243* (2019.01)

(52) U.S. Cl.
CPC ............ *A61K 31/573* (2013.01); *A61P 35/00* (2018.01); *A61K 33/243* (2019.01)

(56) References Cited

U.S. PATENT DOCUMENTS

| | | | |
|---|---|---|---|
| 5,077,056 A | 12/1991 | Bally et al. | |
| 5,192,549 A | 3/1993 | Barenolz et al. | |
| 5,316,771 A | 5/1994 | Barenholz et al. | |
| 5,538,954 A | 7/1996 | Koch et al. | |
| 5,543,152 A | 8/1996 | Webb et al. | |
| 5,593,622 A | 1/1997 | Yoshioka et al. | |
| 5,676,971 A | 10/1997 | Yoshioka et al. | |
| 5,783,568 A | 7/1998 | Schlessinger et al. | |
| 5,785,987 A | 7/1998 | Hope et al. | |
| 5,846,458 A | 12/1998 | Yoshioka et al. | |
| 6,110,491 A | 8/2000 | Kirpotin | |
| 6,210,707 B1 | 4/2001 | Papahadjopoulos et al. | |
| 6,214,388 B1 | 4/2001 | Benz et al. | |
| 6,241,999 B1 | 6/2001 | Ye et al. | |
| 6,355,268 B1 | 3/2002 | Slater et al. | |
| 6,403,569 B1 | 6/2002 | Achterrath | |
| 6,465,008 B1 | 10/2002 | Slater et al. | |
| 6,511,676 B1 | 1/2003 | Boulikas | |
| 6,545,010 B2 | 4/2003 | Bissery | |
| 6,720,001 B2 | 4/2004 | Chen et al. | |
| 6,787,132 B1 | 9/2004 | Gabizon et al. | |
| 6,794,370 B2 | 9/2004 | Achterrath | |
| 7,022,336 B2 | 4/2006 | Papahadjopoulos et al. | |
| 7,060,828 B2 | 6/2006 | Madden et al. | |
| 7,135,177 B2 | 11/2006 | Benz et al. | |
| 7,219,016 B2 | 5/2007 | Rimm et al. | |
| 7,244,448 B2 * | 7/2007 | Madden ................. | A61K 9/127 424/450 |
| 7,244,826 B1 | 7/2007 | Marks et al. | |
| 7,507,407 B2 | 3/2009 | Benz | |
| 7,829,113 B2 | 11/2010 | Okada et al. | |
| 7,842,676 B2 | 11/2010 | Janoff et al. | |
| 7,846,440 B2 | 12/2010 | Schoeberl et al. | |
| 7,846,473 B2 | 12/2010 | Yoshino et al. | |
| 7,850,990 B2 | 12/2010 | Tardi et al. | |
| 7,871,620 B2 | 1/2011 | Benz et al. | |
| 7,892,554 B2 | 2/2011 | Marks et al. | |
| 8,067,432 B2 | 11/2011 | Anderson et al. | |
| 8,147,867 B2 | 4/2012 | Hong et al. | |
| 8,329,213 B2 | 12/2012 | Hong et al. | |
| 8,496,961 B2 | 7/2013 | Hong et al. | |
| 8,658,203 B2 | 2/2014 | Drummond et al. | |
| 8,703,181 B2 | 4/2014 | Hong et al. | |
| 8,992,970 B2 | 3/2015 | Hong et al. | |
| 9,339,497 B2 | 5/2016 | Bayever et al. | |
| 9,364,473 B2 | 6/2016 | Bayever et al. | |
| 9,452,162 B2 | 9/2016 | Bayever et al. | |
| 9,492,442 B2 | 11/2016 | Bayever et al. | |
| 9,511,155 B2 | 12/2016 | Drummond et al. | |
| 9,616,081 B2 | 4/2017 | Okabe | |
| 9,717,723 B2 | 8/2017 | Hong et al. | |
| 9,717,724 B2 | 8/2017 | Bayever et al. | |
| 9,724,303 B2 | 8/2017 | Hong et al. | |
| 9,730,891 B2 | 8/2017 | Hong et al. | |
| 9,737,528 B2 | 8/2017 | Drummond et al. | |
| 9,782,349 B2 | 10/2017 | Hong et al. | |
| 9,895,365 B2 | 2/2018 | Blanchette et al. | |
| 10,350,201 B2 | 7/2019 | Hong et al. | |
| 10,413,510 B2 | 9/2019 | Hong et al. | |
| 10,456,360 B2 | 10/2019 | Drummond et al. | |
| 10,478,428 B2 | 11/2019 | Blanchette et al. | |
| 10,722,508 B2 | 7/2020 | Hong et al. | |
| 10,980,795 B2 | 4/2021 | Bayever et al. | |
| 10,993,914 B2 | 5/2021 | Drummond et al. | |
| 2002/0035091 A1 | 3/2002 | Govindarajan et al. | |
| 2002/0102298 A1 | 8/2002 | Needham | |
| 2002/0146450 A1 | 10/2002 | Slater et al. | |
| 2002/0192275 A1 | 12/2002 | Zalipsky et al. | |
| 2003/0138481 A1 | 7/2003 | Zadi | |
| 2004/0002505 A1 | 1/2004 | Ozawa et al. | |
| 2004/0071768 A1 | 4/2004 | Sarris et al. | |
| 2007/0110798 A1 | 5/2007 | Drummond et al. | |
| 2007/0219268 A1 | 9/2007 | Hausheer | |
| 2007/0265324 A1 | 11/2007 | Wernet et al. | |
| 2008/0108135 A1 | 5/2008 | Marks et al. | |
| 2009/0123419 A1 | 5/2009 | Sherman et al. | |
| 2009/0149397 A1 | 6/2009 | Ossovskaya et al. | |
| 2010/0056761 A1 | 3/2010 | Schoeberl et al. | |
| 2010/0068255 A1 | 3/2010 | Benz et al. | |
| 2011/0059076 A1 | 3/2011 | McDonagh et al. | |
| 2011/0104256 A1 | 5/2011 | Wang et al. | |
| 2011/0123523 A1 | 5/2011 | Schoeberl et al. | |
| 2012/0003160 A1 | 1/2012 | Wolf et al. | |
| 2012/0034295 A1 | 2/2012 | Spiegel et al. | |
| 2012/0045524 A1 | 2/2012 | Wernet et al. | |
| 2012/0269812 A1 | 10/2012 | Baum et al. | |
| 2012/0282325 A1 | 11/2012 | Tong et al. | |
| 2013/0209481 A1 | 8/2013 | Zhou et al. | |
| 2013/0236459 A1 | 9/2013 | Baum et al. | |
| 2013/0274281 A1 | 10/2013 | Bradley | |
| 2014/0065204 A1 | 3/2014 | Hayes et al. | |
| 2014/0170075 A1 | 6/2014 | Drummond et al. | |
| 2015/0182460 A1 | 7/2015 | Hong et al. | |
| 2015/0182521 A1 | 7/2015 | Bayever et al. | |
| 2015/0328156 A1 | 11/2015 | Bayever et al. | |
| 2015/0374682 A1 | 12/2015 | Bayever et al. | |
| 2016/0030341 A1 | 2/2016 | Hong et al. | |
| 2016/0030342 A1 | 2/2016 | Hong et al. | |
| 2016/0058704 A1 * | 3/2016 | Tardi ................... | A61K 9/0019 424/450 |
| 2016/0074382 A1 | 3/2016 | Bayever et al. | |
| 2016/0206615 A1 | 7/2016 | Tangutoori et al. | |
| 2016/0303264 A1 | 10/2016 | Hendricks et al. | |
| 2016/0346272 A1 | 12/2016 | Bayever et al. | |
| 2017/0049767 A1 | 2/2017 | Blanchette et al. | |
| 2017/0049775 A1 | 2/2017 | Bayever et al. | |
| 2017/0202840 A1 | 7/2017 | Bayever et al. | |
| 2017/0333421 A1 | 11/2017 | Adiwijaya et al. | |

FOREIGN PATENT DOCUMENTS

| | | |
|---|---|---|
| CN | 101878229 A | 11/2010 |
| CN | 1980637 B | 2/2014 |
| WO | 1997028156 A1 | 8/1997 |
| WO | 2000023052 A1 | 4/2000 |
| WO | 2003013536 A2 | 2/2003 |
| WO | 2003030864 A1 | 4/2003 |
| WO | 2003101474 A1 | 12/2003 |
| WO | 2004017940 A3 | 4/2004 |
| WO | 2004093795 A3 | 11/2004 |
| WO | 2005000900 A1 | 1/2005 |
| WO | 2005107712 A1 | 11/2005 |
| WO | 2006110816 A2 | 10/2006 |
| WO | 2007076117 A2 | 7/2007 |
| WO | 2009040426 A1 | 4/2009 |

(56) References Cited

FOREIGN PATENT DOCUMENTS

| WO | 2009126920 A3 | 3/2010 |
|---|---|---|
| WO | 2010125462 A2 | 11/2010 |
| WO | 2011066684 A1 | 6/2011 |
| WO | 2011153010 A1 | 12/2011 |
| WO | 2012012454 A1 | 1/2012 |
| WO | 2012031293 A1 | 3/2012 |
| WO | 2012078695 A2 | 6/2012 |
| WO | 2012079582 A1 | 6/2012 |
| WO | 2012146610 A1 | 11/2012 |
| WO | 2013006547 A2 | 1/2013 |
| WO | 2013138371 A1 | 9/2013 |
| WO | 2013158803 A1 | 10/2013 |
| WO | 2013188586 A1 | 12/2013 |
| WO | 2014113167 A1 | 7/2014 |
| WO | 2014157444 A1 | 10/2014 |
| WO | 2016094402 A1 | 6/2016 |
| WO | 2016168451 A1 | 10/2016 |
| WO | 2017031442 A1 | 2/2017 |
| WO | 2017031445 A1 | 2/2017 |
| WO | 2017034957 A1 | 3/2017 |
| WO | 2017066726 A1 | 4/2017 |
| WO | 2017172678 A1 | 10/2017 |
| WO | 2017199093 A1 | 11/2017 |
| WO | 2018083470 A1 | 5/2018 |

OTHER PUBLICATIONS

FDA (https://www.accessdata.fda.gov/drugsatfda_docs/label/2015/207793lbl.pdf). ONIVYDE Highlights of Prescribing Information (Year: 2015).*
Mirtsching et al (Am J Med Sci, 2014, 347(2), 167-169). (Year: 2014).*
Cassileth et al (Arch Intern Med, 1983, 143(7), 1347-1349) (Year: 1983).*
Drug and Therapeutics Bulletin, 43(8), 2005, 57-62. (Year: 2005).*
Drummond, D.c., et al , Cancer Res., vol. 66 (6), pp. 3271-3277, 2006.*
Morise, M., et ak ub Jpn J Clin Oncol, vol. 44 (9), pp. 846-851, 2014.*
Chan, D.C., et al AACR Annual Meeting, Apr. 5-9, 2014.*
U.S. Appl. No. 15/241,128: Nov. 25, 2016 Nonfinal Office Action, 6 pages.
U.S. Appl. No. 15/296,536: Mar. 8, 2017 Nonfinal Office Action, 6 pages.
U.S. Appl. No. 15/331,393: Jan. 19, 2017 Pre-Interview Communication, 4 pages.
U.S. Appl. No. 15/331,393: Mar. 20, 2017: Examiner's Interview Summary and First Action Interview Office Action Summary, 5 pages.
U.S. Appl. No. 15/331,648: Jan. 19, 2017 Pre-Interview Communication, 4 pages.
U.S. Appl. No. 15/331,648: Mar. 17, 2017 Examiner's Interview Summary, 3 pages.
U.S. Appl. No. 15/337,274: Mar. 24, 2017 Nonfinal Office Action, 10 pages.
U.S. Appl. No. 15/341,377: Jan. 30, 2017 Nonfinal Office Action, 12 pages.
U.S. Appl. No. 15/341,377: Apr. 18, 2017 Final Office Action, 13 pages.
U.S. Appl. No. 15/341,619: Apr. 3, 2017 Pre-Interview Communication, 3 pages.
U.S. Appl. No. 15/363,761: Jan. 18, 2017 Nonfinal Office Action, 15 pages.
U.S. Appl. No. 15/363,761: Aug. 1, 2017 Final Office Action, 18 pages.
U.S. Appl. No. 15/363,761: Dec. 14, 2017 Examiner Interview Summary, 3 pages.
U.S. Appl. No. 15/363,923: Feb. 1, 2017 Nonfinal Office Action, 24 pages.
U.S. Appl. No. 15/363,923: Sep. 13, 2017 Final Office Action, 29 pages.
U.S. Appl. No. 15/363,978: Feb. 7, 2017 Nonfinal Office Action, 16 pages.
U.S. Appl. No. 15/363,978: Aug. 21, 2017 Final Office Action, 19 pages.
U.S. Appl. No. 15/363,978: Dec. 14, 2017 Examiner Interview Summary, 3 pages.
U.S. Appl. No. 15/364,021: Mar. 9, 2017 Nonfinal Office Action, 18 pages.
U.S. Appl. No. 15/364,021: Oct. 4, 2017 Final Office Action, 20 pages.
U.S. Appl. No. 15/375,039: Feb. 16, 2018 Nonfinal Office Action, 11 pages.
U.S. Appl. No. 15/403,441: Dec. 21, 2017 Nonfinal Office Action, 9 pages.
U.S. Appl. No. 15/645,645: Dec. 1, 2017 Nonfinal Office Action, 16 pages.
U.S. Appl. No. 15/652,513: Dec. 20, 2017 Nonfinal Office Action, 13 pages.
U.S. Appl. No. 15/661,868: Dec. 1, 2017 Nonfinal Office Action, 15 pages.
U.S. Appl. No. 15/664,930: Dec. 20, 2017 Nonfinal Office Action, 7 pages.
U.S. Appl. No. 15/664,976: Sep. 11, 2018 Nonfinal Office Action, 23 pages.
U.S. Appl. No. 15/664,976: May 21, 2019 Nonfinal Office Action, 11 pages.
U.S. Appl. No. 15/768,352: Feb. 14, 2019 Non-Final Office Action, 15 pages.
U.S. Appl. No. 15/768,352: Jun. 3, 2019 Examiner Interview Summary, 5 pages.
U.S. Appl. No. 15/768,352: Jun. 12, 2019 Notice of Allowance including Examiner's Reasons for Allowance and Examiner Interview Summary, 21 pages.
U.S. Appl. No. 15/768,352: Jul. 12, 2019 Examiner Interview Summary, 4 pages.
U.S. Appl. No. 15/768,352: Aug. 28, 2019 Notice of Allowance including Examiner's Reasons for Allowance and Examiner Interview Summary, 16 pages.
U.S. Appl. No. 15/809,815: Mar. 6, 2018 Nonfinal Office Action, 12 pages.
U.S. Appl. No. 15/809,815: Sep. 11, 2018 Final Office Action, 14 pages.
U.S. Appl. No. 15/809,815: Jul. 8, 2019 Non-Final Office Action, 13 pages.
U.S. Appl. No. 15/852,551: Jan. 11, 2019 Nonfinal Office Action, 5 pages.
U.S. Appl. No. 15/896,389: Jul. 18, 2019 Nonfinal Office Action, 24 pages.
U.S. Appl. No. 15/896,436: Jul. 5, 2019 Nonfinal Office Action, 18 pages.
U.S. Appl. No. 15/967,638: Jan. 14, 2019 Nonfinal Office Action, 14 pages.
U.S. Appl. No. 16/012,351: Mar. 8, 2019 Non-Final Office Action, 13 pages.
U.S. Appl. No. 16/012,372: Mar. 8, 2019 Non-Final Office Action, 8 pages.
U.S. Appl. No. 16/036,885: Sep. 3, 2019 Non-Final Office Action, 15 pages.
U.S. Appl. No. 11/121,294: Aug. 17, 2009 Nonfinal Office Action, 33 pages.
U.S. Appl. No. 11/121,294: Mar. 12, 2010 Final Office Action, 15 pages.
U.S. Appl. No. 11/121,294: May 19, 2010 Advisory Action, 3 pages.
U.S. Appl. No. 11/121,294: Aug. 4, 2010 Nonfinal Office Action, 14 pages.
U.S. Appl. No. 11/121,294: Dec. 6, 2010 Final Office Action, 17 pages.
U.S. Appl. No. 11/121,294: Apr. 13, 2011 Nonfinal Office Action, 10 pages.
U.S. Appl. No. 11/121,294: Jul. 12, 2011 Examiner Interview Summary, 3 pages.

(56) References Cited

OTHER PUBLICATIONS

U.S. Appl. No. 11/121,294: Nov. 23, 2011 Final Office Action, 20 pages.
U.S. Appl. No. 11/601,451: Jan. 11, 2010 Nonfinal Office Action, 14 pages.
U.S. Appl. No. 11/601,451: Aug. 27, 2010 Final Office Action, 17 pages.
U.S. Appl. No. 11/601,451: Jul. 12, 2011 Examiner Interview Summary, 4 pages.
U.S. Appl. No. 13/416,204: May 8, 2012 Pre-Interview Communication, 4 pages.
U.S. Appl. No. 13/416,204: Jun. 29, 2012 Interview Summary and First Action Interview Office Action, 6 pages.
U.S. Appl. No. 13/654,373: Aug. 12, 2013 Nonfinal Office Action and Interview Summary, 10 pages.
U.S. Appl. No. 14/151,632: Apr. 18, 2016 Nonfinal Office Action, 9 pages.
U.S. Appl. No. 14/175,365: Jun. 26, 2014 Nonfinal Office Action, 20 pages.
U.S. Appl. No. 14/406,776: Feb. 26, 2016 Nonfinal Office Action, 9 pages.
U.S. Appl. No. 14/632,422: Jan. 10, 2017 Nonfinal Office Action, 18 pages.
U.S. Appl. No. 14/812,950: Oct. 2, 2015 Pre-Interview Communication, 3 pages.
U.S. Appl. No. 14/844,500: Dec. 16, 2015 Nonfinal Office Action, 25 pages.
U.S. Appl. No. 14/851,111: Feb. 25, 2016 Nonfinal Office Action, 13 pages.
U.S. Appl. No. 14/879,302: Aug. 15, 2016 Nonfinal Office Action, 30 pages.
U.S. Appl. No. 14/879,302: Dec. 15, 2016 Nonfinal Office Action, 14 pages.
U.S. Appl. No. 14/879,358: Dec. 28, 2015 Nonfinal Office Action, 20 pages.
U.S. Appl. No. 14/879,358: Jul. 12, 2016 Nonfinal Office Action, 14 pages.
U.S. Appl. No. 14/964,239: Nov. 4, 2016 Nonfinal Office Action, 21 pages.
U.S. Appl. No. 14/964,239: Apr. 26, 2017 Examiner Interview Summary, 2 pages.
U.S. Appl. No. 14/964,239: Jun. 21, 2017 Nonfinal Office Action, 16 pages.
U.S. Appl. No. 14/964,239: Dec. 11, 2017 Nonfinal Office Action, 15 pages.
U.S. Appl. No. 14/964,571: Feb. 13, 2017 Nonfinal Office Action, 8 pages.
U.S. Appl. No. 14/964,571: Nov. 1, 2017 Final Office Action, 14 pages.
U.S. Appl. No. 14/964,571: Sep. 25, 2018 Nonfinal Office Action, 12 pages.
U.S. Appl. No. 14/964,571: Jun. 12, 2019 Final Office Action, 15 pages.
U.S. Appl. No. 14/965,140: Mar. 10, 2016 Nonfinal Office Action, 24 pages.
U.S. Appl. No. 14/965,140: Jul. 13, 2016 Interview Summary and Nonfinal Office Action, 14 pages.
U.S. Appl. No. 14/965,140: Dec. 19, 2016 Nonfinal Office Action, 9 pages.
U.S. Appl. No. 14/966,458: Dec. 6, 2016 Nonfinal Office Action, 34 pages.
U.S. Appl. No. 14/966,458: Apr. 27, 2017 Examiner Interview Summary, 2 pages.
U.S. Appl. No. 14/979,666: Dec. 9, 2016 Nonfinal Office Action, 20 pages.
U.S. Appl. No. 15/059,640: Dec. 2, 2016 Nonfinal Office Action, 9 pages.
U.S. Appl. No. 15/227,561: Jul. 14, 2017 Nonfinal Office Action, 25 pages.
U.S. Appl. No. 15/227,561: Apr. 26, 2018 Nonfinal Office Action, 13 pages.
U.S. Appl. No. 15/227,561: Dec. 10, 2018 Final Office Action, 18 pages.
U.S. Appl. No. 15/227,631: Jul. 17, 2017 Nonfinal Office Action, 24 pages.
U.S. Appl. No. 15/227,631: Apr. 10, 2018 Nonfinal Office Action, 13 pages.
U.S. Appl. No. 15/227,631: Aug. 31, 2018 Nonfinal Office Action, 15 pages.
U.S. Appl. No. 15/227,631: Dec. 19, 2018 Final Office Action, 15 pages.
U.S. Appl. No. 15/241,106: Oct. 28, 2016 Pre-Interview Communication, 4 pages.
U.S. Appl. No. 15/241,106: Dec. 29, 2016 Nonfinal Office Action, 15 pages.
U.S. Appl. No. 15/241,106: Jul. 10, 2017 Final Office Action, 16 pages.
Ahmad I, et al., "Antibody-Targeted Delivery of Doxorubicin Entrapped in Sterically Stabilized Liposomes Can Eradicate Lung Cancer in Mice," Cancer Res. 53(7):1484-8 (1993).
Ardizzoni A, et al., "Topotecan, A New Active Drug in the Second-Line Treatment of Small-Cell Lung Cancer: A Phase II Study in Patients with Refractory and Sensitive Disease," J Clin Oncol. 15(5):2090-6 (1997).
Chan D, et al., "Evaluating the Pharmacodynamics and Pharmacokinetic Effects of MM-398, a Nanoliposomal Irinotecan (nal-IRI) in Subcutaneous Xenograft Tumor Models of Human Squamous Cell Carcinoma and Small Cell Lung Cancers," Poster presented at AACR Annual Meeting Apr. 5-9, 2014, 6 pages.
Chan D, et al., "Evaluating the Pharmacodynamics and Pharmacokinetic Effects of MM-398, a Nanoliposomal Irinotecan (nal-IRI) in Subcutaneous Xenograft Tumor Models of Human Squamous Cell Carcinoma and Small Cell Lung Cancers," Cancer Res.74(19 Suppl): Abstract 4626 (2014), 2 printed pages.
Chan D, et al., "PEP02 (Liposome Irinotecan) Effectively Inhibits Human Lung Squamous Cell Carcinoma and Small Cell Lung Cancers in Subcutaneous and Orthotopic Xenograft Tumor Models," J Thoracic Oncology. 6(6)(Suppl 2):S420-1 (2011).
Chan D, et al., "PEP02 (Liposome Irinotecan) Effectively Inhibits Human Squamous Cell Carcinoma and Small Cell Lung Cancers in Subcutaneous and Orthotopic Xenograft Tumor Models." Presentation at the 14th World Conference on Lung Cancer, 2011, 11 pages.
Chan D, et al., "PEP02 (Liposome Irinotecan) Effectively Inhibits Human Squamous Cell Carcinoma and Small Cell Lung Cancers in Subcutaneous and Orthotopic Xenograft Tumor Models." Presentation at Santa Monica Lung Cancer Meeting, 2012, 9 pages.
Clinical Trials Identifier NCT00104754: Jul. 20, 2016 update, first posted Mar. 4, 2005, "Phase II Trial of Liposome Encapsulated SN38 (LE-SN38) in the Treatment of Small Cell Lung Cancer." Retrieved from ClinicalTrials.gov archive, 8 printed pages.
Clinical Trials Identifier NCT01770353: Aug. 9, 2013 update, "A Pilot Study in Patients Treated with MM-398 to Determine Tumor Drug Levels and to Evaluate the Feasibility of Ferumoxytol Magnetic Resonance Imaging to Measure Tumor Associated Macrophages." Retrieved from ClinicalTrials.gov archive, 3 printed pages.
Clinical Trials Identifier NCT03088813: Sep. 30, 2019 update, first posted Mar. 23, 2017, "Study of Irinotecan Liposome Injection (ONIVYDE®) in Patients With Small Cell Lung Cancer." Retrieved from ClinicalTrials.gov archive, 8 printed pages.
Eckardt J, et al., "Phase III Study of Oral Compared With Intravenous Topotecan as Second-Line Therapy in Small-Cell Lung Cancer," J Clin Oncol. 25(15):2086-92 (2007).
Hanna N, et al., "Randomized Phase III Trial Comparing Irinotecan/Cisplatin with Etoposide/Cisplatin in Patients with Previously Untreated Extensive-Stage Disease Small-Cell Lung Cancer," J Clin Oncol. 24(13)2038-43 (2006).
Huber R, et al., "Efficacy of a Toxicity-Adjusted Topotecan Therapy in Recurrent Small Cell Lung Cancer," Eur Respir J. 27(6):1183-9 (2006).

(56) References Cited

OTHER PUBLICATIONS

Hycamtin (topotecan hydrochloride) for injection package insert, revision Feb. 28, 2014, retrieved from https://www.accessdata.fda.gov/drugsatfda_docs/label/2014/020671s020lbl.pdf, 23 pages.
Hycamtin (topotecan) for injection package insert, revision Jun. 2, 2015, retrieved from https://www.accessdata.fda.gov/drugsatfda_docs/label/2015/020671s021lbl.pdf, 21 pages.
Kalra A, et al., "Preclinical Activity of Nanoliposomal Irinotecan Is Governed by Tumor Deposition and Intratumor Prodrug Conversion," Cancer Res. 74(23):7003-13 (2014).
Leonard S, et al., "Extended Topoisomerase 1 Inhibition Through Liposomal Irinotecan Results in Improved Efficacy over Topotecan and Irinotecan in Models of Small-Cell Lung Cancer," Anti-Cancer Drugs. 28(10):1086-96 (2017).
Leonard S, et al., "Irinotecan Liposome Injection has Greater Anti-Tumor Activity than Topotecan and Irinotecan in Mouse Models of Small Cell Lung Cancer," Poster presented at AACR 110th Annual World Congress 2017, Washington, DC, Apr. 1-5, 2017, 6 pages.
Leonard S, et al., "Preclinical Support for Evaluation of Irinotecan Liposome Injection (nal-IRI, MM-398) in Small Cell Lung Cancer," Poster presented at 17th World Conference on Lung Cancer, Vienna, Austria, Dec. 4-7, 2016, 5 pages.
Leonard S, et al., "Preclinical Support for Evaluation of Irinotecan Liposome Injection (nal-IRI, MM-398) in Small Cell Lung Cancer," Abstracts from the IASLC 17th World Conference on Lung Cancer held Dec. 4-7, 2016, J Thoracic Oncology. 12(1)(Suppl):S699 (2016), 1 page.
Masuda N, et al., "CPT-11: A New Derivative of Camptothecin for the Treatment of Refractory or Relapsed Small-Cell Lung Cancer," J Clin Oncol. 10(8):1225-9 (1992).
Merrimack Pharmaceuticals, "Merrimack Pharmaceuticals Initiates Cross-Tumor Study to Investigate Potential Predictive Response Markers for a Developmental Nanotherapeutic Chemotherapy," Dec. 19, 2012. Retrieved from http://investors.merrimack.com/news-releases/news-release-details/merrimack-pharmaceuticals-initiates-cross-tumor-study, 2 printed pages.
O'Brien M, et al., "Phase III Trial Comparing Supportive Care Alone With Supportive Care With Oral Topotecan in Patients With Relapsed Small-Cell Lung Cancer," J Clin Oncol. 24(34):5441-7 (2006).
Onivyde [MM-398] package insert, revision Oct. 22, 2015, retrieved from http://www.accessdata.fda.gov/drugsat.fda_docs/label/2015/207793lbl.pdf, 18 pages.
Owonikoko T, et al., "A Systematic Analysis of Efficacy of Second-Line Chemotherapy in Sensitive and Refractory Small-Cell Lung Cancer," J Thorac Oncol. 7(5):866-72 (2012).
Pallis A, et al., "A Multicenter Randomized Phase II Study of the Irinotecan/Gemcitabine Doublet Versus Irinotecan Monotherapy in Previously Treated Patients with Extensive Stage Small-Cell Lung Cancer," Lung Cancer. 65(2):187-91 (2009), Epub Dec. 18, 2008.
Paz-Ares L, et aL., "Liposomal Irinotecan vs Topotecan in Patients with Small Cell Lung Cancer Who Have Progressed On/After Platinum-Based Therapy." Poster presented Sep. 23-26, 2018 at 19th World Conference on Lung Cancer meeting, 9 pages.
Paz-Ares L, et al., "Resilient: Study of Irinotecan Liposome Injection (nal-IRI) in Patients with Small Cell Lung Cancer—Preliminary Findings from Part 1 Dose-Defining Phase," Poster presented at ASCO in Chicago, IL May 31-Jun. 4, 2019, 6 pages.
Paz-Ares L, et al., "Resilient: Study of Irinotecan Liposome Injection (nal-IRI) in Patients with Small Cell Lung Cancer—Preliminary Findings from Part 1 Dose-Defining Phase," Abstract No. 8562, J Clin Oncol. 37(15)(Suppl):8562 (2019).
PCT/IB2017/000681: PCT International Preliminary Report on Patentability dated Nov. 20, 2018, 6 pages.
PCT/IB2017/000681: PCT International Search Report and Written Opinion dated Aug. 25, 2017, 8 pages.
Ramanathan R, et al., "Lesion Characterization with Ferumoxytol MRI in Patients with Advanced Solid Tumors and Correlation with Treatment Response to MM-398, Nanoliposomal Irinotecan (nal-IRI)," Abstract No. 261. Eur. J. Cancer, 50:87 (2014).
Tardi P. et al., "Drug Ratio-Dependent Antitumor Activity of Irinotecan and Cisplatin Combinations In Vitro and In Vivo," Mol Cancer Ther. 8(8):2266-75 (2009).
Von Pawel J, et al., "Randomized Phase III Trial of Amrubicin Versus Topotecan as Second-Line Treatment for Patients with Small-Cell Lung Cancer," J Clin Oncol. 32(35):4012-9 and appendix (1 page) (2014).
Von Pawel J, et al., "Topotecan Versus Cyclophosphamide, Doxorubicin, and Vincristine for the Treatment of Recurrent Small-Cell Lung Cancer," J Clin Oncol. 17(2):658-67 (1999).
Zhao M, et al., "Clinical Observation of Irinotecan or Topotecan as Second-Line Chemotherapy on Treating 43 Patients with Small-Cell Lung Cancer," Chin Oncol. 21(2):156-8 (2011), text in Chinese with Tables 1-3 and Figure 1 in English.
U.S. Appl. No. 11/121,294, filed May 2, 2005, U.S. Pat. No. 8,147,867, Issued.
U.S. Appl. No. 11/601,451, filed Nov. 17, 2006, U.S. Pat. No. 8,658,203, Issued.
U.S. Appl. No. 13/416,204, filed Mar. 9, 2012, U.S. Pat. No. 8,329,213, Issued.
U.S. Appl. No. 13/654,373, filed Oct. 17, 2012, U.S. Pat. No. 8,703,181, Issued.
U.S. Appl. No. 14/151,632, filed Jan. 9, 2014, Abandoned.
U.S. Appl. No. 14/175,365, filed Feb. 7, 2014, U.S. Pat. No. 8,992,970, Issued.
U.S. Appl. No. 14/632,422, filed Feb. 26, 2015, U.S. Pat. No. 9,717,723, Issued.
U.S. Appl. No. 14/879,302, filed Oct. 9, 2015, U.S. Pat. No. 9,730,891, Issued.
U.S. Appl. No. 14/879,358, filed Oct. 9, 2015, Abandoned.
U.S. Appl. No. 14/964,239, filed Dec. 9, 2015, Abandoned.
U.S. Appl. No. 14/965,140, filed Dec. 10, 2015, U.S. Pat. No. 9,724,303, Issued.
U.S. Appl. No. 14/966,458, filed Dec. 11, 2015, U.S. Pat. No. 9,782,349, Issued.
U.S. Appl. No. 14/979,666, filed Dec. 28, 2015, Abandoned.
U.S. Appl. No. 15/227,561, filed Aug. 3, 2016, Abandoned.
U.S. Appl. No. 15/227,631, filed Aug. 3, 2016, Abandoned.
U.S. Appl. No. 15/213,127, filed Jul. 18, 2016, Abandoned.
U.S. Appl. No. 15/296,536, filed Oct. 18, 2016, U.S. Pat. No. 9,737,528, Issued.
U.S. Appl. No. 15/363,761, filed Nov. 29, 2016, U.S. Pat. No. 10,413,510, Issued.
U.S. Appl. No. 15363,923, filed Nov. 29, 2016, Abandoned.
U.S. Appl. No. 15/363,978, filed Nov. 29, 2016, U.S. Pat. No. 10,350,201, Issued.
U.S. Appl. No. 15/364,021, filed Nov. 29, 2016, Abandoned.
U.S. Appl. No. 15/664,976, filed Jul. 31, 2017, Published.
U.S. Appl. No. 15/896,389, filed Feb. 14, 2018, Published.
U.S. Appl. No. 15/896,436, filed Feb. 14, 2018, Published.
U.S. Appl. No. 14/406,776, filed Dec. 10, 2014, U.S. Pat. No. 9,452,162, Issued.
U.S. Appl. No. 14/812,950, filed Jul. 29, 2015, U.S. Pat. No. 9,339,497, Issued.
U.S. Appl. No. 14/844,500, filed Sep. 3, 2015, U.S. Pat. No. 9,364,473, Issued.
U.S. Appl. No. 14/851,111, filed Sep. 11, 2015, U.S. Pat. No. 9,492,442, Issued.
U.S. Appl. No. 15/059,640, filed Mar. 3, 2016, Abandoned.
U.S. Appl. No. 15/241,128, filed Aug. 19, 2016, U.S. Pat. No. 9,717,724, Issued.
U.S. Appl. No. 15/341,377, filed Nov. 2, 2016, Abandoned.
U.S. Appl. No. 15/341,619, filed Nov. 2, 2016, Abandoned.
U.S. Appl. No. 15/652,513, filed Jul. 18, 2017, Abandoned.
U.S. Appl. No. 15/664,930, filed Jul. 31, 2017, Abandoned.
U.S. Appl. No. 16/012,351, filed Jun. 19, 2018, Published.
U.S. Appl. No. 16/012,372, filed Jun. 19, 2018, Published.
U.S. Appl. No. 14/964,571, filed Dec. 9, 2015, Published.
U.S. Appl. No. 15/375,039, filed Dec. 9, 2016, Abandoned.
U.S. Appl. No. 15/928,649, filed Mar. 22, 2018, Abandoned.
U.S. Appl. No. 16/036,885, filed Jul. 16, 2018, Published.

(56) References Cited

OTHER PUBLICATIONS

U.S. Appl. No. 15/337,274, filed Oct. 28, 2016, U.S. Pat. No. 9,895,365, Issued.
U.S. Appl. No. 15/852,551, filed Dec. 22, 2017, Published, Packard.
U.S. Appl. No. 16/586,609, filed Sep. 27, 2019, Pending.
U.S. Appl. No. 15/241,106, filed Aug. 19, 2016, Abandoned.
U.S. Appl. No. 15/809,815, filed Nov. 10, 2017, Published.
U.S. Appl. No. 15/403,441, filed Jan. 11, 2017, Abandoned.
U.S. Appl. No. 15/331,648, filed Oct. 21, 2016, Abandoned.
U.S. Appl. No. 15/331,393, filed Oct. 21, 2016, Abandoned.
U.S. Appl. No. 15/331,318, filed Oct. 21, 2016, Abandoned.
U.S. Appl. No. 15/645,645, filed Jul. 10, 2017, Abandoned.
U.S. Appl. No. 15/655,592, filed Jul. 20, 2017, Abandoned.
U.S. Appl. No. 15/661,868, filed Jul. 27, 2017, Abandoned.
U.S. Appl. No. 15/608,443, filed Feb. 28, 2018, Abandoned.
U.S. Appl. No. 15/768,352, filed Apr. 13, 2018, Published.
U.S. Appl. No. 15/967,633, filed May 1, 2018, Abandoned.
U.S. Appl. No. 15/967,638, filed May 1, 2018, Abandoned.
U.S. Appl. No. 16/510,394, filed Jul. 12, 2019, Pending.
U.S. Appl. No. 16/567,902, filed Sep. 11, 2019, Pending.
U.S. Appl. No. 15/598,633, filed May 18, 2017, Abandoned.
U.S. Appl. No. 15/948,574, filed Apr. 9, 2018, Abandoned.
U.S. Appl. No. 16/302,050, filed Nov. 15, 2018, Published.
U.S. Appl. No. 16/346,436, filed Apr. 30, 2019, Pending.
Pfizer Background Document on the UGT1A1 Polymorphisms and Irinotecan Toxicity: ACPS Nov. 3, 2004 Advisory Committee Meeting, 19 pages.
Pliarchopoulou K, et al., "Pancreatic Cancer: Current and Future Treatment Strategies," Cancer Treat Rev. 35(5):431-6 (2009).
Qin B, et al., "In-vitro Schedule-Dependent Interaction Between Oxaliplatin and 5-Fluorouracil in Human Gastric Cancer Cell Lines," Anti-Cancer Drugs. 17(4):445-53 (2006).
Rahib L, et al., "Projecting Cancer Incidence and Deaths to 2030: The Unexpected Burden of Thyroid, Liver, and Pancreas Cancers in the United States," Cancer Res. 74(11):2913-21 (2014).
Rahma O, et al., "Second-Line Treatment in Advanced Pancreatic Cancer: A Comprehensive Analysis of Published Clinical Trials," Ann Oncol. 24(8):1972-9 (2013), epub doi:10.1093/annonc/mdt166, May 12, 2013, pp. 1-8.
Raymond E, et al., "Multicentre Phase II Study and Pharmacokinetic Analysis of Irinotecan in Chemotherapy-Naive Patients with Glioblastoma," Ann Oncol. 14(4):603-14 (2003).
Reni M, et al., "Salvage Chemotherapy with Mitomycin, Docetaxel, and Irinotecan (MDI Regimen) in Metastatic Pancreatic Adenocarcinoma: A Phase I and II Trial," Cancer Invest. 22(5):688-96 (2004).
Rivory L, et al., "Pharmacokinetic Interrelationships of Irinotecan (CPT-11) and Its Three Major Plasma Metabolites in Patients Enrolled in Phase I/II Trials," Clin Cancer Res. 3(8):1261-6 (1997).
Rombouts S, et al., "FOLFIRINOX in Locally Advanced and Metastatic Pancreatic Cancer: A Single Centre Cohort Study," J Cancer. 7(13):1861-6 (2016).
Rothenberg M, et al., "Phase I and Pharmacokinetic Trial of Weekly CPT-11," J Clin Oncol. 11(11):2194-204 (1993).
Roy A, et al., "A Randomized Phase II Study of PEP02 (MM-398), Irinotecan or Docetaxel as a Second-Line Therapy in Patients With Locally Advanced or Metastatic Gastric or Gastro-Oesophageal Junction Adenocarcinoma," Ann Oncol. 24(6):1567-73 (2013).
Sachdev J, et al., "A Phase 1 Study in Patients with Metastatic Breast Cancer to Evaluate the Feasibility of Magnetic Resonance Imaging with Ferumoxytol as a Potential Biomarker for Response to Treatment with Irinotecan Liposome Injection (nal-IRI, MM-398)." Poster presented at 38th Annual San Antonio Breast Cancer Symposium on Dec. 8, 2015, 10 pages.
Sachdev J, et al., "Characterization of Metastatic Breast Cancer Lesions with Ferumoxytol MRI and Clinical Response to MM-398, Nanoliposomal Irinotecan (nal-IRI), in 3 Subjects." Poster presented at San Antonio Breast Cancer Symposium 2014, 8 pages.
Sachdev J, et al., "Characterization of Metastatic Breast Cancer Lesions with Ferumoxytol MRI and Treatment Response to MM-398, Nanoliposomal Irinotecan (nal-IRI)," Cancer Res.75(9 Suppl): Abstract P5-01-06 (2015), 3 printed pages.
Sachdev J, et al., "Phase I Expansion Study of Irinotecan Liposome Injection (nal-IRI) in Patients with Metastatic Breast Cancer (mBC)." Poster presented at the American Association for Cancer Research Annual Meeting 2019; Mar. 29-Apr. 3, 2019; Atlanta, GA, 9 printed pages.
Sachdev J, et al., Abstract C1048. "Phase I Expansion Study of Irinotecan Liposome Injection (nal-IRI) in Patients with Metastatic Breast Cancer (mBC)," Cancer Res. In Proceedings of the American Association for Cancer Research Annual Meeting 2019; Mar. 29-Apr. 3, 2019; Atlanta, GA. Cancer Res. 2019; 79(13 Suppl):Abstract nr CT048, 4 printed pages.
Sadzuka Y, et al. "Effect of Liposomalization on the Antitumor Activity, Side-Effects and Tissue Distribution of CPT-11," Cancer Lett. 127(1-2): 99-106 (1998).
Saito R, et al., "Distribution of Liposomes into Brain and Rat Brain Tumor Models by Convection-Enhanced Delivery Monitored with Magnetic Resonance Imaging," Cancer Res. 64(7):2572-9 (2004).
Saito R, et al., "Gadolinium-loaded Liposomes Allow for Real-Time Magnetic Resonance Imaging of Convection-Enhanced Delivery in the Primate Brain," Exp Neurol. 196(2):381-9 (2005).
Saito R, et al., "Tissue Affinity of the Infusate Affects the Distribution Volume During Convection-Enhanced Delivery into Rodent Brains: Implications for Local Drug Delivery," J Neurosci Methods. 154(1-2):225-32 (2006).
Saltz L, et al., "Irinotecan Plus Fluorouracil and Leucovorin for Metastatic Colorectal Cancer. Irinotecan Study Group," N Engl J Med. 343(13):905-14 (2000).
Shimada S, et al., "Irinotecan Plus Low-Dose Cisplatin for α-Fetoprotein-Producing Gastric Carcinoma with Multiple Liver Metastases: Report of Two Cases," Surg Today. 32(12):1075-80 (2002).
Siegel R, et al., "Cancer Statistics, 2015," CA Cancer J Clin. 65(1):5-29 (2015).
Slatter J, et al., "Pharmacokinetics, Metabolism, and Excretion of Irinotecan (CPT-11) Following I.V. Infusion of [14C]CPT-11 in Cancer Patients," Drug Metab Dispos. 28(4):423-33 (2000).
Stein S, et al., "Final Analysis of a Phase II Study of Modified FOLFIRINOX in Locally Advanced and Metastatic Pancreatic Cancer," Br J Cancer. 114(7):737-43 (2016).
Tahara M, et al., "The Use of Olaparib (AZD2281) Potentiates SN-38 Cytotoxicity in Colon Cancer Cells by Indirect Inhibition of Rad51-Mediated Repair of DNA Double-Strand Breaks," Mol Cancer Ther. 13(5):1170-80 (2014).
Taïeb J., "FOLFIRI.3, A New Regimen Combining 5-Fluorouracil, Folinic Acid and Irinotecan, For Advanced Pancreatic Cancer: Results of an Association des Gastro-Enterologues Oncologues (Gastroenterologist Oncologist Association) Multicenter Phase II Study," Ann Oncol. 18(3)498-503 (2007), epub Dec 8, 2006.
Takahara N, et al., "Uridine Disphosphate Glucuronosyl Transferase 1 Family Polypeptide A1 Gene (UGT1A1) Polymorphisms are Associated with Toxicity and Efficacy in Irinotecan Monotherapy for Refractory Pancreatic Cancer," Cancer Chemother Pharmacol. 71(1):85-92 (2013), Epub Sep. 29, 2012.
Tanaka R, et al., "Synergistic Interaction Between Oxaliplatin and SN-38 in Human Gastric Cancer Cell Lines In Vitro," Oncol Rep. 14(3):683-8 (2005).
Tentori L, et al., "Influence of MLH1 on Colon Cancer Sensitivity to Poly(ADP-ribose) Polymerase Inhibitor Combined with Irinotecan," Int J Oncol. 43(1):210-8 (2013).
Tsai C, et al., "Nanovector-Based Therapies in Advanced Pancreatic Cancer," J Gastroint Oncol 2(3):185-94 (2011).
Tsubamoto H, et al., "Combination Chemotherapy with Itraconazole for Treating Metastatic Pancreatic Cancer in the Second-line or Additional Setting,". Anticancer Res. 35(7):4191-6 (2015).
U.S. Appl. No. 15/664,976: Nov. 4, 2019 Nonfinal Office Action, 9 pages.
U.S. Appl. No. 15/664,976: May 18, 2020 Final Office Action, 11 pages.
U.S. Appl. No. 15/809,815: Feb. 27, 2020 Final Office Action, 16 pages.

(56) References Cited

OTHER PUBLICATIONS

U.S. Appl. No. 15/896,389: Jan. 31, 2020 Final Office Action, 28 pages.
U.S. Appl. No. 15/896,389: Mar. 26, 2020 Examiner Interview Summary and Applicant slides, 22 pages.
U.S. Appl. No. 15/896,389: Apr. 9, 2020 Advisory Action, 3 pages.
U.S. Appl. No. 15/896,389: Jun. 5, 2020 Notice of Allowance including Examiner's Reasons for Allowance and Examiner Interview Summary, 13 pages.
U.S. Appl. No. 16/012,351: Jan. 7, 2020 Final Office Action, 9 pages.
U.S. Appl. No. 16/012,372: Jan. 7, 2020 Final Office Action, 9 pages.
U.S. Appl. No. 16/012,372: Jul. 27, 2020 Non-Final Office Action, 8 pages.
U.S. Appl. No. 16/302,050: Jan. 17, 2020 Non-Final Office Action, 17 pages.
U.S. Appl. No. 16/510,394: Mar. 6, 2020 Non-Final Office Action, 15 pages.
U.S. Appl. No. 16/567,902: Apr. 27, 2020 Non-Final Office Action, 20 pages.
U.S. Appl. No. 16/567,902: Aug. 10, 2020 Final Office Action, 21 pages.
Ueno H, et al., "A Phase II Study of Weekly Irinotecan as First-Line Therapy for Patients with Metastatic Pancreatic Cancer," Cancer Chemother Pharmacol. 59(4):447-54 (2007), Epub Jul. 20, 2006.
Ulrich-Pur H, et al., "Irinotecan Plus Raltitrexed vs Raltitrexed Alone in Patients with Gemcitabine-Pretreated Advanced Pancreatic Adenocarcinoma," Br J Cancer. 88(8):1180-4 (2003).
Umemura A, et al., "Modified FOLFIRINOX for Locally Advanced and Metastatic Pancreatic Cancer Patients Resistant to Gemcitabine and S-1 in Japan: A Single Institutional Experience," Hepato-Gastroenterology. 61:00-00 doi10.5754/hge14111, pp. 6-12 (2013).
ABRAXANE package insert, revision Dec. 23, 2011, retrieved from https://www.accessdata.fda.gov/drugsatfda_docs/label/2011/021660s025s026s029lbl.pdf, 13 pages.
ABRAXANE package insert, revision Jul. 21, 2015, retrieved from https://www.accessdata.fda.gov/drugsatfda_docs/label/2015/021660s041lbl.pdf, 24 pages.
Adiwijaya B, et al., "Population Pharmacokinetics of Liposomal Irinotecan in Patients With Cancer," Clin Pharmacol Ther. 102(6):997-1005 (2017).
Alagoz M, et al., "DNA Repair and Resistance to Topoisomerase I Inhibitors: Mechanisms, Biomarkers and Therapeutic Targets," Curr Med Chem. 19(23):3874-85 (2012).
Alberts S, et al. "Gemcitabine and Oxaliptatin for Metastatic Pancreatic Adenocarcinoma: A North Central Cancer Treatment Group Phase II Study," Ann Oncol. 14(4):580-5 (2003).
Alcindor T, et al., "Oxaliplatin: A Review in the Era of Molecularly Targeted Therapy," Curr Oncol. 18(1):18-25 (2011).
Alfert M, et al., "A Selective Staining Method for the Basic Proteins of Cell Nuclei," Proc Natl Acad Sci USA. 39(10):991-9 (1953).
American Chemical Society (ACS), http://www.cancer.org/cancer/pancreatccancer/detailedguide/pancreatic-cancer-what-is-pancreatic-cancer, retrieved Dec. 10, 2017, 7 printed pages.
American Chemical Society (ACS), http://www.cancer.org/cancer/pancreaticcancer/detailedguide/pancreatic-cancer-what-is-pancreatic-cancer, retrieved Dec. 1, 2016, 4 printed pages.
Amodeo S, et al., "Can we downstage locally advanced pancreatic cancer to resectable? A phase I/II study of induction oxaliplatin and 5-FU chemoradiation," J Gastrointest Oncol. 9(5):922-35 (2018).
Anders C, et al., "Phase 1 Expansion Study of Irinotecan Liposome Injection (nal-IRI) in Patients with Metastatic Breast Cancer (mBC): Findings from the Cohort with Active Brain Metastasis (BM)." Presentation presented at the Society for Neuro-Oncology Inaugural Conference on Brain Metasteses, Aug. 16-17, 2019, New York, NY, 11 pages.
Anders C, et al., Abstract TRLS-06. "Phase 1 Expansion Study of Irinotecan Liposome Injection (nal-IRI) in Patients with Metastatic Breast Cancer (mBC): Findings from the Cohort with Active Brain Metastasis (BM)," Neuro-Oncology Advances. 1(Suppl 1):i9 doi.org/10.1093/noajnl/vdz014.039 (2019).
Assaf E, et al., "5-Fluorouracil/Leucovorin Combined with Irinotecan and Oxaliplatin (FOLFIRINOX) as Second-Line Chemotherapy in Patients with Metastatic Pancreatic Adenocarcinoma," Oncology. 80(5-6):301-6 (2011).
Author Unknown, "From Antinutrient to Phytonutrient: Phytic Acid Gains Respect." HighBeam Research, Environmental Nutrition, Apr. 1, 2004, 2 printed pages. URL: http://www.highbeam.com/doc/1G1-116341390.html/print (accessed Nov. 4, 2011).
Azrak R, et al., "Therapeutic Synergy Between Irinotecan and 5-Fluorouracil against Human Tumor Xenografts," Clin Cancer Res. 10(3):1121-9 (2004).
Baker J, et al., "Irinophore C, a Novel Nanoformulation of Irinotecan, Alters Tumor Vascular Function and Enhances the Distribution of 5-Fluorouracil and Doxorubicin," Clin Cancer Res. 14(22):7260-71 (2008).
Bendell J, et al., "Treatment Patterns and Clinical Outcomes in Patients With Metastatic Colorectal Cancer Initially Treated with FOLFOX-Bevacizumab or FOLFIRI-Bevacizumab: Results From ARIES, a Bevacizumab Observational Cohort Study," Oncologist. 17(12):1486-95 (2012).
Bernards N, et al., "Liposomal Irinotecan Achieves Significant Survival and Tumor Burden Control in a Triple Negative Breast Cancer Model of Spontaneous Metastasis," Mol Pharm. 15(9):4132-8 (2018).
Bernards N, et al., "Liposomal Irinotecan Injection (nal-IRI) Achieves Significant Survival and Tumor Burden Control in a Triple Negative Breast Cancer Model of Spontaneous Metastasis," Poster presented at the World Molecular Imaging Congress Sep. 13-16, 2017, Philadelphia, Pennsylvania, 5 pages.
Boeck S, et al., "Capecitabine Plus Oxaliplatin (CapOx) versus Capecitabine Plus Gemcitabine (CapGem) versus Gemcitabine Plus Oxaliplatin (mGemOx): Final Results of a Multicenter Randomized Phase II Trial in Advanced Pancreatic Cancer," Ann Oncol. 19(2):340-7 (2008), Epub Oct. 24, 2007.
Brixi-Benmansour H, et al., "Phase II Study of First-line FOLFIRI for Progressive Metastatic Well-differentiated Pancreatic Endocrine Carcinoma," Dig Liver Dis. 43(11):912-6 (2011).
Burris H, et al., "Phase II Trial of Oral Rubitecan in Previously Treated Pancreatic Cancer Patients," Oncologist. 10(3):183-90 (2005).
Butt R, et al., "Postfractionation for Enhanced Proteomic Analyses: Routine Electrophoretic Methods Increase the Resolution of Standard 2D-PAGE," J Proteome Res. 4(3):982-91 (2005).
CAMPTOSAR package insert, revised May 16, 2002, 37 pages.
CAMPTOSAR package insert, revision Dec. 19, 2014, retrieved from https://www.accessdata.fda.gov/drugsatfda_docs/label/2014/020571s048lbl.pdf, initial U.S. approval 1996, 40 printed pages.
CAMPTOSAR package insert, revision May 14, 2010, retrieved from https://www.accessdata.fda.gov/drugsatfda_docs/label/2010/020571s031s032s033s036s037lbl.pdf, 37 pages.
Cantore M, et al., "Combined Irinotecan and Oxaliplatin in Patients with Advanced Pre-Treated Pancreatic Cancer," Oncology 67(2):93-7 (2004).
CAS Registry Record for 23214-92-8 (doxorubicin), entered STN Nov. 16, 1984, 2 pages.
CAS Registry Record for 97682-44-5 (irinotecan), entered STN Aug. 18, 1985, 1 page.
Cereda S, et al., "XELIRI or FOLFIRI as Salvage Therapy in Advanced Pancreatic Cancer," Anticancer Res. 30(11):4785-90 (2010).
Chen L, et al., "Effect of Baseline Carbohydrate Antigen 19-9 (CA19-9) Level on Overall Survival (OS) in NAPOLI-1 Trial: a Phase 3 Study of MM-398 (nal-IRI), with or without 5-Fluorouracil and Leucovorin (5-FU/LV), versus 5-FU/LV in Metastatic Pancreatic Cancer (mPAC) Previously Treated with Gemcitabine-based Therapy." Poster presented at the Gastrointestinal Cancers Symposium of the ASCO meeting of Jan. 21-23, 2016, San Francisco, California, 16 pages.
Chen L, et al., "Effect of Baseline Carbohydrate Antigen 19-9 (CA19-9) Level on Overall Survival (OS) in NAPOLI-1 Trial: a Phase 3 Study of MM-398 (nal-IRI), with or without 5-Fluorouracil and Leucovorin (5-FU/LV), versus 5-FU/LV in Metastatic Pancre-

(56) References Cited

OTHER PUBLICATIONS atic Cancer (mPAC) Previously Treated with Gemcitabine-based Therapy." Poster handout at the Gastrointestinal Cancers Symposium of the ASCO meeting of Jan. 21-23, 2016, San Francisco, California, 2 pages.
Chen L, et al., "Expanded Analyses of NAPOLI-1: Phase 3 Study of MM-398 (nal-IRI), with or without 5-Fluorouracil and Leucovorin, versus 5-Fluorouracil and Leucovorin, in Metastatic Pancreatic Cancer (mPAC) Previously Treated with Gemcitabine-based Therapy." Presented Jan. 15, 2015, ASCO GI, 17 pages.
Chen L, et al., "Expanded Analyses of NAPOLI-1: Phase 3 Study of MM-398 (nal-IRI), With or Without 5-Fluorouracil and Leucovorin, Versus 5-Fluorouracil and Leucovorin, in Metastatic Pancreatic Cancer (mPAC) Previously Treated with Gemcitabine-Based Therapy." Poster presented at the ASCO meeting of May 29-Jun. 2, 2015, Chicago, Illinois, 7 pages.
Chen L, et al., "Phase I Study of Biweekly Liposome Irinotecan (PEP02, MM-398) in Metastatic Colorectal Cancer Failed on First-line Oxaliplatin-based Chemotherapy," J Clin Oncol. 30(4_suppl):Abstract 613 (2012), 6 printed pages.
Chen L, et al., "Safety Across Subgroups in NAPOLI-1:A Phase 3 Study of nal-IRI (MM-398) ± 5-Fluorouracil and Leucovorin (5-FU/LV) Versus 5-FU/LV in Metastatic Pancreatic Cancer (mPAC) Previously Treated with Gemcitabine-Based Therapy." Poster presented at the 18th European Society of Medical Oncology World Congress on Gastrointestinal Cancer; Barcelona, Spain; Jun. 29-Jul. 2, 2016, 10 pages.
Chen L, et al., Abstract PD-023. "Safety Across Subgroups in NAPOLI-1:A Phase 3 Study of nal-IRI (MM-398) ± 5-Fluorouracil and Leucovorin (5-FU/LV) Versus 5-FU/LV in Metastatic Pancreatic Cancer (mPAC) Previously Treated with Gemcitabine-Based Therapy." Annals of Oncology. 27(Suppl 2):ii102-ii117 (2016), 1 page.
Chen P, et al., "Comparing Routes of Delivery for Nanoliposomal Irinotecan Shows Superior Anti-Tumor Activity of Local Administration in Treating Intracranial Glioblastoma Xenografts," Neuro Oncol. 15(2):189-97 (2013), Epub Dec. 21, 2012.
Chibaudel B, et al., "PEPCOL: a GERCOR Randomized Phase II Study of Nanoliposomal Irinotecan PEP02 (MM-398) or Irinotecan with Leucovorin/5-Fluorouracil as Second-Line Therapy in Metastatic Colorectal Cancer", Cancer Med. 5(4):676-83 (2016).
Chibaudel B, et al., "PEPCOL: A Randomized Non-Comparative Phase II Study to Evaluate the Efficacy and Safety of PEP02 (MM-398) or Irinotecan in Combination with Leucovorin and 5-Fluorouracil as Second-Line Treatment for Patients with Unresectable Metastatic Colorectal Cancer. A GERCOR Study." Poster presented at ASCO 2015, 6 pages.
Chiesa M, et al., "A Pilot Phase II Study of Chemotherapy with Oxaliplatin, Folinic Acid, 5-Fluorouracil and Irinotecan in Metastatic Gastric Cancer," Tumori. 93(3)244-7 (2007).
Chiesa MD, et al., "Sequential Chemotherapy with Dose-Dense Docetaxel, Cisplatin, Folinic Acid and 5-Fluorouracil (TCF-dd) Followed by Combination of Oxaliplatin, Folinic acid, 5-Fluorouracil and Irinotecan (COFFI) in Metastatic Gastric Cancer: Results of a Phase II Trial," Cancer Chemother Pharmacol. 67(1):41-8 (2011), epub 2010.
Chou T, et al. "Effect of Composition on the Stability of Liposomal Irinotecan Prepared by a pH Gradient Method," J Biosci Bioeng. 95(4):405-8 (2003).
Chuang V and M. Suno, "Levoleucovorin as Replacement for Leucovorin in Cancer Treatment," Ann Pharmacother. 46(10):1349-57 (2012).
Clarke J, et al., "A Phase 1 Trial of Intravenous Liposomal Irinotecan in Patients with Recurrent High-Grade Glioma," Cancer Chemother Pharmacol. 79(3):603-10 (2017).
Clinical Trials Identifier NCT00311610: Jun. 29, 2016 update, first posted Apr. 6, 2006, "Phase II Trial of LE SN38 in Patients with Metastatic Colorectal Cancer After Progression on Oxaliplatin." Retrieved from ClinicalTrials.gov archive, 8 printed pages.
Clinical Trials Identifier NCT00734682: Jan. 7, 2015 update, first posted Aug. 14, 2008, "A Phase I Trial of Nanoliposomal CPT-11 (NL CPT-11) in Patients With Recurrent High-Grade Gliomas." Retrieved from ClinicalTrials.gov archive, 6 printed pages.
Clinical Trials Identifier NCT00813072: Mar. 2, 2012 update, first posted Dec. 22, 2008, "A Randomized Phase II Study of PEP02, Irinotecan or Docetaxel as a Second Line Therapy in Patients With Locally Advanced or Metastatic Gastric or Gastroesophageal Junction Adenocarcinoma." Retrieved from ClinicalTrials.gov archive, 9 printed pages.
Clinical Trials Identifier NCT00813163: Jan. 11, 2011 update, "A Phase II Study of PEP02 as a Second Line Therapy for Patients With Metastatic Pancreatic Cancer." Retrieved from ClinicalTrials.gov archive, 3 printed pages.
Clinical Trials Identifier NCT00813163: Mar. 1, 2012 update, "A Phase II Study of PEP02 as a Second Line Therapy for Patients With Metastatic Pancreatic Cancer." Retrieved from ClinicalTrials.gov archive, 3 printed pages.
EP2861210: Reply to proprietor's grounds of appeal to opposition decision dated Jul. 27, 2020, D30 (Chen L, et al., "Phase I Study of Biweekly Liposome Irinotecan (PEP02, MM-398) in Metastatic Colorectal Cancer Failed on First-line Oxaliplatin-based Chemotherapy," J Clin Oncol. 30(4_suppl):Abstract 613 (2012), 5 printed pages.).
EP2861210: Reply to proprietor's grounds of appeal to opposition decision dated Jul. 27, 2020, D31 (Cunningham D, et al., "Randomized Phase II Study of PEP02, Irinotecan, or Docetaxel as a Second-Line Therapy in Gastric or Gastroesophageal Junction Adenocarcinoma," J Clin Oncol. 29(4_supp):Abstract 6 (2011), 5 printed pages).
EP2861210: Reply to proprietor's grounds of appeal to opposition decision dated Jul. 27, 2020, D32 (Gerber D, "Miscellaneous Agents—Cytotoxics and Hormonal Agents," J Thorac Oncol. 7(12 Suppl 5):S387-9 (2012)).
EP2861210: Reply to proprietor's grounds of appeal to opposition decision dated Jul. 27, 2020, D33 (Noble C, et al., "Novel Nanoliposomal CPT-11 Infused by Convection-Enhanced Delivery in Intracranial Tumors: Pharmacology and Efficacy," Cancer Res. 66(5):2801-6 (2006)).
EP2861210: Reply to proprietor's grounds of appeal to opposition decision dated Jul. 27, 2020, D34 (Krauze M, et al., "Convection-Enhanced Delivery of Nanoliposomal CPT-11 (Irinotecan) and PEGylated Liposomal Doxorubicin (Doxil) in Rodent Intracranial Brain Tumor Xenografts," Neuro Oncol. 9(4):393-403 (2007)).
EP2861210: Reply to proprietor's grounds of appeal to opposition decision dated Jul. 27, 2020, D35 (Mullard A, "How Much Do Phase III Trials Cost?" Nat Rev Drug Discov. 17(111:777 (2018)).
EP2861210: Reply to proprietor's grounds of appeal to opposition decision dated Jul. 27, 2020, D36 (The Medicines for Human Use (Clinical Trials) Regulations, 2004, 86 pages).
Extra J, et al., "Phase I Study of Oxaliplatin in Patients with Advanced Cancer," Cancer Chemother Pharmacol. 25(4):299-303 (1990).
FDA News Release, "FDA Approves New Treatment for Advanced Pancreatic Cancer." Retrieved from http://ww.fda.gov/NewsEvents/Newsroom/PressAnnouncements/ucm468654.htm, Oct. 22, 2015, 3 printed pages.
Fischel J, et al., "Ternary Combination of Irinotecan, Fluorouracil-Folinic Acid and Oxaliplatin: Results on Human Colon Cancer Cell Lines," Br J Cancer. 84(4):579-85 (2001).
Fitzgerald J, et al., "Systems Pharmacology Identification of Tumour Nanoparticle Permeability as Predictor of Clinical Anti-Cancer Activity of MM-398, Nanoliposomal Irinotecan, nal-IRI." Poster presented at 15th International Conference on Systems Biology. Sep. 14-18, 2014, 10 pages.
Fleming D. "Importance of sequence in chemotherapy administration," retrieved from http://www.oncologynurseadvisor.com/advisor-forum/importance-of-sequence-in-chemotherapy-administration/article/378072/ (2014).
Fuchs C, et al., "Phase III Comparison of Two Irinotecan Dosing Regimens in Second-Line Therapy of Metastatic Colorectal Cancer," J Clin Oncol. 21(5):807-14 (2003).

(56) References Cited

OTHER PUBLICATIONS

Gaddy D, "Preclinical Anti-tumor Activity of Nanoliposomal Irinotecan (Nal-IRI, MM-398) + 5-FU + Oxaliplatin in Pancreatic Cancer." Abstract presented at AACR 2016, 1 page.

Gaddy D, et al., "Preclinical Anti-tumor Activity of Nanoliposomal Irinotecan (nal-IRI, MM-398) + 5-FU + Oxaliplatin in Pancreatic Cancer." Poster presented at AACR 2016, 5 pages.

Gahramanov S, et al., "Pseudoprogression of Glioblastoma After Chemo- and Radiation Therapy: Diagnosis by Using Dynamic Susceptibility-Weighted Contrast-Enhanced Perfusion MR Imaging with Ferumoxytol versus Gadoteridol and Correlation with Survival," Radiology. 266(3):842-52 (2013). doi: 10.1148/radiol.12111472. Epub Nov. 30, 2012.

Gebbia V, et al., "Irinotecan Plus Bolus/Infusional 5-Fluorouracil and Leucovorin in Patients With Pretreated Advanced Jancreatic Carcinoma: A Multicenter Experience of the Gruppo Oncologico Italia Meridionale," Am J Clin Oncol. 33(5):461-64 (2010).

GEMZAR package insert, revision Feb. 4, 2011, retrieved from https://www.accessdata.fda.gov/drugsatfda_docs/label/2011/020509s069lbl.pdf, 21 pages.

GEMZAR package insert, revision May 8, 2014, retrieved from https://www.accessdata.fda.gov/drugsatfda_docs/label/2014/020509s077lbl.pdf, 18 pages.

Genther Williams S, et al., "Treatment with the PARP Inhibitor, Niraparib, Sensitizes Colorectal Cancer Cell Lines to Irinotecan Regardless of MSI/MSS Status," Cancer Cell Int. 15(1):14, doi: 10.1186/s12935-015-0162-8 (2015), pp. 1-11.

Gilbert D, et al., "Topoisomerase I Inhibition in Coloreclal Cancer: Biomarkers and Therapeutic Targets," Br J Cancer. 106(1):18-24 (2012), doi: 10.1038/bjc.2011.498, Epub Nov. 22, 2011.

Globocan Cancer Facts Sheets: All Cancers 2012. Available from: http://globocan.iarc.fr/old/FactSheets/cancers/all-new.asp, accessed on Oct. 3, 2016, 9 printed pages.

Goldstein D, et al., "nab-Paclitaxel Plus Gemcitabine for Metastatic Pancreatic Cancer: Long-Term Survival From a Phase III Trial," J Natl Cancer Inst. 107(2): dju413, pp. 1-10 (2015).

Grant S, et al., "Dose-Ranging Evaluation of the Substituted Benzamide Dazopride When Used as an Antiemetic in Patients Receiving Anticancer Chemotherapy," Cancer Chemother Pharmacol. 31(6):442-44 (1993).

Guichard S, et al., "Combination of Oxaliplatin and Irinotecan on Human Colon Cancer Cell Lines: Activity In Vitro and In Vivo," Anticancer Drugs. 12(9):741-51 (2001).

Hare J, et al., "Treatment of Colorectal Cancer Using a Combination of Liposomal Irinotecan (Irinophore C(TM)) and 5-Fluorouracil," PLoS One. 8(4):e62349, doi: 10.1371/journal.pone.0062359, 12 pages (2013).

Hayashi H, et al., "Phase II Study of Bi-Weekly Irinotecan for Patients with Previously Treated HER2-Negative Metastatic Breast Cancer: KMBOG0610B," Breast Cancer. 20(2):131-6 (2013); doi: 10.1007/s12282-011-0316-z. Epub Nov. 29, 2011.

Hayes M, et al., "Assembly of Nucleic Acid-Lipid Nanoparticles from Aqueous-Organic Monophases," Biochim Biophys Acta. 1758(4):429-42 (2006).

Hong K, et al., "Anti-HER2 Immunoliposomes for Targeted Drug Delivery," Ann N Y Acad Sci. 886:293-6 (1999).

Honig A, et al., "Brain Metastases in Breast Cancer—an In Vitro Study to Evaluate New Systemic Chemotherapeutic Options," Anticancer Res. 25(3A):1531-7 (2005).

Hosein P, et al., "A Retrospective Study of Neoadjuvant FOLFIRINOX in Unresectable or Borderline-Resectable Locally Advanced Adenocarcinoma," BMC Cancer. 12:199, pp. 1-7 (2012).

Hoskins J, et al., "UGT1A1*28 Genotype and Irinotecan-Induced Neutropenia: Dose Matters," J Natl Cancer Inst. 99(17):1290-95 (2007).

Hsueh C-T, et al., "Nanovectors for Anti-Cancer Drug Delivery in the Treatment of Advanced Pancreatic Adenocarcinoma," World J Gastroenterol. 22(31):7080-90 (2016).

Hubner R, et al., "Effects of nal-IRI (MM-398) ± 5-Fluorouracil on Quality of Life (QoL) in NAPOLI-1: A Phase 3 Study in Patients With Metastatic Pancreatic Ductal Adenocarcinoma (mPDAC) Previously Treated with Gemcitabine-Based Therapy." Poster presented at the 18th European Society of Medical Oncology World Congress on Gastrointestinal Cancer; Barcelona, Spain; Jun. 29-Jul. 2, 2016, 9 pages.

Hubner R, et aL, Abstract O-004. "Effects of nal-IRI (MM-398) ± 5-fluorouracil on Quality of Life (QoL) in NAPOLI-1: A Phase 3 Study in Patients with Metastatic Pancreatic Ductal Adenocarcinoma (mPDAC) Previously Treated with Gemcitabine." Annals of Oncology. 27(Suppl 2):ii118-ii128 (2016), 1 page.

Jacobs A, et al., "A Randomized Phase III Study of Rubitecan (ORA) vs. Best Choice (BC) in 409 Patients with Refractory Pancreatic Cancer Report from a North-American Multi-Center Study," J Clin Oncol., 2004 ASCO Annual Meeting Proceedings 22(14S):4013 (2004).

Kalra A, et al., "Evaluating Determinants for Enhanced Activity of MM-398/PEP02; A Novel Nanotherapeutic Encapsulation of Irinotecan (CPT-11)." Poster for abstract 5696 presented at American Association for Cancer Research 103rd Annual Meeting 2012, Mar. 31-Apr. 4, 2012, Chicago, IL, 11 pages.

Kalra A, et al., "Preclinical Activity of Nanoliposomal Irinotecan Is Governed by Tumor Deposition and Intratumor Pro-Drug Conversion," Cancer Res. Author Manuscript Published OnlineFirst Oct. 1, 2014, 31 pages.

Kalra A, et al., "Preclinical Activity of Nanoliposomal Irinolecan Is Governed by Tumor Deposition and Intratumor Prodrug Conversion," Cancer Res. 74(23):7003-13 (2014), published OnlineFirst, OF1-OF11, Oct. 1, 2014, 12 pages.

Kalra A, et al., "Preclinical Activity of Nanoliposomal Irinotecan Is Governed by Tumor Deposition and Intratumor Prodrug Conversion," Cancer Res. Author queries on manuscript, pp. 1-11 (2014), 13 total pages.

Kalra A, et al., "The Tumor Microenvironment Modulates the Delivery and Activation of Liposomal Encapsulated Irinotecan, MM-398," Poster for abstract 5622 presented at the 104th Annual Meeting of the American Association of Cancer Research, Apr. 6-10, 2013, Washington DC, 10 pages.

Kalra A, et al., Abstract 2065: "Magnetic Resonance Imaging with an Iron Oxide Nanoparticle Demonstrates Preclinically the Feasibility of Predicting Intratumoral Uptake and Activity of MM-398, a Nanoliposomal Irinotecan (nal-IRI)." Poster presented at American Association for Cancer Research annual meeting 2014, San Diego, CA, 5 pages.

Kalra A, et al., Abstract 5622. "The Tumor Microenvironment Modulates the Delivery and Activation of Liposomal Encapsulated Irinotecan, MM-398." In Proceedings of the 104th Annual Meeting of the American Association of Cancer Research; Apr. 6-10, 2013. Cancer Res 2013;73(8 Suppl):Abstract nr 5622, doi:10.1158/1538-7445.AM2013-5622, 2 printed pages.

Kalra A, et al., Abstract 5696. "Evaluating Determinants for Enhanced Activity of MM-398/PEP02; A Novel Nanotherapeutic Encapsulation of Irinotecan (CPT-11)." In Proceedings of the 103rd Annual Meeting of the American Association for Cancer Research; Mar. 31-Apr. 4, 2012; Chicago, IL. Cancer Res 2012; 72(8 Suppl):Abstract nr 5696. doi:1538-7445.AM2012-5696, 3 printed pages.

Kalra A., "Magnetic Resonance Imaging (MRI) to Predict Tumor Drug Delivery and Response to Nanoliposomal Therapy." Presentation presented at Tumor Models Boston 2014, 32 pages.

Kambe M, et al., "Phase I Study of Irinotecan by 24-h Intravenous Infusion in Combination with 5-Fluorouracil in Metastatic Colorectal Cancer," Int J Clin Oncol. 17(2):150-4 (2012).

Kang M, et al., "Activity of MM-398, Nanoliposomal Irinotecan (nal-IRI), in Ewing's Family Tumor Xenografts Is Associated with High Exposure of Tumor to Drug and High SLFN11 Expression," Clin Cancer Res. 21(5):1139-50 (2015).

Katsu T, et al., "Ion-Selective Electrode for Transmembrane pH Difference Measurements," Anal. Chem. 73 (8):1849-54 (2001).

Kim J, et al., "Efficient Prioritization of Potential Diagnostic Biomarkers Using a Systems Pharmacology Approach: Case Study of MM-398 (Irinotecan sucrosofate liposome injection)." Presentation presented at the Pharmacokietics UK 2013 Meeting, Oct. 31, 2013, Harrogate, North Yorkshire, 34 pages.

(56) References Cited

OTHER PUBLICATIONS

Kim J, et al., "Efficient Prioritization of Potential Diagnostic Biomarkers Using a Systems Pharmacology Approach: Case Study of MM-398, an Irinotecan Sucrosofate Liposome Injection)." Abstract for Pharmacokietics UK 2013 Meeting, Oct. 30-Nov. 1, 2013, Harrogate, North Yorkshire, 2 pages.

Morgan R, et al., "Human Cell Line (COLO 357) of Metastatic Pancreatic Adenocarcinoma," Int J Cancer 25(5):591-8 (1980).

Mukhtar R, et al., "Elevated PCNA+ Tumor-Associated Macrophages in Breast Cancer are Associated with Early Recurrence and Non-Caucasian Ethnicity," Breast Cancer Res Treat. 130(2):635-44 (2011).

Mullany S, et al., "Effect of Adding the Topoisomerase I Poison 7-ethyl-10-hydroxy-camptothecin (SN-38) to 5-Fluorouracil and Folinic Acid in HCT-8 Cells: Elevated dTTP Pools and Enhanced Cytotoxicity," Cancer Chemother Pharmacol. 42(5):391-9 (1998).

Münstedt K, et al., "Role of Dexamethasone Dosage in Combination with 5-HT3 Antagonists for Prophylaxis of Acute Chemotherapy-Induced Nausea and Vomiting," Br J Cancer. 79(3-4):637-9 (1999).

Murai J, et al., "Identification of Novel PARP Inhibitors Using a Cell-Based TDP1 Inhibitory Assay in a Quantitative High-Throughput Screening Platform," Author manuscript; Published in final edited form as: DNA Repair (Arnst). 21:177-82 (2014), 13 pages.

Murai J, et al., "Rationale for Poly(ADP-ribose) Ploymerase (PARP) Inhibitors in Combination Therapy with Campothecins or Temozolomide Based on PARP Trapping versus Catalytic Inhibition," J Pharmacol Exp Ther. 349(3):408-16 (2014).

National Comprehensive Cancer Network Clinical Practice Guidelines in Oncology (NCCN Guidelines). "Pancreatic Adenocarcinoma." Version I.2016. Mar. 22, 2016 (PANC-9), 133 pages.

Nentwich, F., "Doxorubicin Hydrochloride," In Intravenous Therapy: A Comprehensive Application of Intravenous Therapy and Medication Administration at p. 310. Published by Jones & Bartlett Learning, 1990.

Neuzillet C, et al., "FOLFIRI Regimen in Metastatic Pancreatic Adenocarcinoma Resistant to Gemcitabine and Platinum-Salts," World J Gastroenterol. 18(33):4533-41 (2012).

Neuzillet C., et al., "FOLFIRI Regimen as Second-/Third-line Chemotherapy in Patients with Advanced Pancreatic Adenocarcinoma Refradory to Gemcitabine and Platinum Salts: A Retrospective Series of 70 Patients." J Clin Oncol. 29: 2011 (Suppl 4; Abstract 272). 2011 Gastrointestinal Cancers Symposium (2011), 2 printed pages.

NIH National Cancer Institute, "FDA Approves Irinotecan Liposome to Treat Pancreatic Cancer," Nov. 24, 2015 by NCI Staff, 2 printed pages.

Noble C, et al., "Novel Nanoliposomal CPT-11 Infused by Convection-Enhanced Delivery in Intracranial Tumors: Pharmacology and Efficacy," Cancer Res. 66(5):2801-6 (2006).

Noble C, et al., "Pharmacokinetics, Tumor Accumulation and Antitumor Activity of Nanoliposomal Irinotecan Following Systemic Treatment of Intracranial Tumors," Nanomedicine. 9(14):2099-108 (2014).

O'Dwyer P, et al., "Uridine Diphosphate Glucuronosyltransferase (UGT) 1A1 and Irinotecan: Practical Pharmacogenomics Arrives in Cancer Therapy," J Clin Oncol. 24(28):4534-8 (2006).

Oettle H, et al., "Second-Line Oxaliplatin, Folinic Acid, and Fluorouracil Versus Folinic Acid and Fluorouracil Alone for Gemcitabine-Refractory Pancreatic Cancer: Outcomes From the CONKO-003 Trial," J Clin Oncol. 32(23):2423-9 (2014).

Oh S, et al., "Pilot Study of Irinotecan/Oxaliplatin (IROX) Combination Chemotherapy for Patients with Gemcitabine- and 5-Fluorouracil-Refractory Pancreatic Cancer," Invest New Drugs. 28(3):343-9 (2010), Epub May 15, 2009.

Ohkawa S, et al., "Randomised Phase II Trial of S-1 Plus Oxaliplatin vs S-1 in Patients with Gemcitabine-Refractory Pancreatic Cancer," Br J Cancer. 112(9):1428-34 (2015).

Okusaka T, et al., "Phase II Study of FOLFIRINOX for Chemotherapy-Naive Japanese Patients with Metastatic Pancreatic Cancer," Cancer Sci. 105(10):1321-6 (2014).

Oxaliplatin package insert, revision Nov. 2013, retrieved from https://www.accessdata.fda.gov/drugsatfda_docs/label/2013/022160s009lbl.pdf, 43 pages.

Palomaki G, et al., "Can UGT1A1 Genotyping Reduce Morbidity and Mortality in Patients with Metastatic Colorectal Cancer Treated with Irinotecan? An Evidence-Based Review," Genet Med. 11(1):21-34 (2009).

Park J, et al., "Anti-HER2 Immunoliposomes: Enhanced Efficacy Attributable to Targeted Delivery," Clin Cancer Res. 8(4):1172-81 (2002).

Patton W, "Detection Technologies in Proteome Analysis," J Chromatogr B. 771(1-2):3-31 (2002).

Pavillard V, et al., "Combination of Irinotecan (CPT11) and 5-Fluorouracil with an Analysis of Cellular Determinants of Drug Activity," Biochem Pharmacol. 56(10):1315-22 (1998).

Paz N, et al., "MM-398/PEP02, A Novel Liposomal Formulation of Irinotecan Demonstrates Stromal-Modifying Anti-Cancer Properties," Poster for abstract A63 presented at the AACR Special Conference on Pancreatic Cancer: Progress and Challenges; Jun. 18-21, 2012; Lake Tahoe, NV, 9 pages.

Paz N, et al., Abstract A63. "MM-398/PEP02, A Novel Liposomal Formulation of Irinotecan, Demonstrates Stromal-Modifying Anti-cancer Properties," In Proceedings of the AACR Special Conference on Pancreatic Cancer: Progress and Challenges; Jun. 18-21, 2012; Lake Tahoe, NV. Cancer Res. 2012;72(12 Suppl):Abstract nr A63, 3 printed pages.

PCT/GB2017/053293: PCT International Preliminary Report on Patentability dated May 7, 2019, 7 pages.

PCT/GB2017/053293: PCT International Search Report and Written Opinion dated Feb. 2, 2018, 12 pages.

PCT/US2013/045495: PCT International Preliminary Report on Patentability dated Dec. 16, 2014, 8 pages.

PCT/US2013/045495: PCT International Search Report and Written Opinion dated Aug. 22, 2013, 11 pages.

PCT/US2013/046914: PCT International Preliminary Report on Patentability dated Dec. 23, 2014, 7 pages.

PCT/US2013/046914: PCT International Search Report dated Sep. 2, 2013, 3 pages.

PCT/US2013/075513: PCT International Preliminary Report on Patentability dated Jun. 16, 2015, 7 pages.

PCT/US2013/075513: PCT International Search Report dated Jun. 6, 2014, 2 pages.

PCT/US2014/062007: PCT International Preliminary Report on Patentability dated Apr. 26, 2016, 10 pages.

PCT/US2014/062007: PCT International Search Report dated Jan. 9, 2015, 3 pages.

PCT/US2015/064491: PCT International Preliminary Report on Patentability dated Jun. 13, 2017, 7 pages.

PCT/US2015/064491: PCT International Search Report dated Feb. 19, 2016, 4 pages.

PCT/US2016/027515: PCT International Preliminary Report on Patentability dated Oct. 17, 2017, 8 pages.

PCT/US2016/027515: PCT International Search Report dated Jun. 27, 2016, 4 pages.

PCT/US2016/047727: PCT International Preliminary Report on Patentability dated Feb. 27, 2018, 6 pages.

PCT/US2016/047727: PCT International Search Report and Written Opinion dated Nov. 16, 2016, 8 pages.

PCT/US2016/047814: PCT International Preliminary Report on Patentability dated Feb. 20, 2018, 6 pages.

PCT/US2016/047814: PCT International Search Report dated Nov. 17, 2016, 3 pages.

PCT/US2016/047827: PCT International Preliminary Report on Patentability dated Feb. 20, 2018, 6 pages.

PCT/US2016/047827: PCT International Search Report dated Nov. 17, 2016, 3 pages.

Peddi P, et al., "Multi-Institutional Experience with FOLFIRINOX in Pancreatic Adenocarcinoma," Journal of the Pancreas (JOP). 13(5):497-501 (2012), online access, 11 printed pages.

Peinert S, et al., "Safety and Efficacy of Weekly 5-Fluorouracil/Folinic Acid/Oxaliplatin/Irinotecan in the First-Line Treatment of Gastrointestinal Cancer," Ther Adv Med Oncol. 2(3):161-74 (2010).

(56) References Cited

OTHER PUBLICATIONS

Pelzer U, et al., "A Randomized Trial in Patients With Gemcitabine Refractory Pancreatic Cancer. Final Results of the CONKO 003 Study," J Clin Oncol. 2008 ASCO Annual Meeting Proceedings. 26(155):4508 (2008), 2 printed pages.
Pelzer U, et al., "Second-Line Therapy in Refractory Pancreatic Cancer. Results of a Phase II Study," Onkologie. 32(3):99-102 (2009).
Petrioli R, et al., "Gemcitabine, Oxaliplatin, and Capecitabine (GEMOXEL) Compared with Gemcitabine Alone in Metastatic Pancreatic Cancer: A Randomized Phase II Study," Cancer Chemother Pharmacol. 75(4):683-90 (2015).
Chang T, et al., "Phase I Study of Nanoliposomal Irinotecan (PEP02) in Advanced Solid Tumor Patients," Cancer Chemother Pharmacol. 75(3):579-86 (2015).
Chen L, et al., "Phase I Study of Liposome Encapsulated Irinotecan (PEP02) in Advanced Solid Tumor Patients," J Clin Oncol., 2008 ASCO Annual Meeting Proceedings (Post-Meeting Edition), 26(15S) (May 20 Suppl):2565 (2008), 1 page.
Chen L, et al., "Phase I Study of Liposome Encapsulated Irinotecan (PEP02) in Advanced Solid Tumor Patients," Poster presented at the ASCO meeting of May 30-Jun. 3, 2008, Chicago, Illinois, 9 pages.
Chen L, et al., "Phase I Study of Liposome Irinotecan (PEP02) in Combination with Weekly Infusion of 5-FU/LV in Advanced Solid Tumors," J Clin Oncol., 2010 Asco Annual Meeting Abstracts, 28(15_suppl) (May 20 Suppl):e13024 '2010), 1 page.
Chiang N-J, et al., "A Phase I Dose-Escalation Study of PEP02 (Irinotecan Liposome Injection) in Combination with 6-Fluorouracil and Leucovorin in Advanced Solid Tumors," BMC Cancer. 16(1):907 (2016). doi: 10.1186/s12885-016-2933-6, pp. 1-8.
Clinical Trials Identifier NCT00364143: Jan. 26, 2012 update, first posted Aug. 15, 2006, "A Phase I Study of IHL-305 (Irinotecan Liposome Injection) in Patients With Advanced Solid Tumors." Retrieved from ClinicalTrials.gov archive, 6 printed pages.
Clinical Trials Identifier NCT01688336: Sep. 18, 2012 update, "Phase II Single Arm Clinical Trial of FOLFIRINOX for Unresectable Locally Advanced and Borderline Resectable Pancreatic Cancer." Retrieved from ClinicalTrials.gov archive, 5 printed pages.
Clinical Trials Identifier NCT02631733: Dec. 15, 2015 update, "A Phase I Study of a Combination of MM-398 and Veliparib in Solid Tumors." Retrieved from ClinicalTrials.gov archive, 6 printed pages.
Clinical Trials Identifier NCT02631733: Feb. 16, 2016 update, "A Phase I Study of a Combination of MM-398 and Veliparib in Solid Tumors." Retrieved from ClinicalTrials.gov archive, 6 printed pages.
Clinical Trials Identifier NCT02631733: Jun. 20, 2016 update, "A Phase I Study of a Combination of MM-398 and Veliparib in Solid Tumors." Retrieved from ClinicalTrials.gov archive, 6 printed pages.
Clinical Trials Identifier NCT02631733: Jun. 21, 2016 update, "A Phase I Study of a Combination of MM-398 and Veliparib in Stolid Tumors." Retrieved from ClinicalTrials.gov archive, 6 printed pages.
Clinical Trials Identifier NCT02631733: Jul. 6, 2016 update, "A Phase I Study of a Combination of MM-398 and Veliparib in Solid Tumors." Retrieved from ClinicalTrials.gov archive, 6 printed pages.
Clinical Trials Identifier NCT02631733: Jul. 11, 2016 update, "A Phase I Study of a Combination of MM-398 and Veliparib in Solid Tumors." Retrieved from ClinicalTrials.gov archive, 6 printed pages.
Clinical Trials Identifier NCT02631733: Jul. 19, 2016 update, "A Phase I Study of a Combination of MM-398 and Veliparib in Solid Tumors." Retrieved from ClinicalTrials.gov archive, 6 printed pages.
Clinical Trials Identifier NCT02631733: Aug. 7, 2016 update, "A Phase I Study of a Combination of MM-398 and Veliparib in Solid Tumors." Retrieved from ClinicalTrials.gov archive, 6 printed pages.
Clinical Trials Identifier NCT02631733: Sep. 21, 2016 update, "A Phase I Study of a Combination of MM-398 and Veliparib in Solid Tumors." Retrieved from ClinicalTrials.gov archive, 6 printed pages.
Clinical Trials Identifier NCT02631733: Oct. 4, 2017 update, first posted Dec. 16, 2015, "A Phase I Study of a Combination of MM-398 and Veliparib in Solid Tumors." Retrieved from ClinicalTrials.gov archive, 10 printed pages.

Drummond D, et al., "Optimizing Liposomes for Delivery of Chemotherapeutic Agents to Solid Tumors," Pharmacol Rev. 51(4):691-743 (1999).
Eisenhauer E, et al., "New Response Evaluation Criteria in Solid Tumours: Revised RECIST Guideline (version 1.1)," Eur J Cancer 45(2):228-47 (2009).
Infante J, et al., "Phase I and Pharmacokinetic Study of IHL-305 (PEGylated Liposomal Irinotecan) in Patients with Advanced Solid Tumors," Cancer Chemother Pharmacol. 70(5):699-705 (2012).
Lorusso P, et al., "Phase I Safety, Pharmacokinetic, and Pharmacodynamic Study of the Poly(ADP-ribose) Polymerase (PARP) Inhibitor Veliparib (ABT-888) in Combination with Irinotecan in Patients with Advanced Solid Tumors," Clin Cancer Res. 22(13):3227-37 (2016), Epub Feb. 3, 2016.
Lorusso P, et al., "Phase I Study of the Safety, Pharmacokinetics (PK), and Pharmacodynamics (PD) of the Poly (ADP-ribose) Polymerase (PARP) Inhibitor Veliparib (ABT-888; V) in Combination with Irinotecan (CPT-11; Ir) in Patients (pts) with Advanced Solid Tumors," Supplement ASCO Meeting Library, Jun. 5, 2011, 1 page.
Lorusso P, et al., "Phase I Study of the Safety, Pharmacokinetics (PK), and Pharmacodynamics (PD) of the Poly (ADP-ribose) Polymerase (PARP) Inhibitor Veliparib (ABT-888; V) in Combination with Irinotecan (CPT-11; Ir) in Patients (pts) with Advanced Solid Tumors," Journal of Clinical Oncology 29.15_suppl: Abstract 3000 (2011), 3 printed pages.
Lorusso P, et al., "Phase I Study of the Safety, Pharmacokinetics, and Pharmacodynamics of the Poly(ADP-ribose) Polymerase (PARP) Inhibitor Veliparib (ABT-888) in Combination with Irinotecan (CPT-11) in Patients with Advanced Solid Tumors," Presentation presented at American Society of Clinical Oncology 2011 Meeting, 37 pages.
Ma W, et al., "Nanoliposomal Irinotecan (nal-IRI, nal-IRI) Population Pharmacokinetics (PK) and Its Association with Efficacy and Safety in Patients with Solid Tumors." Poster presented at 2015 European Cancer Congress, Vienna, Austria, Sep. 25, 2015, 7 pages.
Paz-Ares L, et aL, "Efficacy and Safety of Irinotecan Liposome Injection (nal-IRI) in Patients with Small Cell Lung Cancer (SCLC)," Presentation presented at 2019 World Conference on Lung Cancer; Sep. 7-10, 2019; Barcelona, Spain; 9 pages.
Paz-Ares Rodriguez L, et al., Abstract OA03.03. "Initial Efficacy and Safety Results of Irinotecan Liposome Injection (NAL-IRI) in Patients With Small Cell Lung Cancer," 2019 World Conference on Lung Cancer Abstracts; Sep. 7-10, 2019; Barcelona, Spain; pp. 220-221.
Ramanathan R, et al., "Correlation between Ferumoxytol Uptake in Tumor Lesions by MRI and Response to Nanoliposomal Irinotecan in Patients with Advanced Solid Tumors: A Pilot Study," Clin Cancer Res. 23(14):3638-48 (2017).
Ramanathan R, et al., "Lesion Characterization with Ferumoxytol MRI in Patients with Advanced Solid Tumors and Correlation with Treatment Response to MM-398, Nanoliposomal Irinotecan (nal-IRI)." Poster presented at EORTC-NCI-AACR International Conference on Molecular Targets and Cancer Therapeutics on Nov. 20, 2014, 7 pages.
Ramanathan R, et al., "Pilot Study in Patients with Advanced Solid Tumors to Evaluate Feasibility of Ferumoxytol (FMX) as a Tumor Imaging Agent Prior to MM-398, a Nanoliposomal Irinotecan (nal-IRI)." Poster presented at AACR Annual Meeting 2014, San Diego, CA, 9 pages.
Ychou, M, et al., "An Open Phase I Study Assessing the Feasibility of the Triple Combination: Oxaliplatin Plus Irinotecan Plus Leucovorin/5-Fluorouracil Every 2 Weeks in Patients With Advanced Solid Tumors," Ann Oncol. 14(3):481-9 (2003).
Kim J, et al., "Sustained Intratumoral Activation of MM-398 Results in Superior Activity over Irinotecan Demonstrated by Using a Systems Pharmacology Approach." Poster presented at the AACR Pancreatic Cancer Symposium, Jun. 18-21, 2012, New York, New York, 8 pages.
Kim J, et al., "Systems Pharmacology Modeling Identifies Unique Parameters That Drive Tumor SN38 Levels for Liposomal Irinotecan (MM-398) Compared to Irinotecan." Abstract presented at 14th International Conference on Systems Biology; Copenhagen, Denmark; Aug. 29-Sep. 4, 2013, 1 page.

(56) References Cited

OTHER PUBLICATIONS

Kim J, et aL, "Systems Pharmacology Modeling Identifies Unique Parameters That Drive Tumor SN38 Levels for Liposomal Irinotecan (MM-398) Compared to Irinotecan." Poster presented at 14th International Conference on Systems Biology; Copenhagen, Denmark; Aug. 29-Sep. 4, 2013, 11 pages.

Kim J, et al., Abstract A6. "Sustained Intratumoral Activation of MM-398 Results in Superior Activity Over Irinotecan Demonstrated by Using a Systems Pharmacology Approach, " In: Proceedings of the AACR Special Conference on Chemical Systems Biology: Assembling and Interrogating Computational Models of the Cancer Cell by Chemical Perturbations; Jun. 27-30, 2012; Boston, MA. Cancer Res. 2012;72(13 Suppl):Abstract nr A6, 3 printed pages.

Kim J, et. al., "Systems Pharmacology Based Biomarker Potentially Predicts Clinical Anti-Cancer Activity of MM-398, Nanoliposomal Irinotecan, nal-IRI." Poster presented at American Conference on Pharmacometrics, Oct. 12-15 2014, 10 pages.

Kirpotin D, et al. "Antibody Targeting of Long-Circulating Lipidic Nanoparticles Does Not Increase Tumor Locatlization but Does Increase Internalization in Animal Models," Cancer Res. 66(13):6732-40 (2006).

Klinz S, et al., "Identifying Differential Mechanisms of Action for MM-398/PEP02, a Novel Nanotherapeutic Encapsulation of Irinotecan." Poster presented at MCR, Nov. 12-16, 2011, 8 pages.

Klinz S, et al., "Identifying Differential Mechanisms of Action for MM-398/PEP02, a Novel Nanotherapeutic Encapsulation of Irinotecan," Mol Cancer Ther. 10(11 Suppl):Abstract C207. Molecular Targets and Therapeutics Meeting (2011), 2 printed pages.

Klinz S, et al., "Nanoliposomal Irinotecan (nal-IRI) is an Active Treatment and Reduces Hypoxia as Measured Through Longitudinal Imaging Using [18F]FAZA-PET in an Orthotopic Patient-Derived Tumorgraft Model of Pancreatic Cancer." Poster presented at AACR Pancreatic meeting Orlando, FL, May 12-15, 2016, 10 pages.

Klinz S, et al., Abstract C293: "Irinotecan Sucrosofate Liposome Injection, MM-398, Demonstrates Superior Activity and Control of Hypoxia as Measured Through Longitudinal Imaging Using [18F] FAZA PET Compared to Free Irinotecan in a Colon Adenocarcinoma Xenograft Model." Poster presented at AACR-NCI-EORTC International Conference on Molecular Targets and Cancer Therapeutics on Oct. 19, 2013, 7 pages.

Klinz S, et al.,"MM-302 a HER2-targeted Liposomal Doxorubicin, Shows Binding/Uptake and Efficacy in HER2 2+ Cells and Xenograft Models," Cancer Res. 71:Abstract 3637 (2011), 1 printed page.

Ko A, "Nanomedicine Developments in the Treatment of Metastatic Pancreatic Cancer: Focus on Nanoliposomal Irinotecan," Int J Nanomedicine. 11:1225-35 (2016).

Ko A, et al.' "A Multinational Phase 2 Study of Nanoliposomal Irinotecan Sucrosofate (PEP02, MM-398) for Patients with Gemcitabine-Refractory Metastatic Pancreatic Cancer," Br J Cancer. 109(4):920-5 (2013).

Ko A, et al., "A Multinational Phase II Study of PEP02 (Liposome Irinotecan) for Patients with Gemcitabine-Refractory Metastatic Pancreatic Cancer," J Clin Oncol. 29:2011 (Suppl; Abstract 4069). 2011 ASCO Annual Meeting (2011), 2 printed pages.

Ko A, et al., "A Multinational Phase II Study of PEP02 (MM-398), Liposome Irinotecan, for Patients with Gemcitabine-refractory Metastatic Pancreatic Cancer." Poster presented at the American Society of Clinical Oncology meeting, Jun. 3-Jun. 7, 2011, Chicago, Illinois, 9 pages.

Ko A, et al., "Excess Toxicity Associated with Docetaxel and Irinotecan in Patients with Metastatic, Gemcitabine-Refractory Pancreatic Cancer: Results of a Phase II Study," Cancer Invest. 26(1):47-52 (2008).

Köhne C, et al., "Randomized Phase III Study of High-Dose Fluorouracil Given as a Weekly 24-Hour Infusion With or Without Leucovorin Versus Bolus Fluorouracil Plus Leucovorin in Advanced Colorectal Cancer: European Organization of Research and Treatment of Cancer Gastrointestinal Group Study 40952," J Clin Oncol. 21(20):3721-8 (2003).

Korn R, "Advanced Imaging with Ferumoxytol MRI to Predict Drug Delivery." Presentation presented at Pancreatic Cancer 2014, Feb. 22, 2014, 23 pages.

Koshkaryev A, et al., "Differential Tissue Clearance Results in Improved Therapeutic Index for Nanoliposomal Irinotecan (nal-IRI; Onivyde) when Combined with the PARP Inhibitor Veliparib." Poster presented at AACR Meeting on Apr. 16-20, 2016, 5 pages.

Kozuch P, et al., "Irinotecan Combined with Gemcitabine, 5-Fluorouracil, Leucovorin, and Cisplatin (G-FLIP) is an Effective and Noncrossresistant Treatment for Chemotherapy Refractory Metastatic Pancreatic Cancer," Oncologist. 6(6):488-95 (2001).

Krauze M, et al., "Convection-Enhanced Delivery of Nanoliposomal CPT-11 (Irinotecan) and PEGylated Liposomal Doxorubicin (Doxil) in Rodent Intracranial Brain Tumor Xenografts," Neuro Oncol. 9(4):393-403 (2007).

Kummar S, et al. "Phase I Study of PARP Inhibitor ABT-888 in Combination with Topotecan in Adults with Refractory Solid Tumors and Lymphomas," Cancer Res. 71(17):5626-34 (2011), Epub Jul. 27, 2011.

Landry R, et al., "Pharmacokinetic Study of Ferumoxytol: A New Iron Repalcement Therapy in Normal Subjects and Hemodialysis Patients," Am J Nephrol. 25(4):400-10 (2005).

Lee C, et al., "Novel Chondroitin Sulfate-binding Cationic Liposomes Loaded with Cisplatin Efficiently Suppress the Local Growth and Liver Metastasis of Tumor Cells in Vivo," Cancer Res. 62(15):4282-8 (2002).

Lee H, et al., A Novel 64Cu-Liposome PET Agent (MM-DX-929) Predicts Response to Liposomal Chemotherapeutics in Preclinical Breast Cancer Models, Cancer Res. 72(24 Suppl): Abstract nrP4-02-05 (2012), San Antonio Breast Cancer Symposium, Dec. 4-8, 2012, 2 printed pages.

Lee H, et al., A Novel 64Cu-Liposome PET Agent (MM-DX-929) Predicts Response to Liposomal Chemotherapeutics in Preclinical Breast Cancer Models, Poster presented at San Antonio Breast Cancer Symposium, Dec. 4-8, 2012, 13 pages.

Lee H, et al., "Delivery and Anti-Tumor Activity of Nanoliposomal Irinotecan (Nal-IRI, MM-398) in Metastatic Xenograft Models of Triple Negative Breast Cancer." Poster presented at 39th Annual San Antonio Breast Cancer Symposium, Dec. 6-10, 2016, 8 pages.

Lee M, et al., "5-Fluorouracil/Leucovorin Combined wtih Irinotecan and Oxaliplatin (FOLFIRINOX) as Second-Line Chemotherapy in Patients with Advanced Pancreatic Cancer Who Have Progressed on Gemcitabine-Based Therapy," Chemotherapy. 59(4)273-9 (2013).

Lordick F, et al., "Phase II Study of Weekly Oxaliplatin Plus Infusional Fluorouracil and Folinic Acid (FUFOX Regiment) as First-Line Treatment in Metastatic Gastric Cancer," Br J Cancer. 93(2):190-4 (2005).

Lorusso P, et al., "Abstract CT325: Combination of the PARP Inhibitor Veliparib (ABT888) with Irinotecan in Patients with Triple Negative Breast Cancer: Preliminary Activity and Signature of Response." Proceedings: AACR 106th Annual Meeting, Apr. 18-22, 2015, Philadelphia, PA (2015), 3 printed pages.

Louvet C, et al., "Gemcitabine in Combination With Oxaliplatin Compared With Gemcitabine Alone in Locally Advanced or Metastatic Pancreatic Cancer: Results of a GERCOR and GISCAD Phase III Trial," J Clin Oncol. 23(15):3509-16 (2005).

Lynparza™ (olaparib) capsules package insert, © AstraZeneca. 2014, Revised: Dec. 2014, 6 pages.

Maddison J, et al., "Sucralfate," In Small Animal Clinical Pharmacology at p. 474, published by W. B. Saunders (2002).

Mahaseth H, et al., "Modified FOLFIRINOX Regimen With Improved Safety and Maintained Efficacy in Pancreatic Adenocarcinoma," Pancreas. 42(8):1311-5 (2013).

Makrilia N, et al., "Treatment for Refractory Pancreatic Cancer. Highlights from the '2011 ASCO Gastrointestinal Cancers Symposium'. San Francisco, CA, USA, Jan. 20-22, 2011," J Pancreas. 12(2):110-3 (2011).

Mamot C, et al., "Epidermal Growth Factor Receptor-Targeted Immunoliposomes Significantly Enhance the Efficacy of Multiple Anticancer Drugs In Vivo," Cancer Res. 65(24):11631-8 (2005).

(56) References Cited

OTHER PUBLICATIONS

Mamot C, et al., "Extensive Distribution of Liposomes in Rodent Brains and Brain Tumors Following Convection-Enhanced Delivery," J Neurooncol. 68(1):1-9 (2004).

Mans D, et al., "Sequence-Dependent Growth Inhibition and DNA Damage Formation by the Irinotecan-5-Fluorouracil Combination in Human Colon Carcinoma Cell Lines," Eur J Cancer. 35(13):1851-61 (1999).

Mathé G, et al., "A Phase I Trial of Trans-1-diamino-cyclohexane Oxalate-platinum (I-OHP)," Biomed Pharmacother, 40(10):372-376 (1986).

Mathé G, et al., "Oxalato-platinum or 1-OHP, a Third-Generation Platinum Complex: An Experimental and Clinical Appraisal and Preliminary Comparison with Cis-platinum and Carboplatinum," Biomed Pharmacother, 43(4):237-50 (1989).

Maxwell F, et al., "CA 19-9 levels in patients with metastatic pancreatic adenocarcinoma receiving first-line therapy with liposomal irinotecan plus 5-fluorouracil/leucovorin and oxaliplatin (NAPOX)," Poster presented at the American Association for Cancer Research (AACR) Special Conference on Pancreatic Cancer: Advances in Science and Clinical Care, Sep. 6-9, 2019, Boston, MA, 7 pages.

Melis M, et al., "Can We Downstage Regionally Advanced Pancreatic Cancer to Resectable: a Phase I/II Study of Induction Oxaliplatin and 5FU Chemo-Radiation," 52nd Annual Meeting for Society for Surgery of the Alimentary Tract, May 6-10, 2011, http://meetings.ssat.com/abstracts/11ddw/P57.cgi, Abstract P57, 1 printed page.

Merrimack Pharmaceuticals, "Merrimack Announces Inclusion of ONIVYDE (irinotecan liposome injection) as a Category 1 Treatment Option in the 2016 NCCN Guidelines for Pancreatic Adenocarcinoma," Mar. 24, 2016. Retrieved from http://investors.merrimack.com/news-releasesinews-release-details/merrimack-announces-inclusion-onivyder-irinotecan-liposome, 2 printed pages.

Messerer C, et al., "Liposomal Irinotecan: Formulation Development and Therapeutic Assessment in Murine Xenograft Models of Colorectal Cancer," Clin Cancer Res. 10(19):6638-49 (2004).

Miles D, et al., "Combination Versus Sequential Single-Agent Therapy in Metastatic Breast Cancer," Oncologist. 7 (suppl 6)13-19 (2002).

Miller M, et al. "Predicting Therapeutic Nanomedicine Efficacy Using a Companion Magnetic Resonance Imaging Nanoparticule," Sci Transl Med. 7:314ra183 (2015), pp. 1-12, Editor's Summary (1 page), and Supplementary Materials (24 pages).

Miller M, et al., "Tumour-Associated Macrophages Act as a Slow-Release Reservoir of Nano-Therapeutic Pt(IV) Pro-Drug," Nat. Commun. 6:8692, doi: 10.1038/ncomms9692, 13 pages (2015), Supplementary Figures 1-9 (9 pages), Supplementary Table 1 (1 page), and Supplementary References (1 page).

Minami H, et al., "Irinotecan Pharmacokinetics/Pharmacodynamics and UGT1A Genetic Polymorphisms in Japanese: Roles of UGT1A1*6 and *28," Pharmacogenet Genomics. 17(7):497-504 (2007).

Mizuno N., "Randomized Phase II Trial of S-1 versus S-1 Plus Irinotecan (IRIS) in Patients with Gemcitabine-Refractory Pancreatic Cancer," J Clin Oncol. 31(Suppl 4):Abstract 263 (2013), 2 printed pages.

Mohammad A, et al., "Liposomal Irinotecan Accumulates in Metastatic Lesions, Crosses the Blood-Tumor Barrier (BTB), and Prolongs Survival in an Experimental Model of Brain Metastases of Triple Negative Breast Cancer," Pharm Res. 35(2):31; doi.org/10.1007/s11095-017-2278-0 (2018), 10 pages.

Clinical Trials Identifier NCT00813163: Jan. 12, 2015 update, "A Phase II Study of PEP02 as a Second Line Therapy for Patients with Metastatic Pancreatic Cancer." Retrieved from ClinicalTrials.gov archive, 3 printed pages.

Clinical Trials Identifier NCT00813163: Apr. 6, 2017 update, first posted Dec. 22, 2008, "A Phase II Study of PEP02 as a Second Line Therapy for Patients With Metastatic Pancreatic Cancer." Retrieved from ClinicalTrials.gov archive, 6 printed pages.

Clinical Trials Identifier NCT00940758: Jul. 16, 2009 update, "Pharrnacokinetic Study of Biweekly PEP02 (Liposome Irinotecan) in Patients With Metastatic Colorectal Cancer Refractory to First-line Oxaliplatin-based Chemotherapy." Retrieved from ClinicalTrials.gov archive, 3 printed pages.

Clinical Trials Identifier NCT00940758: Feb. 3, 2010 update, "Phase I and Pharmacokinetic Study of Biweekly PEP02 (Liposome Irinotecan) in Patients With Metastatic Colorectal Cancer Refractory to First-line Oxaliplatin-based Chemotherapy." Retrieved from ClinicalTrials.gov archive, 3 printed pages.

Clinical Trials Identifier NCT00940758: Mar. 1, 2012 update, "Phase I and Pharmacokinetic Study of Biweekly PEP02 (Liposome Irinotecan) in Patients With Metastatic Colorectal Cancer Refractory to First-line Oxaliplatin-based Chemotherapy." Retrieved from ClinicalTrials.gov archive, 3 printed pages.

Clinical Trials Identifier NCT00940758: Apr. 6, 2017 update, first posted Jul. 16, 2009, "Phase I and Pharmacokinetic Study of Biweekly PEP02 (Liposome Irinotecan) in Patients With Metastatic Colorectal Cancer Refractory to First-line Dxaliplatin-based Chemotherapy." Retrieved from ClinicalTrials.gov archive, 5 printed pages.

Clinical Trials Identifier NCT01359007: May 23, 2011 update, "A Phase II Study Evaluating the Rate of RO Resection (Microscopically Negative Margins) After Induction Therapy With 5-Fluorouracil, Leucovorin, Oxaliplatin, Irinotecan (FOLFIRINOX) in Patients With Borderline Resectable or Locally Advanced Inoperable Pancreatic Cancer." Retrieved from ClinicalTrials.gov archive, 3 printed pages.

Clinical Trials Identifier NCT01359007: May 28, 2015 update, "A Phase II Study Evaluating the Rate of RO Resection (Microscopically Negative Margins) After Induction Therapy With 5-Fluorouracil, Leucovorin, Oxaliplatln, Irinotecan (Folfirinox) in Patients With Borderline Resectable or Locally Advanced Inoperable Pancreatic Cancer." Retrieved from ClinicalTrials.gov archive, 3 printed pages.

Clinical Trials Identifier NCT01375816: Jun. 16, 2011 update, "A Randomized Phase II Study of PEP02 or Irinotecan in Combination With Leucovorin and 5-Flourouracil in Second Line Therapy of Metastatic Colorectal Cancer" Retrieved from ClinicalTrials.gov archive, 5 printed pages.

Clinical Trials Identifier NCT01375816: Jun. 4, 2015 update, first posted Jun. 17, 2011, "A Randomized Phase II Study of PEP02 or Irinotecan in Combination With Leucovorin and 5-Fluorouracil in Second Line Therapy of Metastatic colorectal Cancer." Retrieved from ClinicalTrials.gov archive, 10 printed pages.

Clinical Trials Identifier NCT01446458: Oct. 4, 2011 update, "Phase I Study of Stereotactic Body Radiation Therapy and 5-Fluorouracil, Oxaliplatin and Irinotecan (FOLFIRINOX) in the Neoadjuvant Therapy of Pancreatic Cancer." Retrieved from ClinicalTrials.gov archive, 5 printed pages.

Clinical Trials Identifier NCT01494506: Dec. 16, 2011 update, "A Randomized, Open Label Phase 3 Study of MM-398 Versus 5-Fluorouracil and Leucovorin in Patients With Metastatic Pancreatic Cancer." Retrieved from ClinicalTrials.gov archive, 3 printed pages.

Clinical Trials Identifier NCT01494506: Aug. 9, 2012 update, "A Randomized, Open Label Phase 3 Study of MM-398, With or Without 5-Fluorouracil and Leucovorin, Versus 5-Fluorouracil and Leucovorin in Patients With Metastatic Pancreatic Cancer Who Have Failed Prior Gemcitabine-based Therapy." Retrieved from ClinicalTrials.gov archive, 3 printed pages.

Clinical Trials Identifier NCT01494506: Aug. 1, 2013 update, "A Randomized, Open Label Phase 3 Study of MM-398, With or Without S~Fluorouracil and Leucovorin, Versus 5 Fluorouracil and Leucovorin in Patients with Metastatic Pancreatic Cancer Who Have Failed Prior Gemcitabine-based Therapy." Retrieved from ClinicalTrials.gov archive, 3 printed pages.

Clinical Trials Identifier NCT01494506: Jun. 16, 2016 update, "A Randomized, Open Label Phase 3 Study of MM-398, With or Without 5-Fluorouracil and Leucovorin, Versus 5 Fluorouracil and Leucovorin in Patients with Metastatic Pancreatic Cancer Who Have Failed Prior Gemcitabine-based Therapy." Retrieved from ClinicalTrials.gov archive, 5 printed pages.

Clinical Trials Identifier NCT01523457: Jan. 31, 2012 update, "Phase II Study of Modified Folfirinox in Advanced Pancreatic Cancer." Retrieved from ClinicalTrials.gov archive, 4 printed pages.

(56) References Cited

OTHER PUBLICATIONS

Clinical Trials Identifier NCT01643499: Jul. 17, 2012 update, "A Genotype-guided Dosing Study of mFOLFIRINOX in Previously Untreated Patients with Advanced Gastrointestinal Malignancies." Retrieved from ClinicalTrials.gov archive, 5 printed pages.

Clinical Trials Identifier NCT01770353: Apr. 26, 2015 update, "A Pilot Study in Patients Treated with MM-398 to Determine Tumor Drug Levels and to Evaluate the Feasibility of Ferumoxytol Magnetic Resonance Imaging to Measure Tumor Associated Macrophages." Retrieved from ClinicalTrials.gov archive, 4 printed pages.

Clinical Trials Identifier NCT01770353: May 6, 2015 update, "A Pilot Study in Patients Treated with MM-398 to Determine Tumor Drug Levels and to Evaluate the Feasibility of Ferumoxytol Magnetic Resonance Imaging to Measure Tumor Associated Macrophages." Retrieved from ClinicalTrials.gov archive, 4 printed pages.

Clinical Trials Identifier NCT01770353: Mar. 22, 2016 update, "A Pilot Study in Patients Treated with MM-398 to Determine Tumor Drug Levels and to Evaluate the Feasibility of Ferumoxytol Magnetic Resonance Imaging to Measure Tumor Associated Macrophages and to Predict Patient Response to Treatment." Retrieved from ClinicalTrials.gov archive, 4 printed pages.

Clinical Trials Identifier NCT01770353: Jul. 7, 2016 update, "A Pilot Study in Patients Treated with MM-398 to Determine Tumor Drug Levels and to Evaluate the Feasibility of Ferumoxytol Magnetic Resonance Imaging to Measure Tumor Associated Macrophages and to Predict Patient Response to Treatment." Retrieved from ClinicalTrials.gov archive, 4 printed pages.

Clinical Trials Identifier NCT01771146: Jan. 17, 2013 update, "A Prospective Evaluation of Neoadjuvant FOLFIRINOX Regimen in Patients with Non-metastatic Pancreas Cancer (Baylor University Medical Center and Texas Oncology Experience)." Retrieved from ClinicalTrials.gov archive, 3 printed pages.

Clinical Trials Identifier NCT01926197: Aug. 19, 2013 update, "A Randomized Phase III Study Evaluating Modified FOLFIRINOX (mFFX) With or Without Stereotactic Body Radiotherapy (SBRT) in the Treatment of Locally Advanced Pancreatic Cancer." Retrieved from ClinicalTrials.gov archive, 3 printed pages.

Clinical Trials Identifier NCT01992705: Nov. 22, 2013 update, "Neoadjuvant Folfirinox and Stereotactic Body Radiotherapy (SBRT) Followed by Definitive Surgery for Patients with Borderline Resectable Pancreatic Adenocarcinoma: A Single-Arm Pilot Study." Retrieved from ClinicalTrials.gov archive, 5 printed pages.

Clinical Trials Identifier NCT02013336: Feb. 6, 2017 update, first posted Dec. 17, 2013, "Phase 1 Dose-escalating Study of MM-398 (Irinotecan Sucrosofate Liposome Injection) Plus Intravenous Cyclophosphamide in Recurrent or Refractory Pediatric Solid Tumors" Retrieved from ClinicalTrials.gov archive, 6 printed pages.

Clinical Trials Identifier NCT02022644: May 8, 2017 update, first posted Dec. 30, 2013, "A Phase I Study of Convection-Enhanced Delivery of Liposomal-Irinotecan Using Real-Time Imaging With Gadolinium in Patients With Recurrent High Grade Glioma." Retrieved from ClinicalTrials.gov archive, 9 printed pages.

Clinical Trials Identifier NCT02028806: Jan. 6, 2014 update, "Phase II Trial to Investigate the Efficacy and Safety of mFOLFIRINOX in Patients with Metastatic Pancreatic Cancer in China." Retrieved from ClinicalTrials.gov archive, 4 printed pages.

Clinical Trials Identifier NCT02047474: Jan. 27, 2014 update, "Phase II Study of Peri-Operative Modified Folfirinox in Localized Pancreatic Cancer." Retrieved from ClinicalTrials.gov archive, 5 printed pages.

Clinical Trials Identifier NCT02109341: Apr. 8, 2014-04-08 update, "Phase I/II Study to Evaluate Nab-paclitaxel in Substitution of CPT11 or Oxaliplatin in FOLFIRINOX Schedule as First Line Treatment on Metastatic Pancreatic Cancer." Retrieved from ClinicalTrials.gov archive, 5 printed pages.

Clinical Trials Identifier NCT02143219: May 20, 2014 update, "Phase-2 Study Evaluating Overall Response Rate (Efficacy) and Autonomy Daily Living Preservation (Tolerance) of 'FOLFIRINOX' Pharmacogenic Dose Adjusted, in Elderly Patients (70 yo. or Older) With a Metastatic Pancreatic Adenocarcinoma." Retrieved from ClinicalTrials.gov archive, 5 printed pages.

Clinical Trials Identifier NCT02148549: May 27, 2014 update, "The Pilot Study of Neoadjuvant Chemotherapy of FIRINOX for Patients With Borderline Resectable Pancreatic Cancer." Retrieved from ClinicalTrials.gov archive, 4 printed pages.

Clinical Trials Identifier NCT02551991: Sep. 30, 2019 update, first posted Sep. 16, 2015, "A Randomized, Open-label, Phase 2 Study of Nanoliposomal Irinotecan (Nal-IRI)-Containing Regimens Versus Nab-Paclitaxel Plus Gemcitabine in Patients With Previously Untreated, Metastatic Pancreatic Adenocarcinoma." Retrieved from ClinicalTrials.gov archive, 5 printed pages.

Clinical Trials Identifier NCT02884128: Aug. 25, 2016 update, "A Study of PEP02 in Combination With 5-fluorouracil (5-FU) and Leucovorin (LV) in Advanced Solid Tumors." Retrieved from ClinicalTrials.gov archive, 3 printed pages.

Clinical Trials Identifier NCT02884128: Aug. 30, 2016 update, first posted Aug. 30, 2016, "A Multi-Center, Open-Label Phase I Dose-Escalation Study of PEP02 in Combination With 5-fluorouracil (5-FU) and Leucovorin (LV) in Advanced Solid Tumors." Retrieved from ClinicalTrials.gov archive, 5 printed pages.

Clinical Trials Identifier NCT02896803: Sep. 11, 2016 update, "A Phase II Trial of Bolus Fluorouracil and Oxaliplatin (mFLOX) as First-line Regimen for Patients With Unresectable or Metastatic Pancreatic Cancer Not Eligible for Infusional Fluorouracil, Irinotecan and Oxaliplatin." Retrieved from ClinicalTrials.gov archive, 4 printed pages.

Clinical Trials Identifier NCT02896907: Sep. 11, 2016 update, "A Pilot Study of Intravenous Ascorbic Acid and Folfirinox in the Treatment of Advanced Pancreatic Cancer." Retrieved from ClinicalTrials.gov archive, 4 printed pages.

Conroy T, et al., "FOLFIRINOX versus Gemcitabine for Metastatic Pancreatic Cancer," N Engl J Med. 364(19):1817-25 (2011).

Conroy T, et al., "Irinotecan Plus Oxaliplatin and Leucovorin-Modulated Fluorouracil in Advanced Pancreatic Cancer—A Groupe Tumeurs Digestives of the Federation Nationale des Centres de Lutte Contre le Cancer Study," J Clin Oncol. 23(6):1228-36 (2005).

Cortés J, et al., Abstract CT154. "Multicenter Open-Label, Phase II Trial, to Evaluate the Efficacy and Safety of Liposomal Irinotecan (nal-IRI) for Progressing Brain Metastases in Patients with HER2-Negative Breast Cancer (The Phenomenal Study)," In Proceedings of the American Association for Cancer Research Annual Meeting 2018; Apr. 14-18, 2018; Chicago, Illinois. Cancer Res. 2018;78(13 Suppl):Abstract nr CT154, 3 printed pages.

Davidson D, et al., "The PARP Inhibitor ABT-888 Synergizes Irinotecan Treatment of Colon Cancer Cell Lines," Invest New Drugs. 31(2);461-8 (2013) DOI: 101007/s10637-012-9886-7; Epub Oct. 9, 2012, 8 pages.

Dawidczyk C, et al., "State-of-the-art in Design Rules for Drug Delivery Platforms: Lessons Learned from FDA-Approved Nanomedicines," J Control Release. 187:133-44 (2014).

Dayyani F, et al., Abstract B14. "CA 19-9 levels in patients with metastatic pancreatic adenocarcinoma receiving first-line therapy with liposomal irinotecan plus 5-fluorouracil/leucovorin and oxaliplatin (NAPOX)," In Proceedings of the AACR Special Conference on Pancreatic Cancer Advances in Science and Clinical Care; Sep. 6-9, 2019; Boston, MA; Cancer Res. 2019; 79(24 Suppl): Abstract nr B14, 3 printed pages.

Dean A, et al., "A Phase 2, Open-Label Dose-Exploration Study of Liposomal Irinotecan (nal-IRI) Plus 5-Flurouracil/Leucovorin (5-FU/LV) plus Oxaliplatin (OX) in Patients With Previously Untreated Metastatic Pancreatic Cancer." Poster presented at the American Society of Clinical Oncology Annual Conference, Chicago, IL, Jun. 1-5, 2018, 11 pages.

Dean A, et al., "A Randomized, Open-label, Phase 2 Study of Nanoliposomal Irinotecan (nal-IRI)-containing Regimens versus nab-Paclitaxel Plus Gemcitabine in Patients with Previously Untreated, Metastatic Pancreatic Adenocarcinoma (mPAC)." Poster presented at the Gastrointestinal Cancers Symposium Asco 2016, 11 pages.

Dean A, et al., "A Randomized, Open-label, Phase 2 Study of Nanoliposomal Irinotecan (nal-IRI)-containing Regimen versus nab-Paclitaxel Plus Gemcitabine in Patients with Previously Untreated,

(56) References Cited

OTHER PUBLICATIONS

Metastatic Pancreatic Adenocarcinoma (mPAC)." Poster handout at the Gastrointestinal Cancers Symposium ASCO 2016, 2 pages.
Dean A, et al., "Nanoliposomal Irinotecan (nal-IRI)-Containing Regimens Versus nab-paclitaxel Plus Gemcitabine as First-Line Therapy in Patients With Metastatic Pancreatic Adenocarcinoma (mPAC): A Randomized, Open-Label Phase 2 Study." Poster presented at the 18th European Society of Medical Oncology World Congress on Gastrointestinal Cancer; Barcelona, Spain; Jun. 29-Jul. 2, 2016, 14 pages.
Dean A, et al., Abstract P-287. "Nanoliposomal Irinotecan (nal-IRI)-Containing Regimens Versus nab-paclitaxel Plus Gemcitabine as First-Line Therapy in Patients With Metastatic Pancreatic Adenocarcinoma (mPAC): A Randomized, Open-Label Phase 2 Study." Annals of Oncology. 27(Suppl 2):ii1-i85 (2016), 1 page.
Delord J, et al., "Population Pharmacokinetics of Oxaliplatin," Cancer Chemother Pharmacol. 51(2):127-31 (2003), Epub Dec. 4, 2002.
Dickinson P, et al., "Canine Model of Convection-Enhanced Delivery of Liposomes Containing CPT-11 Monitored with Real-Time Magnetic Resonance Imaging," J. Neurosurg. 108(5):989-98 (2008).
Dickinson P, et al., "Canine Spontaneous Glioma: A Translational Model System for Convection-Enhanced Delivery," Neuro Oncol. 12(9):928-40; Epub 10:1093/neuonc/noq046, 1-13 (2010).
Dósa E, et al., "Magnetic Resonance Imaging of Intracranial Tumors: Intra-Patient Comparison of Gadoteridol and Ferumoxytol," Neuro Oncol. 13(2):251-60 (2011) doi: 10.1093/neuonc/noq172. Epub 2010.
Douillard J, et al.,"Irinotecan Combined with Fluorouracil Compared with Fluorouracil Alone as First-line Treatment for Metastatic Colorectal Cancer: A Multicentre Randomised Trial," Lancet 355(9209):1041-7 (2000).
DOXIL package insert, revision Apr. 16, 2015, retrieved from https://www.accessdata.fda.gov/drugsatfda_docs/label/2015/050718s048lbl.pdf, 28 pages.
DOXIL package insert, revision Aug. 30, 2013, retrieved from https://www.accessdata.fda.gov/drugsatfda_docs/label/2013/050718s045lbl.pdf, 35 pages.
DOXIL package insert, revision Jun. 10, 2008, retrieved from https://www.accessdata.fda.gov/drugsatfda_docs/label/2008/050718s033lbl.pdf, 34 pages.
Drummond D, et al.: "Development of a Highly Active Nanoliposomal Irinotecan Using a Novel Intraliposomal Stabilization Strategy," Cancer Res. 66(6):3271-77 (2006).
Ducreux M, et al., "Randomized Phase II Study Evaluating Oxaliplatin Alone, Oxaliplatin Combined with Infusional 6-FU, and Infusional 5-FU Alone in Advanced Pancreatic Carcinoma Patients," Ann Oncol. 15(3): 467-73 (2004).
Eloxatin package insert, revision Dec. 28, 2011, retrieved from https://www.accessdata.fda.gov/drugsatfda_docs/label/2011/021492s012lbl.pdf, 51 pages.
English translation of title and abstract for Hasegawa, Y, "Biomarker as Predictive Safety Testing in Oncology", Igaku No Ayumi (Journal of Clinical and Experimental Medicine), 224(13)1171-4 (2008) (original in Japanese).
EP2861210: Communication of Notices of Opposition (R. 79(1) EPC), dated Feb. 16, 2018, 1 page.
EP2861210: Notice of Opposition dated Feb. 5, 2018, 6 pages.
EP2861210: Opposition dated Feb. 5, 2018, Annex to Notice of Opposition, Facts and Arguments, 8 pages.
EP2861210: Opposition dated Feb. 5, 2018, D1 (FUSILEV package insert, 2008, 7 pages).
EP2861210: Opposition dated Feb. 5, 2018, D2 (Gebbia V, et al., "Irinotecan Plus Bolus/Infusional 5-Fluorouracil and Leucovorin in Patients With Pretreated Advanced Pancreatic Carcinoma: A Multicenter Experience of the Gruppo Oncologico Italia Meridionale," Am J Clin Oncol. 33(5):461-64 (2010)).
EP2861210: Opposition dated Feb. 5, 2018, D3 (Zaniboni A, et al., "FOLFIRI as Second-Line Chemotherapy for Advanced Pancreatic Cancer: A GISCAD Multicenter Phase II Study," Cancer Chemother Pharmacol 69(6):1641-5 (2012)).
EP2861210: Opposition dated Feb. 5, 2018, D4 (Neuzillet C, et aL, "FOLFIRI Regimen in Metastatic Pancreatic Adenocarcinoma Resistant to Gemcitabine and Platinum-Salts," World J Gastroenterol. 18(33):4533-41 (2012)).
EP2861210: Opposition dated Feb. 5, 2018, D5 (Yoo C, et al., "A Randomised Phase II Study of Modified FOLFIRI.3 vs Modified FOLFOX as Second-Line Therapy in Patients with Gemcitabine-Refractory Advanced Pancreatic Cancer," Br J Cancer. 101(10):1658-63 (2009)).
EP2861210: Opposition dated Feb. 5, 2018, D6 (Taïeb J., "FOLFIRI. 3, A New Regimen Combining 5-Fluorouracil, Folinic Acid and Irinotecan, for Advanced Pancreatic Cancer: Results of an Association des Gastro-Enterologues Oncologues (Gastroenterologist Oncologist Association) Multicenter Phase II Study," Ann Oncol. 18(3)498-503 (2007), epub Dec 8, 2006).
EP2861210: Opposition dated Feb. 5, 2018, D7 (Chen L, et al., "Phase I Study of Liposome Encapsulated Irinotecan (PEP02) in Advanced Solid Tumor Patients," J Clin Oncol., 2008 ASCO Annual Meeting Proceedings (Post-Meeting Edition), 26(15S) (May 20 Suppl):2565 (2008), 2 pages).
EP2861210: Opposition dated Feb. 5, 2018, D8 (Infante J, et al., "Phase I and Pharmacokinetic Study of IHL-305 (PEGylated Liposomal Irinotecan) in Patients With Advanced Solid Tumors," Cancer Chemother Pharmacol. 70(5): 599-705 (2012)).
EP2861210: Opposition dated Feb. 5, 2018, D9 (Waterhouse D, et al., "Lipid-Based Nanoformulation of Irinotecan: Dual Mechanism of Action Allows for Combination Chemo/Angiogenic Therapy," Nanomedicine 6(9):1645-54 (2011)).
EP2861210: Opposition filed Feb. 5, 2018, D10 (Camptosar package insert, 2012, 39 pages).
EP2861210: Opposition filed Feb. 5, 2018, D11 (Hoskins J, et al., "UGT1A1*28 Genotype and Irinotecan-Induced Neutropenia: Dose Matters," J Natl Cancer Inst. 99(17):1290-95 (2007)).
EP2861210: Opposition dated Feb. 5, 2018, D12 (Tsai C, et al., "Nanovector-Based Therapies in Advanced Pancreatic Cancer," J Gastroint Oncol 2(3):185-94 (2011)).
EP2861210: Opposition dated Feb. 5, 2018, D13 (Ko A, et al., "A Multinational Phase II Study of Liposome Irinotecan (PEP02) for Patients with Gemcitabine-Refractory Metastatic Pancreatic Cancer," J Clin Oncol. 29:2011 (Suppl; Abstract 237). 2011 ASCO Annual Meeting (2011), 2 printed pages).
EP2861210: Opposition dated Feb. 5, 2018, D15 (Clinical Trials Identifier NCT01494506: Jan. 25, 2013 version, "A Randomized, Open Label Phase 3 Study of MM-398, With or Without 5-Fluorouracil and Leucovorin, Versus 5 Fluorouracil and Leucovorin in Patients With Metastatic Pancreatic Cancer Who Have Failed Prior Gemcitabine-based Therapy," Retrieved from ClinicalTrials.gov archive, 1 printed page).
EP2861210: Response to EP Opposition Proceedings filed Aug. 24, 2018, 22 pages.
EP2861210: Response to EP Opposition Proceedings filed Aug. 24, 2018, D15a (Clinical Trials Identifier NCT01494506: Dec. 16, 2011 version, "A Randomized, Open Label Phase 3 Study of MM-398 Versus 5-Fluorouracil and Leucovorin in Patients With Metastatic Pancreatic Cancer." Retrieved from ClinicalTrials.gov archive, 3 printed pages).
EP2861210: Response to EP Opposition Proceedings filed Aug. 24, 2018, D17 (European Commission Implementing Decision granting marketing authorisation for Onivyde, Oct. 14, 2016), 39 pages.
EP2861210: Response to EP Opposition Proceedings filed Aug. 24, 2018, D18 (FDA News Release, "FDA Approves New Treatment for Advanced Pancreatic Cancer." Retrieved from http://www.fda.gov/NewsEvents/Newsroom/PressAnnouncements/ucm468654.htm, Oct. 22, 2015, 3 printed pages).
EP2861210: Response to EP Opposition Proceedings filed Aug. 24, 2018, D19 (Wang-Gillam A, et al., "Nanoliposomal Irinotecan with Flourouracil and Folinic Acid in Metastatic Pancreatic Cancer After Previous Gemcitabine-Based Therapy (NAPOLI-1): a Global,

(56) References Cited

OTHER PUBLICATIONS

Randomised, Open-Label, Phase 3 Trial," Lancet, 387 (10018):545-57 (2016). Epub doi: 10.1016/S0140-6736(15)00986-1, pp. 1-13 (2015)).
EP2861210: Response to EP Opposition Proceedings filed Aug. 24, 2018, D20 (MHRA Public Assessment Report for 5-Fluorouracil, 2006, 60 pages).
EP2861210: Summons to attend oral proceedings including preliminary opinion of the Opposition Division dated Jan. 30, 2019, 12 pages.
EP2861210: Opponent submission in opposition proceedings made following summons to attend oral proceedings, dated May 10, 2019, 20 pages.
EP2861210: Opponent submission in opposition proceedings made following summons to attend oral proceedings, dated May 10, 2019, D1b (Leucovorin calcium injection product label, Nov. 2011, 2 pages).
EP2861210: Opponent submission in opposition proceedings made following summons to attend oral proceedings, dated May 10, 2019, D22 (Chen L, et al., "Phase I Study of Liposome Irinotecan (PEP02) in Combination with Weekly Infusion of 5-FU/LV in Advanced Solid Tumors," J Clin Oncol., 2010 ASCO Annual Meeting Abstracts, 28(15_suppl) (May 20 Suppl):e13024 (2010), 1 page).
EP2861210: Proprietor's Auxiliary Requests in Opposition Proceedings filed Jun. 28, 2019, including cover letter and clean and marked-up AR1, AR2, and AR3, 12 pages.
EP2861210: Minutes of the oral proceedings before the Opposition Division, dated Aug. 28, 2019, 9 pages.
EP2861210: Opposition Division's decision to revoke patent, dated Aug. 28, 2019, 27 pages.
EP2861210: Proprietor's statement of grounds of appeal to opposition decision dated Dec. 30, 2019, 35 pages.
EP2861210: Proprietor's Main and Auxiliary Requests MR, AR1, AR2, and AR3 with Proprietor's Statement of Grounds of Appeal in Opposition Proceedings filed Dec. 30, 2019, 4 pages.
EP2861210: Proprietor's statement of grounds of appeal to opposition decision dated Dec. 30, 2019, D23 (Declaration of Amy McKee M.D.) including D23A (Hoos W, et al., "Pancreatic Cancer Clinical Trials and Accrual in the United Sates." J Clin Oncol. 31(27)3432-8 (2013) and accompanying Appendix Table A1, Table A2, and Figure A1) and D23B (BIO Industry Analysis: Clinical Development Success Rates 2006-2015, Jul. 2016), 44 total pages.
EP2861210: Proprietor's statement of grounds of appeal to opposition decision dated Dec. 30, 2019, D24 (Declaration of Bruce Belanger, Ph.D.), 2 pages.
EP2861210: Reply to proprietor's grounds of appeal following opposition and cover letter, dated Jul. 27, 2020, 35 pages.
EP2861210: Reply to proprietor's grounds of appeal to opposition decision dated Jul. 27, 2020, D15c (EU clinical trial database for NAPOLI-1 study from Oct. 12, 2012, corresponds to D15b), 10 pages.
EP2861210: Reply to proprietor's grounds of appeal to opposition decision dated Jul. 27, 2020, D25 (Chen P, et al., "Comparing Routes of Delivery for Nanoliposomal Irinotecan Shows Superior Anti-Tumor Activity of Local Administration in Treating Intracranial Glioblastoma Xenografts," Neuro Oncol. 15(2):189-97 (2013), Epub Dec. 21, 2012).
EP2861210: Reply to proprietor's grounds of appeal to opposition decision dated Jul. 27, 2020, D26 (Drummond D, et al., "Development of a Highly Active Nanoliposomal Irinotecan Using a Novel Intraliposomal Stabilization Strategy," Cancer Res. 66(6):3271-77 (2006)).
EP2861210: Reply to proprietor's grounds of appeal to opposition decision dated Jul. 27, 2020, D27 (Roy A, et al., "A Randomized Phase II Study of PEP02 (MM-398), Irinotecan or Docetaxel as a Second-Line Therapy in Patients With Locally Advanced or Metastatic Gastric or Gastro-Oesophageal Junction Adenocarcinoma," Ann Oncol. 24(6):1567-73 (2013)).
EP2861210: Reply to proprietor's grounds of appeal to opposition decision dated Jul. 27, 2020, D28 (Svenson S, "Clinical Translation of Nanomedicines," Current Opinion in Solid State and Materials Science. 16(6):287-294 (2012), article in press version, 7 pages).
EP2861210: Reply to proprietor's grounds of appeal to opposition decision dated Jul. 27, 2020, D29 (Makrilia N, et al., "Treatment for Refractory Pancreatic Cancer. Highlights from the '2011 ASCO Gastrointestinal Cancers Symposium'. San Francisco, CA, USA, Jan. 20-22, 2011," J Pancreas. 12(2):110-3 (2011)).
Van Cutsem E, et al., "A Phase lb Dose-Escalation Study of Erlotinib, Capecitabine and Oxaliplatin in Metastatic Colorectal Cancer Patients," Ann Oncol. 19(2):332-9 (2008), Epub Nov. 6, 2007.
Ventura M, et al., "Ferumoxytol as an MR Imaging Surrogate Marker of Liposomal Drug Deposition and Longitudinal Efficacy in a Preclinical Model of Breast Cancer." Poster presented at World Molecular Imaging Congress, Sep. 13-16, 2017, Philadelphia, Pennsylvania, 6 pages.
Ventura M, et al., "Imaging-Based Assessment of the Treatment Efficacy of Nanoliposomal Irinotecan (nal-IRI) in a Triple Negative Breast Cancer Model of Spontaneous Metastasis." Poster presented at Annual World Molecular Imaging Congress, Sep. 7-10, 2016, 8 pages.
Verreault M, et al., "Vascular Normalization in Orthotopic Glioblastoma Following Intravenous Treatment with Lipid-Based Nanoparticulate Formulations of Irinotecan (Irinophore C™), Doxorubicin (Caelyx®) or Vincristine," BMC Cancer. 11:124, pp. 1-18 (2011).
Von Hoff D, et al., "NAPOLI 1: Randomized Phase 3 Study of MM-398 (nal-IRI), With or Without 5-Fluorouracil and Leucovorin, Versus 5-Fluorouracil and Leucovorin, in Metastatic Pancreatic Cancer Progressed on or following Gemcitabine-Based Therapy." Poster presented at the ESMO World Congress on Gastrointestinal Cancer 2014, 11 pages.
Wagener D, et al., "Phase II Trial of CPT-11 in Patients with Advanced Pancreatic Cancer: An EORTC Early Clinical Trials Group Study," Ann Oncol. 6(2):129-32 (1995).
Wählby C, et al., "Sequential Immunofluorescence Staining and Image Analysis for Detection of Large Numbers of Antigens in Individual Cell Nuclei," Cytometry. 47(1):32-41 (2002).
Wainberg Z, et al., "A phase 1/2, open-label, dose-expansion study of liposomal irinotecan (nal-IRI) plus 5-fluorouracil/leucovorin (5-FU/LV) and oxaliplatin (OX) in patients with previously untreated metastatic pancreatic cancer (mPAC)." Presentation presented at the ESMO 21st World Congress on Gastrointestinal Cancer, Barcelona, Spain, Jul. 3-6, 2019, 13 pages.
Wainberg Z, et al., "First-line liposomal irinotecan + 5-fluorouracil/leucovorin + oxaliplatin in patients with pancreatic ductal adenocarcinoma: long-term follow-up results from a phase 1/2 study." Presentation presented at the ESMO World Congress on Gastrointestinal Cancer, Jul. 1-4, 2020, 13 pages.
Wainberg Z, et al., Abstract LBA-1. "First-line liposomal irinotecan + 5 fluorouracil/leucovorin + oxaliplatin in patients with pancreatic ductal adenocarcinoma: Long-term follow-up results from a phase 1/2 study," Ann Oncol. 31(Suppl 3): S241 doi.org/10.1016/j.annonc.2020.04.076 (2020).
Wainberg Z, et al., Abstract SO-005: "A Phase 1/2, Open-Label, Dose-Expansion Study of Liposomal Irinotecan (Nal-IRI) Plus 5-Fluorouracil/Leucovorin (5-FU/LV) and Oxaliplatin (OX) in Patients with Previously Untreated Metastatic Pancreatic Cancer," Ann Oncol. 30(Suppl 4): doi:10.1093/annonc/mdz157 | iv123 (Jul. 2019), 1 page.
Wang-Gillam A, et al., "Nanoliposomal Irinotecan with Flourouracil and Folinic Acid in Metastatic Pancreatic Cancer After Previous Gemcitabine-Based Therapy (NAPOLI-1): A Global, Randomised, Open-Label, Phase 3 Trial," Lancet, 387(10018):545-57 (2016). Epub doi: 10.1016/S0140-6736(15)00986-1, pp. 1-13 (2015).
Wasserman E, et al., "Combination of Oxaliplatin Plus Irinotecan in Patients With Gastrointestinal Tumors: Results of Two Independent Phase I Studies with Pharmacokinetics," J Clin Oncol. 17(6):1751-9 (1999).
Waterhouse D, et al., "Lipid-Based Nanoformulation of Irinotecan: Dual Mechanism of Action Allows for Combination Chemo/Angiogenic Therapy," Nanomedicine 6(9):1645-54 (2011).
Wilson W, et al., "Targeting Hypoxia in Cancer Therapy," Nat Rev Cancer 11(6):393-410 (2011).

(56) References Cited

OTHER PUBLICATIONS

Yeh B, et al., "Structural Basis for Activation of Fibroblast Growth Factor Signaling by Sucrose Octasulfate," Mol Cell Biol. 22(20):7184-92 (2002).
Yi S, et al, "Irinotecan Monotherapy as Second-Line Treatment in Advanced Pancreatic Cancer," Cancer Chemother Pharmacol. 63(6):1141-5 (2009), Epub Oct. 7, 2008.
Yoo C, et al., "A Randomised Phase II Study of Modified FOLFIRI.3 vs Modified FOLFOX as Second-Line Therapy in Patients with Gemcitabine-Refractory Advanced Pancreatic Cancer," Br J Cancer 101(10):1658-63 (2009).
Zander S, et al., "EZN-2208 (PEG-SN38) Overcomes ABCG2-Mediated Topotecan Resistance in BRCA1-Deficient Mouse Mammary Tumors," PLoS One. 7(9):345248 (2012), pp. 1-9.
Zaniboni A, et al., "FOLFIRI as Second-Line Chemotherapy for Advanced Pancreatic Cancer: A GISCAD Multicenter Phase II Study," Cancer Chemother Pharmacol 69(6):1641-5 (2012).
Zeghari-Squalli, N et al., "Cellular Pharmacology of the Combination of the DNA Topoisomerase I Inhibitor SN-38 and the Deaminocyclohexane Platinum Derivative Oxaliplatin," Clin Cancer Res. 5(5):1189-96 (1999).
Zhang Y, et al. "Poly(ADP-ribose) Polymerase and XPF-ERCC1 Participate in Distinct Pathways for the Repair of Topoisomerase I-Induced DNA Damage in Mammalian Cells," Nucleic Acids Res. 39(9):3607-20 (2011).
Zheng J, et al., "[18F]FAZA-PET Detection of Hypoxia Changes following Anti-cancer Therapy." Poster presented at Annual World Molecular Imaging Congress, Sep. 18-21, 2013, 7 pages.
Zheng J, et al., "Longitudinal Tumor Hypoxia Imaging with [18F[FAZA-PET Provides Early Prediction of Nanoliposomal Innotecan (nal-IRI) Treatment Activity," EJNMMI Res 5(1):57, 10 pages (2015).
Zhou X, et al., "Clinical Analysis of Bevacizumab Plus FOLFIRI Regimen as Front-Line Therapy for Chinese Patients with Advanced Colorectal Cancer," J Cancer Ther 2(4):470-4 (2011).
Znojek P, et al., "Preferential Potentiation of Topoisomerase I Poison Cytotoxicity by PARP Inhibition in S Phase," Br J Cancer 111(7):1319-26 (2014).
Schroen A, et al., "Challenges to Accrual Predictions to Phase III Cancer Clinical Trials: A Survey of Study Chairs and Lead Statisticians of 248 NCI Sponsored Trials," Clin Trials. 8(5):591-600 (2011), author manuscript version, 14 pages.
Serwer L, et al., "Investigation of Intravenous Delivery of Nanoliposomal Topotecan For Activity Against Orthotopic Glioblastoma Xenografts," Neuro Oncol. 13(12):1288-95 (2011).
Shi S, et al., "Combinatational Therapy: New Hope for Pancreatic Cancer?" Cancer Lett. 317(2):127-35 (2012). Epub 2011.
Siveke J, et al., "Subgroup Analysis by Measurable Metastatic Lesion (ML) Number and Selected Lesion Locations (LL) at Baseline (BL) in NAPOLI-1: A Phase 3 Study of Liposomal Irinotecan (nal-IRI)±5-Fluorouracil/Leucovorin (5-FU/LV) in Patients With Metastatic Pancreatic Ductal Adenocarcinoma Previously Treated With Gemcitabine-Based Therapy." Poster presented at the American Society of Clinical Oncology Gastrointestinal Cancers Symposium (ASCO GI), San Francisco, CA, Jan. 18-20, 2018, 8 pages.
Siveke J, et al., Abstract 460. "Subgroup Analysis by Measurable Metastatic Lesion (ML) Number and Selected Lesion Locations (LL) at Baseline (BL) in NAPOLI-1: A Phase III Study of Liposomal Irinotecan (nal-IRI)±5-Fluorouracil/Leucovorin (5-FU/LV) in Patients (pts) With Metastatic Pancreatic Ductal Adenocarcinoma (mPDAC) Previously Treated With Gemcitabine-Based Therapy," J Clin Oncol. 36(4_Suppl):460 DOI: 10.1200/JCO.2018.36.4_suppl.460 (2018), 2 printed pages.
Siveke J, et al., Abstract ID0596. "Expanded Analyses of NAPOLI-1: Phase 3 Study of nal-IRI (MM-398), With or Without 5-Fluorouracil (5FU) and Leucovorin (LV), Versus 5-Fluorouracil and Leucovorin (5FU/LV), in Metastatic Pancreatic Cancer (mPAC) Previously Treated With Gemcitabine-Based Therapy," Oncol Res Treat. 39(Suppl 1):170(2016).
Siveke J, et al., Abstract P863. "Effects of Nanoliposomal Irinotecan (nal-IRI;MM-398) ± 5-Fluorouracil und Leucavorin (5-FU/LV) on Quality of Life (QoL) in NAPOLI-1: A Phase 3 Study in Patients (pts) With Metastatic Pancreatic Adenocarcinoma (mPAC) Previously Treated With Gemcitabine-Based Therapy," Oncol Res Threat. 39 (Suppl 3):259 (2016).
Skof E, et al., "Capecitabine Plus Irinotecan (XELIRI Regimen) Compared to 5-FU/LV Plus Irinotecan (FOLFIRI Regimen) As Neoadjuvant Treatment for Patients With Unresectable Liver-Only Metastases of Metastatic Colorectal Dancer: A Randomised Prospective Phase II Trial," BMC Cancer. 9:120 doi: 10.1186/1471-2407-9-120 (2009), 9 pages.
Soares H, et. al., "A Phase II Study of Capecitabine Plus Docetaxel in Gemcitabine-Pretreated Metastatic Pancreatic Cancer Patients:CapTere," Cancer Chemother Pharmacol. 73(4):839-45 (2014).
Sohal D et. al., "Metastatic Pancreatic Cancer: ASCO Clinical Practice Guideline Update," J Clin Oncol. 36 (24)2545-2556 and appendix (2018).
Sohal D, et. al., "Metastatic Pancreatic Cancer: American Society of Clinical Oncology Clinical Practice Guideline," J Clin Oncol. 34(23)2784-96 and Appendix (2016).
Sohal D, et al., "Reply to A. Wang-Gillam et al," J Clin Oncol. 35(6):690-1 (2017). Epub 2016.
Son J, et al., "Glutamine Supports Pancreatic Cancer Growth Through a Kras-Regulated Metabolic Pathway," Nature. 496(7443):101-5 (2013), author manuscript version, 16 pages.
Sousa C and Kimmelman A, "The Complex Landscape of Pancreatic Cancer Metabolism," Carcinogenesis. 35 (7):1441-50 (2014).
Starling N, et al., "A Dose Escalation Study of Gemcitabine Plus Oxaliplatin in Combination With Imatinib for Gemcitabine-Refractory Advanced Pancreatic Adenocarcinoma," Ann Oncol. 23(4):942-7 (2012). Epub 2011.
Stathis A and Moore M, "Advanced Pancreatic Carcinoma: Current Treatment and Future Challenges," Nat Rev Clin Oncol. 7(3):163-72 (2010).
Stathopoulos G and Boulikas T, "Lipoplatin Formulation Review Article," J Drug Deliv. 2012:581363, Article ID 581363, doi:10. 1155/2012/581363, Epub 2011, 10 pages.
Stathopoulos G, et al., "A Multicenter Phase III Trial Comparing Irinotecan-Gemcitabine (IG) With Gemcitabine (G) Monotherapy as First-Line Treatment in Patients With Locally Advanced or Metastatic Pancreatic Cancer," Br J Cancer. 95(5):587-92 (2006).
Stathopoulos G, et al., "Liposomal Oxaliplatin in the Treatment of Advanced Cancer: A Phase I Study," Anticancer Res 26(2B):1489-93 (2006).
Stathopoulos G, et al., "Lipsomal Cisplatin Combined With Gemcitabine in Pretreated Advanced Pancreatic Cancer Patients: A phase I-II Study," Oncol Rep. 15(5):1201-4 (2006).
Takada T et al., "Comparison of 5-Fluorouracil, Doxorubicin and Mitomycin C with 5-Fluorouracil Alone in the Treatment of Pancreatic-Biliary Carcinomas," Oncology. 51(5):396-400 (1994).
Takahara N, et al., "A Retrospective Study of S-1 and Oxaliplatin Combination Chemotherapy in Patients With Refractory Pancreatic Cancer," Cancer Chemother Pharmacol 72(5):985-90 (2013).
Takano S, et al., "Metronomic Treatment of Malignant Glioma Xenografts with Irinotecan (CPT-11) Inhibits Angiogenesis and Tumor Growth," J Neurooncol. 99(2):177-85 (2010).
Tardi P, et al., "Coencapsulation of Irinotecan and Floxuridine Into Low Cholesterol-Containing Liposomes That Coordinate Drug Release In Vivo," Biochim Biophys Acta. 1768(3):678-87 (2007). Epub 2006.
Tempero M, et al., "NCCN Clinical Practice Guidelines in Oncology: Pancreatic Adenocarcinoma," Version 1.2012. National Comprehensive Cancer Network, Inc. (2011), 79 pages.
Tempero M, et al., "NCCN Clinical Practice Guidelines in Oncology: Pancreatic Adenocarcinoma," Version 2.2012. National Comprehensive Cancer Network, Inc. (2011), 94 pages.
Tempero M, et al., "NCCN Clinical Practice Guidelines in Oncology: Pancreatic Adenocarcinoma," Version 2.2014. National Comprehensive Cancer Network, Inc. (2014), 122 pages.
Tempero M, et al., "Pancreatic Adenocarcinoma: Clinical Practice Guidelines in Oncology," J Natl Compr Canc Netw. 8(9):972-1017 (2010).

(56) References Cited

OTHER PUBLICATIONS

Thota R, et al., "Treatment of Metastatic Pancreatic Adenocarcinoma: A Review," Oncology. 28(1):70-4 (2014). Available at cancernetwork.com/view/treatment-metastatic-pancreatic-adenocarcinoma-review, 6 printed pages.
Todaka A, et al., "S-1 Monotherapy as Second-line Treatment for Advanced Pancreatic Cancer after Gemcitabine Failure," Jpn J Clin Oncol. 40(6):567-72 (2010).
Togawa A, et al., "Treatment With an Oral Fluoropyrimidine, S-1, Plus Cisplatin in Patients Who Failed Postoperative Gemcitabine Treatment for Pancreatic Cancer: A Pilot Study," Int J Clin Oncol. 12(4):268-73 (2007).
Tomicki S, et al., "Utilization of Hospital Inpatient Services Among Patients With Metastatic Pancreatic Cancer With Commercial and Medicare Insurance Treated With FDA-Approved/NCCN Category 1 Regimens." Poster presented at the Academy of Managed Care Pharmacy, Nexus (AMCP, Nexus): virtual meeting, week of Oct. 19, 2020, 6 pages.
Toutain P and Bousquet-Melou A, "Plasma terminal half-life," J Vet Pharmacol Ther. 27(6):427-39 (2004).
Tsavaris N, et al., "Second-Line Treatment With Oxaliplatin, Leucovorin and 5-Fluorouracil in Gemcitabine-Pretreated Advanced Pancreatic Cancer: A Phase II Study," Invest New Drugs. 23(4):369-75 (2005).
U.S. Appl. No. 15/664,976: dated Oct. 13, 2020 Notice of Allowance including Examiner's Reasons for Allowance, 13 pages.
U.S. Appl. No. 16/586,609: dated Oct. 5, 2020 Non-Final Office Action, 5 pages.
Vaage J, et al., "Therapy of a Xenografted Human Colonic Carcinoma Using Cisplatin or Doxorubicin Encapsulated in Long Circulating Pegylated Stealth Liposomes," Int J Cancer. 80(1):134-7 (1999).
Van Cutsem E et. al., "Phase III Trial of Bevacizumab in Combination With Gemcitabine and Erlotinib in Patients With Metastatic Pancreatic Cancer," J Clin Oncol. 27(13):2231-7 (2009).
Van Rijswijk R, et al., "Weekly High-Dose 5-Fluorouracil and Folinic Acid in Metastatic Pancreatic Carcinoma: A Phase II Study of the EORTC Gastrointestinal Tract Cancer Cooperative Group," Eur J Cancer. 40(14):2077-81 (2004).
Veal G, et al., "A Phase I Study in Paediatric Patients to Evaluate the Safety and Pharmacokinetics of SPI-77, A Liposome Encapsulated Formulation of Cisplatin," Br J Cancer. 84(8): 1029-35 (2001).
Venook A, "Critical Evaluation of Current Treatments in Metastatic Colorectal Cancer," Oncologist. 10(4):250-61 (2005).
Ventura M, et al., "Efficacy of nal-IRI and Hypoxia Modulation in Orthotopic Patient-Derived Pancreatic Tumor Models of High (OCIP51) and Low (OCIP19) Hypoxia," Presentation presented at the World Molecular Imaging Congress 2017, Philadelphia, Pennsylvania, Sep. 13-16, 2017, 15 pages.
Ventura M, et al., Abstract. "Efficacy of nal-IRI and Hypoxia Modulation in Orthotopic Patient-Derived Pancreatic Tumor Models of High (OCIP51) and Low (OCIP19) Hypoxia," The World Molecular Imaging Congress 2017, Philadelphia, Pennsylvania, Sep. 13-16, 2017, 1 page.
Vickers M, et al., "Comorbidity, Age and Overall Survival in Patients With Advanced Pancreatic Cancer—Results from NCIC CTG PA.3: A Phase III Trial of Gemcitabine Plus Erlotinib or Placebo," Eur J Cancer. 48(10):1434-42 (2012). Epub 2011.
Von Hoff D, et al., "Gemcitabine Plus nab-Paclitaxel Is an Active Regimen in Patients With Advanced Pancreatic Cancer: A PhaseI/II Trial," J Clin Oncol. 29(34):4548-54 (2011).
Von Hoff D, et al., "Increased Survival in Pancreatic Cancer with nab-Paclitaxel plus Gemcitabine," N Engl J Med. 369(18): 1691-703 (2013).
Wainberg Z, et al., "First-Line Liposomal Irinotecan + 5-Fluorouracil/ Leucovorin + Oxaliplatin in Patients With Pancreatic Ductal Adenocarcinoma: Long-Term Follow-Up Results From a Phase 1/2 Study." Poster presented at the European Society for Medical Oncology (ESMO) World Congress on Gastrointestinal Cancer, virtual format, Jul. 1-4, 2020, 7 pages.

Wainberg Z, et al., "NAPOLI-3: An Open-Label, Randomized, Phase 3 Study of First-Line Liposomal Irinotecan + 5 Fluorouracil/ Leucovorin + Oxaliplatin Versus Nab-Paclitaxel + Gemcitabine in Patients With Metastatic Pancreatic Ductal Adenocarcinoma." Poster presented at the American Society of Clinical Oncology (ASCO) Annual Conference, virtual format, May 29-Jun. 2, 2020, 6 pages.
Wainberg Z, et al., Abstract TPS4661. "NAPOLI-3: An Open-Label, Randomized, Phase III Study of First-Line Liposomal Irinotecan + 5 Fluorouracil/Leucovorin + Oxaliplatin Versus Nab-Paclitaxel + Gemcitabine in Patients With Metastatic Pancreatic Ductal Adenocarcinoma," J Clin Oncol. 38(15 Suppl):TPS4461 DOI: 10.1200/ JCO.2020.38.15_suppl. TPS4661 (2020), 2 printed pages.
Walker E and Ko A, "Beyond First-Line Chemotherapy for Advanced Pancreatic Cancer: An Expanding Array of Therapeutic Options?" World J Gastroenterol. 20(9):2224-36 (2014).
Batist G, et al., "Safety Pharmacokinetics, and Efficacy of CPX-1 Liposome Injection in Patients with Advanced Solid Tumors," Clin Cancer Res. 15(2)1692-700 (2009).
Boman N, et al., "Optimization of the Retention Properties of Vincristine in Liposomal Systems," Biochim Biophys Acta. 1152(2):253-58 (1993).
Colbern G, et al., "Encapsulation of the Topoisomerase I Inhibitor GL147211C in Pegylated (STEALTH) Liposomes Pharmacokinetics and Antitumor Activity in HT29 Colon Tumor Xenografts," Clin Cancer Res. 4(12):3077-82 (1998).
Dicko A, et al., "Intra and Inter-Molecular Interactions Dictate the Aggregation State of Irinotecan Co-Encapsulated with Floxuridine Inside Liposomes," Pharm Res. 25(7):1702-13 (2008).
Drummond D, et al., "Pharmacokinetics and In Vivo Drug Release Rates in Liposomal Nanocarrier Development," J Pharm Sci. 97(11):4696-740 (2008).
Emerson D, et al., "Antitumor Efficacy, Pharmacokinetics, and Biodistribution of NX 211: A Low-Clearance Liposomal Formulation of Lurtotecan," Clin Cancer Res 6(7):2903-12 (2000).
EP Patent Application No. 05745505.7: European Search Report dated Sep. 1, 2010, 6 pages.
European Medicines Agency Assessment Report for Onivyde, Committee for Medicinal Products for Human Use (CHMP), Jul. 21, 2016, 107 pages.
Fugit K, et al., "The Role of pH and Ring-opening Hydrolysis Kinetics on Liposomal Release of Topotecan," J Control Release. 174:88-97 (2014), Epub Nov. 12, 2013, Author manuscript, pp. 1-27.
Hattori Y, et al., "Novel Irinotecan-Loaded Liposome Using Phytic Acid with High Therapeutic Efficacy for Colon Tumors," J Control Release. 136(1):30-7 (2009).
Pavillard V, et al., "Determinants of the Cytotoxicity of Irinotecan in Two Human Colorectal Tumor Cell Lines," Cancer Chemother Pharmacol. 49(4):329-35 (2002).
Peikov V, et al., "pH-Dependent Association of SN-38 with Lipid Bilayers of a Novel Liposomal Formulation," Int J Pharm 299(1-2):92-9 (2005).
PharmaEngine, www.pharmaengine.com/pep02.html Webpage titled "PEP02". Aug. 4, 2011, 4 printed pages.
Riviere K, et al., "Anti-Tumor Activity of Liposome Encapsulated Fluoroorotic Acid as a Single Agent and in Combination with Liposome Irinotecan," J Control Release. 153(3):288-96 (2011), Author manuscript, pp. 1-19.
Sadzuka Y, et al., "Effective Irinotecan (CPT-11)-containing Liposomes: Intraliposomal Conversion to the Active Metabolite SN-38." Jpn J Cancer Res. 90(2):226-32 (1999).
Tardi P, et al., "Liposomal Encapsulation of Topotecan Enhances Anticancer Efficacy in Murine and Human Xenograft Models," Cancer Res. 60(13):3389-93 (2000).
Wei H, et al., "Active Loading Liposomal Irinotecan Hydrochloride: Preparation, In Vitro and In Vivo Evaluation," Asian J Pharm Sci. 8(5):303-11 (2013).
Zhang L, et al., PEG-Coated Irinitecan Cationic Liposomes Improve the Therapeutic Efficacy of Breast Cancer in Animals, EurRev Med Pharmacol Sci. 17(24):3347-61 (2013).
Chabot G, "Clinical Pharmacokinetics of Irinotecan," Clin. Pharmacokinet. 33(4):245-59 (1997).

(56) References Cited

OTHER PUBLICATIONS

Chan E, et al., "A Phase 1/2 Study Combining MM-151 + nal-IRI + 5-FU + Leucovorin in RAS/RAF Wild-Type Metastatic Colorectal Cancer." Poster presented at the American Society of Clinical Oncology (ASCO) Annual Meeting, Chicago, Illinois, Jun. 3-7, 2016, 7 pages.
Chan E, et al., Abstract TPS3633. "A Phase 1b/2 Study Combining MM-151 + nal-IRI + 5-FU + Leucovorin in RAS-Wildtype Metastatic Colorectal Cancer (mCRC)," J Clin Oncol. 34(15_Suppl):TPS3633 10.1200/JCO.2016.34.15_suppl.TPS3633 (2016), 4 printed pages.
Chauhan V, et al., "Normalization of Tumour Blood Vessels Improves the Delivery of Nanomedicines in a Size-Dependent Manner," Nat Nanotechnol. 7(6):383-8 (2012), author manuscript version, 15 pages.
Chen J, et al., "Improved Pharmacokinetics and Reduced Toxicity of Brucine After Encapsulation into Stealth Liposomes: Role of Phosphatidylcholine," Int J Nanomedicine 7:3567-77 (2012).
Chen L-T, et al., "CA19-9 Decrease and Overall Survival (OS) in the NAPOLI-1 Trial of Liposomal Irinotecan (nal-IRI) ± 5-Fluorouracil and Leucovorin (5-FU/LV) in Metastatic Pancreatic Ductal Adenocarcinoma (mPDAC) Previously Treated With Gemcitabine-Based Therapy." Poster presented at the European Society for Medical Oncology (ESMO) World Congress on Gastrointestinal Cancer, Barcelona, Spain, Jun. 28-Jul. 1, 2017, 5 pages.
Chen L-T, et al., "CA19-9 Decrease and Overall Survival in the NAPOLI-1 Trial of Liposomal Irinotecan (nal-IRI) ± 5-Fluorouracil and Leucovorin (5-FU/LV) in Metastatic Pancreatic Ductal Adenocarcinoma Previously Treated With Gemcitabine-Based Therapy." Poster presented at the European Society for Medical Oncology Asia 2017 Congress, Singapore, Nov. 17-19, 2017, 8 pages.
Chen L-T, et al., "Early Dose Reduction/Delay and the Efficacy of Liposomal Irinotecan With Fluorouracil and Leucovorin in Metastatic Pancreatic Ductal Adenocarcinoma (mPDAC): A Post Hoc Analysis of NAPOLI-1," Pancreatology. 21(1):192-9 (2021). Epub 2020.
Chen L-T, et al., "Efficacy and Safety of Liposomal Irinotecan (nal-IRI) + 5-Fluorouracil and Leucovorin in Patients With Metastatic Pancreatic Ductal Adenocarcinoma Who Previously Received Gemcitabine-Based Therapy: Post Hoc Analysis of the NAPOLI-1 Trial" Poster presented at the American Society of Clinical Oncology Gastrointestinal Cancers Symposium (ASCO GI), San Francisco, CA, Jan. 19-21, 2017, 9 pages.
Chen L-T, et al., "Final Results of NAPOLI-1: A Phase 3 Study of nal-IRI (MM-398) ± 5-Fluorouracil and Leucovorin 5-FU/LV) vs 5-FU/LV in Metastatic Pancreatic Ductal Adenocarcinoma (mPDAC) Previously Treated With Gemcitabine-Based Therapy." Poster presented at the European Society for Medical Oncology (ESMO) Annual Congress, Copenhagen, Denmark, Oct. 7-11, 2016, 8 pages.
Chen L-T, et al., "Impact of Dose Reduction or Dose Delay on the Efficacy of Liposomal Irinotecan (nal-IRI)+5-Fluorouracil/Leucovorin (5-FU/LV): Survival Analysis From NAPOLI-1." Poster presented at the European Society for Medical Oncology (ESMO) Annual Congress, Munich, Germany, Oct. 19-23, 2018, 9 pages.
Chen L-T, et al., "The Prognostic Value of the Modified Glasgow Prognostic Score (mGPS) in Predicting Overall Survival (OS) in Patients With Metastatic Pancreatic Ductal Adenocarcinoma (mPDAC) Receiving Liposomal Irinotecan (nal-IRI)+5-Fluorouracil and Leucovorin (5-FU/LV)." Poster presented at the European Society for Medical Oncology (ESMO) Annual Congress, Munich, Germany, Oct. 19-23, 2018, 9 pages.
Chen L-T, et al., Abstract 221PD. "Efficacy and Safety of Nanoliposomal Irinotecan (nal-IRI, MM-398, PEP02, BAX-2398) in Patients With Metastatic Pancreatic Cancer in Asia: A Subgroup Analysis of the Phase 3 NAPOLI-1 Study," Ann Oncol. 27(Supp_9):ix69-ix70 doi:10.1093/annonc/mdw582 (2016).
Chen L-T, et al., Abstract 227P. "CA19-9 Decrease and Overall Survival (OS) in the NAPOLI-1 Trial of Liposomal Irinotecan (nal-IRI) ± 5-Fluorouracil and Leucovorin (5-FU/LV) in Metastatic Pancreatic Ductal Adenocarcinoma mPDAC) Previously Treated With Gemcitabine-Based Therapy," Ann Oncol. 28(Suppl_10):x66-x67 doi:10.1093/annonc/mdx660 (2017).
Chen L-T, et al., Abstract 303. "Efficacy and Safety of Liposomal Irinotecan (nal-IRI) + 5-Fluorouracil and Leucovorin (5-FU/LV) in Patients (pts) With Metastatic Pancreatic Ductal Adenocarcinoma (mPDAC) Who Previously Received Gemcitabine (Gem)-Based Therapy: Post Hoc Analysis of the NAPOLI-1 Trial," J Clin Oncol. 35(4 Suppl):303 DOI: 10.1200/JCO.2017.35.4_suppl.303 (2017), 2 printed pages.
Chen L-T, et al., Abstract 3707. "Final Results of NAPOLI-1: A Phase 3 Study of nal-IRI (MM-398) ± 5-Fluorouracil and Leucovorin (5-FU/LV) vs 5-FU/LV in Metastatic Pancreatic Cancer (mPAC) Previously Treated With Gemcitabine-Based Therapy," Ann Oncol. 27(6):207-242 10.1093/annonc/mdw371 (2016), 4 printed pages.
Chen L-T, et al., Abstract 734P. "Impact of Dose Reduction or Dose Delay on the Efficacy of Liposomal Irinotecan (nal-IRI)+5-Fluorouracil/Leucovorin (5-FU/LV): Survival Analysis From NAPOLI-1," Ann Oncol. 29(Suppl_8):viii250-viii251 doi:10.1093/annonc/mdy282 (2018).
Chen L-T, et al., Abstract 749P. "The Prognostic Value of the Modified Glasgow Prognostic Score (mGPS) in Predicting Overall Survival (OS) in Patients With Metastatic Pancreatic Ductal Adenocarcinoma (mPDAC) Receiving Liposomal Irinotecan (nal-IRI)+5-Fluorouracil and Leucovorin (5-FU/LV)," Ann Oncol. 29(Suppl 8):viii255-viii256 doi:10.1093/annonc/mdy282 (2018).
Chen L-T, et al., Abstract PD-017. "CA19-9 Decrease and Overall Survival (OS) in the NAPOLI-1 Trial of Liposomal Irinotecan (nal-IRI) ± 5-Fluorouracil and Leucovorin (5-FU/LV) in Metastatic Pancreatic Ductal Adenocarcinoma (mPDAC) Previously Treated With Gemcitabine-Based Therapy," Ann Oncol. 28(Supp 3):6-7 doi:10.1093/annonc/mdx263 (2017).
Chin V, et al., "Chemotherapy and Radiotherapy for Advanced Pancreatic Cancer (Review)," Cochrane Database Syst Rev. 3(3):CD011044 doi: 10.1002/14651858.CD011044.pub2 (2018), 143 pages.
Choi C, et al., "Effects of 5-Fluorouracil and Leucovorin in the Treatment of Pancreatic-Biliary Tract Adenocarcinomas," Am J Clin Oncol. CCT 23(4): 425-8 (2000), 7 printed pages.
Chu C-J, et al., "Efficiency of Cytoplasmic Delivery by pH-Sensitive Liposomes to Cells in Culture," Pharm Res. 7(8):824-34 (1990).
Clarke J, et al., "A Phase 1 Trial of Intravenous Liposomal Irinotecan in Patients With Recurrent High-Grade Gliomas." Poster presented at the American Society of Clinical Oncology (ASCO) Annual Conference, Chicago, IL, May 29-Jun. 2, 2015, 7 pages.
Clarke J, et al., Abstract 2029. "A Phase I Trial of Intravenous Liposomal Irinotecan in Patients With Recurrent High-Grade Gliomas," J Clin Oncol. 33(15_Suppl):2029 DOI: 10.1200/jco.2015.33.15_suppl.2029 (2015), 2 printed pages.
Clinical Trials Identifier NCT00426127: Dec. 29, 2017 update, first posted Jan. 24, 2007, "Docetaxel and Liposomal Doxorubicin Chemotherapy With Enoxaparin in Patients With Advanced Pancreatic Cancer," Retrieved from ClinicalTrials.gov archive, 8 printed pages.
ClinicalTrials.gov search results for ONIVYDE, retrieved from clinicaltrials.gov website on Jan. 27, 2021, 27 pages.
Cockrum P, et al., "Impact of Dose Reductions on Clinical Outcomes Among Patients With Metastatic Pancreatic Cancer Treated With Liposomal Irinotecan in Oncology Clinics in the US." Poster presented at the American Society of Clinical Oncology Gastrointestinal Cancers Symposium (ASCO GI), San Francisco, CA, Jan. 23-25, 2020, 8 pages.
Cockrum P, et al., Abstract 665. "Impact of Dose Reductions on Clinical Outcomes Among Patients (pts) With Metastatic Pancreatic Cancer (mPC) Treated With Liposomal Irinotecan (nal-IRI) in Oncology Clinics in the United States," J Clin Oncol. 38(4_Suppl):665 DOI: 10.1200/JCO.2020.38.4_suppl.665 (2020), 2 printed pages.
Cockrum P, et al., Abstract e16739. "National Comprehensive Cancer Network (NCCN) Category I/FDA-Approved Metastatic Pancreatic Adenocarcinoma (mPDAC) Treatments in Commercially Insured Patients: An Analysis of Inpatient (IP) and Emergency Room (ER) Admissions," J Clin Oncol. 38(15_Suppl):e16739 DOI: 10.1200/JCO.2020.38.15_suppl.e16739 (2020), 2 printed pages.

(56) References Cited

OTHER PUBLICATIONS

Cockrum P, et al., Abstract PCN134. "An Examination of Quality Metrics: Inpatient and Emergency Department Burden of Commercially Insured Treated Metastatic Pancreatic Cancer (mPC) Patients in the United States (US)," Value in Health. 23(Suppl 1):S46 (2020).
Cockrum P, et al., Abstract PCN167. "An Integrated Delivery Network Focus on Cost Drivers in Chemotherapy: The Economic Burden of Neutropenia and Inpatient Admissions Among Commercially Insured Metastatic Pancreatic Dancer Patients (mPC)," Value in Health. 23(Suppl 1):S52 (2020).
Colucci G, et al., "Randomized Phase III Trial of Gemcitabine Plus Cisplatin Compared With Single-Agent Gemcitabine as First-Line Treatment of Patients With Advanced Pancreatic Cancer: The GIP-1 Study," J Clin Oncol. 28(10):1645-51 (2010).
Comella P, et al., "Irinotecan Plus Leucovorin-Modulated 5-Fluorouracil I.V. Bolus Every Other Week May Be a Suitable Therapeutic Option Also for Elderly Patients With Metastatic Colorectal Carcinoma," Br J Cancer. 89(6):992-6 (2003).
Conroy T et al., Abstract 4010. "Randomized Phase III Trial Comparing Folfirinox (F: 5FU/Leucovorin [LV], Irinotecan [I}, and Oxaliplatin [O]) Versus Gemcitibine (G) as First-Line Treatment for Metastatic Pancreatic Adenocarcinoma (MPA): Preplanned Interim Analysis Results of the PRODIGE 4/ACCORD 11 Trial" J Clin Oncol. 28 (15_Suppl):4010 (2010), 3 printed pages.
Custodio A, et al., "Second-Line Therapy for Advanced Pancreatic Cancer: A Review of the Literature and Future Directions," Cancer Treat Rev. 35(8):676-84 (2009).
Daleke D, et al., "Endocytosis of Liposomes by Macrophages: Binding, Acidification and Leakage of Liposomes Monitored by a New Fluorescence Assay," Biochim Biophys Acta. 1024(2):352-66 (1990).
DaunoXome (daunorubicin citrate liposome injection) package insert, rev. Dec. 2011, 11 pages.
De Jong F, et al., "Effects of nal-IRI (MM-398; a Liposomal Formulation of Irinotecan) ± 5-Fluorouracil (5-FU) on Quality of Life (QoL) in NAPOLI-1: A Phase 3 Study in Patients With Metastatic Pancreatic Ductal Adenocarcinoma Previously Treated With Gemcitabine," Poster presented at the Australian Gastro-Intestinal Trials Group, 18th Annual Scientific Meeting, Melbourne, Australia, Sep. 14-16, 2016, 10 pages.
De Jong F, et al., Abstract. "Effects of nal-IRI (MM-398; a Liposomal Formulation of Irinotecan) ± 5-Fluorouracil (5-FU) on Quality of Life (QoL) in NAPOLI-1: A Phase 3 Study in Patients With Metastatic Pancreatic Ductal Adenocarcinoma (mPDAC) Previously Treated With Gemcitabine," Australian Gastro-Intestinal Trials Group, 18th Annual Scientific Meeting, Melbourne, Australia, Sep. 14-16, 2016, 2 pages.
Dean A, et al., "First-Line (1L) Liposomal Irinotecan + 5-Fluorouracil/Leucovorin (5-FU/LV) + Oxaliplatin (OX) in Patients With Locally Advanced or Metastatic Pancreatic Ductal Adenocarcinoma: Exploratory Subgroup Analyses of Survival by Changes in CA 19-9 Levels." Poster presented at the European Society for Medical Oncology (ESMO) Virtual Congress 2020, Sep. 19-21, 2020, 7 pages.
Dean A, et al., "First-Line Liposomal Irinotecan + 5-Fluorouracil/Leucovorin + Oxaliplatin in Patients With Pancreatic Ductal Adenocarcinoma: Results From a Phase 1/2 Study." Presentation presented at the Clinical Oncology Society of Australia (COSA): Virtual meeting, Nov. 11-13, 2020, 10 pages.
Dean A, et al., "NAPOLI-3: An Open-Label, Randomized, Phase III Study of First-Line Liposomal Irinotecan + 5-Fluorouracil/Leucovorin + Oxaliplatin Versus nab-Paclitaxel + Gemcitabine in Patients With Metastatic Pancreatic Ductal Adenocarcinoma." Presentation presented at the Clinical Oncology Society of Australia (COSA): Virtual meeting, Nov. 11-13, 2020, 10 pages.
Dean A, et al., Abstract 1529P. "First-Line (1L) Liposomal Irinotecan + 5-Fluorouracil/Leucovorin (5-FU/LV) + Oxaliplatin (OX) in Patients With Locally Advanced or Metastatic Pancreatic Ductal Adenocarcinoma (mPDAC) Exploratory Subgroup Analyses of Survival by Changes in CA 19-9 Levels," Ann Oncol. 31(Suppl_4):S881-S897 10.1016/annonc/annonc285 (2020), 3 printed pages.
Dean A, et al., Abstract 222. "First-Line Liposomal Irinotecan + 5-Fluorouracil/Leucovorin + Oxaliplatin in Patients With Pancreatic Ductal Adenocarcinoma: Results From a Phase 1/2 Study," Asia-Pac J Clin Oncol. 16(Suppl. 8):118-119 (2020).
Dean A, et al., Abstract 407. "NAPOLI-3: An Open-Label, Randomized, Phase III Study of First-Line Liposomal Irinotecan + 5-Fluorouracil/Leucovorin + Oxaliplatin Versus nab-Paclitaxel + Gemcitabine in Patients With Metastatic Pancreatic Ductal Adenocarcinoma," Asia-Pac J Clin Oncol. 16(Suppl. 8):202-3 (2020).
Dean A, et al., Abstract 4111. "A Phase 1/2, Open-Label Dose-Escalation Study of Liposomal Irinotecan (nal-IRI) Plus 5- Fluorouracil/Leucovorin (5-FU/LV) and Oxaliplatin (OX) in Patients with Previously Untreated Metastatic Pancreatic Cancer (mPAC)," J Clin Oncol. 36(15_Suppl):4111 10.1200/JCO.2018.36.15_suppl.4111 (2018), 1 page.
Dean A, et al., Abstract. "Expanded Analyses of NAPOLI-1: Phase 3 Study of MM-398 (nal-IRI), With or Without 5-Fluorouracil and Leucovorin (5-FU/LV), Versus 5-FU/LV, in Metastatic Pancreatic Cancer (mPAC) Previously Treated With Gemcitabine-Based Therapy," 18th Annual Scientific Meeting of the Australasian Gastro-Intestinal Trials Group AGITG), Melbourne, Australia, Sep. 14-16, 2016, 2 pages.
Dean A, et al., Abstract. "Liposomal Irinotecan (nal-IRI, MM-398)—Containing Regimens Versus nab-Paclitaxel Plus Gemcitabine as First-Line Therapy in Patients With Metastatic Pancreatic Adenocarcinoma (mPAC): A Randomized, Open-Label Phase 2 Study," 18th Annual Scientific Meeting of the Australasian Gastro-Intestinal Trials Group (AGITG), Melbourne, Australia, Sep. 14-16, 2016, 2 pages.
DeLord J, et al., "A Phase I Clinical and Pharmacokinetic Study of Capecitabine (Xeloda®) and Irinotecan Combination Therapy (XELIRI) in Patients With Metastatic Gastrointestinal Tumours," Br J Cancer. 92(5):820-6 (2005).
Derksen J, et al., "Interaction of Immunoglobulin-Coupled Liposomes with Rat Liver Macrophages In Vitro," Exp Cell Res. 168(1):105-15 (1987).
Batist G, et al., Abstract 2014. "Phase 1 Study of CPX-1, A Fixed Ratio Formulation of Irinotecan (IRI) and Floxuridine (FLOX), in Patients With Advanced Solid Tumors," J Clin Oncol. 24(18_suppl):2014 (2006), 2 printed pages.
Gelmon K, et al., "A Phase 1 Study of OSI-211 Given As an Intravenous Infusion Days 1, 2, and 3 Every Three Weeks in Patients With Solid Cancers," Invest New Drugs. 22(3):263-75 (2004).
Harker-Murray P, et al., Abstract CT146. "Plasma Pharmacokinetics of Liposomal Irinotecan (nal-iri) in Pediatric Oncology Patients with Recurrent or Refractory Solid Tumors: South Plains Oncology Consortium Study 2012-001," In Proceedings of the American Association for Cancer Research Annual Meeting 2017; Apr. 1-5, 2017. Washington, DC. Cancer Res. 2017;77(13 Suppl):Abstract nr CT146, doi: 10.1158/1538-7445.AM2017-CT146, 2 printed pages.
Jones S, et al., Abstract 2547. "Phase I and Pharmacokinetic (PK) Study of IHL-305 (Pegylated Liposomal Irinotecan) in Patients With Advanced Solid Tumors," J Clin Oncol. 27(15_suppl):2547 and Table 1 (2009), 6 printed pages.
Kirpotin D, et al., "Targeting of Liposomes to Solid Tumors: The Case of Sterically Stabilized Anti-HER2 mmunoliposomes," J Liposome Res. 7:391-417 (1997).
Ma W, et al., Abstract 2365. "Nanoliposomal Irinotecan (MM-398, nal-IRI) Population Pharmacokinetics (PK) and its Association With Efficacy and Safety in Patients With Solid Tumors Based on the Phase 3 Study NAPOLI-1 and Five Phase 1 and 2 Studies," Eur J Cancer. 51(3):S458 10.1016/S0959-8049(16)31281-3 (2015).
Ma W, et al., Abstract e13588. "Population Pharmacokinetics and Exposure-Safety Relationship of Nanoliposomal Irinotecan (MM-398, nal-IRI) in Patients With Solid Tumors," J Clin Oncol. 33(15_Suppl):e13588 DOI: 10.1200/co.2015.33.15_suppl.e13588 (2015), 2 printed pages.
Mackenzie M, et al., "A Phase I Study of OSI-211 and Cisplatin as Intravenous Infusions Given on Days 1, 2 and 3 Every 3 Weeks in Patients With Solid Cancers," Ann Oncol. 15(4):665-70 (2004).

(56) References Cited

OTHER PUBLICATIONS

Olszewski A, et al., "Phase I Study of Oxaliplatin in Combination with Gemcitabine, Irinotecan, and 5-Fluorouracil/Leucovorin(G-FLIE) in Patients with Metastatic Solid Tumors Including Adenocarcinoma of the Pancreas," J Gastrointest Cancer. 44(2):182-9 (2013).

Papahadjopoulos D, et al., "Targeting of Drugs to Solid Tumors Using Anti-HER2 Immunoliposomes," J Liposome Res. 8(4):425-42 (1998).

Paz-Ares L, et al., "Resilient part 2: An Open-Label, Randomized, Phase 3 Study of Liposomal Irinotecan Injection in Patients With Small-Cell Lung Cancer Who Have Progressed With Platinum-Based First-Line Therapy." Poster presented at the American Society of Clinical Oncology (ASCO) Annual Conference, virtual format, May 29-Jun. 2, 2020, 7 pages.

Paz-Ares L, et al., Abstract TPS9081. "Resilient part II: An Open-Label, Randomized, Phase III Study of Liposomal Irinotecan Injection in Patients With Small-Cell Lung Cancer Who Have Progressed With Platinum-Based First-Line Therapy," J Clin Oncol. 38(15_Suppl):TPS9081 DOI: 10.1200/JCO.2020.38.15_suppl.TPS9081 (2020), 2 printed pages.

Ponce S, et al., "Resilient Part 1: Pharmacokinetics of Second-Line (2L) Liposomal Irinotecan in Patients with Small Cell Lung Cancer (SCLC)," Poster presented at the European Society for Medical Oncology (ESMO) Virtual Congress 2020, virtual format, Sep. 19-21, 2020, 8 pages.

Ponce S, et al., Abstract 1793P. "Resilient Part 1: Pharmacokinetics of Second-Line (2L) Liposomal Irinotecan in Patients with Small Cell Lung Cancer (SCLC)," Ann Oncol. 31(S4):S1038-S1039 (2020).

Saltz LB, et al., "Phase I Clinical and Pharmacokinetic Study of Irinotecan, Fluorouracil, and Leucovorin in Patients With Advanced Solid Tumors," J Clin Oncol. 14(11):2959-67 (1996).

Spigel D, et al., "Liposomal Irinotecan in Adults with Small Cell Lung Cancer Who Progressed on Platinum-Based Therapy: Subgroup Analyses by Platinum Sensitivity." Poster presented at the International Association for the Study of Lung Cancer (IASLC) 2020 North America Conference on Lung Cancer (NACLC): virtual meeting, Oct. 16-17, 2020, 9 pages.

Spigel D, et al., "RESILIENT Part 1, An Open-Label, Safety Run-In of Liposomal Irinotecan in Adults With Small Cell Lung Cancer (SCLC) Who Have Progressed With Platinum-Based First-Line Therapy: Subgroup Analyses by Platinum Sensitivity." Poster presented at the American Society of Clinical Oncology (ASCO) Annual Conference, virtual format, May 29-Jun. 2, 2020, 6 pages.

Spigel D, et al., Abstract 9069. "RESILIENT Part I, An Open-Label, Safety Run-In of Liposomal Irinotecan in Adults With Small Cell Lung Cancer (SCLC) Who Have Progressed With Platinum-Based First-Line (1L) Therapy: Subgroup Analyses by Platinum Sensitivity," J Clin Oncol 38(15_Suppl):9069 DOI: 10.1200/JCO.2020.38.15_suppl.9069 (2020), 2 printed pages.

Spigel D, et al., Abstract MO01.39. "Liposomal Irinotecan in Adults with Small Cell Lung Cancer Who Progressed on Platinum-Based Therapy: Subgroup Analyses by Platinum Sensitivity," IASLC 2020 North America Conference on Lung Cancer Abstracts, p. 80 (2020).

Stylianopoulos T and Jain R, "Combining Two Strategies to Improve Perfusion and Drug Delivery in Solid Tumors," Proc Natl Acad Sci USA. 110(46):18632-7 (2013).

Villalona-Calero M, et al., "Phase I Study of Low-Dose Suramin as a Chemosensitizer in Patients With Advanced Non-Small Cell Lung Cancer," Clin Cancer Res. 9(9):3303-11 (2003).

Abra R, et al., "The Next Generation of Liposome Delivery Systems: Recent Experience With Tumor-Targeted, Sterically-Stabilized Immunoliposomes and Active-Loading Gradients," J Liposome Res. 12(1-2):1-3 (2002).

Abrams T, et al., "Patterns of Chemotherapy Use in a U.S.-Based Cohort of Patients with Metastatic Pancreatic Cancer," Oncologist. 22(8):925-933 (2017).

Abushahin L, et al., "Multivariable Analysis of Real-World Clinical Outcomes Associated With Dose Reductions (DRs) for Patients (pts) With Metastatic Pancreatic Ductal Adenocarcinoma (mPDAC) Treated with Liposomal Irinotecan." Poster presented at the European Society for Medical Oncology Virtual Congress Sep. 19-21, 2020, 5 pages.

Abushahin L, et al., Abstract 1534P. "Multivariable Analysis of Real-World Clinical Outcomes Associated With Dose Reductions (DRs) for Patients (pts) With Metastatic Pancreatic Ductal Adenocarcinoma (mPDAC) Treated with Liposomal Irinotecan" Ann Oncol. 31(Suppl_4):S881-S897 10.1016/annonc/annonc285 (2020), 2 printed pages.

Abushahin L, et al., Abstract e16780. "Real-World Dosing, Management, and Clinical Outcomes of Patients (pts) With Metastatic Pancreatic Adenocarcinoma (mPDAC) Treated With Liposomal Irinotecan," J Clin Oncol. 38(15_Suppl):e16780 DOI: 10.1200/JCO.2020.38.15_suppl.e16780 (2020), 2 printed pages.

Ahn D, et al., "Real-World Dosing Patterns of Patients With Metastatic Pancreatic Cancer (mPC) Treated With Liposomal Irinotecan (nal-IRI) in US Oncology Clinics." Poster presented at the European Society for Medical Oncology (ESMO), Munich, Germany, Oct. 19-23, 2018, 8 pages.

Ahn D, et al., Abstract 735P. "Real-World Dosing Patterns of Patients (pts) With Metastatic Pancreatic Cancer (mPC) Treated With Liposomal Irinotecan (nal-IRI) in US Oncology Clinics," Ann Oncol. 29(Suppl_8):viii251 doi:10.1093/annonc/mdy282 (2018).

Alese O, et al., "A Phase I/II Study of Trifluridine/Tipiracil (TAS-102) in Combination With Nanoliposomal Irinotecan (NAL-IRI) in Advanced GI Cancers." Poster presented at Chan E, et al., "A Phase 1/2 Study Combining MM-151 + nal-IRI + 5-FU + Leucovorin in RAS/RAF Wild-Type Metastatic Colorectal Cancer." Poster presented at the American Society of Clinical Oncology (ASCO) Annual Meeting, Chicago, Illinois, Jun. 1-5, 2018, 1 page.

Alese O, et al., Abstract TPS4155. "A Phase I/II Study of Trifluridine/Tipiracil (TAS-102) in Combination With Nanoliposomal Irinotecan (NAL-IRI) in Advanced GI Cancers," J Clin Oncol. 36(15_Suppl):TPS4155 DOI: 10.1200/JCO.2018.36.15_suppl.TPS4155 (2018), 5 printed pages.

Allegrini G, et al., "A Pharmacokinetic and Pharmacodynamic Study on Metronomic Irinotecan in Metastatic Colorectal Cancer Patients," Br J Cancer 98(8):1312-19 (2008).

Alves Da Silva A, et al., "Standardization of the Infusion Sequence of Antineoplastic Drugs Used in the Treatment of Breast and Colorectal Cancers," Einstein (Sã Paulo). 16(2):eRW4074 doi: 10.1590/S1679-45082018RW4074 (2018), 9 pages.

Amzal B, et al., "Imputing Missing Values to Estimate Health-Related Quality of Life (HR-QoL) in Metastatic Pancreatic Cancer Treated With 5-Fluorouracil and Leucovorin, With and Without Liposomal Irinotecan (nal-IRI)." Poster presented at the International Society for Pharmacoeconomics and Outcomes Research (ISPOR) Annual Meeting, Boston, MA, May 20-24, 2017, 6 pages.

Amzal B, et al., Abstract PCN179. "Imputing Missing Values to Estimate Health-Related Quality of Life (HR-QoL) in Metastatic Pancreatic Cancer (mpc) Treated With 5-Fluorouracil and Leucovorin, With and Without Liposomal Yinotecan (nal-IRI)," Value in Health. 20(5):A119 (2017).

Anders C, et al., Abstract e12003. "Pharmacokinetic (PK) Characterization of Irinotecan Liposome Injection in Patients (pts) With Metastatic Breast Cancer (mBC)," J Clin Oncol. 37(15_Suppl):e12003 DOI: 10.1200/JCO.2019.37.15_suppl.e12003 (2019), 2 printed pages.

Andre T, et al., "Phase III Study Comparing a Semimonthly With a Monthly Regimen of Fluorouracil and Leucovorin As Adjuvant Treatment for Stage II and III Colon Cancer Patients: Final Results of GERCOR C96.1," Clin Oncol. 25(24):3732-8 (2007).

Aranda E, et al., "Randomized Study of Weekly Irinotecan Plus High-Dose 5-Fluorouracil (FUIRI) Versus Biweekly Irinotecan Plus 5-Fluorouracil/Leucovorin (FOLFIRI) As First-Line Chemotherapy for Patients With Metastatic Colorectal Cancer: A Spanish Cooperative Group for the Treatment of Digestive Tumors Study," Ann Oncol. 20(2):251-7 (2009).

Araneo M, et al., "Biweekly Low-Dose Sequential Gemcitabine, 5-Fluorouracil, Leucovorin, and Cisplatin (GFP): A Highly Active Novel Therapy for Metastatic Adenocarcinoma of the Exocrine Pancreas," Cancer Invest. 21(4):489-96 (2003).

(56) References Cited

OTHER PUBLICATIONS

Atkins K, et al., "A Phase I Study of Nanoliposomal Irinotecan and 5-Fluorouracil/Folinic Acid in Combination With Interleukin-1-alpha Antagonist for Advanced Pancreatic Cancer Patients With Cachexia (OnFX)." Poster presented at the American Society of Clinical Oncology Gastrointestinal Cancers Symposium (ASCO GI), San Francisco, CA, Jan. 23-25, 2020, 1 page.

Atkins K, et al., Abstract TPS780. "A Phase I Study of Nanoliposomal Irinotecan and 5-Fluorouracil/Folinic Acid in Combination With Interleukin-1-alpha Antagonist for Advanced Pancreatic Cancer Patients With Cachexia (OnFX)," J Clin Oncol. 38(4_Suppl):TPS780 DOI: 10.1200/JCO.2020.38.4_suppl.TPS780 (2020), 2 printed pages.

Awasthi N, et al., "Antitumor Efficacy of a Liposomal Formulation of Irinotecan in Preclinical Gastric Cancer Models Augmenting Its Response by Antiangiogenic Agents." Poster presented at the Annual Meeting of the American Association for Cancer Research 2020, Philadelphia, PA, Apr. 27-28, 2020 and Jun. 22-24, 2020, 6 pages.

Awasthi N, et al., Abstract 553. "Antitumor Efficacy of a Liposomal Formulation of Irinotecan in Preclinical Gastric Dancer Models: Augmenting Its Response by Antiangiogenic Agents," In Proceedings of the Annual Meeting of the American Association for Cancer Research 2020; Apr. 27-28, 2020 and Jun. 22-24, 2020. Cancer Res. 2020;80(16 Suppl):Abstract nr 553, DOI: 10.1158/1538-7445.AM2020-553, 2 printed pages.

Barbier S, et al., Abstract e16724. "Differentiation of Liposomal Irinotecan From Dose-Dense Non-Liposomal Irinotecan in Patient-Derived Pancreatic Cancer Xenograft Tumor Models," J Clin Oncol. 38(15 Suppl):e16724 DOI: 10.1200/JCO.2020.38.15_suppl.e16724 (2020), 5 printed pages.

Barenholz Y, "Development of Liposomal Drugs And Nano-Drugs: From Academic Research Via Incubators and Startups to FDA and EMA Approved Products. Part I: Science and Technology," Presentation presented at Barcelona NanoMed, Mar. 4-5, 2014, 89 pages.

Barenholz Y, "Doxil®—The First FDA-Approved Nano-Drug: Lessons Learned," J Control Release. 160(2):117-34 (2012).

Barone C, et al., "Schedule-Dependent Activity of 5-Fluorouracil and Irinotecan Combination in the Treatment of Human Colorectal Cancer: In Vitro Evidence and a Phase I Dose-Escalating Clinical Trial," Br J Cancer. 96(1):21-8 (2007). Epub 2006.

Barzi A, et al., Abstract e16229. "Real World Outcomes of Metastatic Pancreatic Cancer (mPC) Patients (pts) Treated With Liposomal Irinotecan (nal-IRI) in the US," J Clin Oncol. 36(15_Suppl):e16229 DOI: 10.1200/JCO.2018.36.15_suppl.e16229 (2018), 2 printed pages.

Basu S, et al., "Development and Validation of an UPLC-MS/MS Method for the Quantification of Irinotecan, SN 38 and SN-38 Glucuronide in Plasma, Urine, Feces, Liver and Kidney: Application to a Pharmacokinetic Study of Irinotecan in Rats," J Chromatogr B Analyt Technol Biomed Life Sci. 1015-1016: 34-41 (2016).

Batist G, et al., Abstract 2549. "Ratiometric Dosing of Irinotecan (IRI) and Floxuridine (FLOX) in a Phase I Trial: A New Approach for Enhancing the Activity of Combination Chemotherapy," J Clin Oncol. 25(18_suppl):2549 (2007), 5 printed pages.

Becker C, et al., "Multivariate Analysis of Health-Related Quality of Life (HR-QoL) in Metastatic Pancreatic Cancer Treated with 5-Fluorouracil and Leucovorin (5-FU/LV), With and Without Liposomal Irinotecan (nal-IRI)." Poster presented at the International Society for Pharmacoeconomics and Outcomes Research (ISPOR) Annual Meeting, Boston, MA, May 20-24, 2017, 7 pages.

Becker C, et al., Abstract PCN182. "Multivariate Analysis of Health-Related Quality of Life (HR-QoL) in Metastatic Pancreatic Cancer (mPC) Treated with 5-Fluorouracil and Leucovorin, With and Without Liposomal Irinotecan (nal-IRI)," Value in Health. 20(5):A120 (2017).

Becker C, et al., Abstract PCN58. "Budget Impact Analysis of Nanoliposomal Irinotecan for Treatment of Pancreatic Dancer Following Progression on Gemcitabine—A US Payer Perspective," Value in Health 19(7):A718-A719 (2016).

Blanc J, et al., "Subgroup Analysis by Prior Non-Liposomal Irinotecan Therapy in NAPOLI-1: A Phase 3 Study of nal-IRI ± 5-Fluorouracil/Leucovorin in Patients With Metastatic Pancreatic Ductal Adenocarcinoma Previously Treated with Gemcitabine-Based Therapy." Poster presented at the European Society for Medical Oncology Asia 2017 Congress, Singapore, Nov. 17-19, 2017, 8 pages.

Blanc J, et al., Abstract 228P. "Subgroup Analysis by Prior Non-Liposomal Irinotecan Therapy in NAPOLI-1: A Phase 3 Study of nal-IRI ± 5-Fluorouracil/Leucovorin in Patients With Metastatic Pancreatic Ductal Adenocarcinoma Previously Treated with Gemcitabine-Based Therapy," Ann Oncol. 28(Suppl_10):x67-x68 doi:10.1093/annonc/mdx660 (2017).

Blanc J, et al., Abstract PD-18. "Subgroup Analysis by Prior Non-Liposomal Irinotecan Therapy in NAPOLI-1: A Phase 3 Study of nal-IRI ± 5-Fluorouracil/Leucovorin in Patients With Metastatic Pancreatic Ductal Adenocarcinoma Previously Treated With Gemcitabine-Based Therapy," Ann Oncol. 28(Suppl_3):7 doi:10.1093/annonc/mdx263 (2017).

BlueCross Blue Shield of North Carolina Corporate Medical Policy, Bevacizumab in Advanced Adenocarcinoma of the Pancreas, File Name: bevacizumab_in_advanced_adenocarcinoma_of_the_pancreas, Origination: Mar. 2010, Last review: Feb. 2019, 5 pages.

Boeck S and Heinemann V, "Second-Line Therapy in Gemcitabine-Pretreated Patients With Advanced Pancreatic Cancer," J Clin Oncol. 26(7):1178-9 (2008).

Borner M, et al., "A Randomized Phase II Trial of Capecitabine and Two Different Schedules of Irinotecan in First-Line Treatment of Metastatic Colorectal Cancer: Efficacy, Quality-of-Life and Toxicity," Ann Oncol. 16(2): 282-8 (2005).

Boulikas T, "Clinical Overview on Lipoplatin: A Successful Liposomal Formulation of Cisplatin," Expert Opin Investig Drugs. 18(8):1197-218 (2009), author manuscript version, 22 pages.

Bozzuto G and Molinari A, "Liposomes as Nanomedical Devices," Int J Nanomedicine. 10:975-99 (2015).

Brus C and Saif M, "Second Line Therapy for Advanced Pancreatic Adenocarcinoma: Where Are We and Where Are We Going?," J Pancreas (Online) 11(4):321-3 (2010).

Bulbake U, et al., "Liposomal Formulations in Clinical Use: An Updated Review," Pharmaceutics. 9(2):12 doi: 10.3390/pharmaceutics9020012 (2017), 33 pages.

Burris H and Rocha-Lima C, "New Therapeutic Directions for Advanced Pancreatic Cancer: Targeting the Epidermal Growth Factor and Vascular Endothelial Growth Factor Pathways," Oncologist. 13(3):289-98 (2008).

Butowski N, et al., "A Phase 1 Study of CED of Nanoliposomal-Irinotecan Using Real-Time Imaging With Gadolinium in Patients With Recurrent High Grade Glioma." Poster presented at the American Society of Clinical Oncology (ASCO) Annual Conference, Chicago, IL, May 29-Jun. 2, 2015, 4 pages.

Butowski N, et al., Abstract TPS2081. "A Phase I Study of Convection-Enhanced Delivery of Nanoliposomal Irinotecan Using Real-Time Imaging in Patients With Recurrent High Grade Glioma," J Clin Oncol. 33(15_Suppl):2081 DOI: 10.1200/jco.2015.33.15_suppl.tps2081 (2015), 2 printed pages.

Caelyx (doxorubicin), MedBroadcast, accessed Jan. 26, 2021 from medbroadcast.com/drug/getdrug/caelyx, 11 printed pages.

Cao S, et al., "Synergistic Antitumor Activity of Capecitabine in Combination with Irinotecan," Clin Colorectal Cancer. 4(5):336-43 (2005).

Cao Y, et al., "A Gold Nanoparticle Bouquet Held on Plasma Membrane: An Ultrasensitive Dark-Field Imaging Approach for Cancer Cell Analysis," Nanotheranostics. 4(4):201-209 (2020).

Carter K, et al., "Sphingomyelin Liposomes Containing Porphyrin-Phospholipid for Irinotecan Chemophototherapy," Theranostics. 6(13)2329-36 (2016).

Cascinu S, et al., "Pancreatic Cancer: ESMO Clinical Practice Guidelines for Diagnosis, Treatment and Follow-up," Ann Oncol. 21 (Suppl 5):v55-v58 (2010).

Cerenzia W, et al., Abstract e16233. "Identifying Continuing Educational Needs Among Oncologists in Managing Patients With Pancreatic Cancer," J Clin Oncol. 36(15_Suppl):e16233 DOI: 10.1200/JCO.2018.36.15_suppl.e16233 (2018), 2 printed pages.

Pal A, et al., "Preclinical Safety, Pharmacokinetics and Antitumor Efficacy Profile of Liposome-Entrapped SN-38 Formulation," Anticancer Res. 25(1A):331-41 (2005).

(56) References Cited

OTHER PUBLICATIONS

Pan-Canadian Oncology Drug Review (pCODR) Expert Review Committee (pERC) Final Recommendation for Irinotecan Liposome (Onivyde) for Metastaic Pancreatic Cancer, pERC Meeting: Oct. 19, 2017, pERC Reconsideration Meeting: Dec. 17, 2017, pp. 1-14.

Papadatos-Pastos D, et al., "FOLFIRINOX—A New Paradigm in the Treatment of Pancreatic Cancer," Expert Rev Anticancer Ther. 14(10):1115-25 (2014).

Papahadjopoulos D, et al., "Sterically Stabilized Liposomes: Improvements in Pharmacokinetics and Antitumor Therapeutic Efficacy," Proc Natl Acad Sci USA. 88(24):11460-4 (1991).

Papi M, et al., "Clinically Approved PEGylated Nanoparticles Are Covered by a Protein Corona That Boosts the Uptake by Cancer Cells," Nanoscale. 9(29):10327-34 (2017).

Parekh H, et al., "A Phase II, Open-Label Pilot Study Evaluating the Safety and Activity of Nal-IRI in Combination With 5-FU and Oxaliplatin in Preoperative Treatment of Pancreatic Adenocarcinoma (NEO-Nal-IRI Study)." Poster presented at the American Society of Clinical Oncology Gastrointestinal Cancers Symposium (ASCO GI), San Francisco, CA, Jan. 23-25, 2020, 3 pages.

Parekh H, et al., Abstract TPS790. "A Phase II, Open-Label Pilot Study Evaluating the Safety and Activity of Nal-IRI in Combination With 5-FU and Oxaliplatin in Preoperative Treatment of Pancreatic Adenocarcinoma (NEO-Nal-IRI Study) (NCT03483038)," J Clin Oncol. 38(4_Suppl):TPS790 (2020), 2 printed pages.

Park J, English abstract and Table 1 and Figure 1 of "Second Line Chemotherapy for Pancreatic Cancer," Korean J Gastroenterol. 57(4):207-12 (2011).

Park J, et al., "Anti-HER2 Immunoliposomes for Targeted Therapy of Human Tumors," Cancer Lett. 118(2):153-60 (1997).

Park J, et al., "Development of Anti-p185HER2 Immunoliposomes for Cancer Therapy," Proc Natl Acad Sci U S A. 92 (5):1327-31 (1995).

Park J, et al., "Immunoliposomes for Cancer Treatment," Adv Pharmacol. 40:399-435 (1997).

Park J, et al., "Sterically Stabilized Immunoliposomes: Formulations for Delivery of Drugs and Genes to Tumor Cells in Vivo," In Targeting of Drugs 6: Strategies for Stealth Therapeutic Systems, Gregoriadis G, et al., eds., Plenum Press, New York, pp. 41-47 (1998).

Park J, et al., "Tumor Targeting Using Anti-HER2 Immunoliposomes," J Control Release. 74(1-3):95-113 (2001).

Park J, et al., "Anti-HER2 Immunoliposomes for Targeted Drug Delivery," Med Chem Res. 8(7/8):383-91 (1998).

Patankar N, et al., "Topophore C: A Liposomal Nanoparticle Formulation of Topotecan for Treatment of Ovarian Dancer," Invest New Drugs. 31(1):46-58 (2013). Epub 2012.

Patel M, et al., "Effects of Oxaliplatin and CPT-11 on Cytotoxicity and Nucleic Acid Incorporation of the Fluoropyrimidines," J Cancer Res Clin Oncol. 130(8):453-9 (2004).

Pavai S and Yap S, "The Clinical Significance of Elevated Levels of Serum CA19-9," Med J Malaysia. 58(5):667-72 (2003).

PCT/US2005/015349: PCT International Search Report and Written Opinion dated Aug. 18, 2005, 14 pages.

PCT/US2016/057247: PCT International Preliminary Report on Patentability dated Apr. 17, 2018, 8 pages.

PCT/US2016/057247: PCT International Search Report dated Dec. 23, 2016, 4 pages.

Pellino A, et al., "Observational Retrospective Evaluation of Treatment With Liposomal Irinotecan Plus Fluorouracil/Leucovorin for Metastatic Pancreatic Cancer Patients: An Italian Large Real-World Analysis." Poster presented at the American Society of Clinical Oncology Gastrointestinal Cancers Symposium (ASCO GI), San Francisco, CA, Jan. 23-25, 2020, 5 pages.

Pellino A, et al., Abstract 660. "Observational Retrospective Evaluation of Treatment With Liposomal Irinotecan Plus Fluorouracil/Leucovorin for Metastatic Pancreatic Cancer Patients: An Italian Large Real-World Analysis," J Clin Oncol. 38(4_Suppl):660 DOI: 10.1200/JCO.2020.38.4_suppl.660 (2020), 2 printed pages.

Pelzer U, et al., "A Randomized Trial in Patients With Gemcitabine Refractory Pancreatic Cancer. Final Results of the CONKO-003 Study." Presentation presented at the American Society of Clinical Oncology (ASCO) Annual Meeting, Chicago, Illinois, May 30-Jun. 3, 2008, 18 pages.

Pelzer U, et al., "Best Supportive Care (BSC) Versus Oxaliplatin, Folinic Acid and 5-Fluorouracil (OFF) Plus BSC in Patients for Second-Line Advanced Pancreatic Cancer: A Phase III-Study from the German CONKO-Study Group," Eur J Cancer. 47(11):1676-81 (2011).

Pelzer U, et al., Abstract P865. "Quality-Adjusted Time Without Symptoms or Toxicity (Q-TWiST) of Nanoliposomal Irinotecan (nal-IRI;MM-398) Plus 5-Fluorouracil and Leucovorin (5-FU/LV) vs 5-FU/LV alone in patients (pts) With Metastatic Pancreatic Adenocarcinoma (mPAC) Previously Treated With Gemcitabine-Based Therapy," Oncol Res Treat. 39(Suppl 3):260 (2016).

Petrelli F, et al., "What Else in Gemcitabine-Pretreated Advanced Pancreatic Cancer? An Update of Second Line Therapies," Rev Recent Clin Trials. 5(1):43-56 (2010).

Philip P, et al., "Consensus Report of the National Cancer Institute Clinical Trials Planning Meeting on Pancreas Cancer Treatment," J Clin Oncol. 27(33):5660-9 (2009).

Picozzi V, et al., "An Assessment of the Total Cost of Pancreatic Cancer Using Real-World Evidence." Poster presented at the American Society of Clinical Oncology Gastrointestinal Cancers Symposium (ASCO GI), San Francisco, CA, Jan. 23-25, 2020, 6 pages.

Picozzi V, et al., Abstract 773. "An Assessment of the Total Cost of Pancreatic Cancer Using Real-World Evidence," J Clin Oncol 38(4_Suppl):773 DOI: 10.1200/JCO.2020.38.4_suppl.773 (2020), 2 printed pages.

Pillai G, "Nanomedicines for Cancer Therapy: An Update of FDA Approved and Those under Various Stages of Development," SOJ Pharm Pharm Sci. 1(2):13(2014), 13 pages.

Pino M, et al., "Capecitabine and Celecoxib as Second-Line Treatment of Advanced Pancreatic and Biliary Tract Cancers," Oncology. 76(4):254-61 (2009).

Poplin E, et al., "Phase III, Randomized Study of Gemcitabine and Oxaliplatin Versus Gemcitabine (Fixed-Dose Rate Infusion) Compared With Gemcitabine (30-Minute Infusion) in Patients With Pancreatic Carcinoma E6201: A Trial of the Eastern Cooperative Oncology Group," J Clin Oncol. 27(23):3778-85 (2009).

Poplin E, et al., "Phase III Southwest Oncology Group 9415/Intergroup 0153 Randomized Trial of Fluorouracil, Leucovorin, and Levamisole Versus Fluorouracil Continuous Infusion and Levamisole for Adjuvant Treatment of Stage II and High-Risk Stage II Colon Cancer," J Clin Oncol. 23(9):1819-25 (2005).

Rahib L, et al., "Evaluation of Pancreatic Cancer Clinical Trials and Benchmarks for Clinically Meaningful Future Trials: A Systematic Review," JAMA Oncol. 2(9):1209-16 (2016).

Ramnani K, et al., Abstract CT13. "Impact of Treatment Sequence on Overall Survival in Metastatic Pancreatic Dancer Patients Treated with Liposomal Irinotecan in the Real-World Setting," Hematology Oncology Pharmacy Association (HOPA) Annual Conference, Mar. 11-14, 2020, available at eventscribe.com/2020/posters/HOPAahead/SplitViewer.asp?PID=Njg0NzMyODlyNzY, (2020), 2 pages.

Ramsay E, et al., "Irinophore C: A Liposome Formulation of Irinotecan With Substantially Improved Therapeutic Efficacy Against a Panel of Human Xenograft Tumors," Clin Cancer Res. 14(4):1208-17 (2008).

Rea D, et al., "A Phase I/II and Pharmacokinetic Study of Irinotecan in Combination with Capecitabine as First-Line Therapy for Advanced Colorectal Cancer," Ann Oncol. 16(7):1123-32 (2005).

Reni M, et al., "Raltitrexed-Eloxatin Salvage Chemotherapy in Gemcitabine-Resistant Metastatic Pancreatic Cancer," Br J Cancer. 94(6):785-91 (2006).

Renouf D, et al., "A Phase II Study of Erlotinib in Gemcitabine Refractory Advanced Pancreatic Cancer," Eur J Cancer. 50(11):1909-15 (2014).

Reynolds J, et al., "HER2-Targeted Liposomal Doxorubicin Displays Enhanced Anti-Tumorigenic Effects Without Associated Cardiotoxicity," Toxicol Appl Pharmacol. 262(1):1-10 (2012).

Rocha Lima C, et al., "Irinotecan Plus Gemcitabine Results in No Survival Advantage Compared With Gemcitabine Monotherapy in

(56) References Cited

OTHER PUBLICATIONS

Patients With Locally Advanced or Metastatic Pancreatic Cancer Despite Increased Tumor Response Rate," J Clin Oncol. 22(18):3776-83 (2004).
Rosenecker J, et al., "Increased Liposome Extravasation in Selected Tissues: Effect of Substance P," Proc Natl Acad Sci USA. 93(14):7236-41 (1996).
Roth A, et al., "Anti-CD166 Single Chain Antibody-Mediated Intracellular Delivery of Liposomal Drugs to Prostate Cancer Cells," Mol Cancer Ther. 6(10):2737-46 (2007).
Rothenberg M, et al., "Alternative Dosing Schedules for Irinotecan," Oncology. 12(8 Suppl 6):68-71 (1998). Available at cancernetwork.com/view/alternative-dosing-schedules-irinotecan, 16 printed pages.
Rubesova E, et al., "Gd-Labeled Liposomes for Monitoring Liposome-Encapsulated Chemotherapy: Quantification of Regional Uptake in Tumor and Effect on Drug Delivery," Acad Radiol. 9(Suppl 2):S525-7 (2002).
Saif M, et al., "Pharmacokinetically Guided Dose Adjustment of 5-Fluorouracil: A Rational Approach to Improving Therapeutic Outcomes," J Natl Cancer Inst. 101(22):1543-52 (2009).
Saltz L, "Clincial Use of Irinotecan: Current Status and Future Considerations," Oncologist. 2(6):402-9 (1997).
Sancho A, et al., Abstract 15625. "Oxaliplatin and Capecitabine After Gemcitabine Failure in Patients With Advanced Pancreatic, Biliary, and Gallbladder Adenocarcinoma (APBC)," J Clin Oncol. 26(15_suppl): 15625 (2008), 5 printed pages.
Satoh T, et al., "Pharmacokinetic Assessment of Irinotecan, SN-38, and SN-38-Glucuronide: A Substudy of the FIRIS Study," Anticancer Res. 33(9):3845-53 (2013).
Scheithauer W, et al., "Fluorouracil Plus Racemic Leucovorin Versus Fluorouracil Combined With the Pure I-somer of Leucovorin for the Treatment of Advanced Colorectal Cancer: A Randomized Phase III Study," J Clin Oncol. 15(3):908-14 (1997).
Bouché O, et al. "Randomized Multicenter Phase II Trial of a Biweekly Regimen of Fluorouracil and Leucovorin (LV5FU2), LV5FU2 Plus Cisplatin, or LV5FU2 Plus Irinotecan in Patients With Previously Untreated Metastatic Gastric Cancer: A Fédération Francophone De Cancérologie Digestive Group Study—FFCD 9803," J Clin Oncol. 22 (21):4319-28 (2004).
Chiang, N-J, et al., "Development of Nanoliposomal Irinotecan (nal-IRI, MM-398, PEP02) in the Management of Metastatic Pancreatic Cancer," Expert Opin Pharmacother. 17(10):1413-20 (2016).
EP3337478: EPO Notice of Sandoz AG Opposition dated May 6, 2021, 5 pages.
EP3337478: Sandoz AG Opposition dated May 6, 2021, 22 pages.
EP3337478: Sandoz AG Opposition dated May 6, 2021, D1 (History of Changes for Study NCT02551991, retrieved from ClinicalTrials.gov archive on May 3, 2021, 4 pages).
EP3337478: Sandoz AG Opposition dated May 6, 2021, D2 (Abstract 0-0003. Von Hoff D, et al., "NAPOLI1 Randomized Phase 3 Study of MM-398 (nal-IRI), With or Without 5-Fluorouracil and Leucovorin, Versus 5-Fluorouracil and Leucovorin, in Metastatic Pancreatic Cancer Progressed on or Following Gemcitabine-Based Therapy." Ann Oncol. 25(Suppl 2):ii105 (2014)).
EP3337478: Sandoz AG Opposition dated May 6, 2021, D3 (Marsh R, et al., "Pancreatic Cancer and Folfirinox A New Era and New Questions," Cancer Med. 4(6):853-63 (2015)).
EP3337478: Sandoz AG Opposition dated May 6, 2021, D4 (Onivyde [MM-398] package insert, revision Oct. 22, 2015, 18 pages).
EP3337478: Sandoz AG Opposition dated May 6, 2021, D5 (Carnevale J and Ko A, "MM-398 (Nanoliposomal Irinotecan): Emergence of a Novel Therapy for the Treatment of Advanced Pancreatic Cancer," Future Oncol. 12(4):453-64 (2016). Epub 2015).
EP3337478: Sandoz AG Opposition dated May 6, 2021, D6 (Dean A, et al., Abstract TPS482. "A Randomized, Open-Label Phase II Study of Nanoliposomal Irinotecan (nal-IRI)-Containing Regimens Versus nab-Paclitaxel Plus Gemcitabine in Patients With Previously Untreated Metastatic Pancreatic Adenocarcinoma (mPAC)," J Clin Oncol. (4_Suppl):tps482 (2016), DOI: 10.1200/jco.2016.34.4_suppl.tps482, 5 printed pages).
EP3337478: Sandoz AG Opposition dated May 6, 2021, D7 (Zhang H, "Onivyde for the Therapy of Multiple Solid Fumors," Onco Targets Ther. 9:3001-3007 (2016)).
EP3337478: Sandoz AG Opposition dated May 6, 2021, D8 (Gaddy D, et al., "Abstract 4830: Preclinical Anti-tumor Activity of Nanoliposomal Irinotecan (Nal-IRI, MM-398) + 5-FU + Oxaliplatin in Pancreatic Cancer." In: Proceedings of the 107th Annual Meeting of the American Association for Cancer Research; Apr. 16-20, 2016; New Orleans, LA. Cancer Res. 76(14 Suppl):Abstract nr 4830 (2016), 4 printed pages).
EP3337478: Sandoz AG Opposition dated May 6, 2021, D9 (Priyambada P, et al., "Nanotechnology-Based Combinational Drug Delivery: An Emerging Approach for Cancer Therapy," Drug Discov Today. 17(17-18):1044-52 (2012)).
EP3337478: EPO Notice of Generics [UK] Limited Opposition dated May 12, 2021, 5 pages.
EP3337478: Generics [UK] Limited Opposition dated May 12, 2021, 9 pages.
EP3337478: Generics [UK] Limited Opposition dated May 12, 2021, D10 (Conroy T, et al., "FOLFIRINOX versus Gemcitabine for Metastatic Pancreatic Cancer," N Engl J Med. 364(19):1817-25 (2011)).
EP3337478: Generics [UK] Limited Opposition dated May 12, 2021, D11 (Gourgou-Bourgade S, et al., "Impact of FOLFIRINOX Compared With Gemcitabine on Quality of Life With Metastatic Pancreatic Cancer: Results From the Prodige 4/ACCORD 11 Randomized Trial," J Clin Oncol. 31(1):23-9 (2013). Epub 2012.).
EP3337478: Generics [UK] Limited Opposition dated May 12, 2021, D12 (Ko A, et al., "A Multinational Phase 2 Study of Nanoliposomal Irinotecan Sucrosofate (PEP02, MM-398) for Patients with Gemcitabine-Refractory Metastatic Pancreatic Cancer," Br J Cancer. 109(4):920-5 (2013)).
EP3337478: Generics [UK] Limited Opposition dated May 12, 2021, D13 (Hann B, et al., Abstract 5648. "Lipidic Nanoparticle CPT-11 in a Bioluminescent Orthotopic Pancreas Cancer Model," Cancer Res. 67(9 Suppl):5648 (2007), 4 printed pages).
EP3337478: Generics [UK] Limited Opposition dated May 12, 2021, D14 (Chang T, et al., "Phase I Study of Nanoliposomal Irinotecan (PEP02) in Advanced Solid Tumor Patients," Cancer Chemother Pharmacol. 75(3):579-86 (2015).
EP3337478: Generics [UK] Limited Opposition dated May 12, 2021, D15 (Chen L, et al., "Phase I Study of Liposome Irinotecan (PEP02) in Combination with Weekly Infusion of 5-FU/LV in Advanced Solid Tumors," J Clin Oncol., 2010 ASCO Annual Meeting Abstracts, 28(15_suppl) (May 20 Suppl):e13024 (2010), 4 printed pages).
EP3337478: Generics [UK] Limited Opposition dated May 12, 2021, D16 (Pubmed abstract retrieved on May 6, 2021 for Mahaseth H, et al., "Modified FOLFIRINOX Regimen With Improved Safety and Maintained Efficacy in Pancreatic Adenocarcinoma," Pancreas. 42(8):1311-5 (2013), 2 printed pages).
EP3337478: Generics [UK] Limited Opposition dated May 12, 2021, D17 (Drummond D, et al., "Development of a Highly Active Nanoliposomal Irinotecan Using a Novel Intraliposomal Stabilization Strategy," Cancer Res. 66 (6):3271-77 (2006)).
Koizumi W, at al., "Phase I/II Study of Bi-weekly Irinotecan plus Cisplatin in the Treatment of Advanced Gastric Cancer," Anticancer Res. 25(2B):1257-62 (2005).
Morise M, et al., "Low-dose Irinotecan as a Second-line Chemotherapy for Recurrent Small Cell Lung Cancer," Jpn J Clin Oncol. 44(9):846-51 (2014).
Wainberg Z, et al., "First-line Liposomal Irinotecan With Oxaliplatin, 5-Fluorouracil and Leucovorin (NALIRIFOX) in Pancreatic Ductal Adenocarcinoma: A Phase I/II Study," Eur J Cancer. 151:14-24 (2021).
Walker S, et al., "Simulation of Y-Site Compatibility of Irinotecan and Leucovorin at Room Temperature in 5% Dextrose in Water in 3 Different Containers," Can J Hosp Pharm. 58(4):212-22 (2005).
Wang W, et al., "Weekly 24-Hour Infusion of High-dose 5-Fluorouracil and Leucovorin in Patients with Advanced Colorectal Cancer: Taiwan Experience," Jpn J Clin Oncol. 28(1):16-19 (1998).
Wang-Gillam A, et al., "Characteristics of Long-Term Survivors in a Randomized Phase 3 Trial (NAPOLI-1) of Patients With Meta-

(56) References Cited

OTHER PUBLICATIONS static Pancreatic Ductal Adenocarcinoma (mDPAC) Treated With Liposomal Irinotecan (nal-IRI; MM-398) + 5-FU/LV." Poster presented at the American Society of Clinical Oncology Gastrointestinal Cancers Symposium (ASCO GI), San Francisco, CA, Jan. 19-21, 2017, 9 pages.

Wang-Gillam A, et al., "Dose Modifications of Liposomal Irinotecan (nal-IRI) + 5-Fluorouracil/Leucovorin (5-FU/LV) in NAPOLI-1: Impact on Efficacy." Poster presented at the American Society of Clinical Oncology Gastrointestinal Dancers Symposium (ASCO GI), San Francisco, CA, Jan. 18-20, 2018, 8 pages.

Wang-Gillam A, et al., "Nomogram for Predicting Overall Survival in Patients Treated With Liposomal Irinotecan (nal-IRI) ± 5-Fluorouracil/Leucovorin (5-FU/LV) in Metastatic Pancreatic Ductal Adenocarcinoma (mPDAC) Previously Treated With Gemcitabine-Based Therapy in NAPOLI-1." Poster presented at the American Society of Clinical Oncology Gastrointestinal Cancers Symposium (ASCO GI), San Francisco, CA, Jan. 18-20, 2018, 9 pages.

Wang-Gillam A, et al., "Updated Overall Survival Analysis of NAPOLI-1: Phase 3 Study of Nanoliposomal Irinotecan (nal-IRI, MM-398), With or Without 5-Fluorouracil and Leucovorin (5-FU/LV), Versus 5-FU/LV in Metastatic Pancreatic Cancer (mPAC) Previously Treated With Gemcitabine-Based Therapy." Poster presented at the American Society of Clinical Oncology Gastrointestinal Cancers Symposium (ASCO GI), San Francisco, CA, Jan. 21-23, 2016, 11 pages.

Wang-Gillam A, et al., "Updated Overall Survival Analysis of NAPOLI-1: Phase 3 Study of Nanoliposomal Irinotecan (nal-IRI, MM-398), With or Without 5-Fluorouracil and Leucovorin, vs 5-Fluorouracil and Leucovorin in Metastatic Pancreatic Ductal Adenocarcinoma Previously Treated With Gemcitabine." Poster presented at the American Society of Clinical Oncology (ASCO) Annual Meeting, Chicago, Illinois, Jun. 3-7, 2016, 8 pages.

Wang-Gillam A, et al., Abstract 293. "Characteristics of Long-Term Survivors in a Randomized Phase III Trial (NAPOLI-1) of Patients With Metastatic Pancreatic Ductal Adenocarcinoma (mPDAC) Treated With Liposomal Irinotecan (nal-IRI; MM-398) + 5-FU/LV," J Clin Oncol. 35(4_Suppl):293 DOI: 10.1200/JCO.2017.35.4_suppl.293 (2017), 2 printed pages.

Wang-Gillam A, et al., Abstract 388. "Dose Modifications of Liposomal Irinotecan (nal-IRI) + 5-Fluorouracil/Leucovorin (5-FU/LV) in NAPOLI-1: Impacton Efficacy," J Clin Oncol. 36(4_Suppl):388 DOI: 10.1200/JCO.2018.36.4_suppl.388 (2018), 2 printed pages.

Wang-Gillam A, et al., Abstract 4126. "Updated Overall Survival (OS) Analysis of NAPOLI-1: Phase III Study of Nanoliposomal Irinotecan (nal-IRI, MM-398), With or Without 5-Fluorouracil and Leucovorin (5-FU/LV), vs 5-FU/LV in Metastatic Pancreatic Cancer (mPAC) Previously Treated With Gemcitabine (Gem)-Based Therapy," J Clin Oncol. 34 (15_Suppl):4126 DOI: 10.1200/JCO.2016.34.15_suppl.4126 (2016), 5 printed pages.

Wang-Gillam A, et al., Abstract 417. "Updated Overall Survival Analysis of NAPOLI-1: Phase III Study of Nanoliposomal Irinotecan (nal-IRI, MM-398), With or Without 5-Fluorouracil and Leucovorin (5-FU/LV), Versus 5-FU/LV in Metastatic Pancreatic Cancer (mPAC) Previously Rreated With Gemcitabine-Based Therapy," J Clin Oncol. 34 (4_Suppl):417 DOI: 10.1200/jco.2016.34(4_suppl):417 (2016), 2 printed pages.

Wang-Gillam A, et al., Abstract 459. "Nomogram for Predicting Overall Survival (OS) in Patients (pts) Treated With Liposomal Irinotecan (nal-IRI) ± 5-Fluorouracil/Leucovorin (5-FU/LV) in Metastatic Pancreatic Ductal Adenocarcinoma (mPDAC) Previously Treated With Gemcitabine-Based Therapy in NAPOLI-1," J Clin Oncol. 36(4 Suppl):459 DOI: 10.1200/JCO.2018.36.4_suppl.459 (2018), 2 printed pages.

Wang-Gillam A, et al., Abstract e15795. "The Prognostic Value of Baseline Neutrophil-to-Lymphocyte Ratio (NLR) and Platelet-to-Lymphocyte ratio (PLR) for Predicting Clinical Outcome in Patients with Metastatic Pancreatic Ductal Adenocarcinoma (mPDAC) Treated With Liposomal Irinotecan (nalIRI; MM398) + 5-Fluorouracil and Leucovorin (5-FU/LV) vs 5-FU/LV," J Clin Oncol. 35(15_Suppl):e15795 DOI: 10.1200/JCO.2017.35.15_suppl.e15795 (2017), 3 printed pages.

Wang-Gillam A, et al., Abstract e16204. "A Survival Prediction Nomogram for Liposomal Irinotecan (nal-IRI)+5-Fluorouracil/Leucovorin (5-FU/LV) in Patients (pts) With Metastatic Pancreatic Ductal Adenocarcinoma (mPDAC) Previously Treated With Gemcitabine-Based Therapy," J Clin Oncol. 36(15_Suppl):e16204 DOI: 10.1200/JCO.2018.36.15_suppl.e16204 (2018), 2 printed pages.

Wang-Gillam A, et al., letter to editor, "Nanoliposomal Irinotecan in the Clinical Practice Guideline for Metastatic Pancreatic Cancer: Applicability to Clinical Situations," J Clin Oncol. 35(6):689-90 (2017). Epub 2016.

Weng K, et al., "Convection-Enhanced Delivery of Targeted Quantum Dot-Immunoliposome Hybrid Nanoparticles to Intracranial Brain Tumor Models," Nanomedicine (Lond). 8(12):1913-25. 2013.

Weng K, et al., "Targeted Tumor Cell Internalization and Imaging of Multifunctional Quantum Dot-Conjugated Immunoliposomes in Vitro and in Vivo," Nano Lett. 8(9):2851-7 (2008).

Willett C, et al., "Direct Evidence That the VEGF-Specific Antibody Bevacizumab Has Antivascular Effects in Human Rectal Cancer," Nat Med 10(2):145-7 (2004), author manuscript version, 7 pages.

Wulaningsih W, et al., "Irinotecan Chemotherapy Combined With Fluoropyrimidines Versus Irinotecan Alone for Overall Survival and Progression-Free Survival in Patients With Advanced and/or Metastatic Colorectal Cancer," Cochrane Database Syst Rev. 2:CD008593 doi: 10.1002/14651858.CD008593.pub3. (2016), 36 pages.

Xeloda (capecitabine) package insert, Roche, revised Nov. 2000, 19 pages.

Xiong H, et al., "Phase 2 Trial of Oxaliplatin Plus Capecitabine (XELOX) as Second-line Therapy for Patients With Advanced Pancreatic Cancer," Cancer 113(8):2046-52 (2008).

Yamashita Y, et al., "Convection-Enhanced Delivery of a Topoisomerase I Inhibitor (Nanoliposomal Topotecan) and a Topoisomerase II Inhibitor (Pegylated Liposomal Doxorubicin) in Intracranial Brain Tumor Xenografts," Neuro Oncol. 9(1):20-8 (2007). Epub 2006.

Yamashita Y, et al., "Convection-Enhanced Delivery of Liposomal Doxorubicin in Intracranial Brain Tumor Xenografts," Targ Oncol. 1:79-85 (2006).

Yang W, et al. "Development of a Method to Quantify Total and Free Irinotecan and 7-ethyl-10-hydroxycamptothecin (SN-38) for Pharmacokinetic and Bio-Distribution Studies After Administration of Irinotecan Liposomal Formulation," Asian J Pharm Sci. 14(6):687-97 (2019). Epub 2018.

Yang W, et al., "The Influence of Trapping Agents on the Antitumor Efficacy of Irinotecan Liposomes: Head-to-Head Comparison of Ammonium Sulfate, Sulfobutylether--Cyclodextrin and Sucrose Octasulfate," Biomater Sci., 7(1):419-28 (2019).

Yang, et al., "Oxaliplatin Long-Circulating Liposomes Improved Therapeutic Index of Colorectal Carcinoma," BMC Biotechnology. 11:21 doi: 10.1186/1472-6750-11-21 (2011), 8 pages.

Yoo C, et al., "Multicenter Randomized Phase II Trial of 5-Fluorouracil/Leucovorin (5-FU/LV) With or Without Liposomal Irinotecan (nal-IRI) in Metastatic Biliary Tract Cancer (BTC) as Second-Line Therapy After Progression on Gemcitabine Plus Cisplatin (GemCis): NIFTY Trial." Poster presented at the European Society for Medical Oncology (ESMO) 2019 Congress, Barcelona, Spain, Sep. 27-Oct. 1, 2019, 6 pages.

Yoo C, et al., Abstract 829TiP. "Multicenter Randomized Phase II Trial of 5-Fluorouracil/Leucovorin (5-FU/LV) With or Without Liposomal Irinotecan (nal-IRI) in Metastatic Biliary Tract Cancer (BTC) as Second-Line Therapy After Progression on Gemcitabine Plus Cisplatin (GemCis): NIFTY Trial," Ann Oncol. 30(Supp_5):v318 /doi.org/10.1093/annonc/mdz247.155 (2019).

Younis I, et al., "Enterohepatic Recirculation Model of Irinotecan (CPT-11) and Metabolite Pharmacokinetics in Patients With Glioma," Cancer Chemother Pharmacol 63(3):517-24 (2009), author manuscript version, 16 pages.

Yu K, et al., "Hospitalizations and Real-World Clinical Outcomes of Liposomal Irinotecan in a NAPOLI1-Based Regimen Among Patients With Metastatic Pancreatic Ductal Adenocarcinoma (mPDAC): A

(56) References Cited

OTHER PUBLICATIONS

Multi-Center Chart Review," Poster presented at the Academy of Managed Care Pharmacy, Nexus (AMCP, Nexus): virtual meeting, week of Oct. 19, 2020, 9 pages.
Yu K, et al., Abstract C3. "Hospitalizations and Real-World Clinical Outcomes of Liposomal Irinotecan in a NAPOLI1-Based Regimen Among Patients With Metastatic Pancreatic Ductal Adenocarcinoma (mPDAC): A Multi-Center Chart Review," J Manag Care Spec Pharm. 26(10-a):S19 (2020).
Yu K, et al., "A US Multicenter Chart Review Study of Patients With Metastatic Pancreatic Ductal Adenocarcinoma Receiving Liposomal Irinotecan after Gemcitabine-Based Therapy." Poster presented at the International Conference an Pharmacoepidemiology & Therapeutic Risk Management (ICPE) All Access, Sep. 16-17, 2020, 8 pages.
Yu K, et al., "Real-World Treatment Patterns and Effectiveness of Liposomal Irinotecan in a NAPOLI1-Based Regimen Among Patients With Metastatic Pancreatic Ductal Adenocarcinoma (mPDAC): A Multi-Academic Center Chart Review." Poster presented at the European Society for Medical Oncology (ESMO) Virtual Congress 2020, Sep. 19-21, 2020, 9 pages.
Yu K, et al., Abstract 1555P. "Real-World Treatment Patterns and Effectiveness of Liposomal Irinotecan in a NAPOL11-Based Regimen Among Patients With Metastatic Pancreatic Ductal Adenocarcinoma (mPDAC): A MultiAcademic Center Chart Review," Ann Oncol. 31(Suppl_4):S950-S951 doi.org/10.1016/j.annonc.2020.08.2038 (2020), 2 printed pages.
Yu K, et al., Abstract e16733. "A Multicenter Chart Review Study of Patients with Metastatic Pancreatic Ductal Adenocarcinoma Receiving Liposomal Irinotecan after Gemcitabine-Based Therapy," J Clin Oncol. 38(15 Suppl):e16733 DOI: 10.1200/JCO.2020.38.15_suppl.e16733 (2020), 4 printed pages.
Yu K, et al., Abstract PO-3727. "A US Multicenter Chart Review Study of Patients With Metastatic Pancreatic Ductal Adenocarcinoma Receiving Liposomal Irinotecan after Gemcitabine-Based Therapy," International Conference on Pharmacoepidemiology & Therapeutic Risk Management (ICPE), Sep. 14, 2020, available at eventscribe.com/2020/ICPEAllAccess/PosterTitles.asp?pfp=PosterTitles, 1 page.
Yu X, et al., "Targeted Drug Delivery in Pancreatic Cancer," Biochim Biophys Acta. 21805(1):97-104 (2010). Epub 2009, author manuscript version, 16 pages.
Zamboni W, et al., "Phase I and Pharmacokinetic Study of Pegylated Liposomal CKD-602 in Patients with Advanced Malignancies," Clin Cancer Res. 15(4):1466-72 (2009) and correction found at Clin Cancer Res. 15(8):2949-50 (2009).
Zhang K, et al., "Comprehensive Optimization of a Single-Chain Variable Domain Antibody Fragment as a Targeting Ligand for a Cytotoxic Nanoparticle," MAbs. 7(1):42-52 (2015).
Dewhirst M, et al., "Microvascular Studies on the Origins of Perfusion-Limited Hypoxia," Br J Cancer Suppl. 27:S247-51 (1996).
Dieguez G, et al., "Real-World Rates of Hematologic Laboratory Abnormalities and Associated Cost Among Metastatic Pancreatic Cancer Therapeutic Regimens," Poster presented at the American Society of Clinical Oncology Gastrointestinal Cancers Symposium (ASCO GI), San Francisco, CA, Jan. 23-25, 2020, 6 pages.
Dieguez G, et al., Abstract 670. "Real-World Rates of Hematology Lab Abnormalities and Associated Cost Among Metastatic Pancreatic Cancer (mPC) Therapeutic Regimens," J Clin Oncol. 38(4_Suppl):670 DOI: 10.1200/JCO.2020.38.4_suppl.670 (2020), 2 printed pages.
Doris J, et al., Abstract CT12. "The Cost of Adverse Events for FDA-Approved/NCCN Category 1 Treatments for Medicare Fee-For-Service (FFS) Patients With Metastatic Pancreatic Cancer: Focus on Liposomal Irinotecan-Based Regimens," Hematology Oncology Pharmacy Association (HOPA) Annual Conference, Mar. 11-14, 2020, available at eventscribe.com/2020/posters/HOPAahead/SplitViewer.asp?PID=Njg0NzA2NjU1NjE, (2020), 2 pages.
Dos Santos N, et al., "Improved Retention of Idarubicin After Intravenous Injection Obtained for Cholesterol-Free iposomes," Biochim Biophys Acta 1561(2):188-201 (2002).

Drummond D, et al., "Clinical Development of Histone Deacetylase Inhibitors as Anticancer Agents," Annu Rev Pharmacol Toxicol 45:495-528 and C1-C2 (2005).
Drummond D, et al., "Development of a Highly Stable and Targetable Nanoliposomal Formulation of Topotecan," J Control Release. 141(1):13-21 (2010). Epub 2009.
Drummond D, et al., "Improved Pharmacokinetics and Efficacy of a Highly Stable Nanoliposomal Vinorelbine," J Pharmacol Exp Ther 328(1):321-30 (2009) Epub 2008.
Drummond D, et al., "Liposome Targeting to Tumors using Vitamin and Growth Factor Receptors," Vitam Horm. 50:285-332 (2000).
Drummond D, et al., Chapter 8, "Intraliposomal Trapping Agents for Improving In Vivo Liposomal Drug Formulation Stability," In Liposome Technology, Third Edition, vol. 2, Ed. G. Gregoriadis, pp. 149-168 (2006).
Drummond D, et al., Chapter 9, "Liposomal Drug Delivery Systems for Cancer Therapy," In Drug Discovery Systems n Cancer Therapy, Ed. D Brown, Humana Press, Totowa, NJ, pp. 191-213 (2004).
Duffour J, et al., "Efficacy of Prophylactic Anti-Diarrhoeal Treatment in Patients Receiving Campto for Advanced Colorectal Cancer," Anticancer Res. 22(6B): 3727-31 (2002).
Elinzano H, et al., "Nanoliposomal Irinotecan and Metronomic Temozolomide for Patients With Recurrent Glioblastoma BrUOG329, A Phase I Brown University Oncology Research Group Trial," Am J Clin Oncol. 44(2):49-52 (2021). Epub 2020 version, pp. 1-4.
Elinzano H, et al., Abstract e14548. "Nanoliposomal Irinotecan and Metronomic Temozolomide for Patients With Recurrent Glioblastoma: BrUOG329, A Phase IB/IIA Brown University Oncology Research Group (BrUOG) Trial," J Clin Oncol. 38(15_Suppl):e14548 DOI: 10.1200/JC0.2020.38.15_suppl.e14548 (2020), 2 printed pages.
Ettrich T, et al., "Liposomal Irinotecan (nal-IRI) Plus 5-Fluorouracil (5-FU) and Leucovorin (LV) or Gemcitabine Plus Cisplatin in Advanced Cholangiocarcinoma: The AIO-NIFE-Trial, an Open Label, Randomized, Multicenter Phase II Trial," Poster presented at the American Society of Clinical Oncology (ASCO) Annual Meeting, Chicago, Illinois, Jun. 1-5, 2018, 5 pages.
Ettrich T, et al., Abstract TPS4145. "Liposomal Irinotecan (nal-IRI) Plus 5-Fluorouracil (5-FU) and Leucovorin (LV) or Gemcitabine Plus Cisplatin in Advanced Cholangiocarcinoma: The AIO-NIFE-Trial, an Open Label, Randomized, Multicenter Phase II Trial," J Clin Oncol. 36(15_Suppl):TPS4145 DOI: 10.1200/JCO.2018.36.15_suppl.TPS4145 (2018), 2 printed pages.
Falcone A, et al., "Sequence Effect of Irinotecan and Fluorouracil Treatment on Pharmacokinetics and Toxicity in Chemotherapy—Naive Metastatic Colorectal Cancer Patients," J Clin Oncol. 19(15):3456-62 (2001).
Fannon M, et al., "Sucrose Octasulfate Regulates Fibroblast Growth Factor-2 Binding, Transport, and Activity Potential for Regulation of Tumor Growth," J Cell Physiol. 215(2):434-41 (2008), NIH public access author manuscript version, 19 pages.
Farncombe M, "Management of Bleeding in a Patient with Colorectal Cancer: A Case Study," Support Care Cancer. 1(3):159-160 (1993).
FDA, "Draft Guidance on Daunorubicin Citrate," Jul. 2014, 6 pages.
FDA, "Draft Guidance on Doxorubicin Hydrochloride," Recommended Feb. 2010, Revised Nov. 2013, Dec. 2014, 6 pages.
Figer A, et al., "A Comparison of Two Dose Regimens in Pancreatic Cancer," J Chemother. 12(5):442-5 (2000).
Fioravanti A, et al., "Metronomic 5-Fluorouracil, Oxaliplatin and Irinotecan in Colorectal Cancer," Eur J Pharmacol. 519(1-3): 8-14(2009).
Fleming G, et al., "Phase I and Pharmacokinetic Study of 24-Hour Infusion 5-Fluorouracil and Leucovorin in Patients With Organ Dysfunction," Ann Oncol. 14(7): 1142-7 (2003).
Freise C, et al., "Characterization of a Cyclosporine-Containing Liposome," Transplant Proc. 23(1 Pt 1):473-4 (1991).
Freise C, et al., "Increased Efficacy of Cyclosporin Liposomes in a Rat Orthotopic Liver Transplant Model," Surgical Forum. 43:395-7 (1992).
Freise C, et al., "The Increased Efficacy and Decreased Nephrotoxicity of a Cyclosporine Liposome," Transplantation. 57(6):928-932 (1994).

(56) References Cited

OTHER PUBLICATIONS

Gaber M, et al., "Thermosensitive Liposomes: Extravasation and Release of Contents in Tumor Microvascular Networks," Int J Radiat Oncol Biol Phys. 36(5):1177-87 (1996).
Gaber M, et al., "Thermosensitive Sterically Stabilized Liposomes: Formulation and in Vitro Studies on the Mechanism of Doxorubicin Release by Bovine Serum and Human Plasma," Pharm Res. 12(10):1407-16 (1995).
Gaddy D, et al., "A Systematic Literature Review to Identify and Compare Clinical Trials Evaluating Novel Therapeutic Agents in Post-Gemcitabine Advanced Pancreatic Cancer Patients." Poster presented at the International Society for Pharmacoeconomics and Outcomes Research (ISPOR) 18th Annual European Congress, Milan, Italy, Nov. 7-11, 2015, 6 pages.
Gaddy D, et al., "Preclinical Anti-tumor Activity of Nanoliposomal Irinotecan (Nal-IRI, MM-398) Supports Utilization as a Foundation of Front-Line Pancreatic Cancer Regimens." Poster presented at the American Society of Clinical Oncology Gastrointestinal Cancers Symposium (ASCO GI), San Francisco, CA, Jan. 19-21, 2017, 5 pages.
Gaddy D, et al., Abstract 336. "Preclinical Antitumor Activity of Nanoliposomal Irinotecan (Nal-IRI, MM-398) and Utilization as a Foundation of Front-Line Pancreatic Cancer Regimens," J Clin Oncol. 35(4_Suppl):336 DOI: 10.1200/JCO.2017.35.4_suppl.336 (2017), 2 printed pages.
Gaddy D, et al., Abstract PCN29. "A Systematic Literature Review to Identify and Compare Clinical Trials Evaluating Novel Therapeutic Agents in Post-Gemcitabine Advanced Pancreatic Cancer," Value in Health. 18(7):A434 (2015).
Garcia-Alfonso P, et al., "Capecitabine in Combination with Irinotecan (XELIRI), Administered As a 2-Weekly Schedule, As First-Line Chemotherapy For Patients With Metastatic Colorectal Cancer: A Phase II Study of the Spanish GOTI Group," Br J Cancer. 101 (7):1039-43 (2009).
Garcia-Carbonero R and Supko J, "Current Perspectives on the Clinical Experience, Pharmacology, and Continued Development of the Camptothecins," Clin Cancer Res 8(3):641-61 (2002).
Garufi C, et al., "A Phase II Study of Irinotecan Plus Chronomodulated Oxaliplatin, 5-Fluorouracil and Folinic Acid in Advanced Colorectal Cancer Patients," Br J Cancer. 89(10):1870-5 (2003).
Gebbia V, et al., "Second-Line Chemotherapy in Advanced Pancreatic Carcinoma: A Multicenter Survey of the Gruppo Oncologico Italia Meridionale on the Activity and Safety of the FOLFOX4 Regimen in Clinical Practice," Ann Oncol. 18(Suppl 6):vi124-7 (2007).
Geddie M, et al., "Improving the Developability of an Anti-EphA2 Single-Chain Variable Fragment for Nanoparticle Targeting," MAbs. 9(1):58-67 (2017). Epub 2016.
Gemzar (gemcitabine HCI) package insert, revision Apr. 1998, 24 pages.
Giles F, et al., "Phase I and Pharmacokinetic Study of a Low-Clearance, Unilamellar Liposomal Formulation of Lurtotecan, a Topoisomerase 1 Inhibitor, in Patients with Advanced Leukemia," Cancer. 100(7):1149-58 (2004).
Gill S, et al., "Pancreox: A Randomized Phase III Study of Fluorouracil/Leucovorin With or Without Oxaliplatin for Second-Line Advanced Pancreatic Cancer in Patients Who Have Received Gemcitabine-Based Chemotherapy," J Clin Oncol. 34(32):3914-20 and Appendix (2016).
Glassman D, et al., "Nanoliposomal Irinotecan With Flurouracil for the Treatment of Advanced Pancreatic Cancer." Poster presented at the American Society of Clinical Oncology Gastrointestinal Cancers Symposium (ASCO GI), San Francisco, CA, Jan. 18-20, 2018, 7 pages.
Glassman D, et al., Abstract 471. "Nano-Liposomal Irinotecan and 5-FU/LV (N+F) for the Treatment of Advanced PDAC: Memorial Sloan Kettering (MSK) Single Cancer Center Evaluation," J Clin Oncol. 36(4 Suppl):471 DOI: 10.1200/JCO.2018.36.4_suppl.471 (2018), 2 printed pages.

Glimelius B, et al., "A Randomized Phase III Multicenter Trial Comparing Irinotecan in Combination With the Nordic Bolus 5-FU and Folinic Acid Schedule or the Bolus/Infused de Gramont Schedule (Lv5FU2) in Patients With Metastatic Colorectal Cancer," Ann Oncol. 19(5):909-14 (2008).
Glimelius B, et al., "Prediction of Irinotecan and 5-Fluorouracil Toxicity and Response in Patients With Advanced Colorectal Cancer," Pharmacogenomics J. 11(1):61-71 (2011). Epub 2010.
Goldberg R, et al., "A Randomized Controlled Trial of Fluorouracil Plus Leucovorin, Irinotecan, and Oxaliplatin Combinations in Patients With Previously Untreated Metastatic Colorectal Cancer," J Clin Oncol. 22(1):23-30 (2004). Epub 2003.
Gounaris I, et al., "Options for the Treatment of Gemcitabine-Resistant Advanced Pancreatic Cancer," JOP. J Pancreas (Online) 11(2):113-23 (2010).
Gourzoulidis G, et al., "The Cost-Effectiveness of Nanoliposomal Irinotecan and 5-Fluorouracil (5-FU)/Leucovorin (LV) for the Treatment of Patients With Metastatic Adenocarcinoma of Pancreas Who Have Progressed Following the Use of Gemcitabine-Related Therapies in Greece." Poster presented at the Virtual International Society for Pharmacoeconomics and Outcomes Research (ISPOR) European Congress, Milan, Italy, Nov. 16-19, 2020, 9 pages.
Gourzoulidis G, et al., Abstract PCN57. "The Cost-Effectiveness of Nanoliposomal Irinotecan and 5-Fluorouracil K5-FU)/Leucovorin (LV) for the Treatment of Patients With Metastatic Adenocarcinoma of Pancreas Who Have Progressed Following the Use of Gemcitabine-Related Therapies in Greece," Virtual International Society for Pharmacoeconomics and Outcomes Research (ISPOR) European Congress, Milan, Italy, Nov. 16-19, 2020, available at ispor.org/heor-resources/presentations-database/presentation/euro2020-3282/105175, 2 printed pages.
Greiner P, et al., "Pharmacokinetics of (−)-Folinic Acid After Oral and Intravenous Administration of the Racemate," 3rd Clin Pharmacol. 28(3):289-95 (1989).
Guichard S, et al., "Cellular Interactions of 5-Fluorouracil and the Camptothecin Analogue CPT-11 (Irinotecan) in a Human Colorectal Carcinoma Cell Line," Biochem Pharmacol. 55(5):667-76 (1998).
Guichard S, et al., "Sequence-Dependent Activity of the Irinotecan-5FU Combination in Human Colon-Cancer Model HT-29 In Vitro and In Vivo," Int J Cancer. 73(5):729-34 (1997).
Haller D, "Chemotherapy for Advanced Pancreatic Cancer," Int J Radiat Oncol Biol Phys. 56(4 Suppl): 16-23 (2003).
Han S, et al., Abstract ACTR-33. "A Phase I Study of Convection-Enhanced Delivery of Liposomal-Irinotecan Using Real-Time Imaging With Gadolinium In Patients With Recurrent High Grade Glioma," Neuro-Oncology. 18(Suppl_6):vi9 doi.org/10.1093/neuonc/now212.031 (2016).
Hann B, et al., Abstract 5648. "Lipidic Nanoparticle CPT-11 in a Bioluminescent Orthotopic Pancreas Cancer Model," Cancer Res. 67(9 Suppl):5648 (2007), 4 printed pages.
Hare J, "Utilization of Liposomes in Combination Cancer Chemotherapy," PhD thesis, University of Alberta, Department of Pharmacology, 2011, 367 pages.
Hashimoto S, et al., "Depletion of Alveolar Macrophages Decreases Neutrophil Chemotaxis to Pseudomonas Airspace Infections," Am J Physiol. 270(5 Pt 1):L819-28 (1996).
Hay M, et al., "Clinical Development Success Rates for Investigational Drugs," Nature Biotechnol. 32(1):40-51 (2014).
Hayes M, et al., "Genospheres: Self-Assembling Nucleic Acid-Lipid Nanoparticles Suitable for Targeted Gene Delivery," Gene Ther. 13(7):646-51 (2006).
Hayes M, et al., "Increased Target Specificity of Anti-HER2 Genospheres by Modification of Surface Charge and Degree of PEGylation," Mol Pharm. 3(6):726-36 (2006).
Heinemann V, et al., "Randomized Phase III Trial of Gemcitabine Plus Cisplatin Compared With Gemcitabine Alone in Advanced Pancreatic Cancer," J Clin Oncol. 24(24):3946-52 (2006).
Herrera-Restrepo O, et al., "Budget Impact in the USA of Liposomal Irinotecan as a Post-Gemcitabine Treatment Option for Patients With Metastatic Pancreatic Adenocarcinoma (mPC)." Poster presented at the International Society for Pharmacoeconomics and Outcomes Research (ISPOR) Annual Meeting, New Orleans, LA, May 18-22, 2019, 12 pages.

(56) References Cited

OTHER PUBLICATIONS

Herrera-Restrepo O, et al., Abstract PCN80. "Budget Impact in the USA of Liposomal Irinotecan as a Post-Gemcitabine Treatment Option for Patients With Metastatic Pancreatic Adenocarcinoma (mPC)," Value in Health. 22(Suppl 2):S70 (2019).

Hidalgo M, "Pancreatic Cancer," N Engl J Med. 362(17):1605-17 (2010).

Hirsch J, et al., "Comparing Total Cost of Care For Medicare Fee-For-Service Patients With Pancreatic Cancer, By Chemotherapy Regimen." Poster presented at the American Society of Clinical Oncology Gastrointestinal Cancers Symposium (ASCO GI), San Francisco, CA, Jan. 23-25, 2020, 5 pages.

Hirsch J, et al., "Comparing Total Costs of Care for Medicare Fee-For-Service (FFS) Patients With Metastatic Pancreatic Cancer by Chemotherapy Regimen," Poster presented at the Academy of Managed Care Pharmacy, Nexus (AMCP, Nexus): virtual meeting, week of Oct. 19, 2020, 8 pages.

Hirsch J, et al., "The Cost of Adverse Events for FDA-Approved/NCCN Category 1 Treatments for Medicare Fee-For-Service (FFS) Patients With Metastatic Pancreatic Cancer." Poster presented at the Hematology Oncology Pharmacy Association (HOPA) Annual Conference, Tampa, FL, Mar. 11-14, 2020, 6 pages.

Hirsch J, et al., "The Cost of Adverse Events for FDA-Approved/NCCN Category 1 Treatments for Medicare Fee-For-Service Patients With Metastatic Pancreatic Cancer." Poster presented at the American Society of Health-System Pharmacists (ASHP) Midyear 2019 Clinical Meeting and Exhibition, Las Vegas, NV, Dec. 8-12, 2019, 6 pages.

Hirsch J, et al., Abstract 4-138. "The Cost of Adverse Events for FDA-Approved/NCCN Category 1 Treatments for Medicare Fee-For-Service Patients With Metastatic Pancreatic Cancer," American Society of Health-System Pharmacists (ASHP) Midyear Clinical Meeting Professional Poster Abstracts, (2019), 2 pages.

Hirsch J, et al., Abstract 721. "Comparing Total Cost of Care For Medicare FFS Patients With Pancreatic Cancer By Chemotherapy Regimen," J Clin Oncol. 38(4_Suppl):721 DOI: 10.1200/JCO.2020.38.4_suppl.721 (2020), 2 printed pages.

Hirsch J, et al., Abstract e19394. "Comparing Total Cost of Care for Medicare FFS Patients With Pancreatic Cancer by Chemotherapy Regimen," J Clin Oncol. 38(15_Suppl):e19394 DOI: 10.1200/JCO.2020.38.15_suppl.e19394 (2020), 2 printed pages.

Hsu M and Juliano R, "Interactions of Liposomes With the Reticuloendothelial System. II: Nonspecific and Receptor-Mediated Uptake of Liposomes by Mouse Peritoneal Macrophages," Biochim Biophys Acta. 720(4):411-419 (1982).

Huang S, et al., "Liposomes and Hyperthermia in Mice: Increased Tumor Uptake and Therapeutic Efficacy of Doxorubicin in Sterically Stabilized Liposomes," Cancer Res. 54(8):2186-91 (1994).

Huang S, et al., "Light Microscopic Localization of Silver Enhanced Liposome-Entrapped Colloidal Gold in Mouse Tissues," Biochim Biophys Acta. 1069(1):117-21 (1991).

Huang S, et al., "Microscopic Localization of Sterically Stabilized Liposomes in Colon-Carcinoma Bearing Mice," Cancer Res. 52(19):5135-43 (1992).

Huang S, et al., "Pharmacokinetics and Therapeutics of Sterically Stabilized Liposomes in Mice Bearing C-26 Colon Carcinoma," Cancer Res. 52(24):6774-81 (1992).

Hubner R, et al., "Effects of nal-IRI (MM-398) ± 5-Fluorouracil on Quality of Life (QoL) in NAPOLI-1: A Phase 3 Study in Patients With Metastatic Pancreatic Ductal Adenocarcinoma (mPDAC) Previously Treated With Gemcitabine," Presentation presented at the European Society for Medical Oncology (ESMO) World Congress on Gastrointestinal Cancer, Barcelona, Spain, Jun. 29-Jul. 2, 2016, 13 pages.

Hubner R, et al., "Prognostic Value of Baseline Neutrophil-to-Lymphocyte Ratio (NLR) for Predicting Clinical Outcome in Metastatic Pancreatic Ductal Adenocarcinoma (mPDAC) Patients Treated With Liposomal Irinotecan (nal-RI) + 5-Fluorouracil and Leucovorin (5-FU/LV) vs 5-FU/LV Alone." Poster presented at the European Society for Medical Oncology (ESMO) Annual Congress, Madrid, Spain, Sep. 8-12, 2017, 5 pages.

Hubner R, et al., "Time Course of Selected Treatment-Emergent Adverse Events in NAPOLI-1: A Phase 3 Study of Liposomal Irinotecan (nal-IRI; MM-398) ± 5-Fluorouracil and Leucovorin (5-FU/LV) vs 5-FU/LV in Metastatic Pancreatic Cancer Previously Treated With Gemcitabine-Based Therapy." Poster presented at the European Society for Medical Oneology (ESMO) Annual Congress, Copenhagen, Denmark, Oct. 7-11, 2016, 8 pages.

Hubner R, et al., Abstract 242P. "Effects of nal-IRI (MM-398) ± 5-Fluorouracil on Quality of Life (QoL) of Patients With Metastatic Pancreatic Ductal Adenocarcinoma (mPDAC) Previously Treated With Gemcitabine Based Therapy Results From NAPOLI-1 ," Ann Oncol. 27(Supp_9):ix76 doi:10.1093/annonc/mdw582 (2016).

Hubner R, et al., Abstract 3832. "Time Course of Selected Treatment Emergent Adverse Events (TEAES) in NAPOLI-1: A Phase 3 Study of nal-IRI (MM-398) ± 5-Fluorouracil and Leucovorin (5-FU/LV) vs 5-FU/LV in Metastatic Pancreatic Cancer (mPAC) Previously Treated With Gemcitabine-Based Therapy," Ann Oncol. 27(6):207-242 10.1093/annonc/mdw371 (2016), 4 printed pages.

Hubner R, et al., Abstract 741P. "Prognostic Value of Baseline Neutrophil-to-Lymphocyte Ratio (NLR) for Predicting Clinical Outcome in Metastatic Pancreatic Ductal Adenocarcinoma (mPDAC) Patients Treated With Liposomal Irinotecan (nal-IRI) + 5-Fluorouracil and Leucovorin (5-FU/LV) vs 5-FU/LV Alone," Ann Oncol. 28(Suppl_5):253 doi:10.1093/annonc/mdx369 (2017).

Hubner R, et al., Abstract. "Expanded Analyses of NAPOLI-1: Phase 3 Study of nal-IRI (MM-398), With or Without 5-Fluorouracil (5FU) and Leucovorin (LV), Versus 5-Fluorouracil and Leucovorin (5FU/LV), in Metastatic Pancreatic Cancer (mPAC) Previously Treated With Gemcitabine-Based Therapy," 2015 National Cancer Research Institute (NCRI) Cancer Conference, Nov. 1-4, 2015, 2 printed pages.

Hwang J, et al., Abstract 4618. "A Randomized Phase II Study of FOLFOX or FOLFIRI.3 as Second-Line Therapy in Patients With Advanced Pancreatic Cancer Previously Treated With Gemcitabine-Based Chemotherapy," J Clin Oncol. 27(15_Suppl):4618 (2009), 2 printed pages.

Hwang J, et al., "Improving the Toxicity of Irinotecan/5-FU/Leucovorin: A 21-Day Schedule," Oncology. 17(9):37-43 (2003). Available at cancernetwork.com/view/improving-toxicity-irinotecan5-fu-leucovorin-21-day-schedule, 13 printed pages.

Ignatiadis M, et al., "A Multicenter Phase II Study of Docetaxel in Combination with Gefitinib in Gemcitabine-Pretreated Patients with Advanced/Metastatic Pancreatic Cancer," Oncology. 71(3-4):159-63 (2006).

Ignatius R, et al., "Presentation of Proteins Encapsulated in Sterically Stabilized Liposomes by Dendritic Cells initiates CD8+ T-cell Responses in Vivo," Blood. 96(10):3505-13 (2000).

Ilson D, "Nanolipoosomal Irinotecan Effective for Pancreatic Cancer," NEJM journal Watch, available at jwatch.org/na39795/2015/12/08/nanoliposomal-irinotecan-effective-pancreatic-cancer, (2015), 7 printed pages.

Immordino M, et al., "Stealth Liposomes: Review of the Basic Science, Rationale, and Clinical Applications, Existing and Potential," Int J Nanomedicine 1(3):297-315 (2006).

Ioka T, et al., "Liposomal Irinotecan (nal-IRI) Plus 5-Fluorouracil/Levoleucovorin (5-FU/LV) vs 5-FU/LV in Japanese Patients (pts) With Gemcitabine-Refractory Metastatic Pancreatic Cancer (mPAC)." Poster presented at the European Society for Medical Oncology (ESMO) Asia 2019 Congress, Singapore, Nov. 22-24, 2019, 9 pages.

Ioka T, et al., Abstract 132P. "Liposomal Irinotecan (nal-IRI) Plus 5-Fluorouracil/Levoleucovorin (5-FU/LV) vs 5-FU/LV n Japanese Patients (pts) With Gemcitabine-Refractory Metastatic Pancreatic Cancer (mPAC)," Ann Oncol. 30(Suppl_9):ix47-ix48 doi:10.1093/annonc/mdz422 (2019).

Ioka T, et al., Abstract 274TiP. "A Randomized Phase 2 Study of Nanoliposomal Irinotecan (nal-IRI, BAX2398)—Containing Regimen in Japanese Patients With Metastatic Pancreatic Adenocarcinoma (mPAC)," Ann Oncol. 27(Supp_9):ix84-ix85 doi:10.1093/annonc/mdw582 (2016).

(56) References Cited

OTHER PUBLICATIONS

Jameson G, et al., "Adverse Events in Patients with Metastatic Pancreatic Cancer Receiving Liposomal Irinotecan Understanding the Occurrence and How Management Affects Patient Outcomes." Poster presented at the Oncology Nursing Society (ONS) Annual Conference, Washington, DC, May 17-20, 2018, 7 pages.
Jameson G, et al., Abstract 1. "Adverse Events in Patients with Metastatic Pancreatic Cancer Receiving Liposomal Irinotecan: Understanding the Occurrence and How Management Affects Patient Outcomes," Oncology Nursing Society (ONS) 43rd Annual Congress, available at ons.confex.com/ons/2018/meetingapp.cgi/Paper/2970, (2018), 2 pages.
Kalra A, et al., Abstract 2065. "Magnetic Resonance Imaging with an Iron Oxide Nanoparticle Demonstrates the Preclinical Feasibility of Predicting Intratumoral Uptake and Activity of MM-398, a Nanoliposomal Irinotecan (nal-IRI)." In Proceedings of the 105th Annual Meeting of the American Association for Cancer Research; Apr. 5-9, 2014. Cancer Res 2014;74(19 Suppl):Abstract nr 2065, doi:10.1158/1538-7445.AM2014-2065, 1 printed page.
Kang S and Saif M, "Optimal Second Line Treatment Options for Gemcitabine Refractory Advanced Pancreatic Cancer Patients. Can We Establish Standard of Care with Available Data?," JOP. J Pancreas (Online) 9(2):83-90 (2008).
Katopodis O, et al., "Second-Line Chemotherapy With Capecitabine (Xeloda) and Docetaxel (Taxotere) in Previously Treated, Unresectable Adenocarcinoma of Pancreas: The Final Results of a Phase II Trial," Cancer Chemother Pharmacol. 67(2):361-8 (2011). Epub 2010.
Khapzory (levoleucovrin) package insert, revised Oct. 2018, accessed from accessdata.fda.gov/drugsatfda_docs/label/2018/211226s000lbl.pdf, 9 pages.
Kim G, et al., "Clinical Pathway Implications and Real-World Characteristics and Outcomes for Patients With Metastatic Pancreatic Ductal Adenocarcinoma (mPDAC) Treated With First Line Category 1 National Comprehensive Cancer Network (NCCN) Regimens." Poster presented at the European Society for Medical Oncology (ESMO) Virtual Congress 2020, Sep. 19-21, 2020, 6 pages.
Kim G, et al., "Impact of Treatment Sequence on Overall Survival in Metastatic Pancreatic Cancer Patients Treated with Liposomal Irinotecan in the Real-World Setting." Poster presented at the Hematology Oncology Pharmacy Association (HOPA) Annual Conference, Tampa, FL, Mar. 11-14, 2020, 7 pages.
Kim G, et al., Abstract 1564P. "Clinical Pathway Implications and Real-World Characteristics and Outcomes for Patients With Metastatic Pancreatic Ductal Adenocarcinoma (mPDAC) Treated With First Line Category 1 National Comprehensive Cancer Network (NCCN) Regimens," Ann Oncol. 31(Suppl_4):S881-S897 10.1016/annonc/annonc285 (2020), 2 printed pages.
Kim G, et al., Abstract e16740. "Real-World Use of Liposomal Irinotecan-Based Regimens Among Patients (pts) With Metastatic Pancreatic Adenocarcinoma (mPDAC) in the United States (U.S.)," J Clin Oncol. 38(15 Suppl):e16740 DOI: 10.1200/JCO.2020.38.15_suppl.e16740 (2020), 2 printed pages.
Kim H, et al., "Phase II Study of Palliative S-1 in Combination With Cisplatin as Second-Line Chemotherapy for Gemcitabine-Refractory Pancreatic Cancer Patients," Oncol Lett 3(6):1314-8 (2012).
Kim Y, et al., "Phase II Study of 5-Fluorouracil and Paclitaxel in Patients With Gemcitabine-Refractory Pancreatic Dancer," Cancer Chemother Pharmacol. 63(3):529-33 (2009). Epub 2008.
Kindler H, et al., "Arsenic Trioxide in Patients With Adenocarcinoma of the Pancreas Refractory to Gemcitabine: A Phase II Trial of the University of Chicago Phase II Consortium," Am J Clin Oncol. 31(6):553-6 (2008).
Kindler H, et al., "Gemcitabine Plus Bevacizumab Compared With Gemcitabine Plus Placebo in Patients With Advanced Pancreatic Cancer: Phase III Trial of the Cancer and Leukemia Group B (CALGB 80303)," J Clin Oncol. 28 22);3617-22 (2010).

Kipps E, et al., "Liposomal Irinotecan in Gemcitabine-Refractory Metastatic Pancreatic Cancer: Efficacy, Safety and Place in Therapy," Ther Adv Med Oncol. 9(3):159-70 (2017).
Kirpotin D, et al., "Building and Characterizing Antibody-Targeted Lipidic Nanotherapeutics," Methods Enzymol. 502:139-66 (2012).
Kirpotin D, et al., Chapter 4.7, "Targeting of Sterically Stabilized Liposomes to Cancers Overexpressing HER2/neu Proto-Oncogene," In Medical Applications of Liposomes, Lasic D and Papahadjopoulos D, eds., pp. 325-345 (1998).
Klapdor R and Fenner C, "Irinotecan(Campto R): Efficacy as Third/Forth Line Therapy in Advanced Pancreatic Cancer," Anticancer Res. 20(6D): 5209-12 (2000).
Klapdor R, et al., "Reflections on Treatment Strategies for Palliative Chemotherapy of Pancreatic Cancer," Anticancer Res. 27(4A): 1789-94 (2007).
Kline C, et al., "Preliminary Observations Indicate Variable Patterns of Plasma 5-Fluorouracil (5-FU) Levels During Dose Optimization of Infusional 5-FU in Colorectal Cancer Patients," Cancer Biol Ther 12(7):557-68 (2011).
Klinz S, et al., Abstract e16205. "DNA Ddamage With Liposomal Irinotecan (nal-IRI) in Pancreatic Cancer Kenografts: Multimodal Analysis of Deposition Characteristics," J Clin Oncol. 36(15_Suppl):e16205 DOI: 10.1200/JCO.2018.36.15_suppl.e16205 (2018), 2 printed pages.
Ko A, et al., "A Phase II Study of Bevacizumab Plus Erlotinib for Gemcitabine-Refractory Metastatic Pancreatic Cancer," Cancer Chemother Pharmacol. 66(6):1051-7 (2010).
Koeller J, et al., Abstract e16751. "Trends in Real-World Clinical Outcomes Among Patients (pts) With Metastatic Pancreatic Adenocarcinoma (mPDAC) Treated With Liposomal Irinotecan Based Regimens in the United States (US)," J Clin Oncol. 38(15_Suppl):e16751 DOI: 10.1200/JCO.2020.38.15_suppl.e16751 (2020), 2 printed pages.
Krauss W, et al., "Emerging Antibody-Based HER2 (ErbB2/neu) Therapeutics," Breast Dis. 11:113-24 (2000).
Kraut E, et al., Abstract 2017. "Final Results of a Phase I Study of Liposome Encapsulated SN-38 (LE-SN38) Safety, Pharmacogenomics, Pharmacokinetics, and Tumor Response," J Clin Oncol. 23(16_Suppl):2017 (2005), 3 printed pages.
Kulke M, et al., "A Phase II Trial of Irinotecan and Cisplatin in Patients with Metastatic Neuroendocrine Tumors," Dig Dis Sci. 51(6):1033-8 (2006).
Kulke M, et al., "Capecitabine Plus Erlotinib in Gemcitabine-Refractory Advanced Pancreatic Cancer," J Clin Oncol. 25(30):4787-92 (2007).
Kulke M, et al., "Randomized Phase II Study of Gemcitabine Administered at a Fixed Dose Rate or in Combination With Cisplatin, Docetaxel, or Irinotecan in Patients With Metastatic Pancreatic Cancer: CALGB 89904," J Clin Oncol. 27(33):5506-12 (2009).
Lakatos G, et al., "Prognostic Value of Baseline Biliary Stents on Outcomes in Patients With Metastatic Pancreatic Ductal Adenocarcinoma (mPDAC) in the NAPOLI-1 Trial." Poster presented at the European Society for Medical Oncology 20th World Congress on Gastrointestinal Cancer, Barcelona, Spain, Jun. 20-23, 2018, 10 pages.
Lakatos G, et al., Abstract P-151. "Prognostic Value of Baseline Biliary Stents on Outcomes in Patients With Metastatic Pancreatic Ductal Adenocarcinoma (mPDAC) in the NAPOLI-1 Trial," Ann Oncol. 29(Suppl_5):v42 doi:10.1093/annonc/mdy151 (2018).
Lamichhane N, et al., "Liposomes: Clinical Applications and Potential for Image-Guided Drug Delivery," Molecules. 23(2):288 doi: 10:3390/molecules2302028 (2018), 17 pages.
Larsen A, et al., "Influence of Liposomal Irinotecan (nal-IRI) and Non-Liposomal Irinotecan, Alone and in Combination, on Tumor Growth and Angiogenesis in Colorectal Cancer (CRC) Models." Poster presented at the American Society of Clinical Oncology Gastrointestinal Cancers Symposium (ASCO GI), San Francisco, CA, Jan. 18-20, 2018, 9 pages.
Larsen A, et al., Abstract 771. "Influence of Liposomal Irinotecan (nal-IRI) and Non-Liposomal Irinotecan, Alone and in Combination, on Tumor Growth and Angiogenesis in Colorectal Cancer (CRC) Models," J Clin Oncol. 36(4_Suppl):711 DOI: 10.1200/JCO. 2018.36.4_suppl.711 (2018), 2 printed pages.

(56) References Cited

OTHER PUBLICATIONS

Latimer H, et al., Abstract C5. "Utilization of Hospital Inpatient Services Among Patients With Metastatic Pancreatic Cancer With Commercial and Medicare Insurance Treated With FDA-Approved/NCCN Category 1 Regimens," J Manag Care Spec Pharm. 26(10-a):S20 (2020).
Le A, et al., "Conceptual Framework for Cutting the Pancreatic Cancer Fuel Supply," Clin Cancer Res. 18 (16):4285-90 (2012).
Lecovorin Calcium package insert, Teva, revised Oct. 2009, 6 pages.
Lee H, et al., "(64)Cu-MM-302 Positron Emission Tomography Quantifies Variability of Enhanced Permeability and Retention of Nanoparticles in Relation to Treatment Response in Patients with Metastatic Breast Cancer," Clin Cancer Res. 23(15)4190-4202 (2017).
Lee H, et al., "A Gradient-Loadable (64)Cu-Chelator for Quantifying Tumor Deposition Kinetics of Nanoliposomal Therapeutics by Positron Emission Tomography," Nanomedicine. 11(1):155-65 (2015). Epub 2014.
Lee K, et al., Abstract P-153. "Decreased Appetite (DA) at Baseline Impacts Prognosis in the NAPOLI-1 Phase 3 Study in Metastatic Pancreatic Ductal Adenocarcinoma (mPDAC)," Ann Oncol. 29(Suppl_5):v42-v43 doi: 10.1093/annonc/mdy151 (2018).
Lee K-H, et al., "Decreased Appetite (DA) at Baseline Impacts Prognosis in the NAPOLI-1 Phase 3 Study in Metastatic Pancreatic Ductal Adenocarcinoma (mPDAC)." Poster presented at the European Society for Medical Oncology 20th World Congress on Gastrointestinal Cancer, Barcelona, Spain, Jun. 20-23, 2018, 9 pages.
Leonard S, et al., "Deposition Characteristics and Resulting DNA Damage Patterns of Liposomal Irinotecan (nal-IRI) in Pancreatic Cancer Xenografts." Poster presented at the American Society of Clinical Oncology Gastrointestinal Cancers Symposium (ASCO GI), San Francisco, CA, Jan. 18-20, 2018, 9 pages.
Leonard S, et al., Abstract 335. "Deposition Characteristics and Resulting DNA Damage Patterns of Liposomal Irinotecan (nal-IRI) in Pancreatic Cancer Xenografts," J Clin Oncol. 36(4_Suppl):335 DOI: 10.1200/JCO.2018.36.4_suppl.335 (2018), 2 printed pages.
Li J and Saif M, "Any Progress in the Management of Advanced Pancreatic Cancer? Highlights from the 45th ASCO Annual Meeting." JOP. J Pancreas (Online) 10(4):361-5 (2009).
Li J, et al., "Any Second-Line Therapy for Advanced Pancreatic Cancer? Highlights from the 2010 ASCO Gastrointestinal Cancers Symposium " JOP. J Pancreas (Online). 11(2):151-3 (2010).
Liu B, et al., "Mapping Tumor Epitope Space by Direct Selection of Single-Chain Fv Antibody Libraries on Prostate Cancer Cells," Cancer Res. 64(2):704-10 (2004).
Liu B, et al., "Recombinant Full-Length Human IgG1s Targeting Hormone-Refractory Prostate Cancer," J Mol Med (Berl). 85(10):1113-23 (2007).
Liu J-J, et al., "Simple and Efficient Liposomal Encapsulation of Topotecan by Ammonium Sulfate Gradient: Stability, Pharmacokinetic and Therapeutic Evaluation," Anticancer Drugs 13(7):709-17 (2002).
Löhr J, et al., "Cationic Liposomal Paclitaxel Plus Gemcitabine or Gemcitabine Alone in Patients With Advanced-Pancreatic Cancer: A Randomized Controlled Phase II Trial," Ann Oncology. 23(5):1214-22 (2012). Epub 2011.
Lundberg B, et al., "Conjugation of Apolipoprotein B with Liposomes and Targeting to Cells in Culture," Biochim Biophys Acta. 1149(2):305-12 (1993).
Mabro M, et al., "A Phase II Study of FOLFIRI-3 (Double Infusion of Irinotecan Combined With LV5FU) After FOLFOX in Advanced Colorectal Cancer Patients," Br J Cancer. 94(9):1287-92 (2006).
Mabro M, et al., "Bimonthly Leucovorin, Infusion 5-Fluorouracil, Hydroxyurea, and Irinotecan (FOLFIRI-2) for Pretreated Metastatic Colorectal Cancer," Am J Clin Oncol. 26(3):254-8 (2003).
Macarulla Mercadé T, et al., "NAPOLI-1 Phase 3 Trial Outcomes by Prior Surgery, and Disease Stage, in Patients With Metastatic Pancreatic Ductal Adenocarcinoma (mPDAC)." Poster presented at the European Society for Medical Oncology Annual Congress, Munich, Germany, Oct. 19-23, 2018, 7 pages.
Macarulla Mercadé T, et al., "Prognostic Effect of Primary Tumour Location in the NAPOLI-1 Phase 3 Study in Metastatic Pancreatic Ductal Adenocarcinoma (mPDAC)." Poster presented at the European Society for Medical Oncology 19th World Congress on Gastrointestinal Cancer, Barcelona, Spain, Jun. 20-23, 2018, 10 pages.
Macarulla Mercadé T, et al., "Selected Subgroup Analyses of Liposomal Irinotecan in Patients With Metastatic Pancreatic Ductal Adenocarcinoma in the Global NAPOLI-1 Phase III Trial." Presentation presented at the European Society for Medical Oncology (ESMO) 20th World Congress on Gastrointestinal Cancer, Barcelona, Spain, Jun. 20-23, 2018, 16 pages.
Macarulla Mercade T, et al., "Subgroup Analysis by Baseline Pain Intensity (BPI) and Baseline Analgesic Use (BAU) in NAPOLI-1, A phase 3 Study of Liposomal Irinotecan (nal IRI)±5-Fluorouracil/Leucovorin (5-FU/LV) in Patients With Metastatic Pancreatic Ductal Adenocarcinoma Previously Treated With Gemcitabine-Based Therapy." Poster presented at the American Society of Clinical Oncology Gastrointestinal Cancers Symposium (ASCO GI), San Francisco, CA, Jan. 18-20, 2018, 8 pages.
Macarulla Mercadé T, et al., "Subgroup Analysis by Baseline Weight-Associated Parameters: A phase 3 Study of Liposomal Irinotecan (nal-IRI)±5-Fluorouracil/Leucovorin (5-FU/LV) in Patients With Metastatic Pancreatic Ductal Adenocarcinoma Previously Treated With Gemcitabine-Based Therapy." Poster presented at the American Society of Clinical Oncology Gastrointestinal Cancers Symposium (ASCO GI), San Francisco, CA, Jan. 18-20, 2018, 7 pages.
Macarulla Mercadé T, et al., "The Effect of Best Response to Prior Anticancer Therapy on Efficacy Outcomes in the NAPOLI-1 Trial of Patients With Metastatic Pancreatic Ductal Adenocarcinoma (mPDAC) Previously Treated with Gemcitabine-Based Therapy." Poster presented at the European Society for Medical Oncology 20th World Congress an Gastrointestinal Cancer, Barcelona, Spain, Jun. 20-23, 2018, 10 pages.
Macarulla Mercadé T, et al., Abstract 379. "Subgroup Analysis by Baseline Pain Intensity (BPI) and Analgesic Use (BAU) in NAPOLI-1: A phase III Study of Liposomal Irinotecan (nal IRI)±5-Fluorouracil/ Leucovorin (5-FU/LV) in Patients (pts) With Metastatic Pancreatic Ductal Adenocarcinoma (mPDAC) Previously Treated With Gemcitabine-Based Therapy," J Clin Oncol. 36(4_Suppl):379 DOI: 10.1200/JCO.2018.36.4_suppl.379 (2018), 4 printed pages.
Macarulla Mercadé T, et al., Abstract 410. "Subgroup Analysis by Baseline (BL) Weight-Associated Parameters A phase III Study of Liposomal Irinotecan (nal-IRI)±5-Fluorouracil/Leucovorin (5-FU/LV) in Patients (pts) With Metastatic Pancreatic Ductal Adenocarcinoma (mPDAC) Previously Treated With Gemcitabine-Based (Gem) Therapy," J Clin Oncol. 36(4_Suppl):410 DOI: 10.1200/JCO.2018.36.4_suppl.410 (2018), 2 printed pages.
Macarulla Mercadé T, et al., Abstract 733P. "NAPOLI-1 Phase III Trial Outcomes by Prior Surgery, and Disease Stage, in Patients With Metastatic Pancreatic Ductal Adenocarcinoma (mPDAC)," Ann Oncol. 29(Supp_8)viii249-viii250 doi:10.1093/annonc/mdy282 (2018).
Macarulla Mercadé T, et al., Abstract O-004. "Selected Subgroup Analyses of Liposomal Irinotecan (nal-IRI) in Patients With Metastatic Pancreatic Ductal Adenocarcinoma (mPDAC) in the Global NAPOLI-1 Phase III Trial," Ann Oncol. 29(Suppl_5)v101 doi:10.1093/annonc/mdy149(2018).
Macarulla Mercadé T, et al., Abstract P-150. "Prognostic Effect of Primary Tumour Location in the NAPOLI-1 Phase 3 Study in Metastatic Pancreatic Ductal Adenocarcinoma (mPDAC)," Ann Oncol. 29(Suppl_5)v41-v42 doi:10.1093/annonc/mdy151 (2018).
Macarulla Mercadé T, et al., Abstract P-152. "The Effect of Best Response to Prior Anticancer Therapy on Efficacy Outcomes in the NAPOLI-1 Trial of Patients With Metastatic Pancreatic Ductal Adenocarcinoma (mPDAC) Previously Treated with Gemcitabine-Based Therapy," Ann Oncol. 29(Suppl 5):v42 doi:10.1093/annonc/mdy151 2018).

(56) References Cited

OTHER PUBLICATIONS

Macarulla T, et al., "Integrated Population Pharmacokinetic Modelling of Liposomal Irinotecan in Patients With Various Tumour Types, Including Untreated Metastatic Pancreatic Cancer (mPC)." Poster presented at the European Society for Medical Oncology (ESMO) Congress 2019, Barcelona, Spain, Sep. 27-Oct. 1, 2019, 6 pages.

Macarulla T, et al., "Subgroup Analysis by Prior Lines of Metastatic Therapy in NAPOLI-1, A Global, Randomized Phase 3 Study of Liposomal Irinotecan ± 5-Fluorouracil and Leucovorin, vs. 5-Fluorouracil and Leucovorin in Patients With Metastatic Pancreatic Ductal Adenocarcinoma Who Have Progressed Following Gemcitabine-Based Therapy." Poster presented at the American Society of Clinical Oncology (ASCO) Annual Conference, Chicago, IL, Jun. 2-6, 2017, 7 pages.

Macarulla T, et al., Abstract 4127. "Subgroup Analysis by Prior Lines of Metastatic Therapy (mtx) in NAPOLI-1: A Global, Randomized Phase 3 Study of Liposomal Irinotecan (nal-IRI) ± 5-Fluorouracil and Leucovorin (5-FU/LV), vs. 5-FU/LV in Patients (pts) With Metastatic Pancreatic Ductal Adenocarcinoma (mPDAC) Who Have Progressed Following Gemcitabine-Based Therapy," J Clin Oncol. 35(15_Suppl):4127 DOI: 10.1200/JCO.2017.35.15_suppl.4127 (2017), 2 printed pages.

Macarulla T, et al., Abstract 691P. "Integrated Population Pharmacokinetic Modelling of Liposomal Irinotecan in Patients With Various Tumour Types, Including Untreated Metastatic Pancreatic Cancer (mPC)," Ann Oncol. 30 (Suppl_5):v263 doi:10.1093/annonc/mdz247 (2019).

Malet-Martino M and Martino R, "Clinical Studies of Three Oral Prodrugs of 5-Fluorouracil (Capecitabine, UFT, S-1): A Review," Oncologist. 7(4):288-323 (2002).

Mamot C, et al., "Epidermal Growth Factor Receptor (EGFR)-Targeted Immunoliposomes Mediate Specific and Efficient Drug Delivery to EGFR and EGFRvIII Overexpressing Tumor Cells," Cancer Res. 63(12):3154-61 (2003).

Mamot C, et al., "Liposome-Based Approaches to Overcome Anticancer Drug Resistance," Drug Resist Updat. 6(5):271-9 (2003).

Mancini R and Modlin J, "Chemotherapy Administration Sequence: A Review of the Literature and Creation of a Sequencing Chart," J Hematol Oncol Pharm 1 (1):17-25 (2011).

Markham C, et al., "A Phase II Irinotecan-Cisplatin Combination in Advanced Pancreatic Cancer," Br J Cancer. 89(10):1860-4 (2003).

Martin L, et al., "VEGF Remains an Interesting Target in Advanced Cancreas Cancer (APCA): Results of a Multi-Institutional Phase II Study of Bevacizumab, Gemcitabine, and Infusional 5-Fluorouracil in Patients With APCA," Ann Oncol. 23(11):2812-20 (2012).

Mathijssen R, et al., "Clinical Pharmacokinetics and Metabolism of Irinotecan (CPT-11)," Clin Cancer Res. (8):21 82-94 (2001).

Matrisian, et al., "The Past, Present, and Future of Pancreatic Cancer Clinical Trials," American Society of Clinical Oncology Educational Book. 35:e205-15 (2016).

Matsusaka S, et al., "Differential Effects of Two Fluorouracil Administration Regimens for Colorectal Cancer," Onco Rep. 10(1):109-13 (2003).

Mayer L, et al.,"Ratiometric Dosing of Anticancer Drug Combinations: Controlling Drug Ratios After Systemic Administration Regulates Therapeutic Activity in Tumor-Bearing Mice," Mol Cancer Ther. 5(7):1854-63 (2006).

McNamara M, et al., "NET-02: A Multi-Centre, Randomized, Phase II Trial of Liposomal Irinotecan (nal-IRI) and 5-Fluorouracil (5-FU)/Folinic Acid or Docetaxel as Second-Line Therapy in Patients (pts) With Progressive Poorly Differentiated Extra-Pulmonary Neuroendocrine Carcinoma (PD-EP-NEC)." Poster presented at the 17th Annual European Neuroendocrine Tumor Society (ENETS) Conference for the Diagnosis and Treatment of Neuroendocrine Tumor Disease, Virtual Conference, Mar. 11-13, 2020, 4 pages.

McNamara M, et al., Abstract P04. NET-02: A Phase II Trial of Liposomal Irinotecan (nal-IRI) and 5-Fluorouracil (5-FU)/Folinic Acid or Docetaxel as Second-Line Therapy in Patients (pts) With Progressive Poorly Differentiated Extra-Pulmonary Neuroendocrine Carcinoma (PD-EP-NEC), In Abstracts of the 17th Annual European Neuroendocrine Tumor Society (ENETS) Conference for the Diagnosis and Treatment of Neuroendocrine Tumor Disease, Virtual Conference, Mar. 11-13, 2020, p. 374.

Meerum Terwogt J, et al., "Phase I and Pharmacokinetic Study of SPI-77, a Liposomal Encapsulated Dosage Form of Cisplatin," Cancer Chemother Pharmacol 49(3):201-10 (2002).

Melisi D, et al., Abstract B04. "Effects of Nanoliposomal Irinotecan (nal-IRI; MM-398) ± 5-Fluorouracil and Leucavorin 5-FU/LV) on Quality of Life (QoL) in Patients (pts) With Metastatic Pancreatic Adenocarcinoma (mPAC) Previously Treated With Gemcitabine-Based Therapy: Results From the Phase 3 NAPOLI-1 Study," Ann Oncol. 27(Supp_4):iv18 doi:10.1093/annonc/mdw333.4 (2016).

Messerer C, et al., "Liposomal Encapsulation of Irinotecan and Potential for the Use of Liposomal Drug in the Treatment of Liver Metastases Associated with Advanced Colorectal Cancer," MS Thesis, University of British Columbia, 2000, 90 pages.

Moore M, et al., "Erlotinib Plus Gemcitabine Compared With Gemcitabine Alone in Patients With Advanced Pancreatic Cancer: A Phase III Trial of the National Cancer Institute of Canada Clinical Trials Group," J Clin Oncol. 25 (15):1960-6 (2007).

Muldoon L, et al., "Comparing Service Utilization and Costs for Medicare FFS Patients With Metastatic Pancreatic Cancer by Chemotherapy Regimen and Line of Therapy." Poster presented at the International Society for Pharmacoeconomics and Outcomes Research (ISPOR) Annual Meeting, New Orleans, LA, May 18-22, 2019, 6 pages.

Muldoon L, et al., Abstract e18357. "Treatment Patterns, Survival Rate, and Parts A and B Costs by Line of Therapy for FDA-Approved/NCCNCategory 1 Treatments for Patients With Metastatic Pancreatic Cancer," J Clin Oncol. 37(15_Suppl):e18357 DOI: 10.1200/JCO.2019.37.15_suppl.e18357 (2019), 2 printed pages.

Muldoon L, et al., Abstract PCN302. "Comparing Service Utilization and Costs for Medicare FFS Patients With Metastatic Pancreatic Cancer by Chemotherapy Regimen and Line of Therapy," Value in Health. 22(Suppl 2):S113-5114(2019).

Munzone E, "Adverse Side Effects Associated to Metronomic Chemotherapy," Presentation presented at Aiom Cancer Metronomic Therapy, Feb. 26, 2016, Milan, 32 pages.

Myocet liposomal, Summary of product characteristics and labelling and package leaflet, European Medicines Agency, available at ema.europa.eu/en/documents/product-information/myocet-liposomal-previously-myocet-epar-product-nformation_en.pdf, Date of first authorisation: Jul. 13, 2000, Date of latest renewal: Jul. 2, 2010, 37 pages.

Nakai Y, et al., "Inhibition of Renin-Angiotensin System Affects Prognosis of Advanced Pancreatic Cancer Receiving Gemcitabine," Br J Cancer. 103(11):1644-8 (2010).

Nakajima T, et al., "Synergistic Antitumor Activity of the Novel SN-38-Incorporating Polymeric Micelles, NK012, Combined With 5-Fluorouracil in a Mouse Model of Colorectal Cancer, As Compared With That of Irinotecan Plus 5-Fluorouracil," Int J Cancer. 122(9):2148-53 (2008).

Nardi M, et al., Abstract 14520. "Metronomic Irinotecan and Standard FOLFIRI Regimen as First-Line Chemotherapy n Metastatic Colorectal Cancer (MCRC). Final Results of Phase II Study," J Clin Oncol. 25(18_suppl):14520 (2007), 1 printed page.

National Cancer Institute, "Irinotecan Hydrochloride Liposome,"Posted: Oct. 27, 2015, Updated:Mar. 28, 2019, available at cancer.gov/about-cancer/treatment/drugs/irinotecan-hydrochloride-liposome, 2 pages.

Neesse A, et al., "Stromal Biology and Therapy in Pancreatic Cancer," Gut. 60(6):861-8 (2011). Epub 2010.

Nelson R, "Lipsomal Irinotecan Boosts Survival in Pancreatic Cancer," Medscape, available at medscape.com/Viewarticle/838501, 2015, 2 printed pages.

Nieto J, et al., "Metastatic Pancreatic Cancer 2008: Is the Glass Less Empty?," Oncologist. 13(5):562-76 (2008) and erratum found at Oncologist 13(6):738 (2008).

Noble C, et al., "Development of Ligand-Targeted Liposomes for Cancer Therapy," Expert Opin Ther Targets. 8(4):335-53 (2004).

(56) References Cited

OTHER PUBLICATIONS

Noordhuis P, et al., "5-Fluorouracil Incorporation into RNA and DNA in Relation to Thymidylate Synthase Inhibition of Human Colorectal Cancers," Ann Oncol. 15(7):1025-32 (2004).
Novarino A, et al., "Oxaliplatin, 5-Fluorouracil, and Leucovorin as Second-Line Treatment for Advanced Pancreatic Cancer," Am J Clin Oncol. 32(1):44-8 (2009).
Oberstein P and Olive K, "Pancreatic Cancer: Why Is It So Hard to Treat?" Ther Adv Gastroenterol. 6(4):321-7 (2013).
Oettle H and Lehmann T, "Gemcitabine-Resistant Pancreatic Cancer: A Second-Line Option," Lancet. 387(10018):507-8 (2016). Epub 2015.
Ogata Y, et al., "Dosage Escalation Study of S-1 and Irinotecan in Metronomic Chemotherapy against Advanced Colorectal Cancer," Kurume Med J 56(1-2):1-7 (2009).
Oncology NEWS International, "Experts Debate Bolus vs Continuous Infusion 5-FU." Feb. 1, 2003, vol. 12, Issue 2, 3 printed pages.
O'Reilly E, et al., "Impact of Prior Irinotecan Exposure on Outcomes of Metastatic Pancreatic Cancer Patients." Poster presented at the American Society of Clinical Oncology Gastrointestinal Cancers Symposium (ASCO GI), San Francisco, CA, Jan. 23-25, 2020, 6 pages.
O'Reilly E, et al., "Real-World Patterns of Care Among Patients With Metastatic Pancreatic Cancer." Poster presented at the American Society of Clinical Oncology Gastrointestinal Cancers Symposium (ASCO GI), San Francisco, CA, Jan. 23-25, 2020, 6 pages.
O'Reilly E, et al., Abstract 666. "Real-World Patterns of Care Among Patients With Metastatic Pancreatic Cancer (mPC)," J Clin Oncol. 38(4_Suppl):666 DOI: 10.1200/JCO.2020.38.4_suppl.666 (2020), 2 printed pages.
O'Reilly E, et al., Abstract 667. "Impact of Prior Irinotecan Exposure on Outcomes of Metastatic Pancreatic Cancer (mPC) Patients," J Clin Oncol. 38(4_Suppl):667 DOI: 10.1200/JCO.2020.38.4_suppl.667 (2020), 2 printed pages.
O'Reilly E, et al., "A Cancer and Leukemia Group B Phase II Study of Sunitinib Malate in Patients with Previously Treated Metastatic Pancreatic Adenocarcinoma (CALGB 80603)," Oncologist. 15(12):1310-9 (2010).
O'Reilly S, "Topotecan: What Dose, What Schedule, What Route?" Clin Cancer Res. 5(1):3-5 (1999).
De Forni M., et al., "Phase 1 and Pharmacokinetic Study of the Camptothecin Derivative Irinotecan, Administered on a Weekly Schedule in Cancer Patients," Cancer Research 54:4347-4354 (1994).

* cited by examiner

DMS-53 SCLC Mouse Xenograft (s.c.)

| Response @ Day 42** | PD | SD | PR | CR |
|---|---|---|---|---|
| Control | 100% (5/5) | 0% (0/5) | 0% (0/5) | 0% (0/5) |
| NaI-IRI | 0% (0/5) | 0% (0/5) | 100% (5/5) | 0% (0/5) |
| Topotecan | 100% (5/5) | 0% (0/5) | 0% (0/5) | 0% (0/5) |

NCI-H1048 SCLC Mouse Xenograft (s.c.)

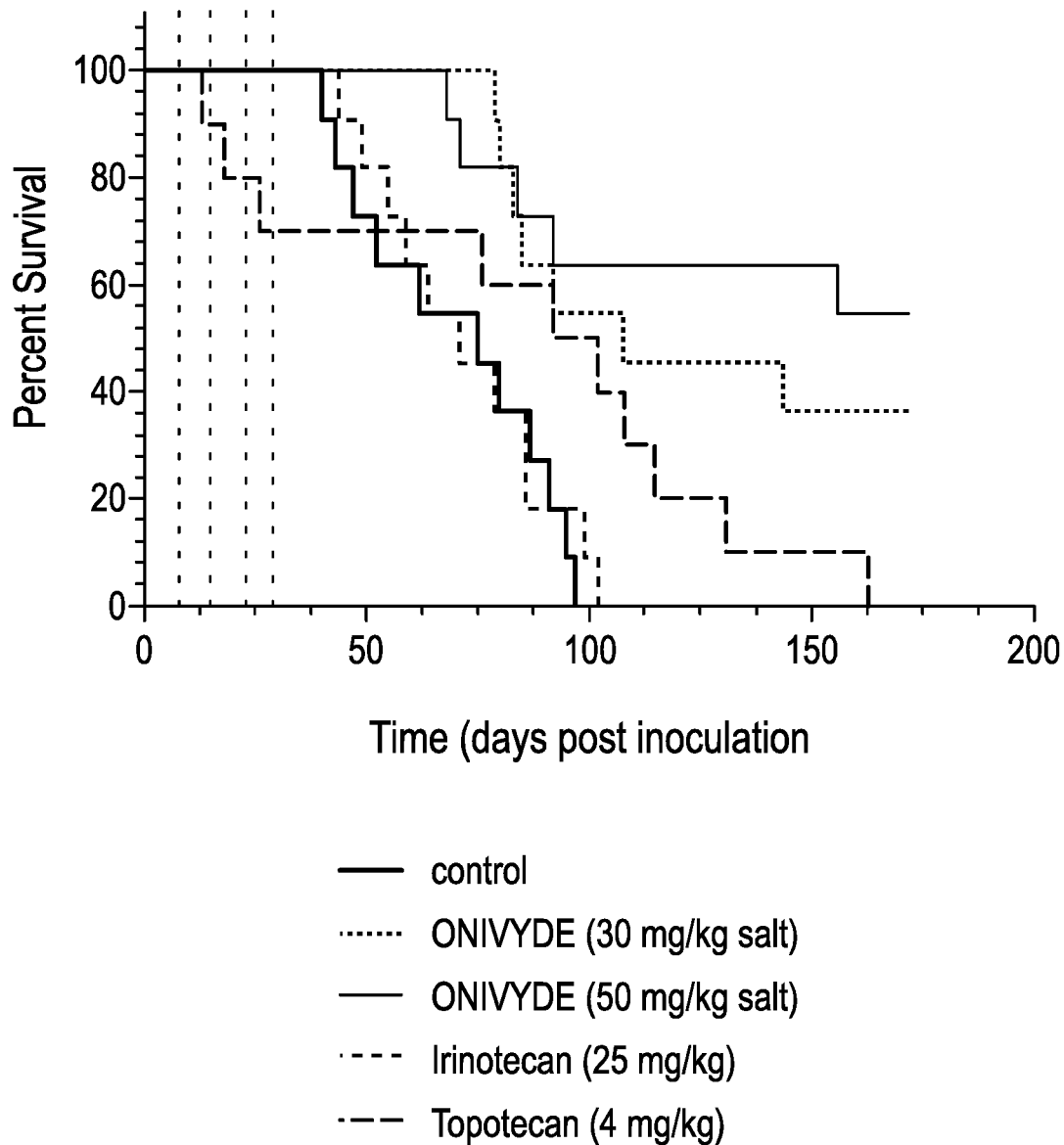

| Number of complete response (Nal-IRI) | | | |
|---|---|---|---|
| Nal-IRI Dose: | 8 mg/kg | 16 mg/kg | 32 mg/kg |
| Day 38 | 0/10 (0%) | 1/10 (10%) | 5/10 (50%) |
| Day 42 | 8/10 (80%) | 9/10 (90%) | 9/10 (90%) |
| Day 46 | 10/10 (100%) | 10/10 (100%) | 10/10 (100%) |

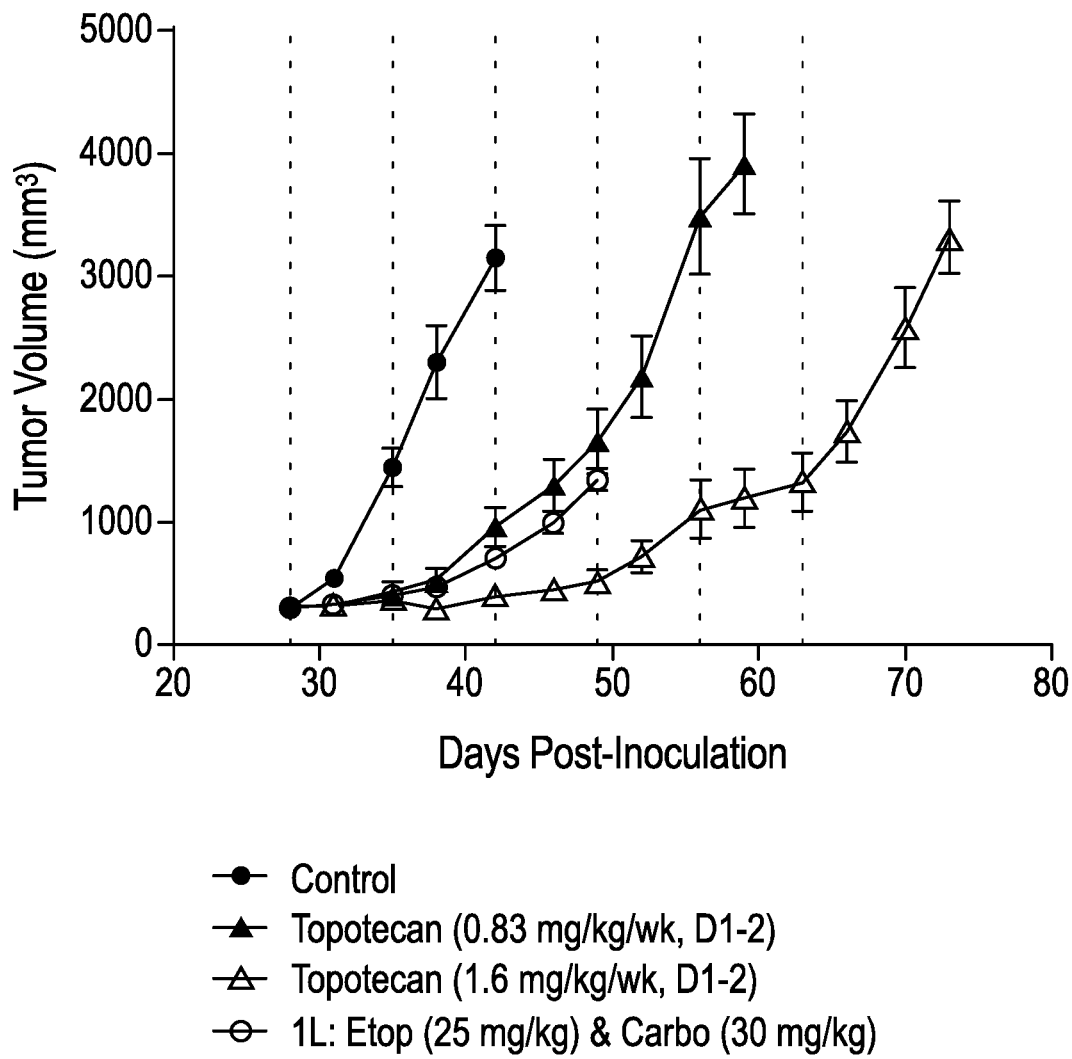

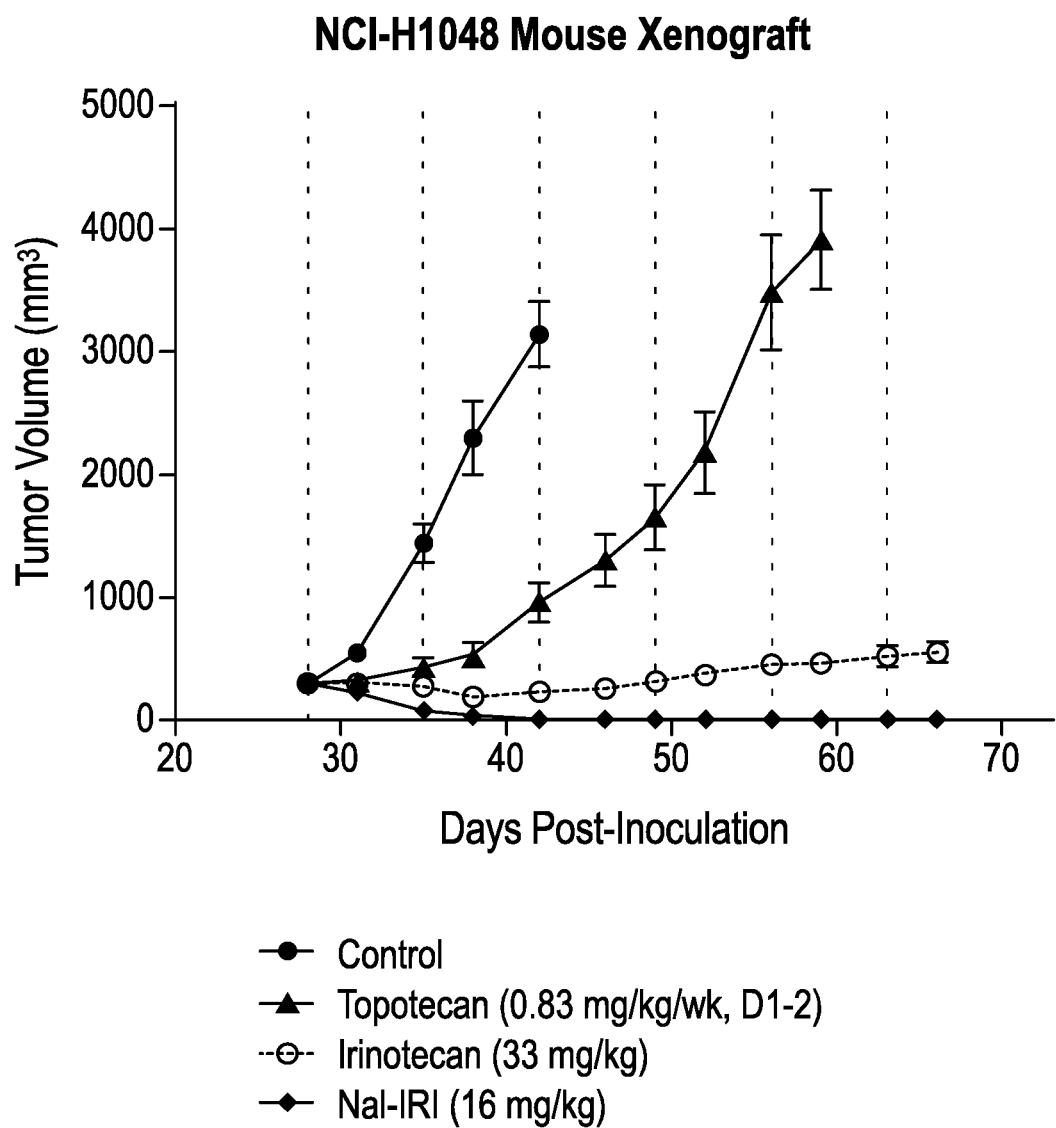

FIG. 16D

| Response at Day 98** | CR | PR | SD | PD |
|---|---|---|---|---|
| Control | 0% (0/6) | 0% (0/6) | 0% (0/6) | 100% (6/6) |
| Nal-IRI | 100% (7/7) | 0% (0/7) | 0% (0/7) | 0% (0/7) |
| Topotecan | 0% (0/7) | 0% (0/7) | 0% (0/7) | 100% (7/7) |

** Response rates determined based on tumor volume change from baseline:
CR: $\Delta TV < -95\%$
PR: $-95\% \leq \Delta TV < -30\%$
SD: $-30\% \leq \Delta TV < 30\%$
PD: $\Delta TV \geq 30\%$

FIG. 17C

| Response at Day 98** | CR | PR | SD | PD |
|---|---|---|---|---|
| Control | 0% (0/5) | 0% (0/5) | 0% (0/5) | 100% (5/5) |
| Nal-IRI | 0% (0/5) | 60% (3/5) | 40% (2/5) | 0% (0/5) |
| Topotecan | 0% (0/5) | 0% (0/5) | 0% (0/5) | 100% (5/5) |

** Response rates determined based on tumor volume change from baseline:
CR: $\Delta TV < -95\%$
PR: $-95\% \leq \Delta TV < -30\%$
SD: $-30\% \leq \Delta TV < 30\%$
PD: $\Delta TV \geq 30\%$

NANOLIPOSOMAL IRINOTECAN FOR USE IN TREATING SMALL CELL LUNG CANCER

CROSS-REFERENCE TO RELATED APPLICATIONS

This application is a national phase entry pursuant to 35 U.S.C. § 371 of International Application No. PCT/IB2017/000681, filed May 17, 2017, which claims the benefit of priority of U.S. Provisional Application No. 62/337,961 (filed May 18, 2016), U.S. Provisional Application No. 62/345,178 (filed Jun. 3, 2016), U.S. Provisional Application No. 62/362,735 (filed Jul. 15, 2016), U.S. Provisional Application No. 62/370,449 (filed Aug. 3, 2016), U.S. Provisional Application No. 62/394,870 (filed Sep. 15, 2016), U.S. Provisional Application No. 62/414,050 (filed Oct. 28, 2016), U.S. Provisional Application No. 62/415,821 (filed Nov. 1, 2016), U.S. Provisional Application No. 62/422,807 (filed Nov. 16, 2016), U.S. Provisional Application No. 62/433,925 (filed Dec. 14, 2016), U.S. Provisional Application No. 62/455,823 (filed Feb. 7, 2017), and U.S. Provisional Application No. 62/474,661 (filed Mar. 22, 2017), each of which is incorporated herein by reference in its entirety.

TECHNICAL FIELD

The present invention relates to the treatment of patients diagnosed with small cell lung cancer (SCLC), including patients with SCLC disease progression after treatment with a platinum-based therapy.

BACKGROUND

Small-cell lung cancer (SCLC) is a highly malignant cancer that most commonly arises within the lung, although it can arise in other body sites. SCLC usually presents as large, rapidly developing lesions arising from the centrally located tracheobronchial airways and invading the mediastinum. Typically, patients present with a cough or dyspnea, wheezing, and/or chest pain. Weight loss, fatigue and anorexia occur in up to one third of the patients. At the time of diagnosis, two thirds of the patients with SCLC have one or more clinically detectable distant metastases.

Initial (first line) treatment of SCLC can include administration of a platinum-based therapy such as 4-6 treatment cycles of cisplatin or carboplatin, in combination with etoposide or irinotecan. Current subsequent (second line) therapy upon SCLC disease progression (after first line therapy) has been reported to provide overall survival of about 7.7 months (sensitive patients) and 5.4 months (refractory patients) based on (Owonikoko, T K, et al., J Thorac Oncol. 2012 May; 7(5):866-72). One second line therapy is the administration of topotecan (e.g., HYCAMTIN, topotecan hydrochloride injection), reported in certain regimens to provide an overall survival of 7.8 months (9.9 months in sensitive patients, 5.7 months in refractory patients) (Owonikoko, T K, et al., J Thorac Oncol. 2012 May; 7(5):866-72). For example, of second line SCLC treatment with topotecan at 1.5 mg/m$^2$ administered on days 1-5 once in a three (3)-week treatment cycle provided overall response rates of about 7-24%, progression free survival (PFS) of about 3.1-3.7 months, and overall survival (OS) of 5.0-8.9 months (accompanied by grade 3 or greater neutropenia rates of 28-88% and grade 3 or greater diarrhea of less than about 5%) (PMIDs 16481389, 17135646, 17513814, 9164222, 10080612, 25385727). Another reported SCLC second line therapy is the administration of non-liposomal irinotecan at 300 mg/m$^2$ once every three (3) weeks, providing mixed overall response rates of 0-33%, PFS of 1.7-2.8 months, and OS of 4.6-6.9 months (accompanied by grade 3 or greater neutropenia rates of 21-23% and grade 3 or greater diarrhea of less than about 0-13%) (PMID 19100647, 1321891).

Irinotecan is an active agent in the treatment of SCLC (e.g., listed in NCCN and ESMO guidelines) but it is not approved in the US or EU. Furthermore, it failed in a PHASE III registration-directed study in combination with a platinum in first line SCLC (PMID: 16648503). No targeted treatment has been successful to date in significantly improving the outcome of patients. The research of novel treatments for this disease is therefore urgently needed.

SUMMARY

The present disclosure provides methods of treating patients with small cell lung cancer after disease progression following platinum-based therapy, by administering a therapeutically effective amount of liposomal irinotecan. In particular, a liposomal irinotecan such as MM-398 (ONIVYDE), can be administered once every two weeks to patients diagnosed with SCLC after disease progression following platinum-based therapy. In some embodiments, the liposomal irinotecan can be administered to patients diagnosed with SCLC disease progression on or after first-line platinum based chemotherapy (carboplatin or cisplatin), immunotherapy, and/or chemo-radiation including platinum-based chemotherapy for treatment of limited or extensive stage SCLC.

A human patient diagnosed with small cell lung cancer (SCLC) after disease progression following platinum-based therapy for the SCLC can be treated once every two weeks with an antineoplastic therapy consisting of a single dose of 90 mg/m$^2$ of irinotecan (free base) encapsulated in irinotecan liposomes. In another embodiment, a human patient who is known to be homozygous for the UGT1A1*28 allele and is diagnosed with small cell lung cancer (SCLC) after disease progression following platinum-based therapy for the SCLC can be treated with an antineoplastic therapy consisting of a single reduced dose (e.g., 50-70 mg/m$^2$, including 50 mg/m$^2$ or 70 mg/m$^2$) of irinotecan (free base) encapsulated in liposomes, administered once every two weeks. In another embodiment, a human patient who has previously experienced a Grade 3+ adverse event while or after receiving liposomal irinotecan after being diagnosed with small cell lung cancer (SCLC), and after disease progression following platinum-based therapy for the SCLC, can be treated with an antineoplastic therapy consisting of a single reduced dose (e.g., 50-70 mg/m$^2$, including 50 mg/m$^2$ or 70 mg/m$^2$) of irinotecan (free base) encapsulated in liposomes, administered once every two weeks.

The liposomal irinotecan can be a pharmaceutically acceptable liposome formulation of irinotecan, comprising irinotecan in a delivery form having a diameter of about 100 nm, such as a liposomal irinotecan (Example 1). Various suitable liposomal irinotecan preparations can be manufactured as disclosed herein (Example 8). Preferably, the liposomal irinotecan is the product MM-398 (ONIVYDE®) (Example 9). In the present disclosure MM-398 is used interchangeably with MM-398 liposomal irinotecan.

BRIEF DESCRIPTION OF THE DRAWINGS

FIG. 8C shows the percent survival of rats in the H841 rat orthotopic xenograft model of SCLC that are treated with control, Onivyde (30 or 50 mg/kg salt), irinotecan (25 mg/kg) or topotecan (4 mg/kg) at days post inoculation.

FIG. 10A is a graph showing Treatment Naïve SCLC Model NCl-H1048 (Nal-IRI 16 mg/kg clinically equivalent dose per BSA=1×~90 mg/m² MM-398; Topotecan 0.83 mg/kg/wk, D1-2, q2w clinically equivalent dose per BSA=1×~1.5 mg/m² Topotecan, q3w, D1-5); FIG. 10B shows the number of complete response (Nal-IRI). NCI-H1048 is a chemo-sensitive model (established from pleural effusion metastases of SCLC). All nal-IRI-treated animals have complete response (CR) after 2-3 doses—but dose response is observed at early time-point. IRI-treated animals progress after initially responding to treatment; while nal-IRI treated animals remain CR to date.

FIGS. 11A and 11B describe a 2 L SCLC xenograft model created through treatment with Carboplatin+Etoposide. FIG. 11C is a graph showing Treatment Naïve SCLC Model NCl-H1048 (Topotecan 0.83 mg/kg/wk, D1-2, q2w clinically equivalent dose per BSA=1×~1.5 mg/m² Topotecan, q3w, D1-5; 1 L Etoposide (25 mg/kg) & Carbo (30 mg/kg) clinically equivalent dose per BSA=1×~100 mg/m² Etoposide D1-3+AUC6 Carbo D1, q4w); 11B is a schematic of 1L and 2L treatments. 1 L regimen results in similar anti-tumor activity as topotecan treatment at clinically relevant doses (based on BSA/BW calculation). After 3 cycles of 1 L treatment, mice were randomized for further 2 L treatments.

FIG. 13A is a graph showing DMS-114 SCLC Mouse Xenograft (s.c.); FIG. 13B is a chart showing Nal-IRI (Day 74) tumor volume change. Nal-IRI is superior to irinotecan and topotecan at clinically relevant doses. SCLC tumors respond to irinotecan early on but became less responsive after 2-3 cycles.

FIGS. 14A-4C are graphs showing SCLC tumors treated with TOP1 inhibitors remain responsive to nal-IRI. FIG. 14A. DMS-114: Treatment Naïve.

FIGS. 15A-15C are graphs showing that duration of exposure maybe crucial for TOP1 inhibitor activity. FIG. 15A is DMS-114 SCLC Mouse Xenograft (s.c.); FIG. 15B is Hypothesized Tumor Exposure; FIG. 15C is NCl-H1048 Mouse Xenograft. At the same dose intensity, bolus (given on day 1) topotecan has less anti-tumor activity compared to fractionated topotecan (days 1 & 2). This may be indicative that prolonged exposure of TOP1 inhibitor above a therapeutic threshold is more beneficial than high $C_{max}$ because irinotecan is a pro-drug (CPT-11), the active metabolite SN-38 may also have a longer duration than topotecan.

FIGS. 16A-16D show NCl-H1048 SCLC Mouse Xenograft (s.c.) FIG. 16A. Tumor Volume; FIG. 16B. Survival; FIG. 16C. Body Weight Change; FIG. 16D. Response at Day 98.

FIGS. 17A-7C show NDMC-53 SCLC Mouse Xenograft (s.c.) FIG. 17A. Tumor Volume; FIG. 17C response at Day 98 post inoculation with control, NaI-IRI (16 mg/kg salt) or topotecan (0.83 mg/kg/wk, D1-2)

FIG. 18A. Plasma; FIG. 18B. Tumor.

FIG. 20A. DMS-114: Topotecan-Treated; FIG. 20B. DMS- 114: Treatment Naïve. DMS114 tumors treated with topotecan are responsive to nal-IRI (16 mg/kg) but not irinotecan (33 mg/kg).

FIG. 21A shows the change in Tumor Volume; FIG. 21B is a survival graph.

FIG. 22A CPT-11 plasma (sustained plasma levels), FIG. 22B. SN-38 plasma (moderately sustained plasma levels), FIG. 22C CPT-11 tumor (sustained intra-tumor levels), and FIG. 22D SN-38 tumor (enhanced intra-tumor activation to SN38).

DETAILED DESCRIPTION

Figure 1:
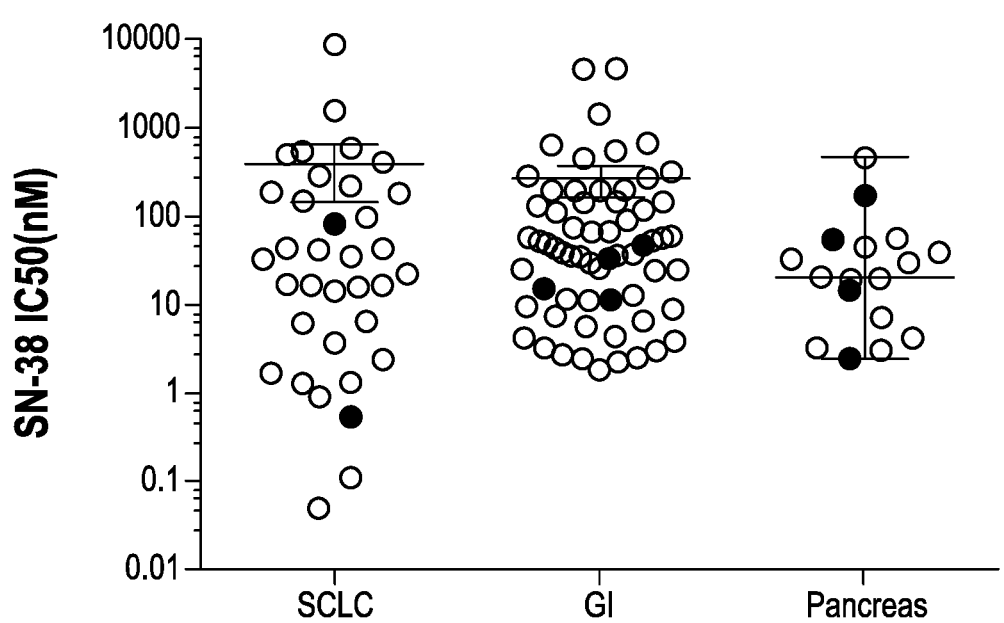
FIG. 1 is a graph showing the drug sensitivity data to SN-38 from the Sanger database were plotted for SCLC, gastrointestinal, and pancreatic cancer cell lines (Example 2).

MM-398 is a liposomal encapsulation of irinotecan that provides sustained tumor exposure of SN-38 and therefore provides certain advantages over nonliposomal irinotecan. The approved regimen of MM-398 in patients with pancreatic cancer is in combination with 5-FU/LV. However, 5-FU is not an active agent used in the treatment of SCLC. To date, the treatment of patients with SCLC with MM-398 has not been disclosed. Applicants have discovered certain methods and uses of MM-398 monotherapy in patients with SCLC, including the methods and uses disclosed herein.

The discovery of these methods and uses of MM-398 for use in patients with SCLC was based in part on preclinical data and clinical pharmacology analysis described herein. The methods and uses are designed to balance increased efficacy with increased toxicity predicted at higher doses. Preclinical data herein indicate the activity of MM-398 in models of SCLC. Clinical pharmacology analysis supports increased toxicity at increased doses and specifically supports the safety profile of the 90 mg/m$^2$ dose. Finally, preclinical efficacy data at mouse dose levels equivalent to 90 mg/m$^2$ in humans are shown to be superior to topotecan.

A human patient diagnosed with small cell lung cancer (SCLC) after disease progression following platinum-based therapy for the SCLC can be treated with an antineoplastic therapy consisting of a single dose of a therapeutically effective amount of irinotecan encapsulated in liposomes. The liposomal irinotecan can be a pharmaceutically acceptable liposome formulation of irinotecan, comprising irinotecan in a delivery form having a diameter of about 100 nm, such as an liposomal irinotecan (Example 1), including PEGylated liposomes. Various suitable liposomal irinotecan preparations can be manufactured as disclosed herein (Example 8). Preferably, the liposomal irinotecan is the product MM-398 (ONIVYDE) (Example 9).

As used herein, 90 mg/m$^2$ irinotecan refers to the free base, encapsulated in liposomes (dose based on the amount of irinotecan free base) and is equivalent to 100 mg/m$^2$ of the irinotecan hydrochloride anhydrous salt). Converting a dose based on irinotecan hydrochloride trihydrate to a dose based on irinotecan free base is accomplished by multiplying the dose based on irinotecan hydrochloride trihydrate with the ratio of the molecular weight of irinotecan free base (586.68 g/mol) and the molecular weight of irinotecan hydrochloride trihydrate (677.19 g/mol). This ratio is 0.87 which can be used as a conversion factor. For example, an 80 mg/m$^2$ dose based on irinotecan hydrochloride trihydrate is equivalent to a 69.60 mg/m$^2$ dose based on irinotecan free base (80×0.87). In the clinic this is rounded to 70 mg/m$^2$ to minimize any potential dosing errors.

Doses of nal-IRI in some studies were calculated based on the equivalent dose of irinotecan hydrochloride trihydrate (salt); in this specification, unless specified otherwise, the doses are based on irinotecan as the free base. Accordingly, 50 mg/m$^2$ based on irinotecan as free base is equivalent to 60 mg/m$^2$ based on irinotecan as the hydrochloride trihydrate, 70 mg/m$^2$ based on irinotecan as free base is equivalent to 80 mg/m$^2$ based on irinotecan as the hydrochloride trihydrate, 90 mg/m$^2$ based on irinotecan as free base is equivalent to 100 mg/m$^2$ based on irinotecan as the hydrochloride trihydrate, and 100 mg/m$^2$ based on irinotecan as free base is equivalent to 120 mg/m$^2$ based on irinotecan as the hydrochloride trihydrate, in accordance with Table 1.

TABLE 1

| Salt | Free base |
| --- | --- |
| 180 | 150 |
| 120 | 100 |
| 100 | 90 |
| 80 | 70 |
| 60 | 50 |
| 50 | 45 |
| 40 | 35 |

The pharmacokinetic parameters of total Irinotecan and total SN-38 following administration of MNI-398 90 mg/m$^2$ as a single agent or part of combination chemotherapy are presented in Table 2.

TABLE 2

Total Irinotecan and Total SN-38
Pharmacokinetic Parameters in Patients with Solid Tumors.

| Dose (mg/m$^2$) | Total Irinotecan | | | Total SN-38 | |
| --- | --- | --- | --- | --- | --- |
| | $C_{max}$ [µg/mL] | $AUC_{0-\infty}$ [h · µg/mL] | $t_{1/2}$ [h] | $C_{max}$ [ng/mL] | $t_{1/2}$ [h] |
| Max (125%) | 60.5 | 2216.5 | 25.8 | 8.8 | 67.8 |
| 90 | 48.4 | 1773.2 | 25.8 | 7.0 | 67.8 |
| Min (80%) | 38.7 | 1418.6 | 25.8 | 5.6 | 67.8 |

Over the dose range of 50 to 150 mg/m$^2$, the $C_{max}$ and AUC of total irinotecan increases with dose. Additionally, the $C_{max}$ of total SN-38 increases proportionally with dose; however, the AUC of total SN-38 increases less than proportionally with dose. Higher plasma SN-38 $C_{max}$ was associated with increased likelihood of experiencing neutropenia.

The $C_{max}$ of SN-38 increases proportionally with liposomal irinotecan dose but the AUC of SN-38 increases less than proportionally with dose, enabling new methods of dosage adjustment. For example, the value of the parameter associated with adverse effects ($C_{max}$) decreases by a relatively greater extent than the value of the parameter associated with the effectiveness of treatment (AUC). Accordingly, when an adverse effect is seen, a reduction in the dosing of the liposomal irinotecan can be implemented that maximizes the difference between the reduction in $C_{max}$ and in AUC. The discovery means that in treatment regimens, a given SN-38 AUC can be achieved with a surprisingly low SN-38 $C_{max}$. Likewise, a given SN-38 $C_{max}$ can be achieved with a surprisingly high SN-38 AUC.

Direct measurement of irinotecan liposome showed that 95% of irinotecan remains liposome encapsulated, and the ratios between total and encapsulated forms did not change with time from 0 to 169.5 hours post-dose.

In some embodiments, the liposomal irinotecan can be characterized by the parameters in Table 2. In some embodiments, the liposomal irinotecan can be MM-398 or a product that is bioequivalent to MM-398. In some embodiments, the liposomal irinotecan can be characterized by the parameters in Table 3, including a $C_{max}$ and/or AUC value that is 80-125% of the corresponding value in Table 2. The pharmacokinetic parameters of total irinotecan for various alternative liposomal irinotecan formulations administering 90 mg/m² irinotecan free base once every two weeks is provided in Table 3.

TABLE 3

Total Irinotecan Pharmacokinetic Parameters in Alternative Liposomal Irinotecan Formulations

| | Total Irinotecan | |
|---|---|---|
| Dose (mg/m²) | $C_{max}$ [μg/mL] (n = 25) | $AUC_{0-\infty}$ [h · μg/mL] (n = 23) |
| 90 | 38.7-60.5 | 1418.6-2216.5 |

Figure 2A:
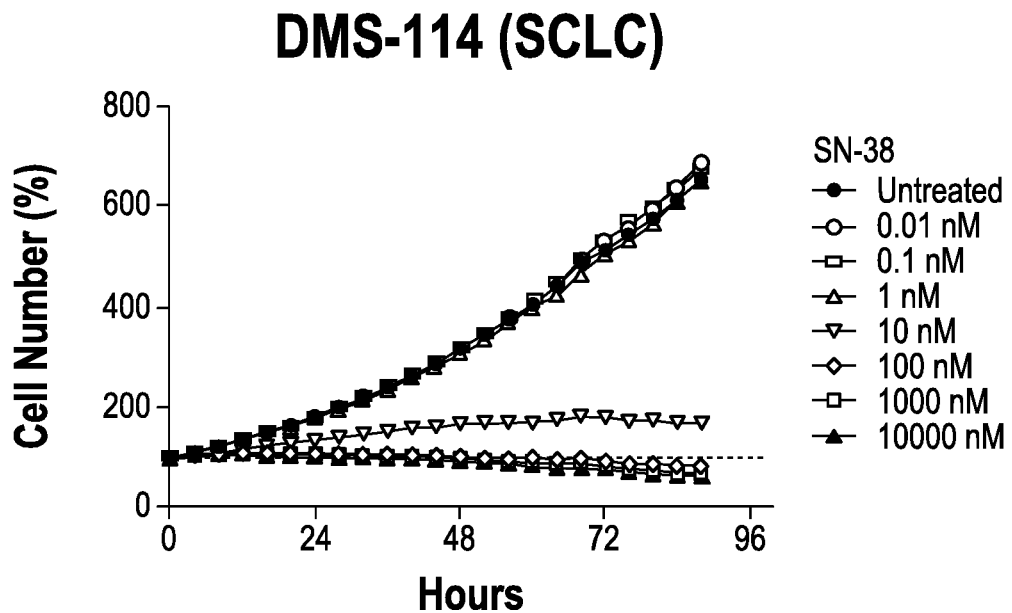
FIGS. 2A and 2B are kinetic growth curves of DMS114 and NCI-H1048 SCLC cell lines acquired on an Incucyte instrument over 88 hours at various SN-38 concentrations
Figure 2B:
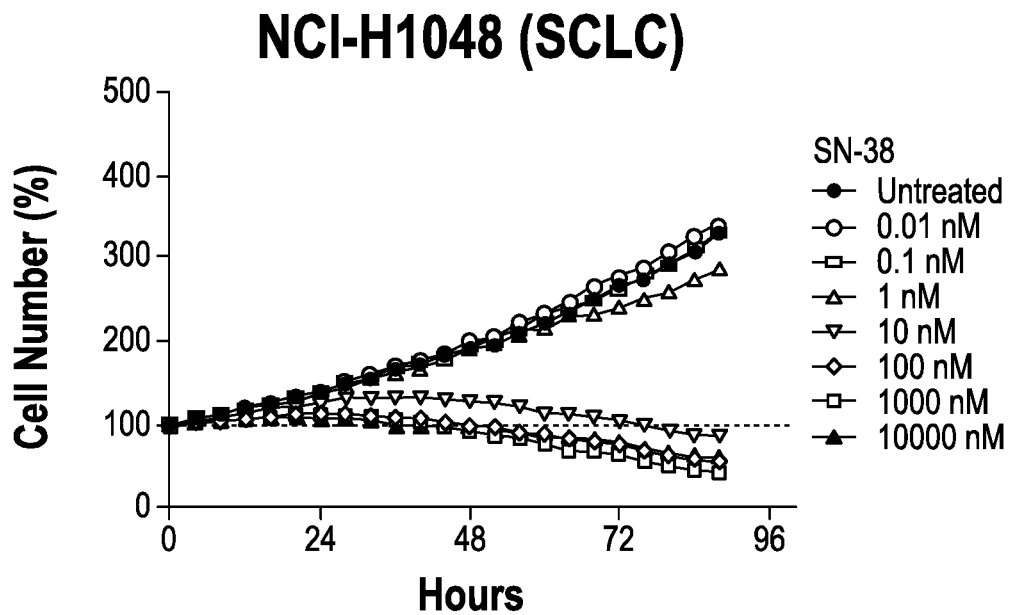

$C_{max}$: Maximum plasma concentration
$AUC_{0-\infty}$: Area under the plasma concentration curve extrapolated to time infinity
$t_{1/2}$: Terminal elimination half-life The activity of the active metabolite of irinotecan, SN-38, against various SCLC cell lines was investigated in in vitro growth and viability assays (Example 2). An analysis of this data indicated that SCLC cell lines have similar sensitivity to SN-38 as pancreatic and gastrointestinal cancer cell lines (FIG. 1). In addition, SN-38 induced a decrease in cell viability of >90% in four tested SCLC cell lines, the IC50 was variable and spanned several orders of magnitude. FIGS. 2A and 2B show the cell growth inhibition kinetics of SN-38 in 2 SCLC cell lines, as described in Example 2.

Figure 3:
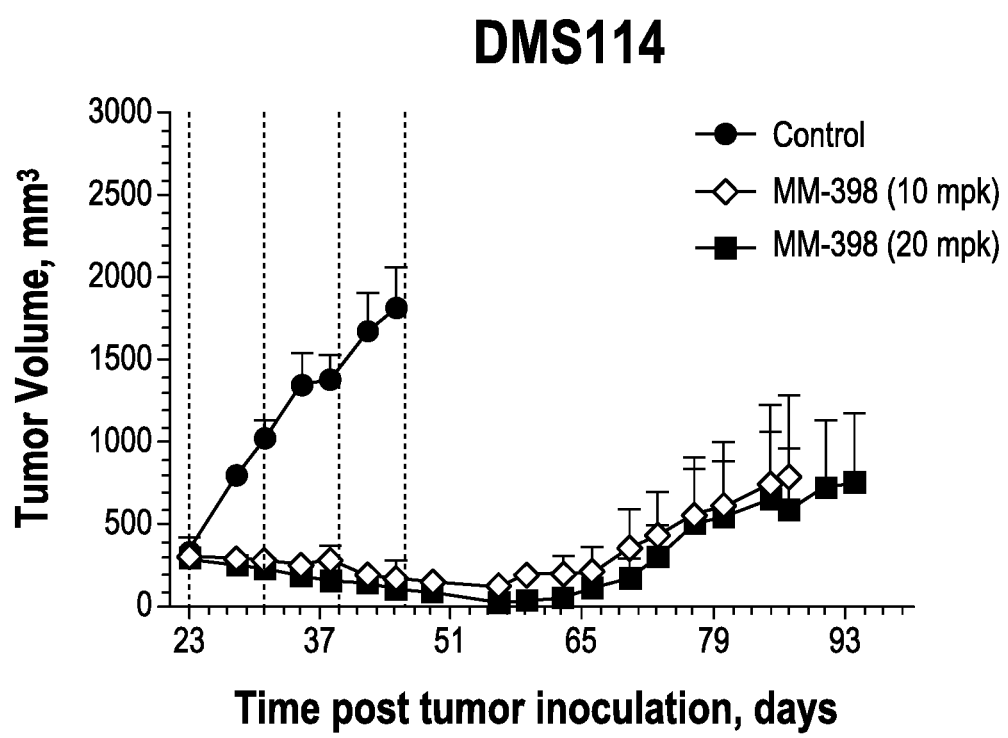
FIG. 3 is a graph showing the anti-tumor activity of MM-398 in the DMS114 xenograft model of SCLC. MM-398 was administered IV at 10 or 20 mg/kg irinotecan hydrochloride trihydrate starting on Day 23 and given weekly for 4 weeks and compared to saline control (black circles).

The activity of MM-398 as a single agent was investigated in xenograft models of SCLC (Example 3). As shown in FIG. 3, anti-tumor activity was seen at all dose levels tested in the DMS-114 model.

Figure 4:
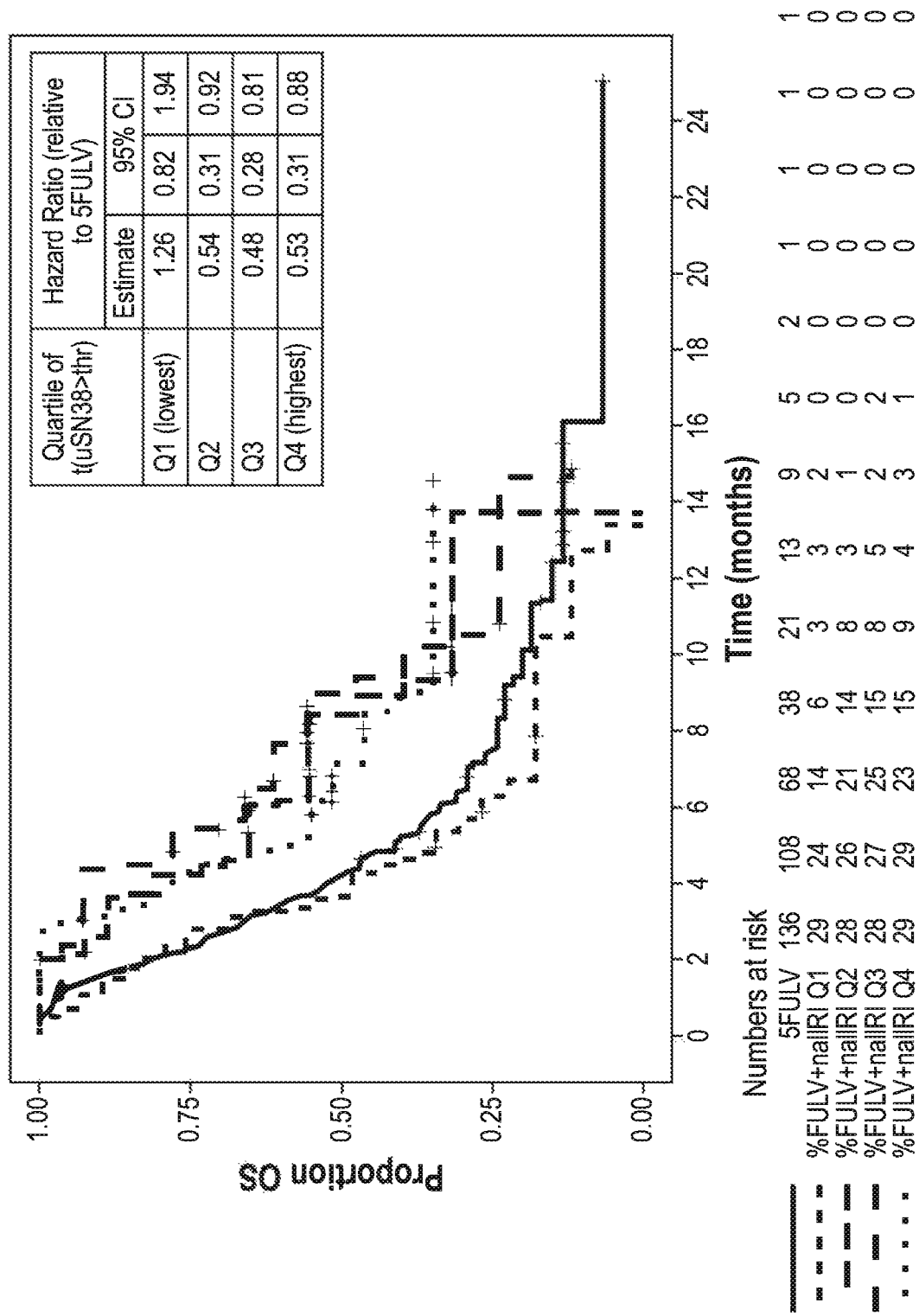
FIG. 4 is a Kaplan-Meier Plot of overall survival by quartiles of unencapsulated SN-38 (uSN38) time above threshold in the MM-398+5FU/LV arm of NAPOLI-1. Q1-Q4 represent the quartiles of uSN38 time above threshold. Q1 represents the shortest time and Q4 represents the longest time.

The estimated association between MM-398 exposure and efficacy was evaluated in pancreatic cancer patients (Example 4). The relationship between OS and quartiles of time (uSN38>0.03 ng/mL) for the MM-398+5FU/LV is provided in FIG. 4.

As described in Examples 6 and 7, an antineoplastic therapy consisting of liposomal irinotecan in a pharmaceutically acceptable injectable form can be administered once every two weeks to patients with SCLC disease that has progressed after having received previous antineoplastic therapy (e.g., prior platinum-based therapies alone or with other chemotherapeutic agents). The dose of liposomal irinotecan (e.g., 50-90 mg/m² irinotecan (free base) encapsulated in irinotecan liposomes) and dose frequency (e.g., once every 2 weeks) of liposomal irinotecan can be selected or modified for certain patients. The dose can be selected to provide a tolerable patient dose, including a dose providing acceptably low levels of grade 3 or greater neutropenia (FIG. 6A) and/or diarrhea (FIG. 6B), as described in Example 6. During the antineoplastic therapy, the patient may receive other agents that are not antineoplastic agents, such as anti-emetic agents. The antineoplastic therapy can be administered in the absence of topotecan.

In some embodiments, the invention is a method of treating a human patient diagnosed with small cell lung cancer (SCLC) after disease progression following platinum-based therapy for the SCLC, the method comprising administering to the human patient an antineoplastic therapy once every two weeks, the antineoplastic therapy consisting of a single dose of liposomal irinotecan providing 90 mg/m² (free base) of irinotecan encapsulated in irinotecan liposomes. In some embodiments, the invention is a method of treating a human patient diagnosed with small cell lung cancer (SCLC) after disease progression following platinum-based therapy for the SCLC, the method comprising administering to the human patient an antineoplastic therapy once every two weeks, the antineoplastic therapy consisting of a single dose of liposomal irinotecan providing 70 mg/m² (free base) of irinotecan encapsulated in irinotecan liposomes. In some embodiments, the invention is a method of treating a human patient diagnosed with small cell lung cancer (SCLC) after disease progression following platinum-based therapy for the SCLC, the method comprising administering to the human patient an antineoplastic therapy once every two weeks, the antineoplastic therapy consisting of a single dose of liposomal irinotecan providing 50 mg/m² (free base) of irinotecan encapsulated in irinotecan liposomes.

The methods of treatment can include determining whether a patient meets one or more inclusion criteria specified in Example 7, and then administering the antineoplastic therapy consisting of liposomal irinotecan. For example, an antineoplastic therapy can consist of administering a therapeutically effective dose (e.g., 50-90 mg/m² irinotecan (free base) encapsulated in liposomes) and dose frequency (e.g., once every 2 weeks) of liposomal irinotecan to a patient who has been treated for SCLC with a platinum-based therapy (e.g., cisplatin and/or carboplatin alone or in combination with etoposide).

In addition, the methods of treatment can include determining whether a patient meets one or more exclusion criteria specified in Example 7, and not administering the antineoplastic therapy consisting of liposomal irinotecan. Methods of treating SCLC disclosed herein can include administering the antineoplastic therapy to a patient who does not meet one or more exclusion criteria in Example 7. For example, an antineoplastic therapy can consist of administering a therapeutically effective dose (e.g., 50-90 mg/m² irinotecan (free base) encapsulated in liposomes) and dose frequency (e.g., once every 2 weeks) of liposomal irinotecan to a patient who has not been treated for SCLC with irinotecan or topotecan.

Certain subgroup of patients diagnosed with SCLC may optionally be treated with a reduced dose of the liposomal irinotecan, including patients who have higher levels of bilirubin or patients with UGT1A1*28 7/7 homozygous allele. The reduced dose refers to a dose of less than 90 mg/m² of irinotecan (free base) encapsulated in liposomes administered once every two weeks to the patient receiving the reduced dose. In some examples, the reduced dose can be a dose of 50-90 mg/m², including a reduced dose of 50 mg/m², a reduced dose of 60 mg/m², a reduced dose of 70 mg/m² or a reduced dose of 80 mg/m² irinotecan (free base) administered once every two weeks to patients diagnosed with SCLC and receiving the reduced dose. For those patients who start with 70 mg/m², the first dose reduction should be to 50 mg/m² and then to 43 mg/m². The exact determination of the appropriate dose will be dependent on the observed pharmacokinetics, efficacy, and safety in that subpopulation.

In some examples, the liposomal irinotecan can be administered to patients diagnosed with SCLC disease progression on or after immunotherapy and/or after first-line platinum based chemotherapy (carboplatin or cisplatin) or chemo-radiation including platinum-based chemotherapy for treatment of limited or extensive stage SCLC. In some examples, the patient can receive some form of immunotherapy for SCLC prior to administration of the liposomal irinotecan. Examples of immunotherapy can include atezolizumab, avelimumab, nivolumab, pembrolizumab, ipilimumab, tremelimumab and/or durvalumab. In one example, a patient receives nivolumab for SCLC (e.g., according to a treatment regimen in NCT02481830) prior to receiving the liposomal irinotecan as disclosed herein. In one example, a patient receives ipilimumab for SCLC (e.g., according to a treatment regimen in NCT01331525, NCT02046733, NCT01450761, NCT02538666 or NCT01928394) prior to receiving the liposomal irinotecan as disclosed herein. The immunotherapy can include molecules that bind to CTLA4, PDL1, PD1, 41BB and/or OX40 including the publicly available compounds in the Table 4 below or other compounds that bind to the same epitope or have the same or similar biological functions.

TABLE 4

| Antibody | Antibody Sequence (literature reference) |
|---|---|
| α-PDL1 | 10F.9G2, Bioxcell |
| α-41BB | LOB12.3, Bioxcell |
| α-CTLA4 | 9H10, Bioxcell |
| α-OX40 | OX-86, Bioxcell |

The use of a combination of liposomal irinotecan and an immunotherapy can be used for the treatment of cancer in a host in need thereof, in an amount and in a schedule of administration that is therapeutically synergistic in the treatment of said cancer. The immunotherapy can be an antibody or combination of antibodies binding to and/or acting upon alpha-PDL1, alpha-41BB, alpha-CTLA4, alpha-OX40 and/or PD1.

In some embodiments, the treatment of cancer in a host in need thereof comprises the administration of MM-398 without the administration of steroids.

The treatment schedule can comprise administering MM-398 once every two or three weeks or two out of three weeks at 43, 50, 70, 80 or 90 mg/m² liposomal irinotecan (free base) in combination with an immunotherapy (e.g., in combination with an antibody to alpha-PDL1, PD1, alpha-41BB, alpha-CTLA4 and/or alpha-OX40). For example, the treatment schedule can comprise administering a (e.g., 28-day) treatment cycle to a human host diagnosed with SCLC, where the treatment cycle includes administration of: a total of 43, 50, 70, 80 or 90 mg/m² liposomal irinotecan (free base) followed by the administration of 3 mg/kg nivolumab, once every two weeks; and repeating said treatment cycle until a progression or an unacceptable toxicity is observed. In another example, the treatment schedule can comprise administering a (e.g., 28-day) treatment cycle to a human host diagnosed with SCLC, where the treatment cycle includes administration of: a total of 43, 50, 70, 80 or 90 mg/m² liposomal irinotecan (free base) once every two or three weeks or two out of three weeks, followed by the administration of 2 mg/kg pembrolizumab, once every two or three weeks (where the first dose of liposomal irinotecan and pembrolizumab are given on the same day); and repeating said treatment cycle until a progression or an unacceptable toxicity is observed. The treatment schedule can comprise administering MM-398 once every two weeks at 90 mg/m² liposomal irinotecan (free base).

A method of treating a human patient diagnosed with small cell lung cancer (SCLC) after disease progression following platinum-based therapy for the SCLC, can consist of administering to the human patient an antineoplastic therapy once every two weeks, the antineoplastic therapy consisting of a single dose of liposomal irinotecan providing 50, 70 or 90 mg/m² (free base) of irinotecan encapsulated in irinotecan liposomes. When the patient is known to be homozygous for the UGT1A1*28 allele, each dose of irinotecan liposome can be reduced (e.g., 50, or 70 mg/m²). When the patient is not homozygous for the UGT1A1*28 allele, and is not otherwise reduced, each dose of irinotecan liposome can be 90 mg/m². The method can further comprise administering a corticosteroid and an anti-emetic to the patient prior to the administration of the irinotecan liposome.

A method of treating a human patient not homozygous for the UGT1A1*28 allele and diagnosed with small cell lung cancer (SCLC) after disease progression following prior therapy for the SCLC, can comprise administering to the human patient an antineoplastic therapy once every two weeks, the antineoplastic therapy consisting of a single dose of liposomal irinotecan providing 90 mg/m² of irinotecan (free base) encapsulated in a irinotecan liposomes. The method can further comprise administering a corticosteroid and an anti-emetic to the patient prior to the administration of the irinotecan liposome.

Prior to receiving the antineoplastic therapy of liposomal irinotecan, the patient can be a patient who has progressed on a platinum-based regimen and who has also (optionally) received a single line of immunotherapy either in maintenance or 2 L setting. The patient can be a patient who was not treated with topotecan for the SCLC prior to receiving the liposomal irinotecan antineoplastic therapy. The patient can previously receive immunotherapy induction, followed and/or accompanied by one or more maintenance doses of chemotherapy, prior to administration of the liposomal irinotecan.

The treatment schedule can comprise administering MM-398 once every three weeks at 100-130 mg/m² liposomal irinotecan (free base) in combination with an immunotherapy (e.g., in combination with an antibody to alpha-PDL1, PD1, alpha-41BB, alpha-CTLA4 and/or alpha-OX40). For example, the treatment schedule can comprise administering a treatment cycle to a human host diagnosed with SCLC, where the treatment cycle includes administration of: a total of 100, 110, 120, or 130 mg/m² liposomal irinotecan (free base) followed by the administration of 3 mg/kg nivolumab, once every three weeks; and repeating said treatment cycle until a progression or an unacceptable toxicity is observed. The treatment schedule can comprise administering a treatment cycle to a human host diagnosed with SCLC, where the treatment cycle includes administration of: a total of 100, 110, 120, or 130 mg/m² liposomal irinotecan (free base) once every three weeks combined with the administration of 3 mg/kg nivolumab, once every two or three weeks (where the first dose of liposomal irinotecan and nivolumab are given on the same day); and repeating said treatment cycle until a progression or an unacceptable toxicity is observed. In another example, the treatment schedule can comprise administering a treatment cycle to a human host diagnosed with SCLC, where the treatment cycle includes administration of: a total of 100, 110, 120, or 130 mg/m² liposomal irinotecan (free base) followed by the administration of 2 mg/kg pembrolizumab, once every three weeks; and repeating said treatment cycle until a progression or an unacceptable toxicity is observed. The treatment schedule can comprise administering a treatment cycle to a human host diagnosed with SCLC, where the treatment cycle includes administration of: a total of 100, 110, 120, or 130 mg/m² liposomal irinotecan (free base) once every three weeks combined with the administration of 2 mg/kg pembrolizumab, once every two or three weeks (where the first dose of liposomal irinotecan and pembrolizumab are given on the same day); and repeating said treatment cycle until a progression or an unacceptable toxicity is observed. The treatment schedule can comprise administering a treatment cycle to a human host diagnosed with SCLC, where the treatment cycle includes administration of: a total of 100, 110, 120, or 130 mg/m² liposomal irinotecan (free base) once every two out of three weeks combined with the administration of 2 mg/kg pembrolizumab, once every two or three weeks (where the first dose of liposomal irinotecan and pembrolizumab are given on the same day); and repeating said treatment cycle until a progression or an unacceptable toxicity is observed. The treatment schedule can comprise administering MM-398 once every three weeks at 110 mg/m² liposomal irinotecan (free base), in combination with a therapeutically effective amount of an immunotherapy (e.g., in combination with an antibody to alpha-PDL1, PD1, alpha-41BB, alpha-CTLA4 and/or alpha-OX40). The treatment schedule can comprise administering MM-398 once every three weeks at 100 mg/m² liposomal irinotecan (free base), in combination with a therapeutically effective amount of an immunotherapy (e.g., in combination with an antibody to alpha-PDL1, PD1, alpha-41BB, alpha-CTLA4 and/or alpha-OX40). The treatment schedule can comprise administering MM-398 once every three weeks at 120 mg/m² liposomal irinotecan (free base), in combination with a therapeutically effective amount of an immunotherapy (e.g., in combination with an antibody to alpha-PDL1, PD1, alpha-41BB, alpha-CTLA4 and/or alpha-OX40). The treatment schedule can comprise administering MM-398 once every three weeks at 130 mg/m² liposomal irinotecan (free base), in combination with a therapeutically effective amount of an immunotherapy (e.g., in combination with an antibody to alpha-PDL1, PD1, alpha-41BB, alpha-CTLA4 and/or alpha-OX40).

In some embodiments, liposomal irinotecan is administered after disease progression following platinum-based therapy for the SCLC in combination with one or more of prexasertib, aldoxorubicin, lurbinectedin and Rova-T. In some embodiments the liposomal irinotecan can be administered to a patient who has previously received a PD-1 directed therapeutic (e.g., nivolumab, pembrolizumab), a PD-L1 directed therapeutic (e.g., atezolizumab or durvalumab), or a Notch ADC compound (e.g., Rova-T) as a first-line (1 L) therapy for the SCLC. In some embodiments the liposomal irinotecan can be administered in combination with a Chk1 directed therapeutic (e.g., prexasertib), a Topo-2 directed therapeutic (e.g., aldozurubicin), a DNA inhibitor (e.g., lurbinectedin) or a Notch ADC compound (e.g., Rova-T). In other embodiments the liposomal irinotecan can be administered in the absence (i.e., without) a Chk1 directed therapeutic (e.g., prexasertib), a Topo-2 directed therapeutic (e.g., aldozurubicin), a DNA inhibitor (e.g., lurbinectedin) or a Notch ADC compound (e.g., Rova-T). In some embodiments the liposomal irinotecan can be administered to a patient who has previously received cisplatin or carboplatin for SCLC, and the liposomal irinotecan is administered in the absence of (i.e., without) cisplatin or carboplatin (for second or subsequent lines of therapy).

In some embodiments, methods of treating SCLC can comprise administering a treatment cycle to a human host diagnosed with SCLC, where the treatment cycle includes administration of: a total of 90 mg/m² liposomal irinotecan (free base) or 120 mg/m² liposomal irinotecan (free base) once every three weeks combined with the administration of 3 mg/kg nivolumab once every two weeks starting on the same day as the first administration of the liposomal irinotecan, and repeating said treatment cycle until a progression or an unacceptable toxicity is observed. In another example, the treatment schedule can comprise administering a treatment cycle to a human host diagnosed with SCLC, where the treatment cycle includes administration of: a total of 90 mg/m² liposomal irinotecan (free base) or 120 mg/m² liposomal irinotecan (free base) once every three weeks combined with the administration of 2 mg/kg pembrolizumab once every three weeks starting on the same day as the first administration of the liposomal irinotecan; and repeating said treatment cycle until a progression or an unacceptable toxicity is observed.

The patient can be administered antineoplastic therapy for treatment of SCLC comprising 90 mg/m² liposomal irinotecan once every two weeks, without the administration of another antineoplastic agent (e.g., without the administration of topotecan).

Preferably, the antineoplastic therapy for previously treated (e.g. second line) SCLC provides a median time to progression of progression free survival of greater than 15 weeks (e.g., at least about 20-25 weeks, including about 21-24 weeks, about 22-24 weeks, about 23 weeks or about 24 weeks), a median overall survival of greater than 30 weeks (e.g., at least about 30-50 weeks, including about 40-50 weeks, about 44-48 weeks, about 45-47 weeks, about 46 weeks or about 47 weeks), with a hazard ratio of less than 1, and preferably less than 0.7, 0.6 or 0.5 (e.g., including hazard ratio of about 0.6-0.7). Preferably, the antineoplastic therapy provides a major adverse event (grade 3+) occurring in >5% of the population of less than 50% for neutropenia (e.g., about 10-50%, including about 20%), less than 50% for thrombocytopenia (e.g., less than 10%, including 1-10%, 1-5%, less than 5%, and about 2%, about 3% and about 4%), and less than 30% for anemia (e.g., less than 10%, including 1-10%, 1-8%, less than 8%, and about 5-7%, about 6% and about 5%).

A method of treating a human patient diagnosed with small cell lung cancer (SCLC) after disease progression following platinum-based therapy for the SCLC, can consist of administering to the human patient an antineoplastic therapy once every two weeks, the antineoplastic therapy consisting of a single dose of liposomal irinotecan providing 90 mg/m² (free base) of irinotecan encapsulated in irinotecan liposomes (or reduced doses of 50-70 g/m² (free base) of irinotecan as the liposomal irinotecan to patients who have experienced adverse events during or after a prior administration of liposomal irinotecan and/or patients known to be homozygous for the UGT1A1*28 allele), where the antineoplastic therapy in a clinical trial of at least 300 patients (e.g., about 400-450 patients), where the antineoplastic therapy in a clinical trial of at least 300 patients (e.g., about 400-450 patients) results in major adverse event (grade 3+) occurring in >5% of the population of less than 50% for neutropenia (e.g., about 10-50%, including about 20%), less than 50% for thrombocytopenia (e.g., less than 10%, including 1-10%, 1-5%, less than 5%, and about 2%, about 3% and about 4%), and less than 30% for anemia (e.g., less than 10%, including 1-10%, 1-8%, less than 8%, and about 5-7%, about 6% and about 5%).

A method of treating a human patient diagnosed with small cell lung cancer (SCLC) after disease progression following platinum-based therapy for the SCLC, can consist of administering to the human patient an antineoplastic therapy once every two weeks, the antineoplastic therapy consisting of a single dose of liposomal irinotecan providing 90 mg/m$^2$ (free base) of irinotecan encapsulated in irinotecan liposomes (or reduced doses of 50-70 g/m$^2$ (free base) of irinotecan as the liposomal irinotecan to patients who have experienced adverse events during or after a prior administration of liposomal irinotecan and/or patients known to be homozygous for the UGT1A1*28 allele), where the antineoplastic therapy in a clinical trial of at least 300 patients (e.g., about 400-450 patients) results in one or more of the following: median time to progression of progression free survival of greater than 15 weeks (e.g., at least about 20-25 weeks, including about 21-24 weeks, about 22-24 weeks, about 23 weeks or about 24 weeks), a median overall survival of greater than 30 weeks (e.g., at least about 30-50 weeks, including about 40-50 weeks, about 44-48 weeks, about 45-47 weeks, about 46 weeks or about 47 weeks), with a hazard ratio of less than 1, and preferably less than 0.7, 0.6 or 0.5 (e.g., including hazard ratio of about 0.6-0.7).

When the patient is known to be homozygous for the UGT1A1*28 allele, each dose of irinotecan liposome can be reduced (e.g., 50, or 70 mg/m$^2$). When the patient is not homozygous for the UGT1A1*28 allele, and is not otherwise reduced, each dose of irinotecan liposome can be 90 mg/m$^2$. The method can further comprise administering a corticosteroid and an anti-emetic to the patient prior to the administration of the irinotecan liposome.

In some embodiments, the liposomal irinotecan can be administered to patients diagnosed with small cell lung cancer (SCLC) disease progression following treatment with one or more camptothecin compounds or topoisomerase I (Topo-1) inhibitors. Examples of camptothecin compounds or topoisomerase I (Topo-1) inhibitors include, but are not limited to, camptothecin, 9-aminocamptothecin, 7-ethylcamptothecin, 10-hydroxycamptothecin, 7-ethyl 10-hydroxy camptothecin, 9-nitrocamptothecin, 10,11-methylenedioxycamptothecin, 9-amino-10,11-methylenedioxycamptothecin, 9-chloro-10,11-methylenedioxycamptothecin, irinotecan (CPT-11), topotecan, lurtotecan, silatecan, etirinotecan pegol, rubitecan, exatecan, FL118, belotecan, gimatecan, indotecan, indimitecan, (7-(4-methylpiperazinomethylene)-10,11-ethylenedioxy-20(S)-camptothecin, 7-(4-methylpiperazinomethylene)-10,11-methylenedioxy-20(S)-camptothecin, and 7-(2-N-isopropylamino)ethyl)-(20S)-camptothecin.

In some embodiments the liposomal irinotecan can be administered to patients diagnosed with SCLC disease progression following treatment with irinotecan (CPT-11), topotecan, or both. In some embodiments the liposomal irinotecan can be administered to patients diagnosed with SCLC disease progression following treatment with irinotecan (CPT-11). In some embodiments the liposomal irinotecan can be administered to patients diagnosed with SCLC disease progression following treatment with topotecan. In some embodiments the liposomal irinotecan can be administered to patients diagnosed with SCLC disease progression following treatment with non-liposomal irinotecan.

In some embodiments, the platinum-based therapy is administered in combination with etoposide or non-liposomal irinotecan. In some embodiments, the platinum-based therapy is administered in combination with etoposide. In some embodiments, the platinum-based therapy is administered in combination with non-liposomal irinotecan. One embodiment is a method of treating a human patient diagnosed with small cell lung cancer (SCLC) following disease progression on or after camptothecin-based therapy for the SCLC, the method comprising administering to the human patient an antineoplastic therapy once every two weeks, the antineoplastic therapy consisting of a 90 mg/m$^2$ (free base) dose of MM-398 liposomal irinotecan. In some embodiments, the camptothecin-based therapy comprises the prior, discontinued administration of topotecan or non-liposomal irinotecan to treat the human patient diagnosed with SCLC. In some embodiments, the camptothecin-based therapy comprises the prior, discontinued administration of non-liposomal irinotecan administered to the human patient at a 300 mg/m$^2$ dose once every three weeks. In some embodiments, the camptothecin-based therapy comprises the prior, discontinued administration of non-liposomal irinotecan administered to the human patient at a 1.5 mg/m$^2$ dose of topotecan on days 1, 2, 3, 4, and 5 in a three week treatment cycle.

In some embodiments, the human patient diagnosed with SCLC is platinum sensitive. In some embodiments the human patient diagnosed with SCLC is platinum resistant.

A first aspect of the present disclosure is a method of treating a human patient diagnosed with small cell lung cancer (SCLC) following disease progression on or after first-line platinum-based therapy for the SCLC. One embodiment of the first aspect is a method of treating a human patient diagnosed with small cell lung cancer (SCLC) following disease progression on or after first-line platinum-based therapy for the SCLC, the method comprising administering to the human patient an antineoplastic therapy once every two weeks, the antineoplastic therapy consisting of a 90 mg/m2 (free base) dose of MM-398 liposomal irinotecan.

In one embodiment of the first aspect the platinum-based therapy comprises the prior, discontinued administration of cisplatin or carboplatin to treat the human patient diagnosed with SCLC. In another embodiment the human patient has a blood ANC greater than 1,500 cells/microliter without the use of hematopoietic growth factors, prior to the administration of the MM-398 liposomal irinotecan. Another embodiment is a method of treating a human patient diagnosed with small cell lung cancer (SCLC) following disease progression on or after first-line platinum-based therapy for the SCLC. Yet another embodiment is a method of treating a human patient diagnosed with small cell lung cancer (SCLC) following disease progression on or after first-line platinum-based therapy for the SCLC, the method comprising administering to the human patient an antineoplastic therapy once every two weeks, the antineoplastic therapy consisting of a 90 mg/m2 (free base) dose of MM-398 liposomal irinotecan wherein the human patient has a blood platelet count of greater than 100,000 cells per microliter, prior to the administration of the MM-398 liposomal irinotecan.

In some embodiments of the first aspect the human patient has a blood hemoglobin greater than 9 g/dL, prior to the administration of the MM-398 liposomal irinotecan. In some embodiments the human patient has a serum creatinine of less than or equal to 1.5×ULN and a creatinine clearance of greater than or equal to 40 mL/min prior to the administration of the MM-398 liposomal irinotecan.

In some of the embodiments of the first aspect the human patient has not received a topoisomerase I inhibitor prior to administration of the MM-398 liposomal irinotecan. In yet other embodiments of the first aspect the human patient has not received more than a single platinum-based therapy prior to administration of the MM-398 liposomal irinotecan.

Embodiments of the first aspect may comprise a method wherein the antineoplastic therapy comprises the steps of: (a) preparing a pharmaceutically acceptable injectable composition by combining dispersion of MM-398 liposomal irinotecan containing 4.3 mg irinotecan free base/mL of the dispersion with a 5% Dextrose Injection (D5W) or 0.9% Sodium Chloride Injection to obtain the injectable composition having a final volume of 500 mL and 90 mg/m$^2$ (free base) of the MM-398 liposomal irinotecan (±5%); and (b) administering the injectable composition from step (a) containing the MM-398 irinotecan liposome to the patient in a 90-minute infusion.

In any embodiment of the first aspect the method may further comprise administering to the human patient dexamethasone and a 5-HT3 blocker prior to each administration of the antineoplastic therapy, and optionally further administering an antiemetic to the human patient.

A second aspect of the present disclosure is a method of treating a human patient who is not homozygous for the UTG1A1*28 allele and is diagnosed with small cell lung cancer (SCLC) following disease progression on or after first-line platinum-based therapy for the SCLC. One embodiment of the second aspect is a method of treating a human patient who is not homozygous for the UTG1A1*28 allele and is diagnosed with small cell lung cancer (SCLC) following disease progression on or after first-line platinum-based therapy for the SCLC, the method comprising administering to the human patient an antineoplastic therapy once every two weeks in a six-week cycle, the antineoplastic therapy consisting of a 90 mg/m2 (free base) dose of MM-398 liposomal irinotecan.

In some embodiments of the second aspect the platinum-based therapy comprises the prior, discontinued administration of cisplatin or carboplatin to treat the human patient diagnosed with SCLC.

One embodiment of the second aspect is a method of treating a human patient who is not homozygous for the UTG1A1*28 allele and is diagnosed with small cell lung cancer (SCLC) following disease progression on or after first-line platinum-based therapy for the SCLC, wherein the method comprises administering to the human patient an antineoplastic therapy once every two weeks in a six-week cycle, the antineoplastic therapy consisting of a 90 mg/m2 (free base) dose of MM-398 liposomal irinotecan, wherein the human patient has one or more of the following prior to the administration of the MM-398 liposomal irinotecan: (a) a blood ANC greater than 1,500 cells/microliter without the use of hematopoietic growth factors; (b) a blood platelet count of greater than 100,000 cells per microliter; (c) a blood hemoglobin greater than 9 g/dL; and (d) a serum creatinine of less than or equal to 1.5×ULN and a creatinine clearance of greater than or equal to 40 mL/min.

In some embodiments of the second aspect the human patient has not received a topoisomerase I inhibitor prior to administration of the MM-398 liposomal irinotecan; and the human patient has not received a more than a single platinum-based therapy prior to administration of the MM-398 liposomal irinotecan. In some embodiments the method comprises administering the antineoplastic therapy for at least three six-week cycles.

In some embodiments of the second aspect the antineoplastic therapy comprises the steps of: (a) preparing a pharmaceutically acceptable injectable composition by combining dispersion of MM-398 liposomal irinotecan containing 4.3 mg irinotecan free base/mL of the dispersion with a 5% Dextrose Injection (D5W) or 0.9% Sodium Chloride Injection to obtain the injectable composition having a final volume of 500 mL and 90 mg/m2 (free base) of the MM-398 liposomal irinotecan (±5%); and (b) administering the injectable composition from step (a) containing the MM-398 irinotecan liposome to the patient in a 90-minute infusion. This embodiment may further comprise administering to the human patient dexamethasone and a 5-HT3 blocker prior to each administration of the antineoplastic therapy, and optionally further administering an antiemetic to the human patient.

A third aspect of the disclosure provides methods of treating a human patient diagnosed with small cell lung cancer (SCLC) following disease progression on or after a first-line platinum-based therapy for the SCLC selected from the group consisting of cisplatin or carboplatin. One embodiment of the third aspect is a method of treating a human patient diagnosed with small cell lung cancer (SCLC) following disease progression on or after a first-line platinum-based therapy for the SCLC selected from the group consisting of cisplatin or carboplatin. The method comprising administering to the human patient an antineoplastic therapy once every two weeks for a total of at least three six-week cycles, the antineoplastic therapy consisting of a 90 mg/m2 (free base) dose of MM-398 liposomal irinotecan; wherein the human patient is not homozygous for the UTG1A1*28 allele and has the following prior to the administration of each antineoplastic therapy of MM-398 liposomal irinotecan: (a) a blood ANC greater than 1,500 cells/microliter without the use of hematopoietic growth factors; (b) a blood platelet count of greater than 100,000 cells per microliter; (c) a blood hemoglobin greater than 9 g/dL; and (d) a serum creatinine of less than or equal to 1.5×ULN and a creatinine clearance of greater than or equal to 40 mL/min. In some embodiments of the third aspect the human patient has not received a topoisomerase I inhibitor prior to administration of the MM-398 liposomal irinotecan and has not received a more than a single platinum-based therapy prior to administration of the MM-398 liposomal irinotecan; and the method further comprises administering to the human patient dexamethasone and a 5-HT3 blocker prior to each administration of the antineoplastic therapy, and optionally further administering an antiemetic to the human patient.

In one embodiment of the third aspect the antineoplastic therapy comprises the steps of: (a) preparing a pharmaceutically acceptable injectable composition by combining dispersion of MM-398 liposomal irinotecan containing 4.3 mg irinotecan free base/mL of the dispersion with a 5% Dextrose Injection (D5W) or 0.9% Sodium Chloride Injection to obtain the injectable composition having a final volume of 500 mL and 90 mg/m2 (free base) of the MM-398 liposomal irinotecan (±5%); and (b) administering the injectable composition from step (a) containing the MM-398 irinotecan liposome to the patient in a 90-minute infusion.

EXAMPLES

Example 1: Liposomal Irinotecan

The liposomal irinotecan composition preferably comprises or consists of phosphatidylcholine, cholesterol, and a polyethyleneglycol-derivatized phosphatidyl-ethanolamine. The liposomal irinotecan can include unilamellar lipid bilayer vesicles comprising the phosphatidylcholine and cholesterol, encapsulating irinotecan sucrose octasulfate. The irinotecan liposomes in the liposomal irinotecan composition have a diameter of 110 nm (±20%). The liposomal irinotecan can comprise irinotecan sucrose octasulfate encapsulated in liposomes having a unilamellar lipid bilayer vesicle, approximately 110 nm in diameter, which encapsulates an aqueous space containing irinotecan in a gelated or precipitated state as the sucrose octasulfate salt; wherein the vesicle is composed of 1,2-distearoyl-sn-glycero-3-phosphocholine (DSPC) (e.g., about 6.8 mg/mL), cholesterol (e.g., about 2.2 mg/mL), and methoxy-terminated polyethylene glycol (MW 2000)-distearoylphosphatidyl ethanolamine (MPEG-2000-DSPE) (e.g., about 0.1 mg/mL). Each mL also contains 2-[4-(2-hydroxyethyl) piperazin-1-yl]ethanesulfonic acid (HEPES) as a buffer (e.g., about 4.1 mg/mL) and sodium chloride as an isotonicity reagent (e.g., about 8.4 mg/mL).

The lipid membrane of the liposomal irinotecan can be composed of phosphatidylcholine, cholesterol, and a polyethyleneglycol-derivatized phosphatidyl-ethanolamine in a suitable molar ratio (e.g., of about 3:2:0.015, and/or in the amount of approximately one polyethyleneglycol (PEG) molecule for 200 phospholipid molecules). ONIVYDE® (also referred to herein as MM-398 or nal-IRI) is a preferred liposomal irinotecan, comprising small unilamellar lipid bilayer vesicle (SUV), approximately 110 nm in diameter that encapsulates an aqueous space which contains irinotecan in a gelated or precipitated state as the sucrosofate salt. The ONIVYDE liposomal irinotecan comprises irinotecan sucrose octasulfate encapsulated in liposomes having a unilamellar lipid bilayer vesicle, approximately 110 nm in diameter, which encapsulates an aqueous space containing irinotecan in a gelated or precipitated state as the sucrose octasulfate salt; wherein the vesicle is composed of 1,2-distearoyl-sn-glycero-3-phosphocholine (DSPC) (6.8 mg/mL), cholesterol (2.2 mg/mL), and methoxy-terminated polyethylene glycol (MW 2000)-distearoylphosphatidyl ethanolamine (MPEG-2000-DSPE) (0.1 mg/mL). Each mL also contains 2-[4-(2-hydroxyethyl) piperazin-1-yl]ethanesulfonic acid (HEPES) as a buffer (4.1 mg/mL) and sodium chloride as an isotonicity reagent (8.4 mg/mL). ONIVYDE is a sterile, white to slightly yellow opaque isotonic liposomal dispersion.

The liposomal irinotecan can be supplied as a sterile, white to slightly yellow, opaque liposomal dispersion in a 10 mL single use glass vial, containing 43 mg/10 mL irinotecan free base. The liposomal dispersion in the vial can be diluted prior to intravenous infusion over 90 minutes.

The present disclosure provides for use of liposomal irinotecan (e.g., ONIVYDE described in Example 9) for the treatment of SCLC once every two weeks at a total dose of 90 mg/m$^2$ irinotecan (free base), encapsulated in liposomes (dose based on the amount of irinotecan free base; equivalent to 100 mg/m$^2$ of the irinotecan hydrochloride anhydrous salt) IV over 90 minutes, every 2 weeks (preferably, in a 6-week cycle). The recommended starting dose of ONIVYDE in patients known to be homozygous for the UGT1A1*28 allele is 50 mg/m$^2$ (free base) administered by intravenous infusion over 90 minutes. The dose of ONIVYDE may be increased to 70 mg/m$^2$ as tolerated in subsequent cycles. There is no recommended dose of ONIVYDE for patients with serum bilirubin above the upper limit of normal.

Example 2

Topoisomerase I inhibition has potent effects on a wide range of cancer cell lines. Reference data in the Wellcome Trust Sanger Institute database of the "Genomics of Drug Sensitivity in Cancer" project are available for 663 cancer cell lines screened for sensitivity to SN-38 (URL www.cancerrxgene.org/translation/Drug/1003). An analysis of this data indicated that SCLC cell lines have similar sensitivity to SN-38 as pancreatic and gastrointestinal cancer cell lines (FIG. 1). Within this dataset, cancer cell lines of gastrointestinal (HT-29, HCT-116, LoVo, MKN45) or pancreatic (AsPC-1, BxPC3, CFPAC-1, MiaPaCa-2) origin for which significant in vivo anti-tumor efficacies of MM-398 have been observed are highlighted by filled circles. SCLC cell lines DMS114 and NCI-H1048 (see below) are also shown as filled circles.

The activity of the active metabolite of irinotecan, SN-38, against various SCLC cell lines was investigated in in vitro growth and viability assays. SN-38 induced a decrease in cell viability of >90% in four tested SCLC cell lines (DMS53, DMS114, NCI-H1048, SW1271), the IC50 was variable and spanned several orders of magnitude. FIGS. 2A and 2B show the cell growth inhibition kinetics of SN-38 in 2 SCLC cell lines (DMS-114 and NCI-H1048) using an IncuCyte® ZOOM System over a time-course of 88 hours. Effective cell growth inhibition was observed between 1-10 nM, while cell killing was observed after prolonged incubation times at concentrations≥10 nM. This range of SN-38 therapeutic threshold coincides with the amount of SN-38 measured from patient tumor biopsies at 72 h post-MM-398 administration (range: 3-163 nM). These data suggest that the prolonged duration of SN-38 in tumors as a result of MM-398 pharmacological characteristics would provide effective activity in SCLC. Preclinical experiments have demonstrated that MM-398 greatly increased the availability of SN-38 in the tumor and showed dose-dependent anti-tumor efficacy at much lower doses than non-liposomal irinotecan.

Example 3

The activity of MM-398 as a single agent was investigated in xenograft models of SCLC. DMS114 cells were inoculated subcutaneously in NCR nu/nu mice. When tumors reached ~300 mm$^3$ in volume, mice were treated with 10 or 20 mg/kg of MM-398 irinotecan hydrochloride, administered intravenously on a weekly basis for 4 weeks. Dose levels were selected to correspond to what is believed to be the clinically relevant mouse dose, based on PK modeling and comparison with clinical PK data. As shown in FIG. 3, anti-tumor activity was seen at all dose levels tested in the DMS114 model. Animals with tumors receiving 10 or 20 mg/kg showed tumor regression that was sustained for approximately 20-27 days past the last dose of MM-398 (2/5 and 4/5 complete regressions at 10 and 20 mg/kg dose, respectively).

Example 4: Association Between Exposure and Efficacy

Figure 5:
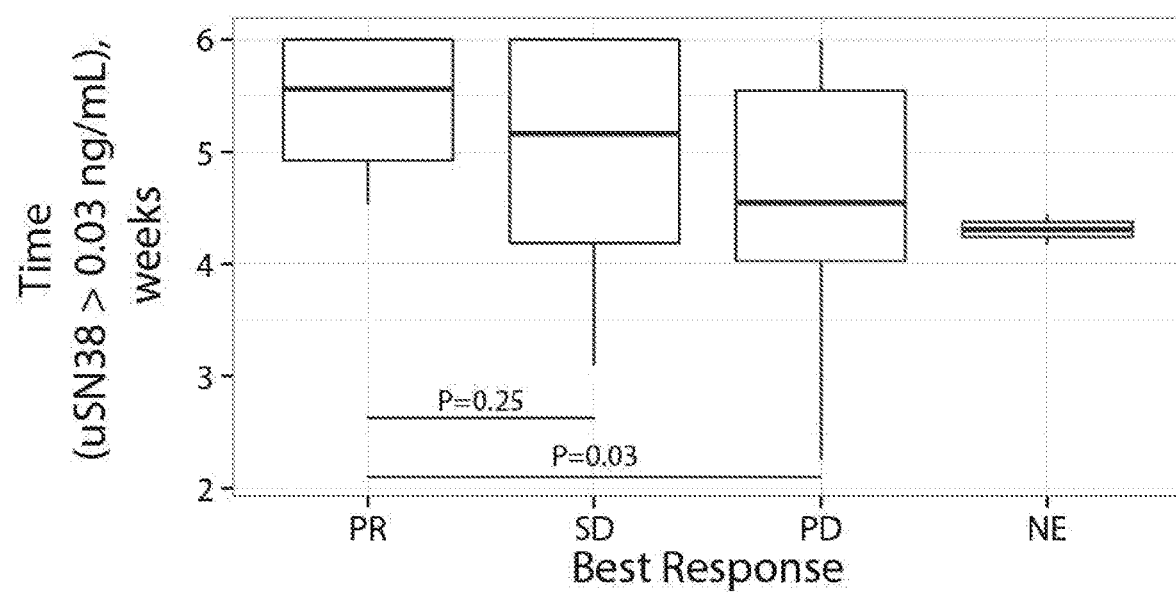
FIG. 5 is a graph showing the association between best response and duration of uSN38>0.03 ng/mL for MM-398+5FU/LV arm in NAPOLI-1.

While the association between MM-398 exposure and efficacy is to be studied in SCLC, data analysis in pancreatic cancer patients indicates benefits in increased exposure to SN-38. In the MM-398+5FU/LV treatment arm of NAPOLI-1, longer overall survival (OS) and progression free survival (PFS) were associated with longer time uSN38>0.03 ng/mL and higher Cavg of tIRI, tSN38 and uSN38, with the highest association observed for the time when uSN38>0.03 ng/mL. $C_{max}$ of tIRI, tSN38, or uSN38 was not predictive of OS (P=0.81-0.92). The relationship between OS and quartiles of time (uSN38>0.03 ng/mL) for the MM-398+5FU/LV is provided in FIG. 4. Longer duration of uSN38>0.03 ng/mL was associated with a higher probability of achieving objective response in the MM-398+5FU/LV arm (FIG. 5) This association was not observed in the MM-398 monotherapy arm dosed at 100 mg/m2 every 3 weeks (P=0.62). The lack of association in the monotherapy arm may be attributed partly in the difference of the dose intervals (MM-398 dose in the monotherapy arm is 100 mg/m2 every 3 weeks, MM-398 dose in the MM-398+5-FU/LV arm is 70 mg/m2 every 2 weeks).

Example 5: Association Between Exposure and Safety with MM-398

Figure 6A:
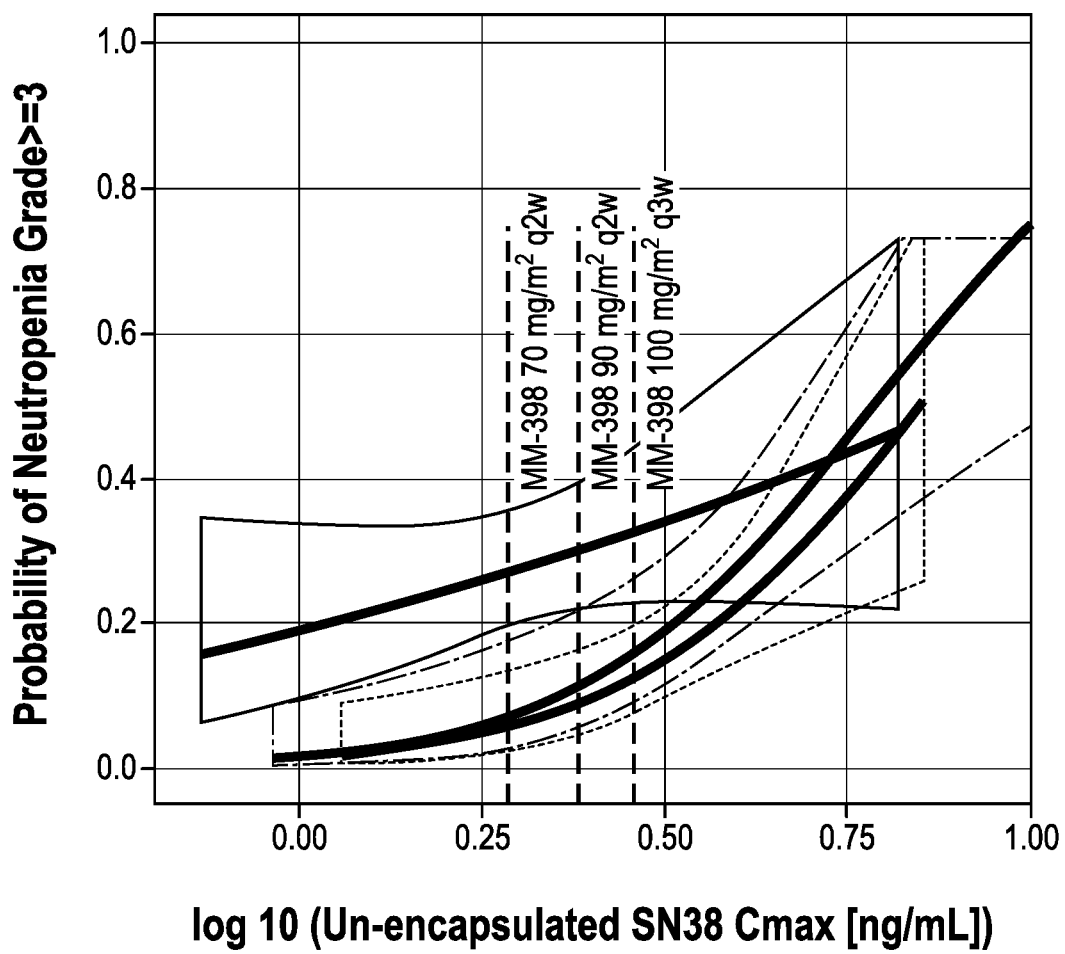
FIG. 6A is a graph showing the association between unencapsulated SN-38 Cmax and Neutropenia Grade≥3 in patients treated with MM-398.
Figure 6B:
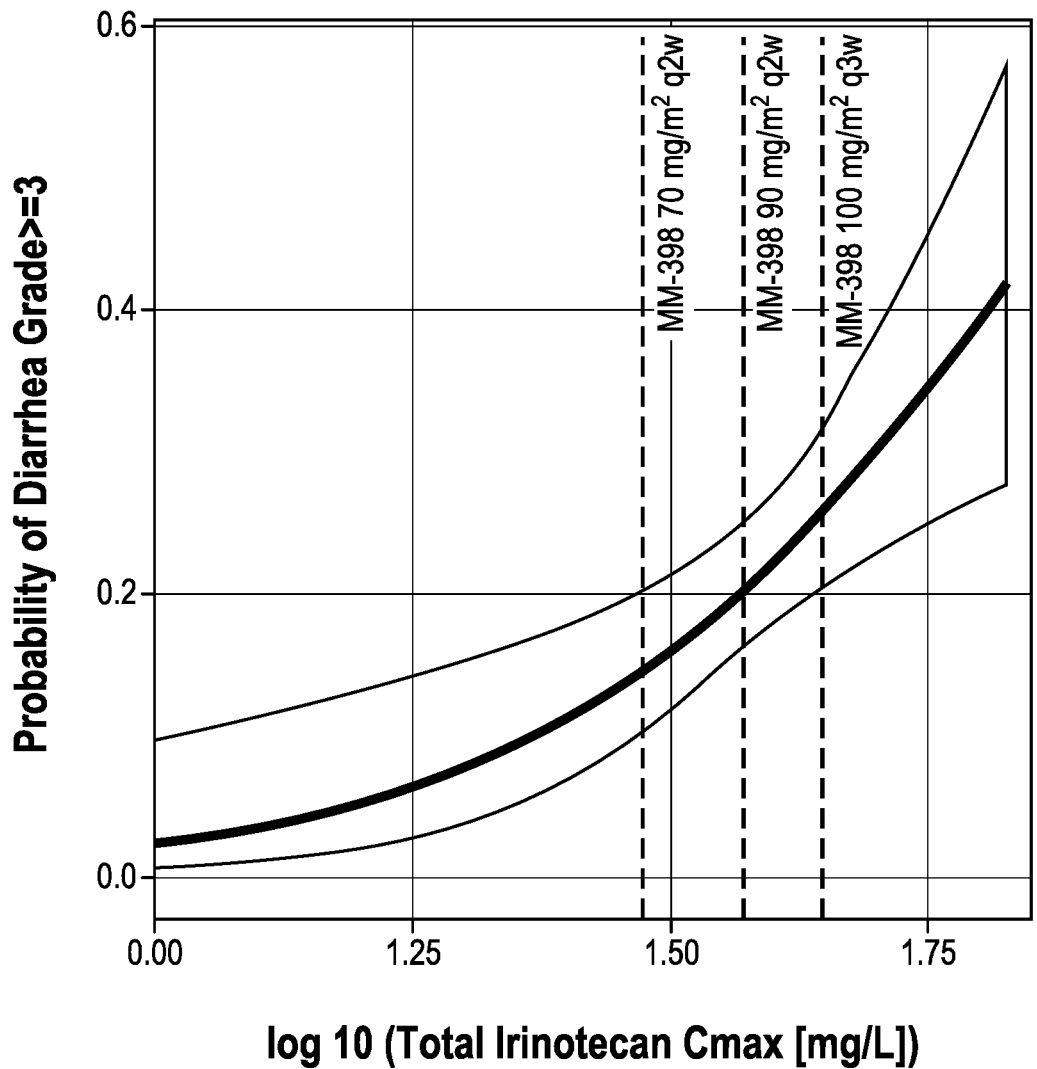
FIG. 6B is a graph showing the association between total irinotecan Cmax and Diarrhea grade≥3 in patients treated with MM-398.

The association between exposure and safety was evaluated based on data in 353 patients treated with Onivyde. Higher un-encapsulated SN-38 $C_{max}$ was associated with higher probability of both incidence and severity of neutropenia treatment-emergent adverse events (FIG. 6A). Higher total irinotecan $C_{max}$ was associated with higher probability of observing grade 3+ diarrhea (FIG. 6B). Moreover, different probabilities of observing grade 3+ neutropenia were seen with and without co-administration with 5FU/LV. These associations were used to evaluate the predicted safety with alternative dose regimens to be tested in SCLC.

Example 6: Prediction of Safety for a Dose of 90 mg/m²

Based on these exposure-safety associations for neutropenia (FIG. 6A) and diarrhea (FIG. 6B), the predicted rate of grade 3+ neutropenia and diarrhea is provided in Table 5. Compared to a dose of 70 mg/m² (free base) as monotherapy, a dose of 90 mg/m² (free base) is predicted to increase grade 3+ neutropenia from 8.4% to 11.1% and diarrhea from 14.3% to 20.0%. These rates were derived based on data with the majority (73%) of patients with pancreatic cancer disease who may have higher risk of diarrhea as compared to patients with SCLC.

TABLE 5

Predicted neutropenia and diarrhea grade 3 or Higher by Irinotecan Liposome Injection Dose

| Adverse Event code | Dose (mg/m2) | Predicted rates |
|---|---|---|
| Neutropenia grade >=3 | 70 | 8.4% |
|  | 90 | 11.1% |
|  | 100 | 13.9% |
| Diarrhea grade >=3 | 70 | 14.3% |
|  | 90 | 20.0% |
|  | 100 | 25.8% |

Example 7: A Randomized, Open Label Phase 3 Study of nal-IRI (ONIVYDE® or MNI-398) in Patients with Small Cell Lung Cancer Who Have Progressed On or After Platinum-Based First-Line Therapy Overview of Study Design. This is an open label, randomized Phase 3 study of irinotecan liposome injection versus IV topotecan in patients with small cell lung cancer who have progressed on or after platinum-based first line therapy. The study will be conducted in two parts.

Part 1:

Part 1a The objectives of Part 1a are to: 1) describe the safety and tolerability of irinotecan liposome injection monotherapy administered every 2 weeks and 2) to determine the irinotecan liposome injection monotherapy dose (90 mg/m² or 70 mg/m² administered every two weeks) for the Part 1b and Part 2 of this study.

Part 1b is a parallel study of nal-IRI (N=25) and IV topotecan (N=25) for the purpose of characterizing preliminary efficacy and safety of irinotecan liposome injection and IV topotecan. The objectives of Part 1b are to describe the 1) progression free survival rate at 12 weeks, 2) objective response rate (ORR), 3) progression free survival (PFS), 4) overall survival (OS), and 5) safety profile.

Part 2: a randomized, efficacy study of the nal-IRI (N=210) versus topotecan (N=210). The primary objective of Part 2 is to compare overall survival following treatment with irinotecan liposome injection with overall survival following treatment with IV topotecan.

The secondary objectives of Part 2 are to compare the following between the treatment arms: 1) progression free survival (PFS), 2) objective response rate (ORR), 3) proportion of patients with symptom improvement in cough, in dyspnea and in fatigue as measured by the European Organization for Research and Treatment of Cancer Quality of Life Questionnaire (EORTC QLQ-C30) and Lung Cancer 13 (LC13) and 4) safety profile.

Exploratory Objectives (Part 1 and Part 2) include: 1) To describe QTcF following treatment with irinotecan liposome injection (Part 1 only), 2) To explore the biomarkers associated with efficacy and safety following treatment with irinotecan liposome injection, 3) To describe the association between UGT1A1 genotype, SN-38 concentration (irinotecan liposome injection treated patients only) and safety, 4) To evaluate the relationship between plasma pharmacokinetics of irinotecan liposome injection and efficacy and safety in this patient population, 5) To compare the rate of development/time to development of CNS progression and development of new CNS metastases, 6) To compare time to treatment failure (TTF) between treatment arms and 7) To compare patient-reported outcomes (PROs) between treatment arms using EORTC-QLQ-C30, EORTC-QLQ-LC13 and EQ-5D-5L.

Both Part 1 and Part 2 will consist of three phases: a screening phase, a Treatment/Active follow-up phase and a long term follow-up phase. The Treatment/Active follow-up phase is the period for the first dose of the study drug through the decision to permanently discontinue study drug treatment. The Long Term follow-up phase is a monthly follow-up for overall survival.

Part 1a

The initial number of patients to be enrolled in the Part 1a safety run-in is 6 patients evaluable for safety. This initial cohort of patients will be treated with irinotecan liposome injection 70 mg/m² every 2 weeks. Dose limiting toxicities (DLTs) will be evaluated during the first 28 days of treatment (or 14 days after the 2nd dose of study treatment if there is a treatment delay) to determine if the dose is tolerable. If 2 or more patients receiving irinotecan liposome injection 70 mg/m² every 2 weeks have DLTs then the dose will be declared not tolerable. In all other cases an additional cohort of 6 patients treated with irinotecan liposome injection starting at 90 mg/m² will be enrolled. The 90 mg/m² cohort will only be enrolled if the overall experience in the initial 6 patients treated in the 70 mg/m² cohort is judged to be safe enough to reasonably expect that the 90 mg/m² dose will be tolerable in the assessment of the Part 1 investigators and the Sponsor. Evaluation of DLTs will follow the same guidelines as the first cohort. If 2 or more patients have DLTs at the 90 mg/m² dose then that dose will be considered to exceed the optimal safety and tolerability criteria, and 70 mg/m² will be designated as the dose for Part 1b and Part 1b will initiate administering 70 mg/m² of irinotecan liposome injection. If there is 0 or 1 DLT within the safety evaluation period with the 90 mg/m² dose, then the decision of which dose to use for Part 1b will be made by Part 1 investigators and the Sponsor based on the entire safety experience of both cohorts.

All patients who received study drug will be evaluable for DLT and safety. The following adverse events should be considered as DLTs if they occur during the first 28 days of treatment (or 14 days after the 2nd dose of study treatment if there is a treatment delay according to section 6.2) and are deemed related to the study treatment by the investigator: Grade 4 neutropenia or thrombocytopenia that does not resolve within 7 days and grade 4 anemia of any duration Inability to begin subsequent treatment course within 14 days of the scheduled date, due to drug-related toxicity Grade 3-4 neutropenia complicated by fever≥38.5° C. (i.e. febrile neutropenia) and/or by infection Any grade 4 non-hematologic toxicity with the exception of the following:
  Fatigue/asthenia<2 weeks
  Nausea and vomiting lasting ≤3 days duration (only considered dose limiting if they last >72 hours after treatment with an optimal anti-emetic treatment)
  Diarrhea≤3 days duration (only considered dose limiting if diarrhea lasts >72 hours after treatment with an optimal anti-diarrheal regimen)

Grade 3 non-hematologic toxicity with the exception of the following:
  Any gastrointestinal disorder and dehydration (with associated signs and symptoms) unless grade 3 toxicity persists despite optimal medical management for >72 hours,
  Pain unless grade 3 toxicity persists despite optimal medical management,
  Fatigue, fever, flu like symptoms, infections and infestations
  Infusion reaction (and associated symptoms) unless it occurs following steroid premedication
  Hepatic and kidney function abnormalities, and electrolyte abnormalities if they persist, despite optimal medical management The determination whether an adverse event is considered a DLT will be made following discussion between the investigators and the Sponsor and confirmed by the safety review committee (i.e. The Part 1a Investigators and the Medical Monitor(s) of the Sponsor). Other adverse events that are deemed related to study treatment can also be considered a DLT event at the discretion of the safety review committee. Safety review meetings between investigators and sponsor will occur regularly during Part 1a of the study with at least monthly meetings, or more frequently, if required.

Part 1b

Following the determination of the nal-IRI dose in Part 1a, Part 1b of the study will be initiated. In Part 1b, approximately 50 eligible patients will be randomized in a 1:1 ratio between the experimental arm (Arm 1a: 90 mg/m² of nal-IRI, every 2 weeks), and the control arm (Arm 1b: topotecan 1.5 mg/m2 IV for 5 days, every 21 days). Patients will be randomized to the treatment arms using an Interactive Web Response System (IWRS) at a central location. In order to reduce imbalance with regard to prognostic factors used for stratification in the randomization for Part 2, randomization in Part 1b will use a minimization procedure accounting for the Part 2 stratification factors.

Platinum resistant patients are defined as patients with disease that either progressed during first-line platinum containing therapy or within 90 days of its completion. Platinum sensitive patients are defined as patients with disease that progressed after 90 days of completion of first line platinum containing therapy. To retain a distribution of platinum sensitivity to first-line treatment groups in accordance with previously published studies (von Pawel, 2014), no more than 30 patients will be randomized from either platinum sensitive or platinum resistant patients in Part 1b.

Safety and efficacy results from Part 1b will determine if the study proceeds (or not) to Part 2. The study will be stopped if both of the following stopping criteria are met:

PFS (based on investigator assessment) rate at 12 weeks for irinotecan liposome injection is less than 50% AND PFS (based on investigator assessment) rate at 12 weeks for IV topotecan exceeds that of irinotecan liposome injection by at least 5 percentage points If the stopping criteria are not met, the final decision to proceed to Part 2 will be made by the Sponsor in consultation with the academic steering committee of the study after consideration of all available efficacy and safety data from Part 1 of the study.

Part 2:

If the stopping criteria from Part 1b are not met and the decision is made to proceed to Part 2 of the study, approximately 420 eligible patients will be randomized in a 1:1 ratio between the experimental arm (Arm 2a: 90 mg/m² of irinotecan liposome injection), and the control arm (Arm 2b: IV topotecan). Patients will be randomized to the treatment arms using an Interactive Web Response System (IWRS) at a central location. Randomization will be stratified, based on the following factors:
  Disease stage (limited vs extensive) at diagnosis
  Region (North America vs Asia vs Other)
  Platinum sensitivity (sensitive vs resistant)
  Performance status (ECOG 0 vs. 1)
  Prior immunotherapy (yes vs. no)

Only region and platinum sensitive vs. resistant will be used for the efficacy analysis.

Tumor responses will be measured and recorded, every 6 weeks (+/−1 week) by using the RECIST guidelines (version 1.1). The tumor assessment at baseline is CT with contrast (chest/abdomen required and pelvis if clinically indicated) and brain MRI with contrast (CT of brain is acceptable). Each follow-up tumor assessment should use the same assessment as performed at baseline, unless medically contraindicated. All patients will have imaging of the brain at baseline and at each assessment. Patients who discontinue study treatment, for reasons other than objective disease progression, should continue to be followed-up until radiological documentation of progressive disease. The Sponsor will collect and store all tumor measurement images on all patients throughout the study; however, local radiologist and/or PI assessment will determine disease progression. A review of the scans may be performed by the Sponsor for an independent analysis, including analysis of PFS and/or ORR. All patients will be followed at least monthly until death or study closure, whichever occurs first.

A quality of life assessment will be performed using the EORTC-QLQ-C30, EORTC-QLQ-LC13, and the EuroQoL five-dimension, five level health status questionnaire (EQ-5D-5L) in Part 1b and Part 2 only. Both instruments will be administered before randomization and prior to dosing at 6 week intervals following start of treatment and at treatment discontinuation and at the 30-day follow-up visit.

Adverse events (AEs) will be evaluated according to the National Cancer Institute's Common Terminology Criteria for Adverse Events version 4.03 (CTCAE v4.03). For summary of AEs, events will be coded using the latest MedDRA dictionary version.

The primary analysis is planned when at least 333 OS events have occurred. An interim analysis for futility is planned to occur at 30% information time, after at least 100 OS events have occurred. In the event that the trial continues, an interim analysis will be conducted when at least 210 OS events (63% information time, at 50% of anticipated death events) have occurred to assess the potential for early stopping due to efficacy of the experimental treatment regimen.

A regular review of safety data will be conducted for Part 2 by an independent Data Monitoring Committee (DMC). The DMC will consist of oncology and statistical experts independent of the Sponsor. The first safety review of the DMC will take place in Part 2 after the 30th patient is treated for at least one cycle or after the 30th patient discontinued study drug, whichever occurs first. The timing and details of subsequent data reviews will be detailed in the DMC charter. Items reviewed on a regular basis will include (but not limited to) safety events, results of PK testing, and UGT1A1*28 genotype from central testing with particular attention to determine whether any study procedure needs to be modified for patients who are homozygous for UGT1A1*28.

Pharmacokinetics

Plasma samples for PK will be collected in Cycle 1 only at the following time points:

Part 1a, and Part 1b, Arm 1a (nal-IRI arm; cycle 1 only):
Day 1: Pre-dose
Day 1: End of nal-IRI infusion
Day 2: Approximately 24 hours after end of infusion
Day 8: Cycle 1, Day 8 (+/−1 day), at any time of day
Day 15: Pre-dose
Day 15: End of nal-IRI infusion
Part 1b, Arm 1b (topotecan arm; cycle 1 only):
Day 1: Pre-dose
Day 1: End of topotecan infusion
Day 1, 2 or 3: Two additional samples between 1.5 and 4 hours after the start of infusion. Each sample must be collected at least 1 hour apart. It is preferred to collect these samples on day 1; however these two additional samples can be collected on day 2 or day 3.
Part 2, Arm 2a (irinotecan liposome injection arm; cycle 1 only):
Day 1: Pre-dose
Day 1: End of irinotecan liposome injection infusion
Day 1: Between 2.5 and 6 hours after the start of infusion
Day 2-6 (Optional): anytime between 1 and 5 days after the start of infusion
Day 8: Cycle 1 Day 8 (+/−1 day), at any time of day.

Study Population

Inclusion Criteria

Disease Specific Inclusion Criteria 1) histopathologically or cytologically confirmed small cell lung cancer according to the International Association for the Study of Lung Cancer (IASLC) histopathological classification. Mixed or combined subtypes according to the IASLC are not allowed; 2) Evaluable disease as defined by RECIST v1.1 guidelines (patients with non-target lesions only are eligible) 3) Progression on or after first-line platinum based chemotherapy (carboplatin or cisplatin) or chemo-radiation including platinum-based chemotherapy for treatment of limited or extensive stage SCLC; and 4) Recovered from the effects of any prior chemotherapy, surgery, radiotherapy or other anti-neoplastic therapy (recovered to grade 1 or better, with the exception of alopecia).

Hematologic, Biochemical and Organ Function Inclusion Criteria: Adequate bone marrow reserves as evidenced by:
ANC>1,500 cells/µl without the use of hematopoietic growth factors; and
Platelet count>100,000 cells/µl; and
Hemoglobin>9 g/dL; transfusions are allowed
Adequate hepatic function as evidenced by:
Serum total bilirubin within normal range for the institution
Aspartate aminotransferase (AST) and alanine aminotransferase (ALT)≤2.5×ULN (≤5×ULN is acceptable if liver metastases are present)
Adequate renal function as evidenced by a serum creatinine≤1.5×ULN and creatinine clearance≥40 mL/min. Actual body weight should be used for calculating creatinine clearance using the Cockcroft-Gault Equation(except for patients with body mass index (BMI)>30 kg/m2 when lean body weight should be used instead):

$$\text{Serum Creatinine (mg/min)} \frac{(140 - \text{Age(years)}) \times (\text{Weight(kg)})}{72 \times \text{Serum Creatinine (mg/dL)}} \times \text{Sex}$$

Where Sex=1 for males and 0.85 for females.
ECG without any clinically significant findings
Recovered from the effects of any prior chemotherapy, surgery, radiotherapy or other anti-neoplastic therapy
Required to participate in the translational research component of the trial, unless prohibited by local regulations, and provide archived tumor tissue (if available)
At least 18 years of age
Able to understand and sign an informed consent (or have a legal representative who is able to do so)
Patients must meet all the inclusion criteria listed above and none of the following exclusion criteria:

General Exclusion Criteria

1) Any medical or social condition deemed by the Investigator to be likely to interfere with a patient's ability to sign informed consent, cooperate and participate in the study, or interfere with the interpretation of the results;

2) Pregnant or breast feeding; females of child-bearing potential must test negative for pregnancy at the time of enrollment based on a urine or serum pregnancy test. Both male and female patients of reproductive potential must agree to use a highly effective method of birth control, during the study and for 4 months following the last dose of study drug.

Disease Specific Exclusion Criteria

1) Prior treatment regimens with irinotecan, topotecan or any other topoisomerase I inhibitor including investigational topoisomerase I inhibitors;

2) Patients with large cell neuroendocrine carcinoma;

3) Patients who have had more than one regimen of prior cytotoxic chemotherapy

4) More than one line of immunotherapy (e.g. nivolumab, pembrolizumab, ipilimumab, atezolizumab, tremelimumab and/or durvalumab). One line of immunotherapy is defined as the following: monotherapy or combination of immunotherapy agents given as either (i) in combination with chemotherapy followed by immunotherapy maintenance in the first line setting, (ii) only as a maintenance following response to first-line chemotherapy or (iii) immunotherapy given as second line treatment following progression;

5) Patients with a history of immunotherapy induced colitis;

6) Any prior systemic treatment other than 1 line of platinum-containing regimen or immunotherapy as described above;

7) Patients with the following CNS metastasis:

i) Patients who have developed new or progressive brain metastasis following prophylactic and/or therapeutic cranial radiation (whole brain stereotactic radiation).

ii) Patients with symptomatic CNS metastasis (a patient with brain metastasis who received cranial radiotherapy is eligible if asymptomatic for neurological symptoms for ≥2 weeks after cranial radiotherapy and is off corticosteroids for treatment of CNS metastasis. Patients with asymptomatic brain metastases are eligible to be enrolled directly to the study).

iii) Patients with carcinomatous meningitis;

8) Unable to discontinue the use of strong CYP3A4 or UGT1A1 inhibitors at least 1 week or strong CYP3A4 inducers at least 2 weeks prior to receiving the first dose of irinotecan liposome injection;

9) Presence of another active malignancy; or

10) Investigational therapy administered within 4 weeks, or within a time interval less than at least 5 half-lives of the investigational agent, whichever is less, prior to the first scheduled day of dosing in this study.

Hematologic, Biochemical and Organ Function Exclusion Criteria

1) Severe arterial thromboembolic events (e.g. myocardial infarction, unstable angina pectoris, stroke) less than 6 months before inclusion; 2) NYHA Class III or IV congestive heart failure, ventricular arrhythmias, or uncontrolled blood pressure; 3) Active infection (e.g. acute bacterial infection, tuberculosis, active hepatitis B or active HIV) which in the investigator's opinion might compromise the patient's participation in the trial or affect the study outcome; 4) Known hypersensitivity to any of the components of irinotecan liposome injection, other liposomal products, or topotecan; or Clinically significant gastrointestinal disorder including hepatic disorders, bleeding, inflammation, occlusion, or diarrhea>grade 1.

Length of Study

It is intended that patients will be treated until disease progression or unacceptable toxicity. Following treatment discontinuation, patients will return to the study site for a 30 day follow up visit. After this visit, patients will continue to be followed for overall survival status by phone or a visit to the study site once every month until death or study closure, whichever occurs first.

Method of Assigning Patients to Treatment Groups

Part 1a:

After all screening assessments have been completed and the first patient reported outcome assessment has been completed, eligible patients will enter Part 1a.

Part 1b:

Part 1b will be initiated following dose selection in Part 1a.

After all screening assessments have been completed and the first patient reported outcome assessment has been completed, eligible patients will be randomized using a computerized interactive web response system (IWRS), in a 1:1 ratio, to one of the following treatment arms: Randomization in Part 1b will use a minimization procedure (McEntegart, 2003) accounting for the Part 2 stratification factors.

Arm 1a (experimental arm): irinotecan liposome injection

Arm 1b (control arm): IV topotecan

Randomization must occur within 7 days of planned dosing.

Part 2:

Part 2 will be initiated upon passing the stopping criteria and based on the decision of the Sponsor in consultation with the academic steering committee.

After all screening assessments have been completed and the first patient reported outcome assessment has been completed, eligible patients will be randomized using a computerized interactive web response system (IWRS), in a 1:1 ratio, to one of the following treatment arms:

Arm 2a (experimental arm): irinotecan liposome injection

Arm 2b (control arm): IV topotecan

Randomization must occur within 7 days of planned dosing. The randomization will be stratified based on the following prognostic factors:

Region (North America vs. Asia vs. Other)

Platinum sensitivity (sensitive vs. resistant)

Disease stage (limited vs. extensive) at diagnosis

Performance status (ECOG 0 vs. 1)

Prior immunotherapy (yes vs. no)

Platinum resistant patients are defined as patients with disease that either progressed during first-line platinum containing therapy or within 90 days of its completion. Platinum sensitive patients are defined as patients with disease that progressed after 90 days of completion of first line platinum containing therapy.

Administration of Irinotecan Liposome Injection

Part 1a:

Irinotecan liposome injection will be administered at a dose of 70 mg/m2 (strength expressed based on irinotecan free base; approximately equivalent to 80 mg/m2 of the anhydrous salt) IV over 90 minutes, every 2 weeks in a 6-week cycle. Should the 70 mg/m2 dose be deemed tolerable and 90 mg/m2 is explored, irinotecan liposome injection should be administered at 90 mg/m2 (strength expressed based on irinotecan free base; approximately equivalent to 100 mg/m2 of the anhydrous salt) IV over 90 minutes, every 2 weeks in a 6-week cycle.

Part 1b & 2:

Irinotecan liposome injection will be administered at a dose of 90 mg/m2 (strength expressed based on irinotecan free base; approximately equivalent to 100 mg/m2 of the anhydrous salt): IV over 90 minutes, every 2 weeks in a 6-week cycle (unless deemed unacceptable in Part 1).

Prior to administration, the appropriate dose of irinotecan liposome injection must be diluted in 5% Dextrose Injection (D5W) or 0.9% Sodium Chloride Injection to a final volume of 500 mL. Care should be taken not to use any diluents other than D5W or 0.9% sodium chloride.

UGT1A1*28 Monitoring

UGT1A1*28 genotype will be collected on all patients and assessed centrally. Results will be provided to the site and to the Sponsor. Sites will also be asked to include the result from the UGT1A1*28 genotyping on the SAE reporting form.

All patients treated with irinotecan liposome injection, regardless of the results of the UGT1A1*28 genotype, will be treated with the same starting dose of irinotecan liposome injection and will follow the same dose reduction rules. During the regular safety monitoring of patients during the study, as will be conducted by the sponsor medical monitor(s) and by the DMC (in Part 2), the safety and PK of UGT1A1*28 homozygous patients will be compared to those who are non-homozygous for UGT1A1*28 to determine whether any different dosing strategy (such as a lower starting dose and/or different dose reduction for irinotecan liposome injection) is required for patients who are homozygous for UGT1A1*28. The first safety DMC meeting will occur after the 30th patient completed once cycle of treatment or discontinued treatment, whichever occurs first. No association between UGT1A1*28 and safety is expected in patients treated with topotecan.

Study Treatments

Irinotecan Liposome Injection:

Part 1a: (Safety Run-In)

Irinotecan liposome injection 70 mg/m$^2$ (strength expressed as irinotecan free base; approximately equivalent to 80 mg/m$^2$ of the anhydrous salt) IV over 90 minutes, every 2 weeks in a 6 week cycle) OR irinotecan liposome injection 90 mg/m$^2$ (strength expressed as irinotecan free base; approximately equivalent to 100 mg/m$^2$ of the anhydrous salt) IV over 90 minutes, every 2 weeks in a 6 week cycle.

Part 1b and Part 2:

Arm 1a and 2a (Experimental Arm):

Irinotecan liposome injection 90 mg/m$^2$ (strength expressed as irinotecan free base; approximately equivalent to 100 mg/m$^2$ of the anhydrous salt): IV over 90 minutes, every 2 weeks in a 6 week cycle (unless deemed unacceptable in Part 1).

Arm 1b and 2b (Control Arm):

Topotecan 1.5 mg/m$^2$: IV over 30 minutes daily for 5 consecutive days, every 3 weeks in a 6 week cycle.

Irinotecan Liposome Injection:

Part 1a, Part 1b Arm 1a and Part 2 Arm 2a:

Supportive care measures should follow the guidelines outlined in the prescribing information for ONIVYDE®. Up to two dose reductions of irinotecan liposome injection are permitted for toxicities. The use of prophylactic G-CSF (both short and long acting growth factor is acceptable, based on investigator preference) with the second or later doses of irinotecan liposome injection is allowed, based on investigator judgment.

Topotecan:

Part 1b Arm 1b and Part 2 Arm 2b (IV Topotecan)

The intended dose for topotecan is 1.5 mg/m2 IV for 5 consecutive days every 3 weeks. The dose, administration and dose reductions should follow the guidance as outlined in the prescribing information for IV topotecan.

Patients randomized to treatment with topotecan should be considered for prophylactic G-CSF in all cycles starting 24 hours following the last dose (both short and long acting growth factor is acceptable, based on investigator preference). Up to two dose reductions of topotecan per patient are permitted for toxicities. Dose delays are permitted to allow recovery from treatment-associated toxicities. Prophylactic antibiotics are recommended for patients at high risk of infectious complications.

Investigational Product:

Irinotecan liposome injection (also known as nal-IRI, pegylated liposomal irinotecan hydrochloride trihydrate, MM-398, PEP02, BAX2398 and ONIVYDE®) is a sterile, white to slightly yellow opaque isotonic liposomal dispersion. Each 10 mL single-dose vial contains 43 mg irinotecan free base at a concentration of 4.3 mg/mL. The liposome is a unilamellar lipid bilayer vesicle, approximately 110 nm in diameter, which encapsulates an aqueous space containing irinotecan in a gelated or precipitated state as the sucrose octasulfate salt. It will be supplied as sterile, single-use vials containing 43 mg irinotecan free base at a concentration of 4.3 mg/mL. Irinotecan liposome injection must be stored refrigerated (2 to 8° C., 36 to 46° F.) with protection from light. Do not freeze.

Part 1a

A dose will be decided to be acceptable for proceeding to Part 1b if the number of patients with DLTs does not exceed 1 in a cohort of 6 patients. Based on this rule, the probabilities to proceed to Part 1b at a dose as a function of true DLT probability rate are shown in Table 6.

TABLE 6

| True rate of unacceptable Toxicity | Probability to advance to randomization |
|---|---|
| 0.05 | 0.97 |
| 0.10 | 0.89 |
| 0.15 | 0.77 |
| 0.20 | 0.65 |
| 0.25 | 0.53 |
| 0.30 | 0.42 |
| 0.35 | 0.32 |
| 0.40 | 0.23 |

Part 1b

The purpose of Part 1b is to provide a pilot sample of safety and efficacy data in a randomized setting. The sample size for Part 1b was selected for practical purposes to enable curtailment of the study if irinotecan liposome injection is observed to be substantially inferior to topotecan with regard to benefit/risk.

An efficacy rule, based on the observed PFS rate at 12 weeks, is implemented in this protocol as a formal stopping rule, while additional data will also be considered and may also result in a decision to not proceed to Part 2. The operating characteristics of the formal stopping rule, given the study design in Part 1b, are described below.

Using a binomial distribution to approximate and assuming the true proportion of progression-free patients at 12 weeks within the control group is 0.55, the probability that the study would be stopped, as a function of the true rate for the irinotecan liposome injection arm, is shown in Table 7.

TABLE 7

| Irinotecan liposome injection PFS rate at 12 weeks | Absolute Δ to control | Probability stop given rules |
|---|---|---|
| 0.75 | 0.20 | 0.002 |
| 0.70 | 0.15 | 0.011 |
| 0.65 | 0.10 | 0.038 |
| 0.60 | 0.05 | 0.101 |
| 0.55 | 0 | 0.211 |
| 0.50 | −0.05 | 0.363 |
| 0.45 | −0.10 | 0.536 |

TABLE 7-continued

| Irinotecan liposome injection PFS rate at 12 weeks | Absolute Δ to control | Probability stop given rules |
|---|---|---|
| 0.40 | −0.15 | 0.698 |
| 0.35 | −0.20 | 0.827 |

A final treatment comparison of PFS will be carried out via a log-rank test when tumor assessments have been completed for all patients in Part 1b. If the censoring rate is assumed to be 10%, it is expected that 45 events would have occurred at the time of the final analysis. If the PFS hazard ratio is 0.64 (e.g. irinotecan liposome injection extends median PFS from 3.5 to 5.5 months), then this analysis would have approximate 75% power to detect the treatment difference with a one-sided level 0.20 test.

Part 2

The primary endpoint is overall survival (OS).

A total of 420 patients will be randomized in a 1:1 ratio to the two treatment arms. Follow-up until at least 333 OS events are observed across the two treatment arms provides at least 85% power to detect a true hazard ratio of HR≤0.714 (mOS: 7.5 v 10.5 months) using a stratified log-rank test (stratified by region (North America vs. Asia vs. Other) and platinum sensitivity (sensitive vs. resistant)) with overall 1-sided significance level of 0.025 (adjusted for interim analyses).

Assuming enrollment over 25 months with a ramp-up to 21 patients per month and lost-to-follow-up rate of 5% across both treatment arms, the timing of the primary analysis is expected to be at 39 months.

An interim analysis for futility will be conducted when approximately 30% of the planned final number of OS events (i.e., 100 of 333 OS events) has been observed in the intent-to-treat (ITT) population. In the event that the study proceeds, a second interim analysis will occur to evaluate both futility and efficacy when approximately 210 OS events (63% of planned OS events and 50% of expected events in the entire study population) have occurred.

General:

Categorical variables will be summarized by frequency distributions (number and percentages of patients) and continuous variables will be summarized by descriptive statistics (mean, standard deviation, median, minimum, maximum).

The efficacy and safety of nal-IRI in Part 1 will be reported descriptively using the same outcome measures as in Part 2. In addition, adverse events occurring in Part 1 of the study will be described in detail.

Patients enrolled and treated with study drug in Part 1 will comprise the Part 1 safety population. The safety and efficacy of these patients will be presented descriptively.

Patients randomized in Part 2 will comprise the intent-to-treat (ITT) population. This will be the population that is evaluated in comparison to evaluate the efficacy of the experimental arm. In the ITT analyses of efficacy, each patient will be considered according to the randomized treatment assignment. Patients who received any part of any study drug will define the Part 2 safety population.

For stratified analyses, stratification factors will be the randomization stratification factors of region (North America, Asia, Other) and platinum sensitivity (sensitive, resistant). Classification of stratification factors will be according to the randomization.

Primary Efficacy Analysis (Part 2):

OS is defined as the number of months from the date of randomization to the date of death. Patients without observed death at the time of the primary analysis will have OS censored according to the last recorded date alive.

The primary analysis will be performed using a stratified log-rank test comparing the OS difference between two treatment arms with 1-sided level of significance at 0.025. Stratification factors will include the randomization stratification factors and classification will be according to the randomization. Kaplan-Meier methods will be used to estimate median OS (with 95% confidence intervals) and to display OS time graphically. A stratified Cox proportional hazards model will be used to estimate hazard ratio and its corresponding 95% confidence interval. Sensitivity analyses for OS will be described in the Statistical Analysis Plan (SAP).

Key Secondary Analyses (Part 2):

Key secondary endpoints are PFS, ORR, proportion of patients with symptom improvement in dyspnea, in cough, and in fatigue.

Key secondary endpoints will tested no more than once. If the primary endpoint of OS is statistically significant at the interim, testing of secondary endpoints will be tested at the interim. Otherwise secondary endpoints will be tested at the final OS analysis if OS if found to be statistically significant at that analysis. Hypothesis testing of key secondary endpoints will be conducted in a stage wise hierarchical manner (Glimm, E, et al., Statistics in Medicine 2010 29:219-228).

The nominal level for comparison of PFS will depend on whether the test is performed at the interim or at the planned final analysis and will incorporate an α-spending function similar to that used for OS. If OS and PFS are both significant, then ORR and EORTC-QLQ symptoms will be tested at 1-sided 0.025 level (nominal α adjusted based on spending function, as described for PFS) with each p-value adjusted using the Benjamini-Hochberg correction (Benjamini & Hochberg, J. Royal Statistical Soc. B 2005 57, 289-300) for one-sided α level testing of 4 planned comparisons. Adjusted p-values will be reported, using SAS PROC MULTTEST with FDR option or equivalent algorithm. Any parameter which is not statistically significant will be regarded as descriptive and exploratory.

Progression-Free Survival:

Progression-free survival is the time from randomization to the first documented objective disease progression (PD) using RECIST v1.1 or death due to any cause, whichever occurs first. Determination of PFS will be per investigator assessment. If neither death nor progression is observed, data will be censored on the date of the last observed tumor assessment date. Patients without a valid tumor response evaluation at randomization will be censored on the date of randomization. Patients starting a new anti-cancer treatment prior to documented PD will be censored at the date of the last observed tumor assessment prior to start of the new treatment. Patients with documented PD or death after an unacceptable long interval (i.e., 2 or more missed or indeterminate scheduled assessments) will be censored at the time of the last observed non-PD tumor assessment date prior to progression or death.

The difference in PFS between treatments will be evaluated using a stratified log-rank test. Kaplan-Meier methods will be used to estimate median PFS (with 95% confidence intervals) and to display PFS time graphically. A stratified Cox proportional hazards model will be used to estimate the PFS hazard ratio and its corresponding 95% confidence interval.

The difference in PFS between treatments will be evaluated using a stratified log-rank test (stratified by region and platinum sensitivity). Kaplan-Meier methods will be used to estimate median PFS (with 95% confidence intervals) and to display PFS time graphically. A stratified Cox proportional hazards model will be used to estimate the PFS hazard ratio and its corresponding 95% confidence interval. Sensitivity analyses for PFS will be described in the SAP.

Objective Response:

Objective response rate (ORR) is the proportion of patients who achieve partial response or complete response according to RECIST v1.1 guidelines. An estimate of the ORR and its 95% CI will be calculated. The difference in ORR between treatment groups will be compared using Cochran-Mantel-Haenszel method, stratified by region and platinum sensitivity.

Proportion of Patients with Improvement of Lung Cancer Symptoms:

This secondary analysis will consider the patient-reported EORTC-QLQ-LC13 symptom scales for cough, dyspnea, and fatigue, as these are considered most clearly to be disease-related and evaluable for treatment impact with regard to the proportion of patients with improvement. The remaining EORTC-QLQ symptom domains will be assessed in exploratory analyses.

Symptom improvement is defined as achievement and 6-week maintenance of symptom subscale scores at least 10 percentage points of scale (following transformation to 0-100 scale) below baseline. Response classifications will be tabulated by treatment group and statistical analyses will compare the proportions of responders for a given symptom.

For each symptom, the proportion of patients with improvement will be tabulated by treatment group with 95% confidence intervals based on a Normal approximation. The difference in the proportion of patients with symptom improvement will be presented with corresponding 95% confidence intervals. The proportion of patients with improvement in a symptom will be compared between treatment regimens using Cochran-Mantel-Haenszel method, stratified by region and platinum sensitivity.

Safety Analysis:

Safety analyses (adverse events and laboratory analyses) will be performed using the safety population, defined as all patients receiving any study drug. Treatment assignment will be according to actual treatment received. Adverse events will be coded using the latest MedDRA dictionary. Severity will be graded according to the NCI CTCAE version 4.03.

Treatment-emergent adverse events (TEAEs) are defined as any adverse events reported from the date of first study drug exposure to 30 days after the last date of study drug exposure. Frequency and percentages of patients will be summarized for: any grade TEAE, grade 3 or higher TEAE, study-drug related TEAE, serious TEAE, TEAE leading to dose modification, and TEAE leading to study drug discontinuation. Adverse events will be summarized by System Organ Class and preferred term. All adverse event data will be listed by patient.

Laboratory data will be summarized according to parameter type. Where applicable, toxicity grading for laboratory safety parameters will be assigned based on NCI CTCAE version 4.03 criteria.

QTcF Analyses:

The potential of QTcF prolongation with irinotecan liposome injection treatment will be evaluated in patients receiving irinotecan liposome injection in Part 1 of this study. For the primary QTcF prolongation analysis, the predicted changes in QTcF will be obtained from the exposure-QTcF relationship using mixed-effect modeling. Sensitivity analyses will be conducted by evaluating by time point and categorical analyses.

EORTC-QLQ Outcomes

Analysis of the EORTC-QLQ-C30 questionnaires will be performed in accordance with the EORTC guidelines (Fayers, 2001). The subscales of the EORTC QLQ-C30 and the QLQ-LC13 will be scored based on the EORTC scoring manual. Scores will be standardized such that higher scores on the EORTC QLQ-C30 or the QLQ-LC13 will represent higher ("better") levels of functioning and/or a higher ("worse") level of symptoms.

Analysis methods for the proportion of patients with symptom improvement are as described in Key Secondary Analysis (section 11.5.2.3).

Frequency tables by treatment group will be reported for the proportion of patients with symptom improvement for each QLQ-C30 and QLQ-LC13 subscale. Details of additional EORTC-QLQ analyses will be provided in the Statistical Analysis Plan.

Raw standardized subscale scores and changes from baseline in over time will be reported. Mean change scores will be compared between treatment groups descriptively and may be explored via longitudinal modeling (i.e., covariate analysis and repeated measures modeling)

EQ-5D-5L:

Raw score and change from baseline in over time will be reported. Mean change scores will be compared between treatment groups descriptively and explored via longitudinal modeling (i.e., covariate analysis and repeated measures modeling).

Time to CNS Progression:

Is defined as time from randomization to development of CNS progression as defined by the RANO-BM working group (Lin et al Lancet Oncology 2015). Time to CNS progression will be described by Kaplan-Meier methods and treatments will be compared using stratified log-rank test.

Pharmacokinetics (PK) and Pharmacodynamics (PD) Analysis:

Plasma pharmacokinetics (PK) of total irinotecan, SN-38, and topotecan will be quantified from the concentration samples using nonlinear mixed effect modeling. The initial PK analysis will use the empirical Bayesian estimation, however, additional covariate analyses will be performed to evaluate alternative baseline factors specific to SCLC. The resulting PK estimates will be used to evaluate the association between PK and PD (efficacy and safety endpoints). Topotecan PK will be used to provide additional data to understand the results from Part 1b, by comparing the distribution and the association of PK to efficacy/safety in this study to historical values.

Dose Modifications

All dose modifications should be based on worst preceding toxicity.

TABLE 8

Recommended Dose Modifications for Irinotecan Liposome Injection

| Toxicity NCI CTCAE v4.03 Grade[b] | Occurrence | Starting Dose | |
|---|---|---|---|
| | | 70 mg/m² | 90 mg/m² |
| Neutropenia, leukopenia, or thrombocytopenia Grade 3 or 4 Neutropenic fever | First occurrence Second occurrence Third occurrence | 50 mg/m² 43 mg/m² Discontinue | 70 mg/m² 50 mg/m² treatment |

A new cycle of therapy should not begin until the absolute neutrophil count is ≥1500/mm³ (1.5 × 10⁹/L)
A new cycle of therapy should not begin until the platelet count is ≥100,000/mm³ (100 × 109/L)

| Nonhematological toxicities: | | | |
|---|---|---|---|
| All nonhematological toxicities (except asthenia and anorexia): Grade 3 or 4 | Withhold ONIVYDE. Initiate loperamide for late onset diarrhea of any severity. Administer intravenous or subcutaneous atropine 0.25 to 1 mg (unless clinically contraindicated) for early onset diarrhea of any severity. Upon recovery to < Grade 1, resume ONIVYDE as below: | | |
| | First occurrence Second occurrence Third occurrence | 50 mg/m² 43 mg/m² Discontinue | 70 mg/m² 50 mg/m² treatment |

A new cycle of therapy should not begin until serum chemistry parameters resolve to ≤ Grade 1
A new cycle of therapy should not begin until nonhematological toxicities resolve to ≤ Grade 1
For Grade ≥ 3 nausea and vomiting, reduce dose only if occur despite optimal anti-emetic therapy
Asthenia and Grade 3 anorexia do not require any dose modifications

| Interstitial lung disease | First occurrence | Discontinue treatment |
|---|---|---|
| Severe hypersensitivity reaction | First occurrence | Discontinue treatment |

[a]All doses mentioned are based on irinotecan free base
[b]National Cancer Institute Common Terminology Criteria for Adverse Events, version 4.03

Topotecan for Injection

Topotecan should only be started in patients with a baseline neutrophil count of greater than or equal to 1,500/mm3 (1.5×109/L) and a platelet count greater than or equal to 100,000/mm³ (100×10⁹/L).

Topotecan should not be administered in subsequent cycles unless the neutrophil count is ≥1×10⁹/l, the platelet count is ≥100×10⁹/l, and the hemoglobin level is ≥9 g/dl (after transfusion if necessary). Treatment should be delayed to allow sufficient time for recovery and upon recovery, treatment should be administered according to the guidelines in Table 9 below.

Dose reduction of topotecan should occur in case of the following toxicities:

Grade 4 neutropenia (ANC<500/mm3 or <0.5×109/L);

Grade 4 thrombocytopenia (platelet count<25,000/mm3 or <0.5×109/L)

Grade 3 or 4 non-hematological toxicity except nausea and vomiting. In case of nausea and vomiting, dose reduction should occur if Grade 3 or 4 toxicity occurs despite optimal medical management Dose reduction decisions should be based on worst preceding toxicity. Moving from dose level 0 to dose level 2 is permitted. Prophylactic antibiotics are recommended for patients at high risk of infectious complications.

Up to two dose reductions of topotecan per patient are permitted for toxicities as shown in Table 9. If a third dose reduction is needed to manage a toxicity, topotecan treatment should be discontinued.

TABLE 9

Recommended topotecan Dose Modification Scheme for Subsequent Cycles

| Dose Level | Dose Modifications |
|---|---|
| 0 | 1.5 mg/m² IV days 1-5 |
| −1 | 1.25 mg/m² IV days 1-5 |
| −2 | 1.0 mg/m² IV days 1-5 |

The dose of topotecan in patients should be reduced to 0.75 mg/m2/day for five consecutive days if the creatinine clearance is between 20 and 39 mL/min.

Topotecan should be discontinued if a new diagnosis of interstitial lung disease is confirmed.

Example 8: Liposomal Irinotecan Manufacturing

The liposomal irinotecans can be prepared in a multi-step process. First, lipids are dissolved in heated ethanol. The lipids can include DSPC, cholesterol and MPEG-2000-DSPE combined in a 3:2:0.015 molar ratio. Preferably, the liposomes can encapsulate irinotecan sucrose octasulfate (SOS) encapsulated in a vesicle consisting of DSPC, cholesterol and MPEG-2000-DSPE combined in a 3:2:0.015 molar ratio. The resulting ethanol-lipid solution is dispersed in an aqueous medium containing substituted amine and polyanion under conditions effective to form a properly sized (e.g. 80-120 nm) essentially unilamellar liposome containing the substituted amine (in the ammonium form) and polyanion encapsulated within a vesicle formed from the dissolved lipids. The dispersing can be performed, e.g., by mixing the ethanolic lipid solution with the aqueous solution containing a substituted amine and polyanion at the temperature above the lipid transition temperature, e.g., 60-70° C., and extruding the resulting hydrated lipid suspension (multilamellar liposomes) under pressure through one or more track-etched, e.g. polycarbonate, membrane filters with defined pore size, e.g. 50 nm, 80 nm, 100 nm, or 200 nm. The substituted amine can be triethylamine (TEA) and the polyanion can be sucrose octasulfate (SOS) combined in a stoichiometric ratio (e.g., TEA8SOS) at a concentration of about 0.4-0.5N. All or substantially all non-entrapped TEA or SOS is then removed (e.g., by gel-filtration, dialysis or ultrafiltration) prior to contacting the liposome with irinotecan under conditions effective to allow the irinotecan to enter the liposome in exchange with TEA leaving the liposome. The conditions can include one or more conditions selected from the group consisting of: addition of the osmotic agent (e.g., 5% dextrose) to the liposome external medium to balance the osmolality of the entrapped TEA-SOS solution and/or prevent osmotic rupture of the liposomes during the loading, adjustment and/or selection of the pH (e.g. to 6.5) to reduce the drug and/or lipid degradation during the loading step, and increase of the temperature above the transition temperature of the liposome lipids (e.g., to 60-70° C.) to accelerate the transmembrane exchange of TEA and irinotecan. The loading of irinotecan by exchange with TEA across the liposome preferably continues until all or substantially all of the TEA is removed from the liposome, thereby exhausting its concentration gradient across the liposome. Preferably, the irinotecan liposome loading process continues until the gram-equivalent ratio of irinotecan to sucrooctasulfate is at least 0.9, at least 0.95, 0.98, 0.99 or 1.0 (or ranges from about 0.9-1.0, 0.95-1.0, 0.98-1.0 or 0.99-1.0). Preferably, the irinotecan liposome loading process continues until the TEA is at least 90%, at least 95%, at least 98%, at least 99% or more of the TEA is removed from the liposome interior. The irinotecan can form irinotecan sucrosofate within the liposome, such as irinotecan and sucrose octasulfate in a molar ratio of about 8:1. Next, any remaining extra-liposomal irinotecan and TEA is removed to obtain the irinotecan liposome using, e.g., gel (size exclusion) chromatography, dialysis, ion exchange, or ultrafiltration methods. The liposome external medium is replaced with injectable, pharmacologically acceptable fluid, e.g., buffered isotonic saline. Finally, the liposome composition is sterilized, e.g., by 0.2-micron filtration, dispensed into dose vials, labeled and stored, e.g., upon refrigeration at 2-8° C., until use. The liposome external medium can be replaced with pharmacologically acceptable fluid at the same time as the remaining extra-liposomal irinotecan and TEA is removed. The extra-liposomal pH of the composition can be adjusted or otherwise selected to provide a desired storage stability property (e.g., to reduce formation of the lyso-PC within the liposome during storage at 4° C. over 180 days), for example by preparing the composition at a pH of about 6.5-8.0, or any suitable pH value there between (including, e.g., 7.0-8.0, and 7.25). Irinotecan liposomes with the extra-liposomal pH values, irinotecan free base concentration (mg/mL) and various concentrations of sucrose octasulfate can be prepared as provided in more detail as described herein.

DSPC, cholesterol (Chol), and PEG-DSPE were weighed out in amounts that corresponded to a 3:2:0.015 molar ratio, respectively (e.g., 1264 mg/412.5 mg/22.44 mg). The lipids were dissolved in chloroform/methanol (4/1 v/v), mixed thoroughly, and divided into 4 aliquots (A-D). Each sample was evaporated to dryness using a rotary evaporator at 60° C. Residual chloroform was removed from the lipids by placing under vacuum (180 µtorr) at room temperature for 12 h. The dried lipids were dissolved in ethanol at 60° C., and pre-warmed TEA8SOS of appropriate concentration was added so that the final alcohol content was 10% (v/v). The lipid concentration was 75 mM. The lipid dispersion was extruded at about 65° C. through 2 stacked 0.1 µm polycarbonate membranes (Nucleopore) 10 times using Lipex thermobarrel extruder (Northern Lipids, Canada), to produce liposomes with a typical average diameter of 95-115 nm (determined by quasielastic light scattering). The pH of the extruded liposomes was adjusted with 1 N NaOH to pH 6.5 as necessary. The liposomes were purified by a combination of ion-exchange chromatography and size-exclusion chromatography. First, Dowex™ IRA 910 resin was treated with 1 N NaOH, followed by 3 washes with deionized water and then followed by 3 washes of 3 N HCl, and then multiple washes with water. The liposomes were passed through the prepared resin, and the conductivity of the eluted fractions was measured by using a flow-cell conductivity meter (Pharmacia, Upsalla, Sweden). The fractions were deemed acceptable for further purification if the conductivity was less than 15 µS/cm. The liposome eluate was then applied to a Sephadex G-75 (Pharmacia) column equilibrated with deionized water, and the collected liposome fraction was measured for conductivity (typically less than 1 µS/cm). Cross-membrane isotonicity was achieved by addition of 40% dextrose solution to a final concentration of 5% (w/w) and the buffer (Hepes) added from a stock solution (0.5 M, pH 6.5) to a final concentration of 10 mM.

A stock solution of irinotecan was prepared by dissolving irinotecan.HCl trihydrate powder in deionized water to 15 mg/mL of anhydrous irinotecan-HCl, taking into account water content and levels of impurities obtained from the certificate of analysis of each batch. Drug loading was initiated by adding irinotecan at 500 g/mol liposome phospholipid and heating to 60±0.1° C. for 30 min in a hot water bath. The solutions were rapidly cooled upon removal from the water bath by immersing in ice cold water. Extraliposomal drug was removed by size exclusion chromatography, using Sephadex G75 columns equilibrated and eluted with Hepes buffered saline (10 mM Hepes, 145 mM NaCl, pH 6.5). The samples were analyzed for irinotecan by HPLC and phosphate by the method of Bartlett (see Phosphate Determination). For storage, the samples were divided into 4 mL aliquots and the pH was adjusted as indicated in the Results using 1 N HCl or 1 N NaOH, sterile filtered under aseptic conditions, and filled into sterile clear glass vials that were sealed under argon with a Teflon® lined threaded cap and placed in a thermostatically controlled refrigerator at 4° C. At defined time points, an aliquot was removed from each sample and tested for appearance, size, drug/lipid ratio, and drug and lipid chemical stability. The liposome size was determined in the diluted samples by dynamic light scattering using Coulter Nano-Sizer at 90 degree angle, and presented as Mean±Standard deviation (nm) obtained by the method of cumulants.

Example 9: ONIVYDE (MM-398) Liposomal Irinotecan

One preferred example of a storage stable liposomal irinotecan described herein is the product that will be marketed as ONIVYDE (irinotecan liposome injection). ONIVYDE is a topoisomerase inhibitor, formulated with irinotecan hydrochloride trihydrate into a liposomal dispersion, for intravenous use. ONIVYDE indicated for the treatment of metastatic adenocarcinoma of the pancreas after disease progression following gemcitabine-based therapy.

ONIVYDE is a storage stabilized liposome having a pH of about 7.25. The ONIVYDE product contains irinotecan sucrosofate encapsulated in a liposome, obtained from an irinotecan hydrochloride trihydrate starting material. The chemical name of irinotecan is (S)-4,11-diethyl-3,4,12,14-tetrahydro-4-hydroxy-3,14-dioxo1H-pyrano[3',4':6,7]-indolizino[1,2-b]quinolin-9-yl-[1,4'bipiperidine]-1'-carboxylate. The dosage of ONIVYDE can be calculated based on the equivalent amount of irinotecan trihydrate hydrochloride starting material used to prepare the irinotecan liposomes, or based on the amount of irinotecan in the liposome. There are about 866 mg of irinotecan per gram of irinotecan trihydrate hydrochloride. For example, an ONIVYDE dose of 80 mg based on the amount of irinotecan hydrochloride trihydrate starting material actually contains about 0.866×(80 mg) of irinotecan free base in the final product (i.e., a dose of 80 mg/m$^2$ of ONIVYDE based on the weight of irinotecan hydrochloride starting material is equivalent to about 70 mg/m$^2$ of irinotecan free base in the final product). ONIVYDE is a sterile, white to slightly yellow opaque isotonic liposomal dispersion. Each 10 mL single-dose vial contains 43 mg irinotecan free base at a concentration of 4.3 mg/mL. The liposome is a unilamellar lipid bilayer vesicle, approximately 110 nm in diameter, which encapsulates an aqueous space containing irinotecan in a gelated or precipitated state as the sucrose octasulfate salt. The vesicle is composed of 1,2-distearoyl-sn-glycero-3-phosphocholine (DSPC) 6.81 mg/mL, cholesterol 2.22 mg/mL, and methoxy-terminated polyethylene glycol (MW 2000)-distearoylphosphatidyl ethanolamine (MPEG-2000-DSPE) 0.12 mg/mL. Each mL also contains 2-[4-(2-hydroxyethyl)piperazin-1-yl]ethanesulfonic acid (HEPES) as a buffer 4.05 mg/mL and sodium chloride as an isotonicity reagent 8.42 mg/mL. Each vial of ONIVYDE contains 43 mg/10 mL irinotecan free base as a white to slightly yellow, opaque, liposomal dispersion in a single-dose vial.

In one example, an ONIVYDE unit dosage form is a pharmaceutical composition comprising an amount of irinotecan encapsulated liposomes that provide a total amount of about 90 mg/m$^2$ of irinotecan free base, or an amount of irinotecan equivalent to 100 mg/m$^2$ irinotecan hydrochloride trihydrate. The unit dosage form can be an intravenous formulation obtained by diluting a unit dosage form (e.g., a vial) at a concentration of about 4.3 mg irinotecan free base/mL injectable fluid into a total volume of about 500 mL. ONIVYDE is prepared for administering by diluting the isotonic liposomal dispersion from the vial as follows: withdraw the calculated volume of ONIVYDE from the vial. ONIVYDE is diluted into 500 mL 5% Dextrose Injection, USP or 0.9% Sodium Chloride Injection, USP and mix diluted solution by gentle inversion; protect diluted solution from light and administer diluted solution within 4 hours of preparation when stored at room temperature or within 24 hours of preparation when stored under refrigerated conditions [2° C. to 8° C. (36° F. to 46° F.)].

Example 10

Figure 7A:
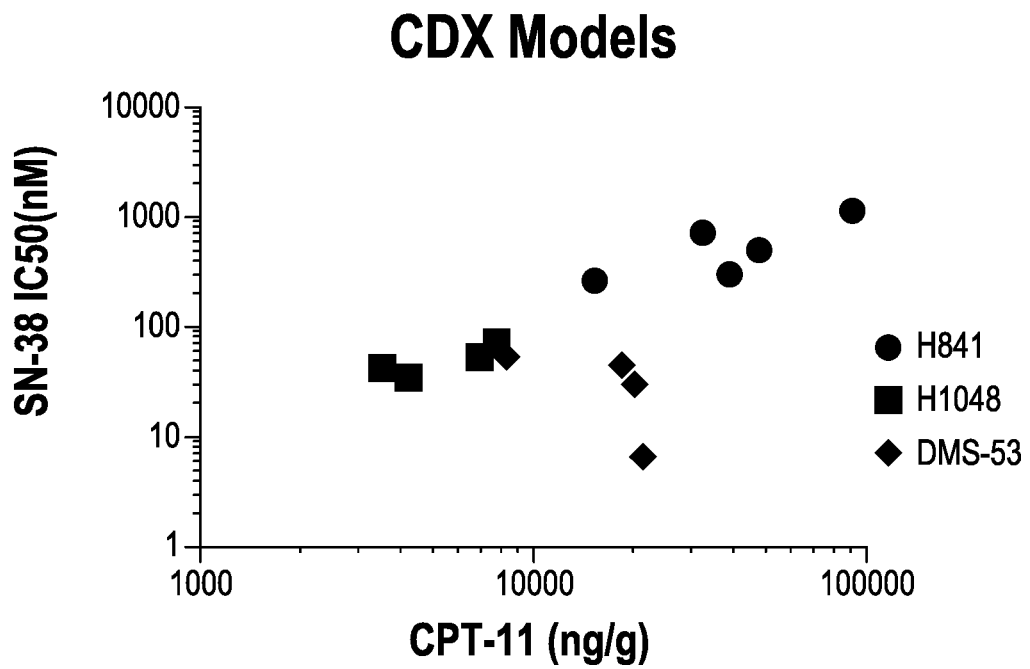
FIG. 7A is a graph showing carboxylesterase (CES) activity; increased tumor SN-38 levels were associated with increased tumor deposition, as assessed by tumor CPT-11 at 24 h post administration in SCLC mouse xenograft models.
Figure 7B:
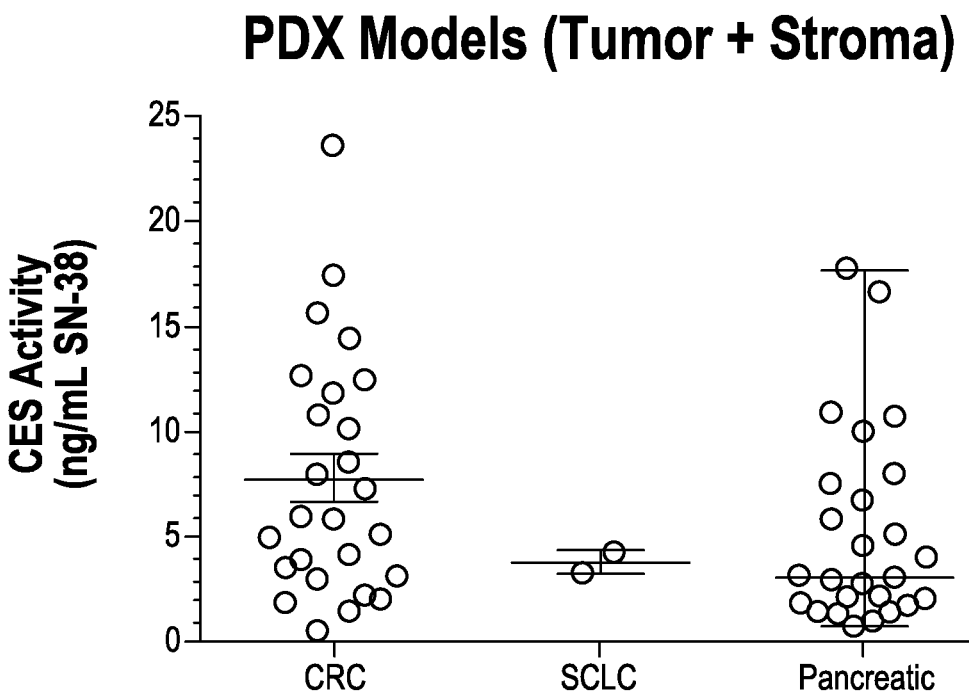
FIG. 7B is a graph showing carboxylesterase (CES) activity; SCLC PDX tumors have CES activity comparable to other indications in which irinotecan is active.
Figure 7C:
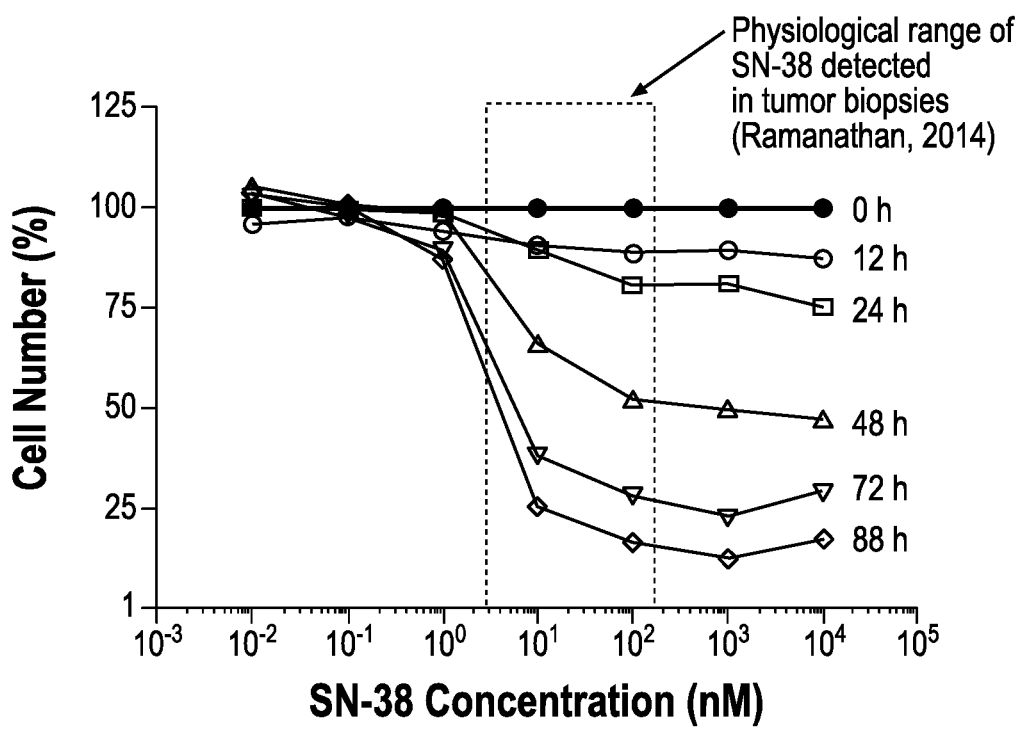
FIG. 7C is a graph showing cell sensitivity; Nal-IRI tumor deposition is consistent with range of SN-38 sensitivity in H1048 SCLC cells.
Figure 7D:
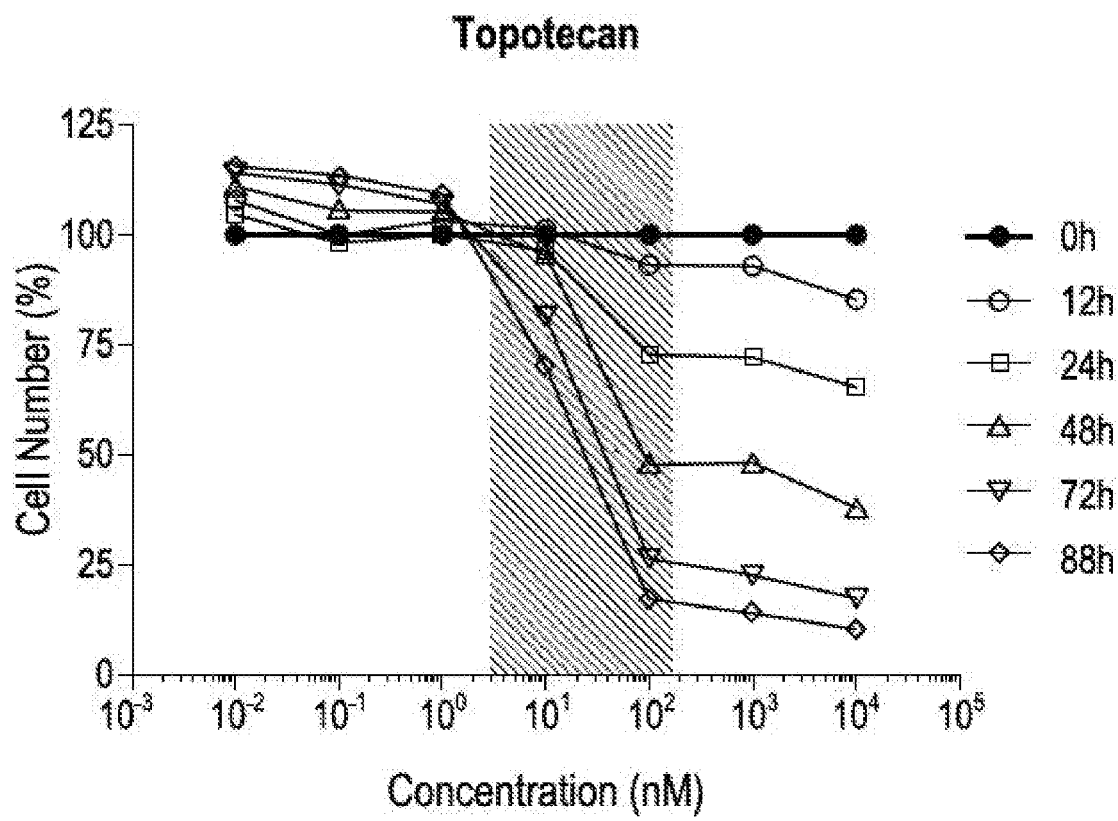
FIG. 7D is a graph showing cell sensitivity; cytotoxicity of Topo1 inhibitors increases with exposure.
Figure 7E:
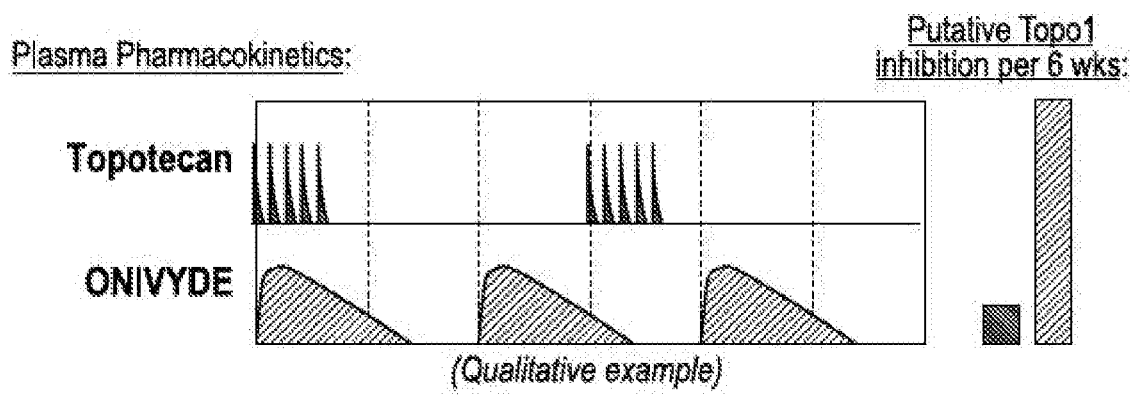
FIG. 7E is a chart showing that topotecan administration is severely limited by toxicity, thus limiting sustained inhibition of topo1 in comparison to Onivyde mediated prolonged SN-38 exposure.

The ability of Nal-IRI to deliver irinotecan and SN-38 to tumors was evaluated in SCLC cell-line derived xenograft (CDX) models (NCI-H1048, DMS-114, H841) in comparison to patient-derived xenograft (PDX) models (CRC, SCLC and pancreatic). Irinotecan liposome injection was administered intravenously to mice bearing xenograft tumors. At 24 hours post administration, mice were sacrificed and tumors were harvested. Irinotecan and SN-38 in tumors were measured by high performance liquid chromatography (HPLC). Data were normalized to injected dose per tumor weight. FIG. 7A shows the increased tumor SN-38 levels were associated with increased tumor deposition, as assessed by tumor CPT-11 at 24 hours post administration in SCLC mouse xenograft models (H841, H1048 and DMS-53). FIG. 7B shows the carboxylesterase (CES) activity in CRC, SCLC, and pancreatic PDX tumors showing that SCLC PDX tumors have CES activity comparable to other indications in which irinotecan is active. Treatment with SN-38 decreased cell viability by >90% in SCLC cell lines (DMS114, NCI-H1048). As shown in FIG. 7C (for NCI-H1048 cells) effective cell growth inhibition was observed between 1-10 nM, with increased cell killing with increased time of exposure over a time-course of up to 88 hours. The concentration range of SN-38 in which cell killing begins to occur coincides with the amount of SN-38 measured from tumor biopsies taken from patients with various solid tumors 72 hours after administration of irinotecan liposome injection (range: 3-163 nM; Ramanathan et al., Eur. J. Cancer, 2014 November; 50:87) is overlaid on the time-dependent SN-38 growth inhibition curves (shown in the area within the dashed lines). Similar effects were seen in DMS-114 cells. Cell growth inhibition kinetics of SN-38 in the cell lines was determined using IncuCyte® ZOOM System. FIG. 7D is a graph showing cell sensitivity; cytotoxicity of Topo1 inhibitors increases with exposure. FIG. 7E is a chart showing that topotecan administration is severely limited by toxicity, thus limiting sustained inhibition of topo1 in comparison to Onivyde mediated prolonged SN-38 exposure.

Figure 8A:
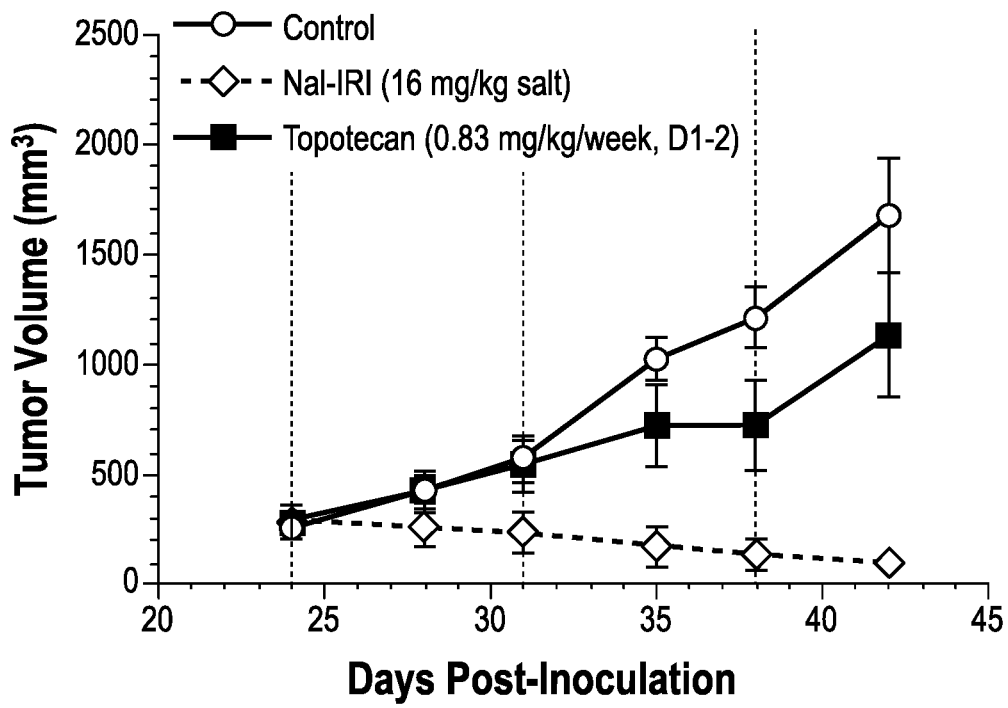
FIG. 8A shows the anti-tumor activity of MM-398 in the DMS-53 xenograft model of SCLC.
Figure 8B:
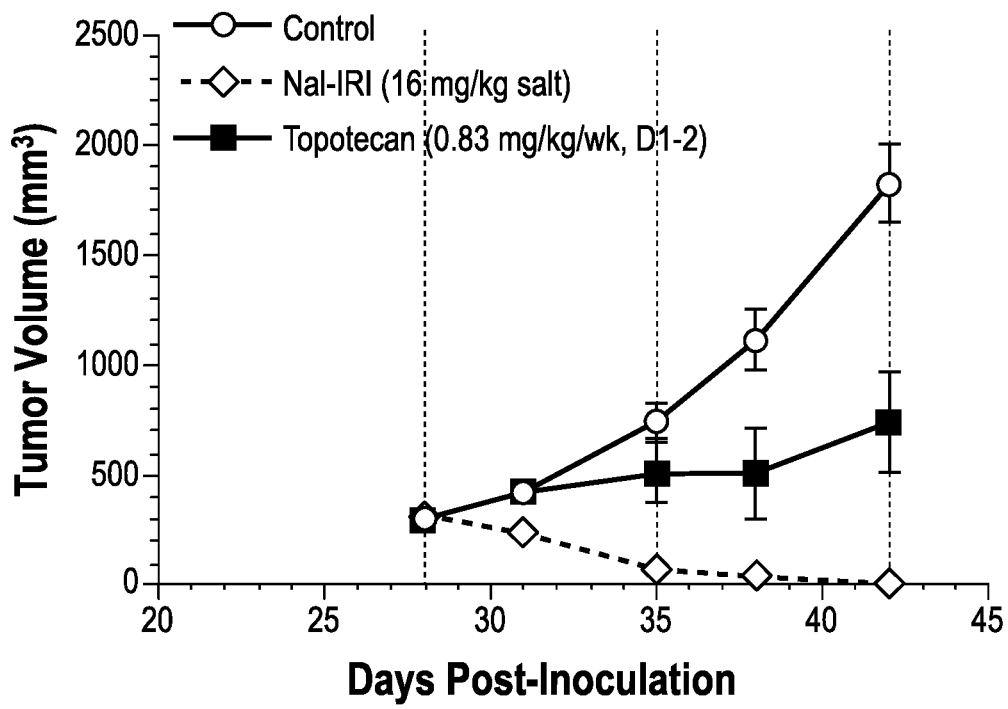
FIG. 8B shows the anti-tumor activity of MM-398 in the HCl-H1048 xenograft model of SCLC.

Example 11: Preclinical Support for Evaluation of Irinotecan Liposome Injection (nal-IRI, MM-398) in Patients with Small Cell Lung Cancer Anti-tumor activity of nal-IRI as a monotherapy was evaluated in DMS-53 and NCI-H1048 xenograft models. Cells were implanted subcutaneously into right flanks of NOD-SCID mice; treatments were initiated when tumors had reached approximately 280 mm$^3$. Nal-IRI was dosed at 16 mg/kg salt, q1w, which is equivalent to a proposed clinical dose of 90 mg/m$^2$ free base, q2w. Topotecan was dosed at 0.83 mg/kg/week, Day 1-2 every 7 days, which approximates a clinical dose intensity of 1.5 mg/m$^2$ (Day 1-5 every 21 days). Tumor metabolite levels of nal-IRI and non-liposomal irinotecan were measured at 24 hours post-injection, using previously established high performance liquid chromatography methods. The results for the monotherapy treatment in DMS-53 are shown in FIG. 8A and the results in NCI-H1048 are shown in FIG. 8B. In FIGS. 8A and 8B the vertical dotted lines indicate days of dosing and the response rates are determined based on tumor volume change from base line: CR: change in tumor volume (TV) <−95%; PR: −95%≤change in TV<−30%; SD: −30%≤change in TV<30%; PD: change in TV≥30%. Nal-IRI displayed significantly greater anti-tumor activity than topotecan based on tumor growth kinetics and overall survival. Furthermore, 7 out of 7 mice in NCI-H1048 model treated with nal-IRI experienced complete tumor regressions after 4 cycles of treatment and maintained for at least 50 days after last dose, compared to 0 out of 7 mice treated with topotecan.

Carboxylesterase activity and sensitivity to SN-38 in SCLC models were comparable to that in indications where nal-IRI or irinotecan HCl has proven to be efficacious clinically (e.g. pancreatic cancer, colorectal cancer). Nal-IRI was found to deliver irinotecan to tumors in SCLC tumors to a similar or greater extent than other tumor types. The tumor irinotecan and SN-38 levels of nal-IRI (16 mg/kg salt) were 12 to 57-fold and 5 to 20-fold higher than nonliposomal irinotecan (30 mg/kg salt), respectively. Nal-IRI demonstrated anti-tumor activity in both xenograft models of SCLC at clinically relevant dose levels, and resulted in complete or partial responses after 4 cycles of treatment, compared to topotecan which have limited tumor growth control.

The anti-tumor activity of MM-398 (Onivyde) in the H841 rat orthotopic xenograft model of SCLC is shown in FIG. 8C which is a graph showing the percent survival of rats treated with control, Onivyde (30 or 50 mg/kg salt), irinotecan (25 mg/kg) or topotecan (4 mg/kg) for days post inoculation. Rats treated with Onivyde at both 30 and 50 mg/kg showed longer survival times that those treated with control, irinotecan or topotecan. MM-398 has anti-tumor activity in multiple SCLC xenograft models. At clinically relevant doses (16 mg/kg/wk MM-398, 0.8 mg/kg/wk topotecan), MM-398 had greater anti-tumor activity and prolonged survival than topotecan.

These studies demonstrated that nal-IRI is more active than topotecan at clinically relevant doses in SCLC preclinical models, and thus support a proposed randomized Phase 3 trial of nal-IRI versus topotecan in patients with SCLC that have progressed on prior platinum-based therapy.

Example 12

Figure 9A:
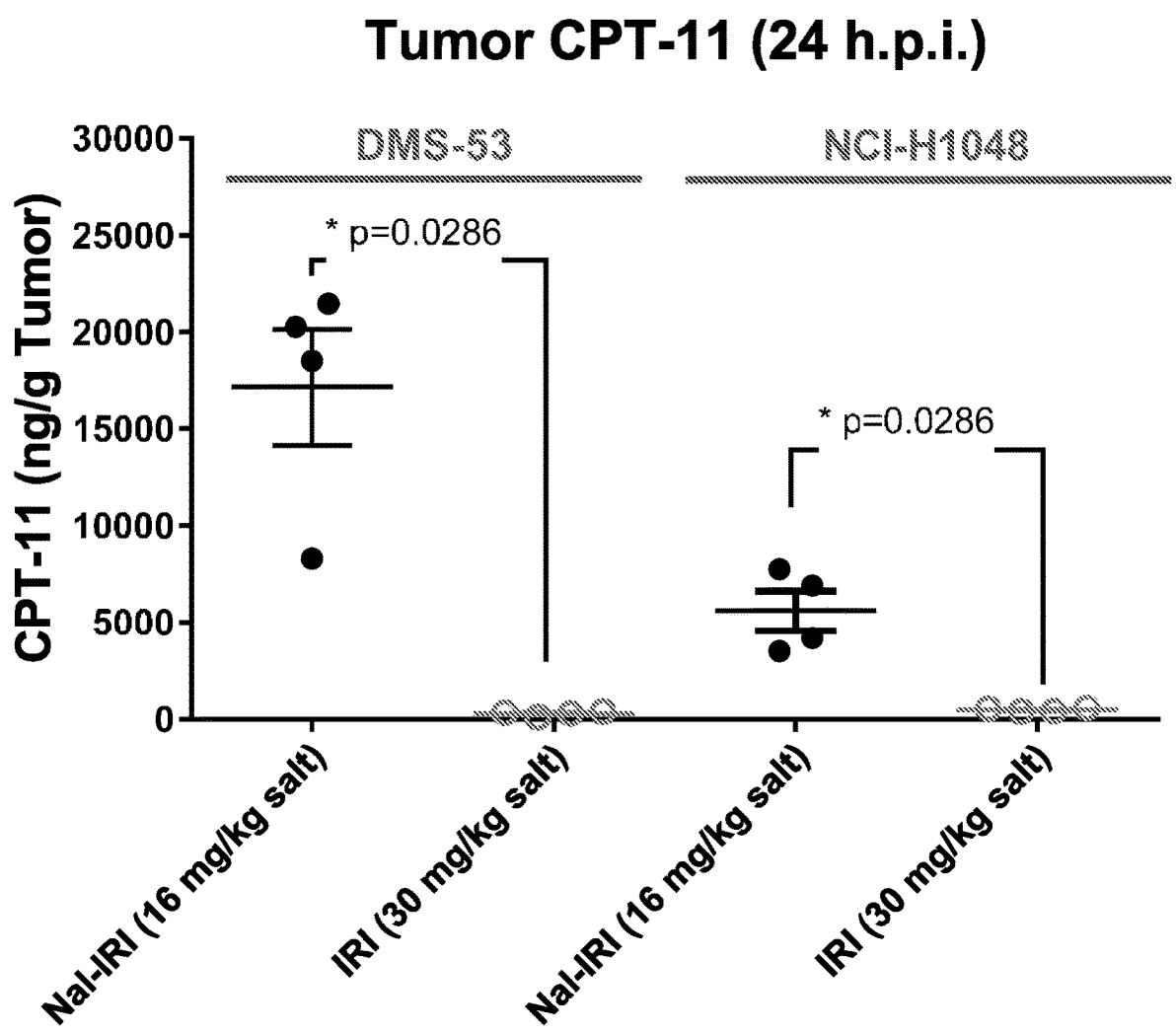
FIGS. 9A and 9B are graphs showing the tumor metabolite levels in SCLC xenograft models treated with MM-398 and nonliposomal Irinotecan. At 24 hours post-injection, (FIG. 9A) CPT-11 and (FIG. 9B) active metabolite SN-38 in tumors were significantly higher for mice treated with MM-398 at 16 mg/kg (salt) compared to nonliposomal irinotecan at 30 mg/kg (salt).
Figure 9B:
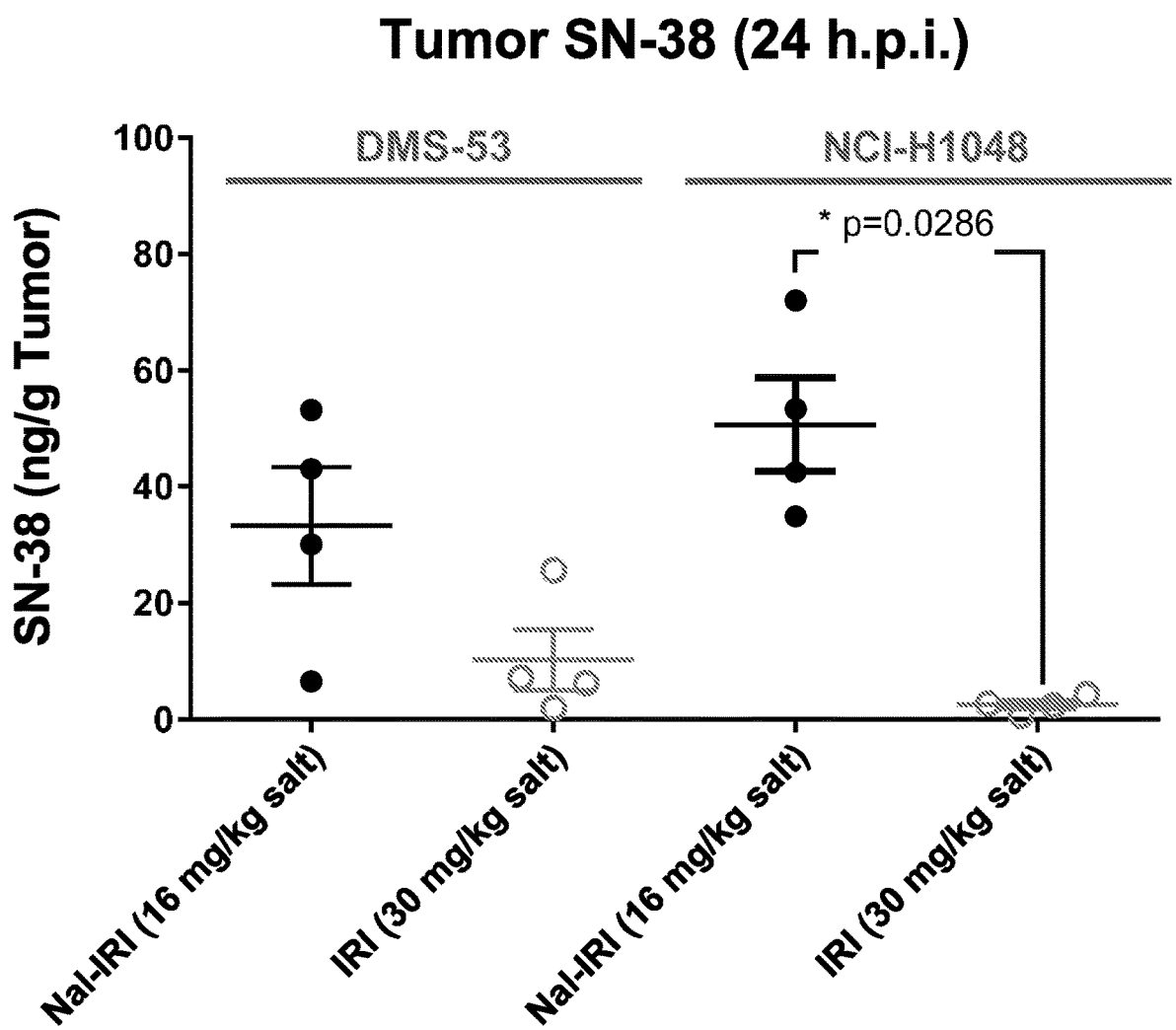
Figures 10A, 10B:
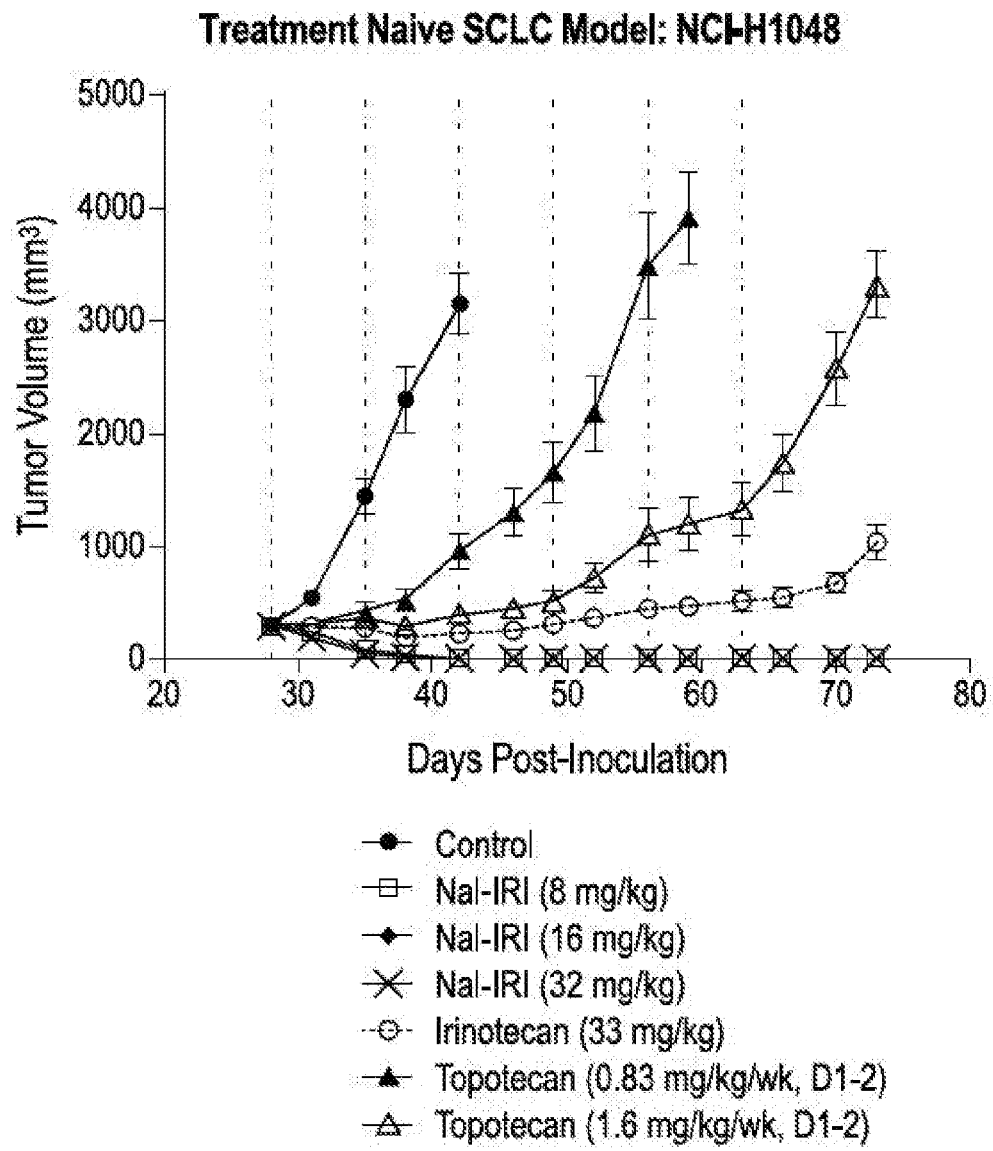
FIGS. 10A and 10B are graphs showing that Nal-IRI is superior to all comparator treatment arms in treatment naïve SCLC xenograft models.
Figure 11B:
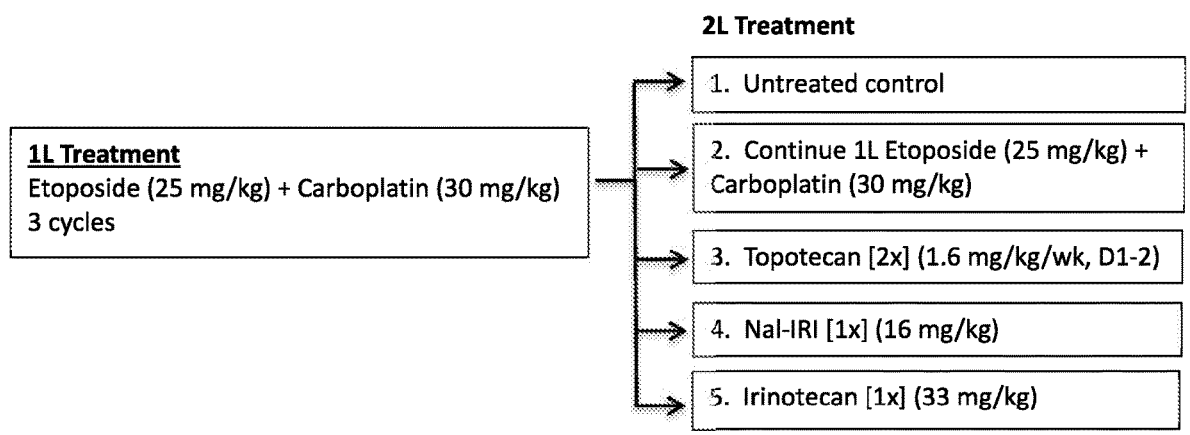
Figure 12:
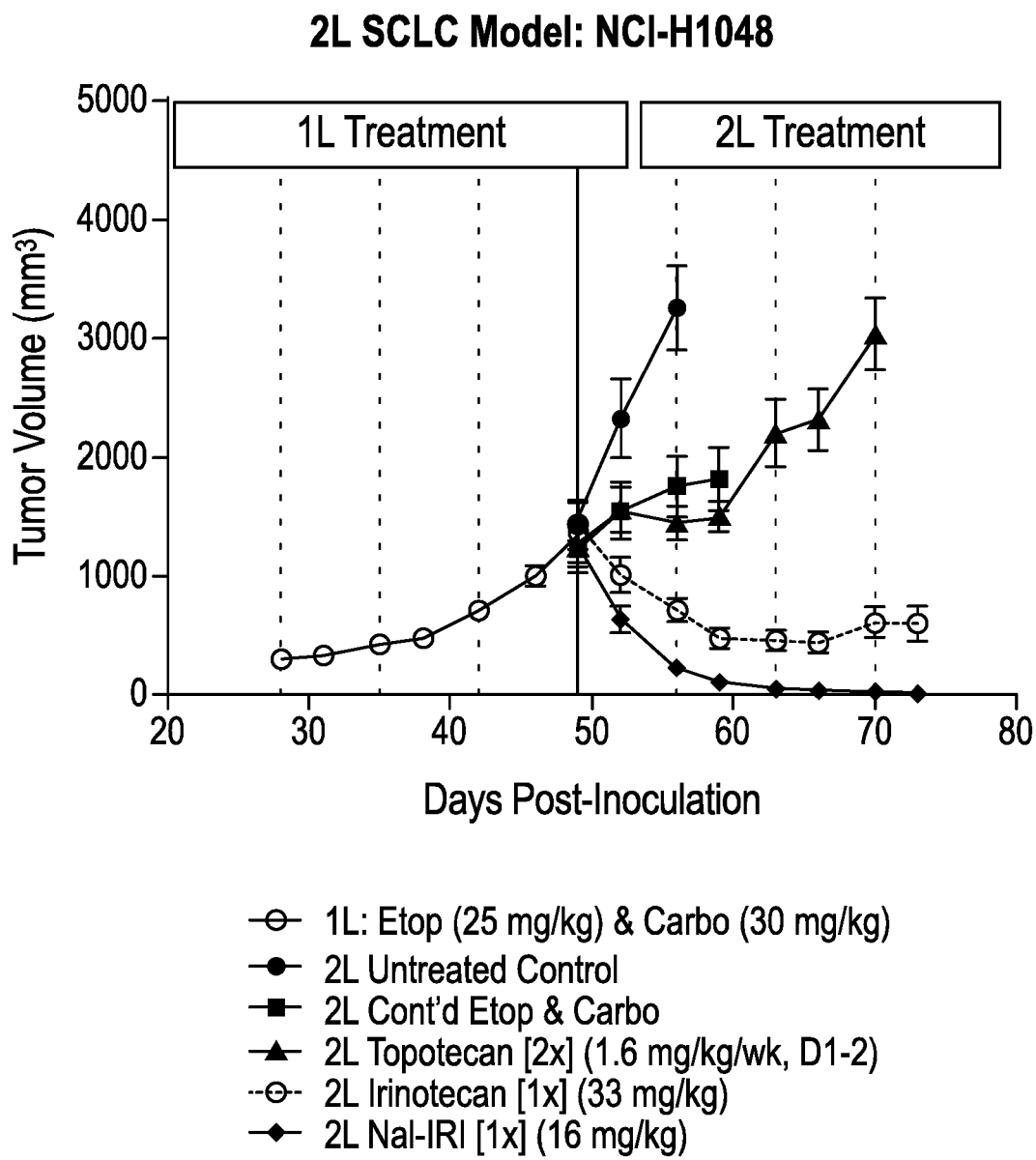
FIG. 12 is a graph showing that Nal-IRI remains effective in platinum-treated SCLC tumors and is superior to topotecan and irinotecan: 2 L SCLC Model: NCl-H1048. In platinum-treated SCLC tumors: Nal-IRI remains active and is trending towards complete response; IRI treatment is active but after 3rd cycle some tumors are trending regrowth; Topotecan (at 2× clinically relevant dose) seems to be active after 1-2 cycles but progress quickly after 3rd dose; Etoposide+carboplatin is not tolerable by the 5th cycle.
Figure 13A:
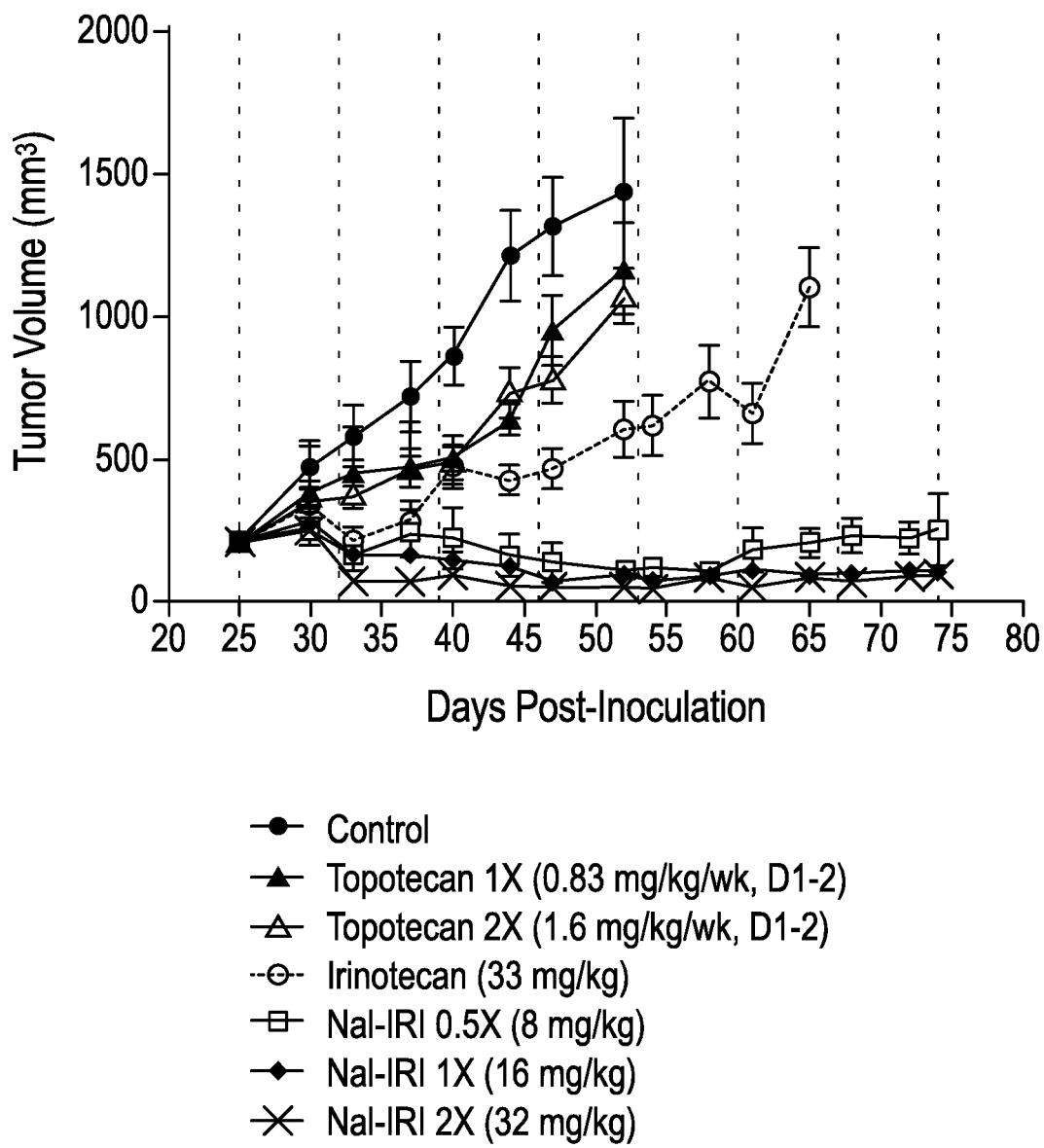
FIGS. 13A and 13B are graphs showing that Nal-IRI is also superior to topotecan and irinotecan in another SCLC xenograft model (DMS-114)
Figure 13B:
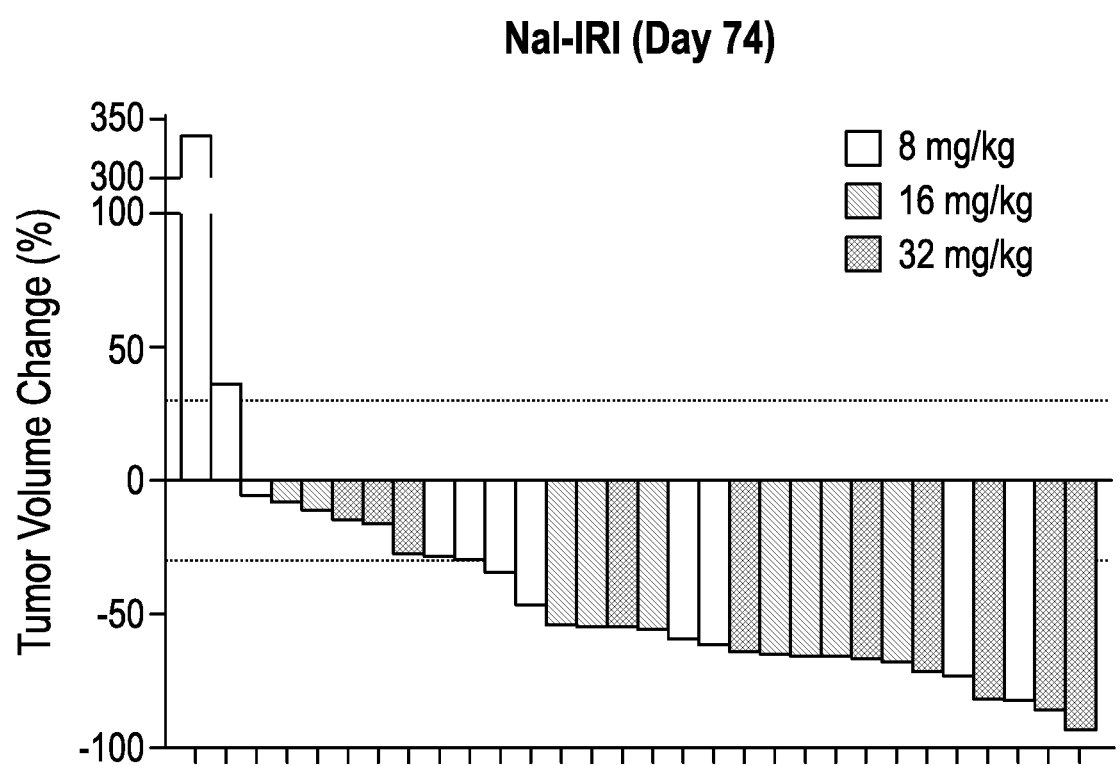
Figure 14A:
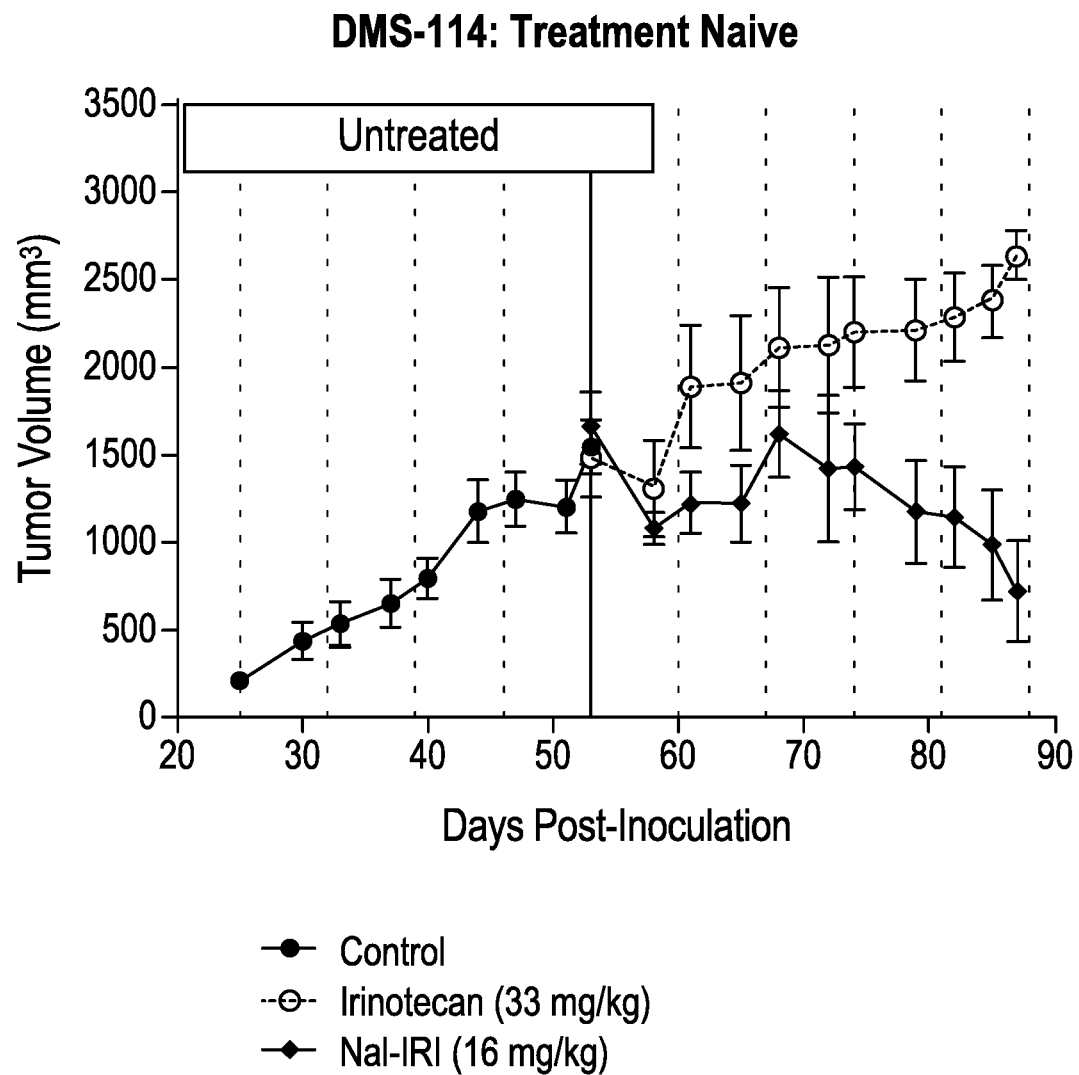
Figure 14B:
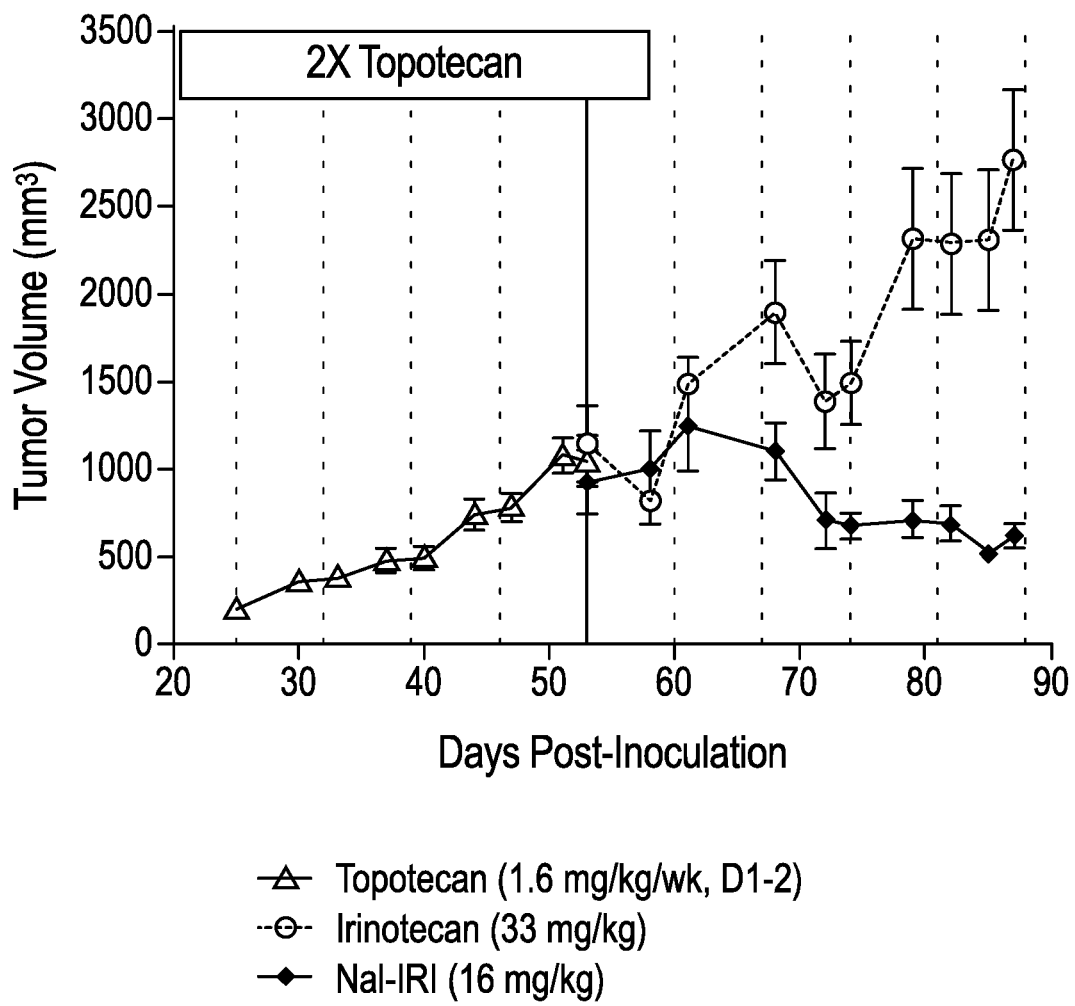
FIG. 14B. DMS-114: Topotecan-Treated.
Figure 14C:
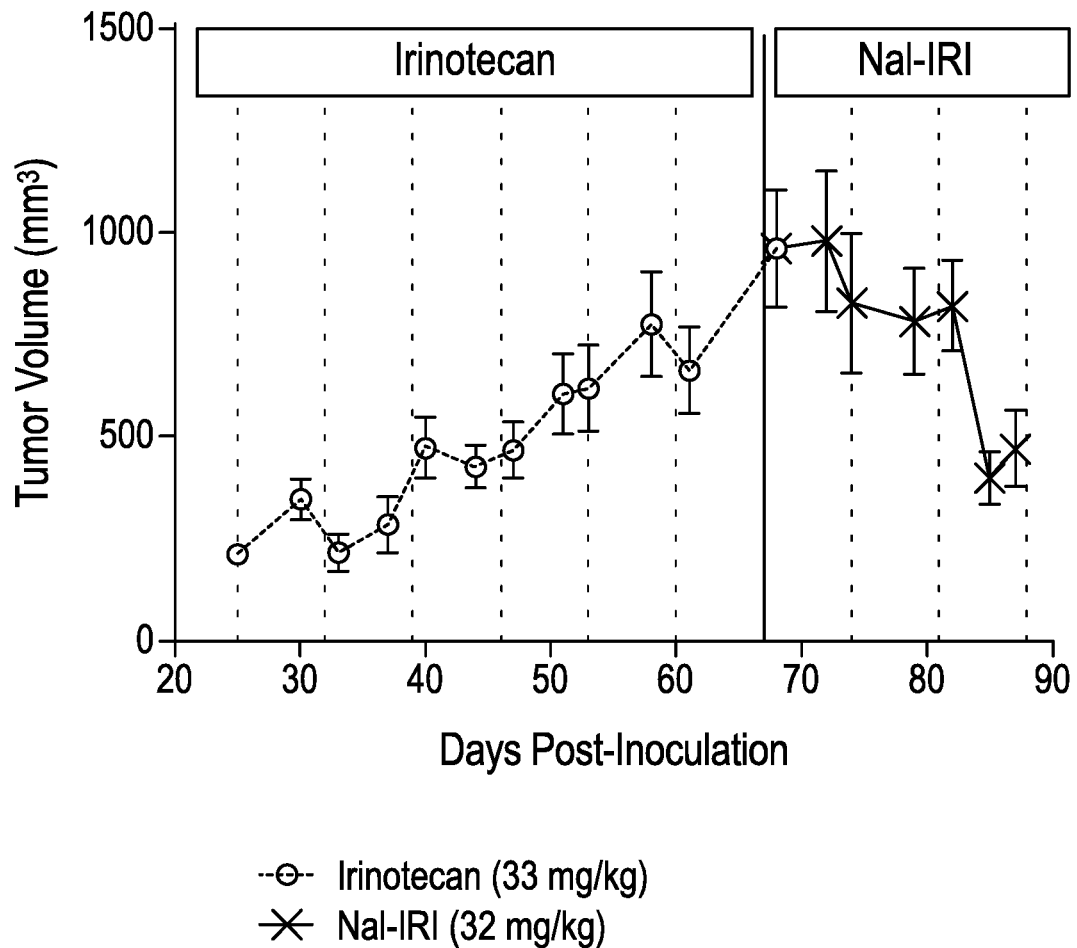
FIG. 14C. DMS-114: Irinotecan-Treated. DMS114 tumors treated with topotecan are responsive to nal-IRI (16 mg/kg) but not irinotecan (33 mg/kg).
Figure 15A:
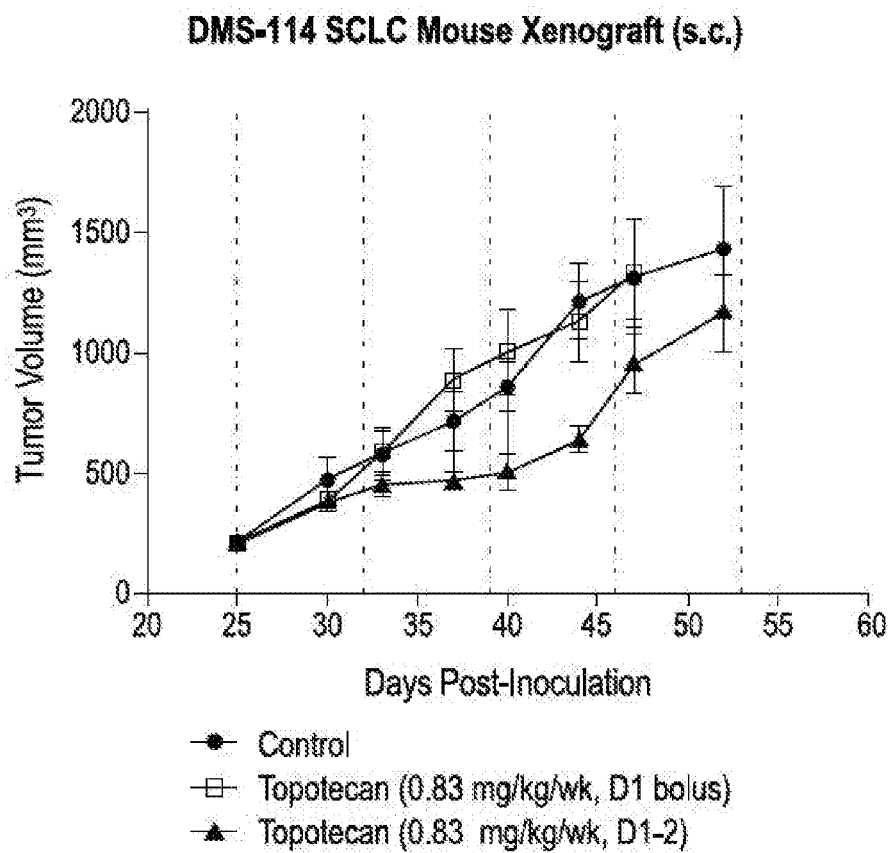
Figure 15B:
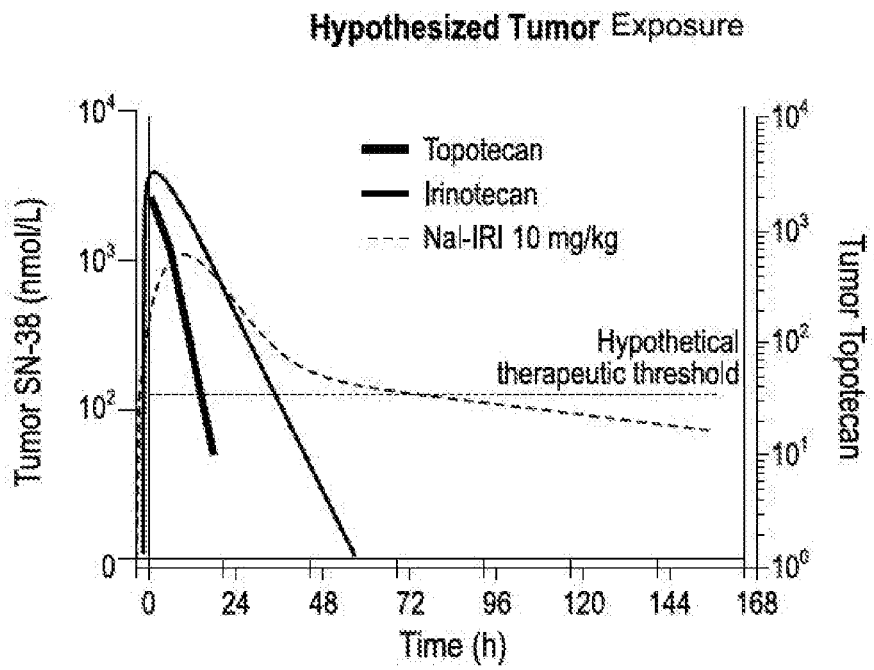
Figure 16A:
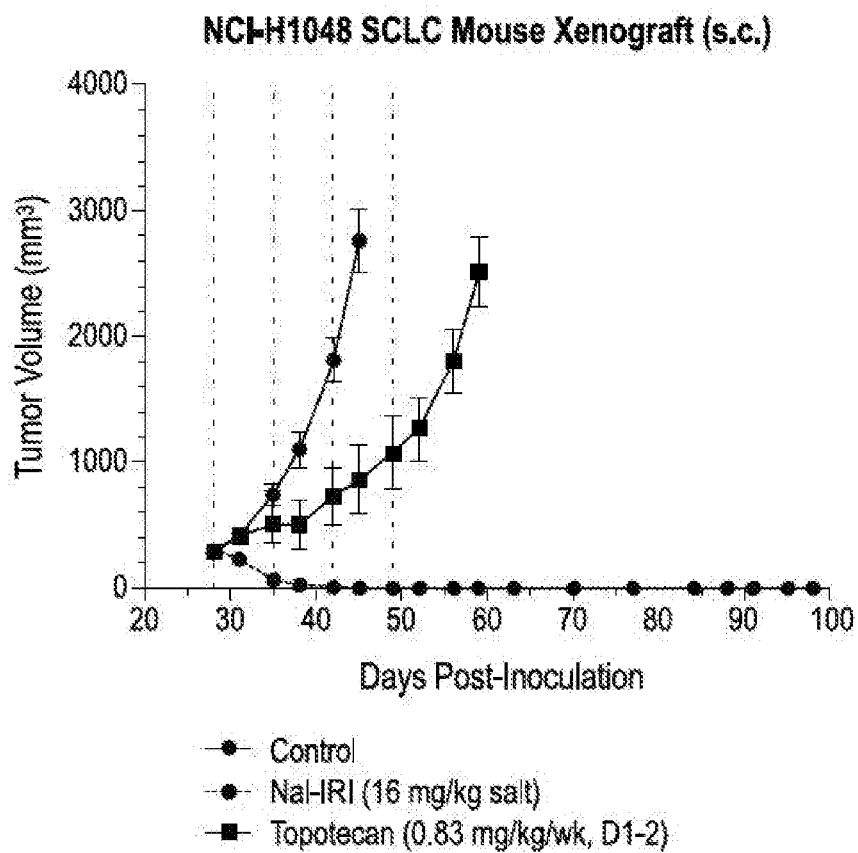
Figure 16B:
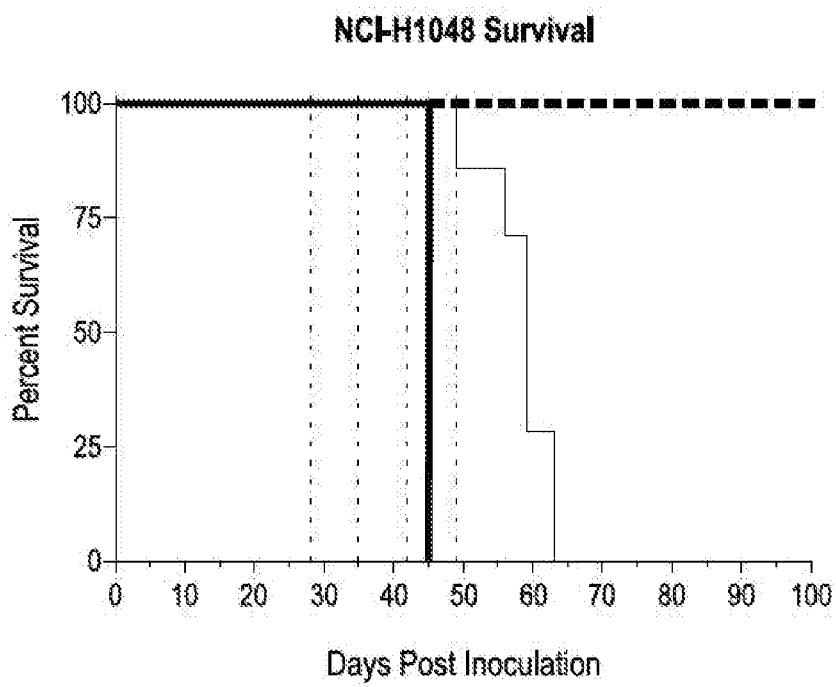
Figure 16C:
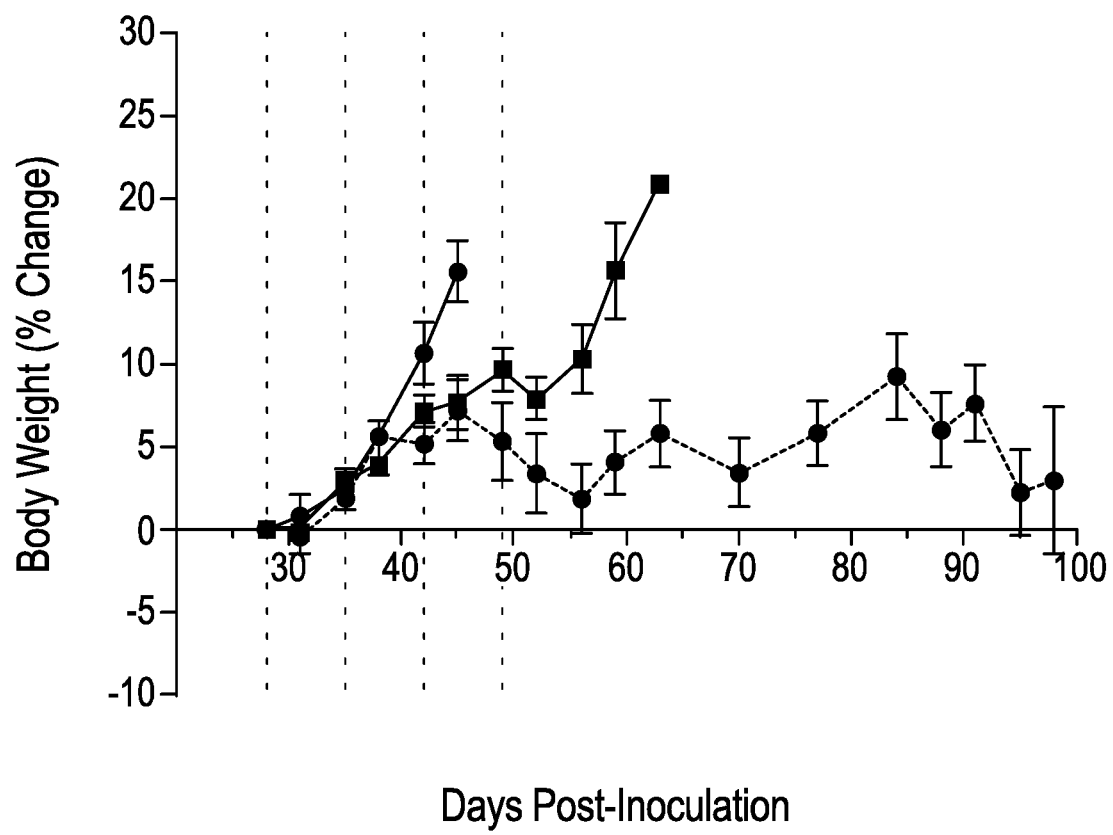
Figure 17A:
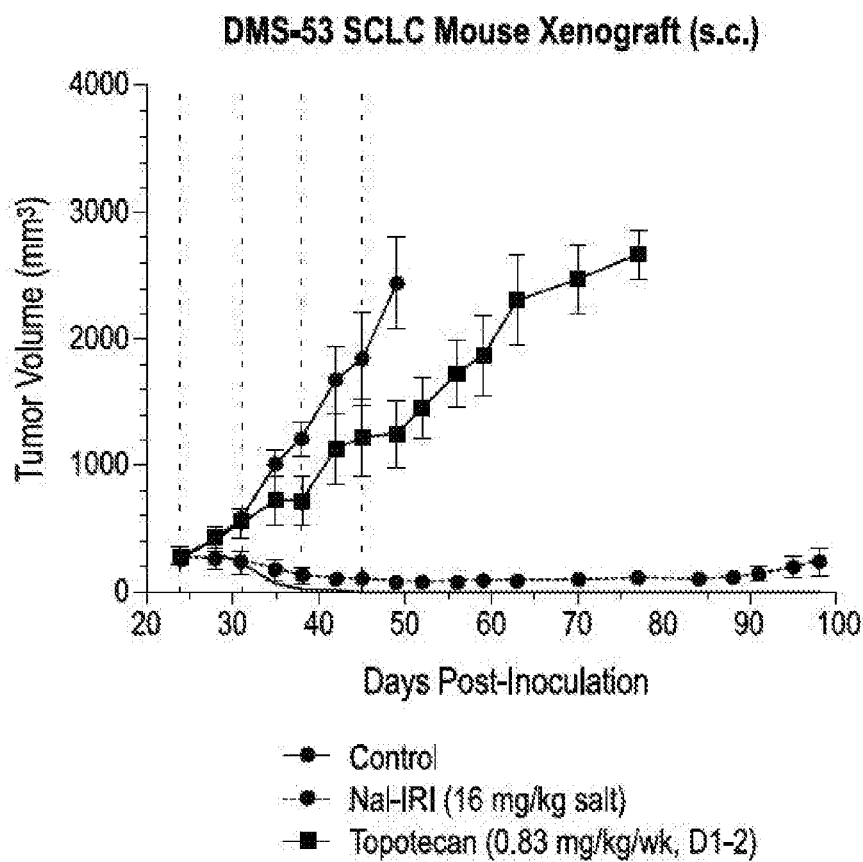
Figure 17B:
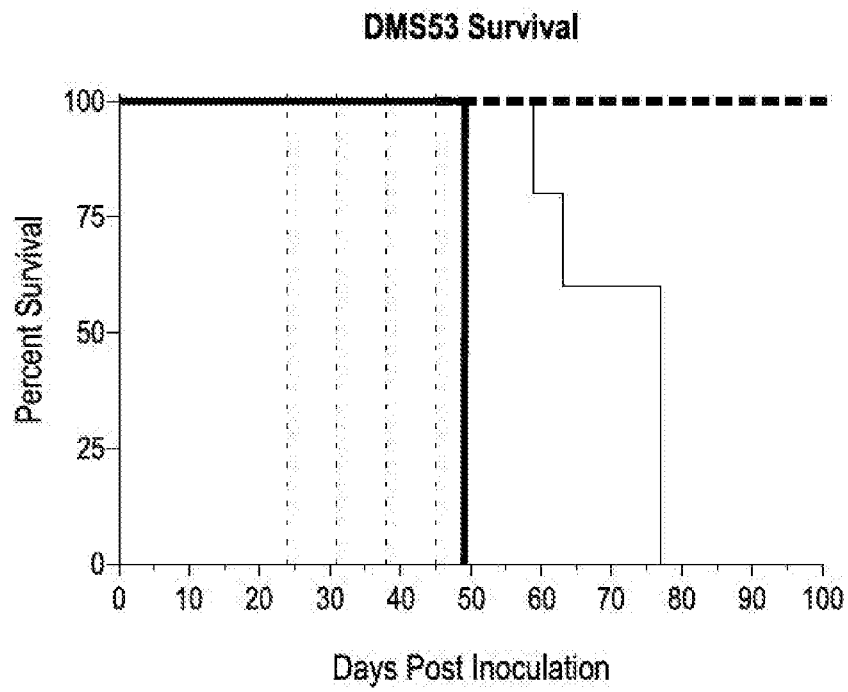
FIG. 17B. Survival.
Figure 18A:
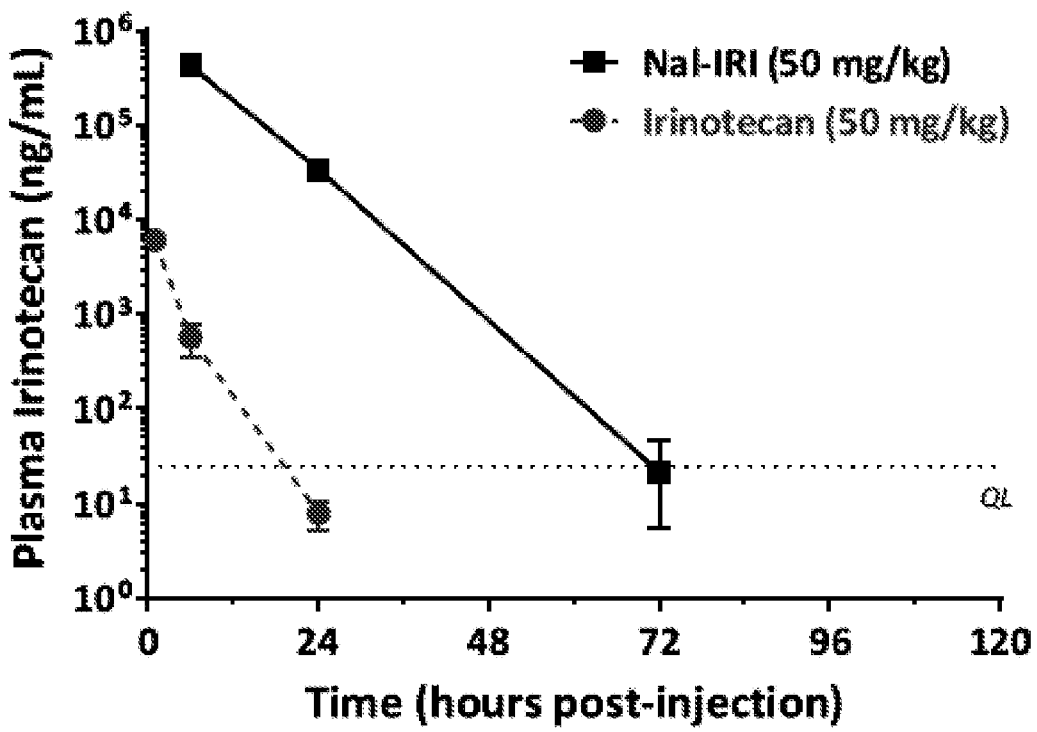
FIGS. 18A and 18B are graphs showing that Nal-IRI increases exposure and sustains delivery of irinotecan and SN-38 (active metabolite) in BxPC-3 mouse xenograft tumors.
Figure 18B:
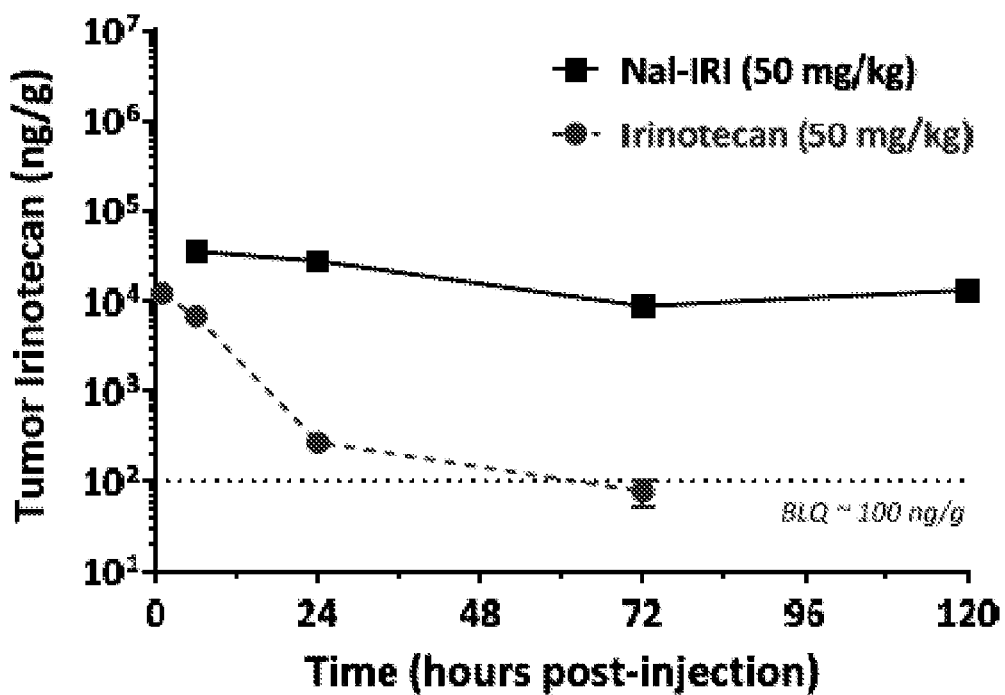

Tumor metabolites levels of nal-IRI were compared to non-liposomal irinotecan in SCLC tumor bearing xenograft models DMS-53 and NCI-H1048 (FIGS. 9A and 9B). Based on body-surface area dosing and scaled to body weight, the clinically-relevant doses of nal-IRI and non-liposomal irinotecan HCl in mice are approximately 16 mg/kg (salt) and 30 mg/kg (salt), respectively. Nal-IRI dosed at 16 mg/kg salt (q1w) is equivalent to a proposed clinical dose of 90 mg/m$^2$ free base, q2w. Irinotecan HCl dosed at 30 mg/kg, q1w, approximates a clinical dose intensity of 300 mg/m$^2$, q3w, which resulted in similar efficacy as topotecan (current standard of care) in second-line SCLC patients (Zhao M L, Bi Q, Ren H X, Tian Q, Bao M L. Clinical observation of irinotecan or topotecan as second-line chemotherapy on treating 43 patients with small-cell lung cancer. Chin Oncol. 2011; 21:156-158).

Using high performance liquid chromatography methods, tumor levels of CPT-11 (FIG. 9A) and the active metabolites SN-38 (FIG. 9B) were measured at 24 hours post-injection (intravenous via tail vein). In both SCLC models, nal-IRI delivered irinotecan to tumors to a greater extent than non-liposomal irinotecan HCl. The tumor CPT-11 and SN-38 levels of nal-IRI (16 mg/kg salt) were 12 to 57-fold and 5 to 20-fold higher than non-liposomal irinotecan (30 mg/kg salt), respectively. The increased tumor CPT-11 and SN-38 delivered by nal-IRI is attributed to the extended circulation as a result of liposomal encapsulation, as well as local activation of liposomal-irinotecan in the tumors (PMID 25273092: Preclinical activity of nanoliposomal irinotecan is governed by tumor deposition and intratumor prodrug conversion. Kalra A V1, Kim J1, Klinz S G1, Paz N1, Cain J1, Drummond D C1, Nielsen U B1, Fitzgerald J B)

Figure 19:
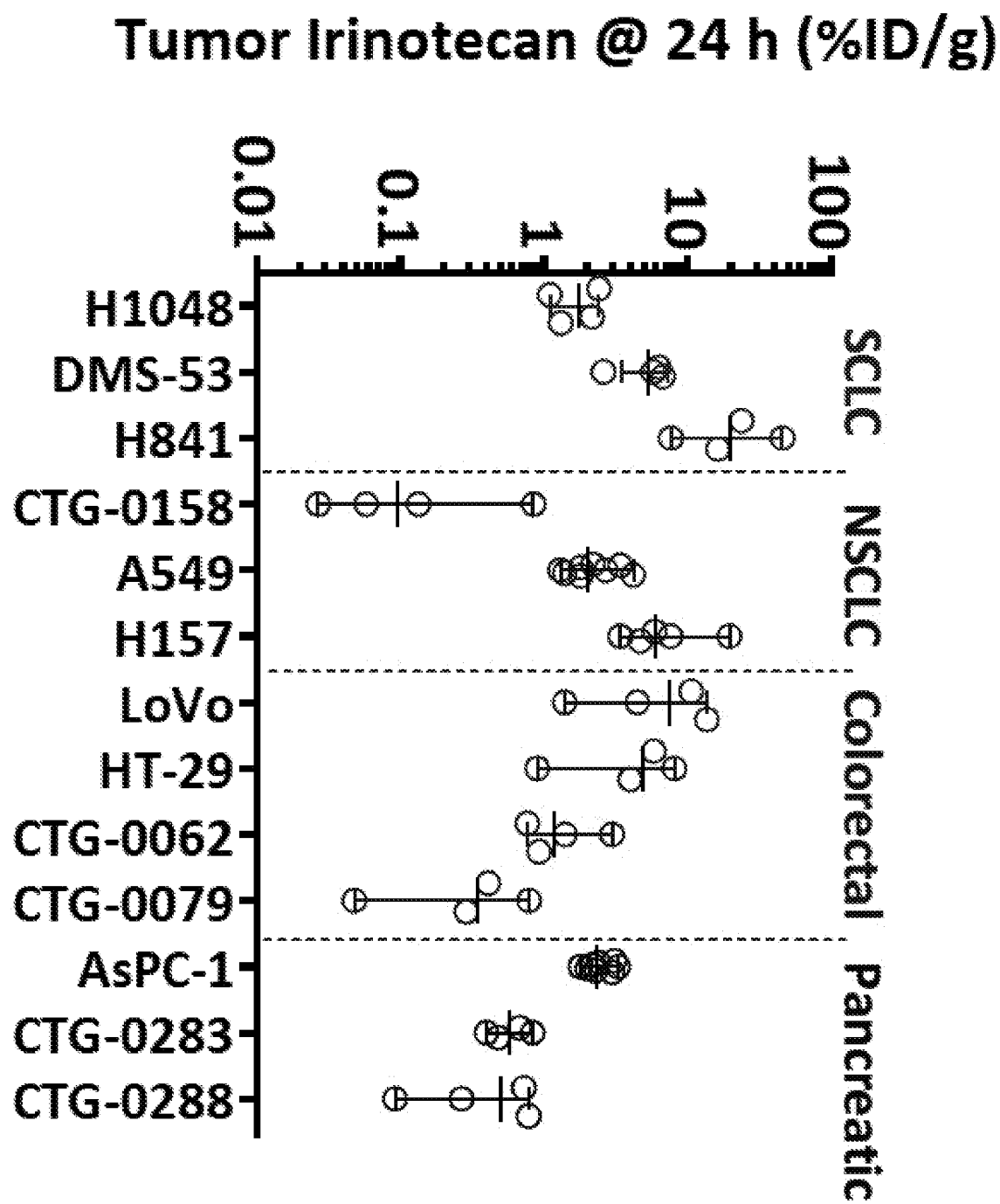
FIG. 19 is a graph showing that Nal-IRI effectively delivers irinotecan to tumors in preclinical models of SCLC.
Figure 20A:
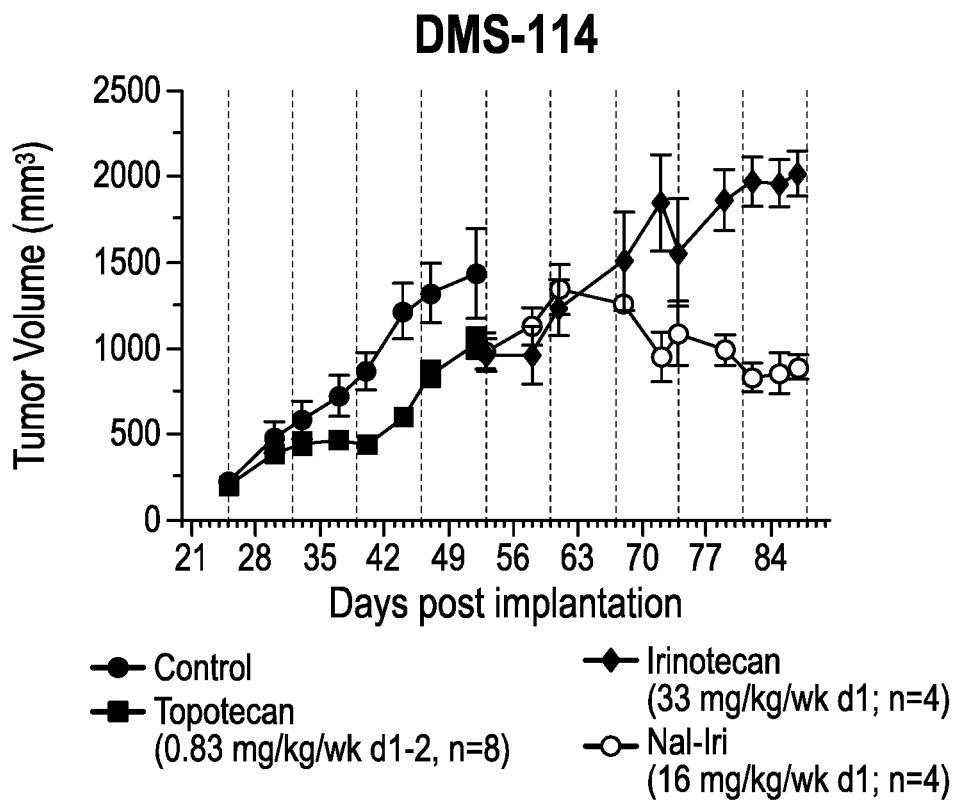
FIGS. 20A and 20B are graphs showing SCLC Tumors treated with TOP1 inhibitors remain responsive to nal-IRI.
Figure 20B:
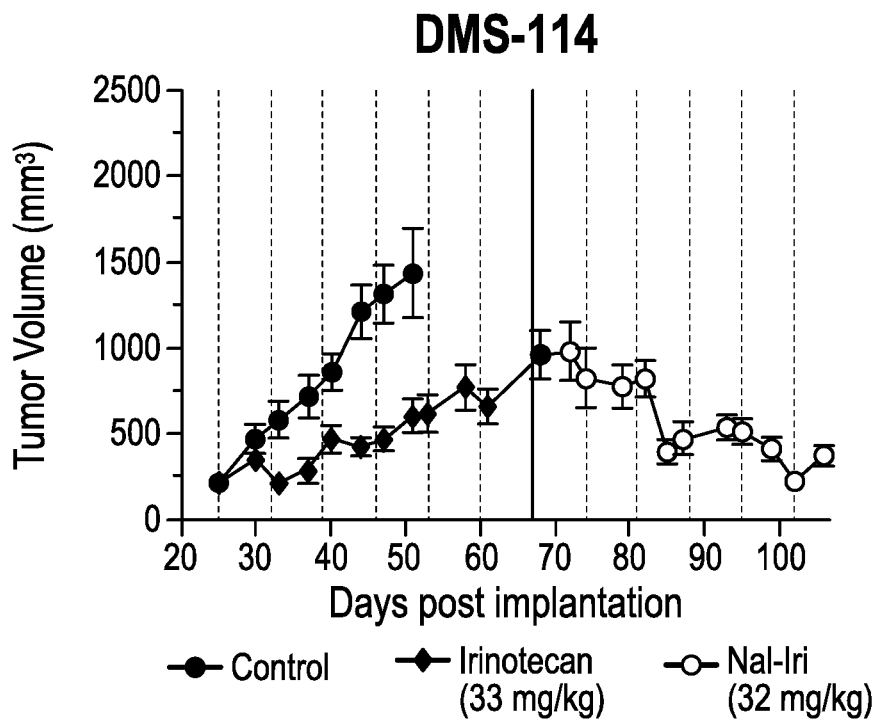

Example 13: Irinotecan Liposome Injection-Mediated Tumor Delivery of Irinotecan and SN-38 In Vivo The ability of MM-398 to deliver irinotecan and SN-38 to tumors was evaluated in SCLC cell-line derived xenograft (CDX) models (NCI-H1048, DMS-114, H841) in comparison to CDX and patient-derived xenograft (PDX) models of other tumor types. Irinotecan liposome injection was administered intravenously to mice bearing xenograft tumors. At 24 hours post administration, mice were sacrificed and tumors were harvested. Irinotecan and SN-38 in tumors were measured by high performance liquid chromatography (HPLC). Data were normalized to injected dose per tumor weight. As shown in FIG. 19, tumors derived from SCLC cell lines have similar or higher levels of irinotecan liposome injection deposition, as assessed by irinotecan content, than other tumor types. Furthermore, analysis of SN-38 levels indicates that increased irinotecan delivery was associated with increased levels of SN-38. These findings are consistent with a proposed mechanism of liposome deposition and local conversion of irinotecan to SN-38 within the tumor.

Example 14: Anti-Tumor Activity of Irinotecan Liposome Injection, Non-Liposomal Irinotecan and Topotecan in a Preclinical Model of Second Line SCLC Nal-IRI is designed for extended circulation relative to non-liposomal irinotecan and to exploit leaky tumor vasculature for enhanced drug delivery to tumors. Following tumor deposition, nal-IRI is taken up by phagocytic cells followed by irinotecan release and conversion to its active metabolite, SN-38, in the tumors. Sustained inhibition of topoisomerase 1 (TOP1) by extended SN-38 delivery is hypothesized to enable superior anti-tumor activity compared to traditional TOP1 inhibitors. Topotecan, a TOP1 inhibitor, is currently a standard of care for second-line treatment of small cell lung cancer (SCLC).

As described below, mice bearing NCI-H1048 SCLC tumors were treated with a carboplatin plus etoposide, a first line regimen in SCLC. Once the tumors escaped growth control by carboplatin plus etoposide, mice were randomized to either continue treatment with carboplatin plus etoposide or switch to second line treatment with either irinotecan liposome injection, non-liposomal irinotecan or topotecan.

Figure 21A:
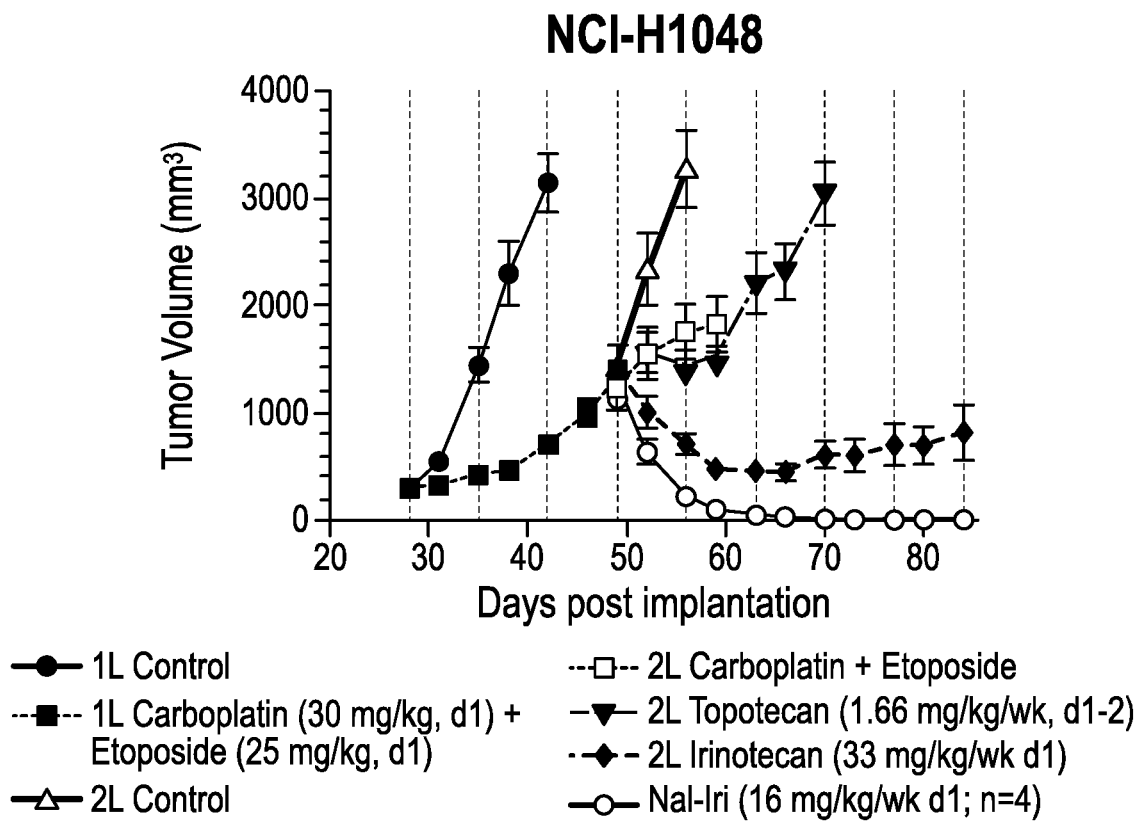
FIGS. 21A and 21B are graphs showing that Nal-IRI remains effective in platinum-treated SCLC tumors and is superior to topotecan and irinotecan in a 2 L SCLC Model: NCl-H1048.
Figure 21B:
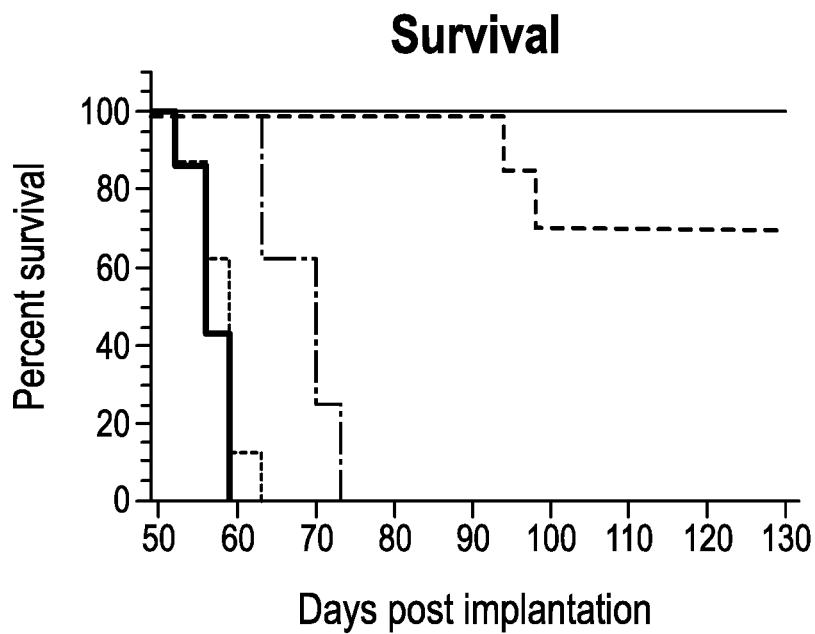
Figure 22A:
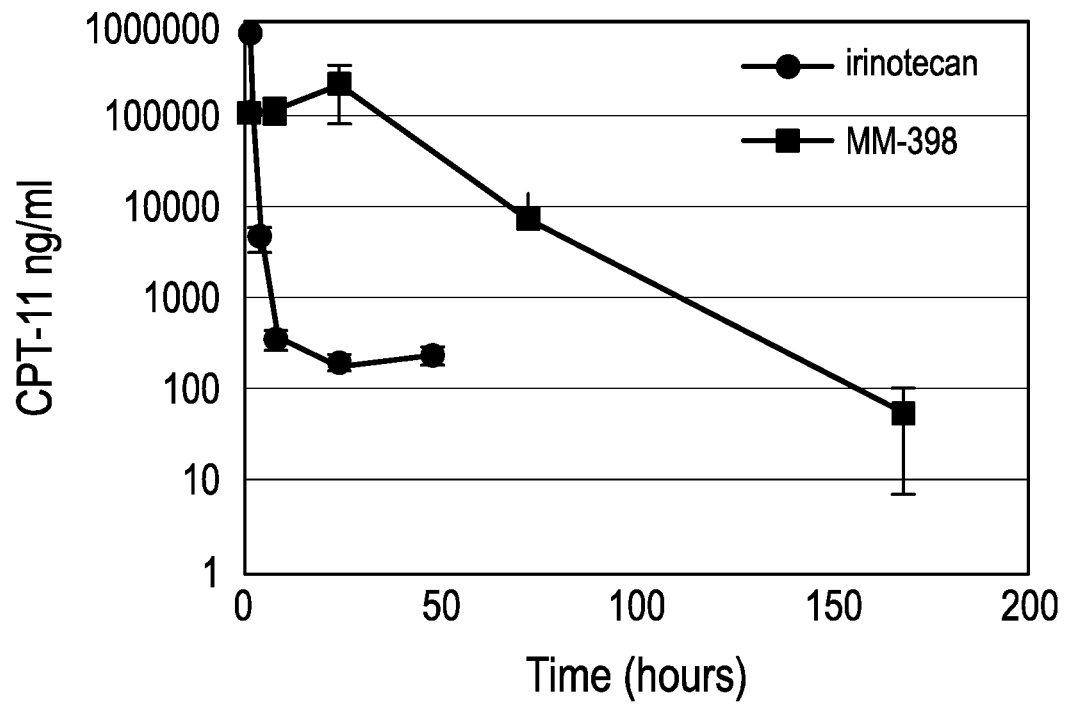
FIGS. 22A-22D are graphs showing pre-clinical evidence that MM-398 has improved circulation and tumor circulation in a HT29 CRC xenograft model—MM-398 40 mg/kg.
Figure 22B:
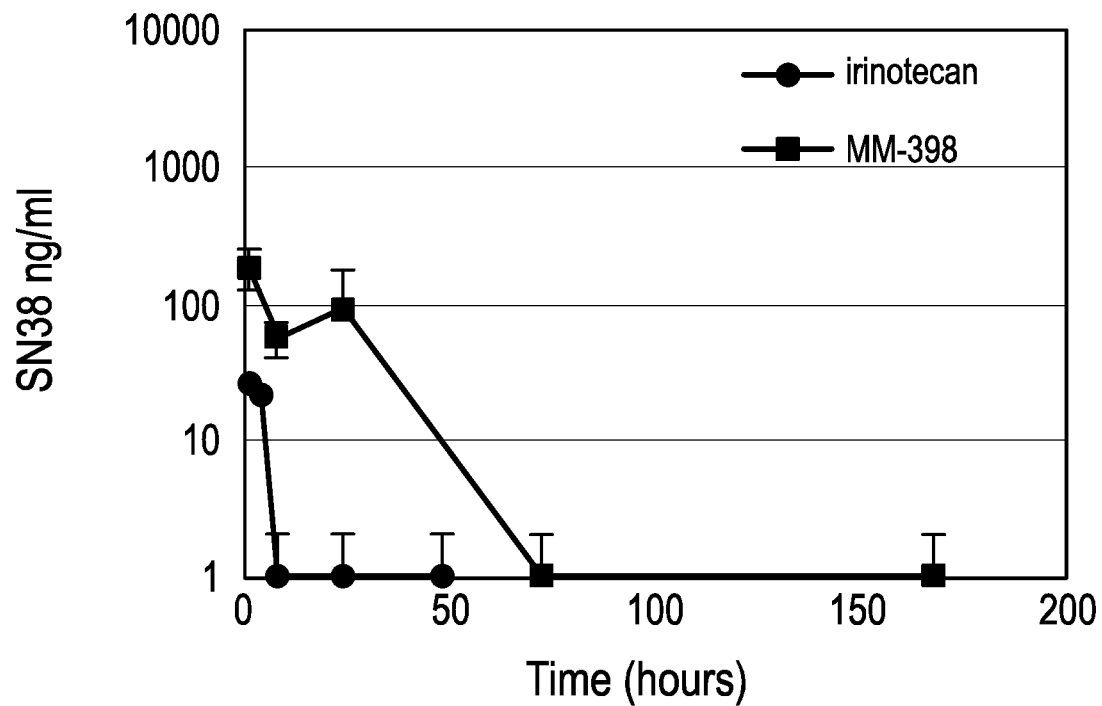
Figure 22C:
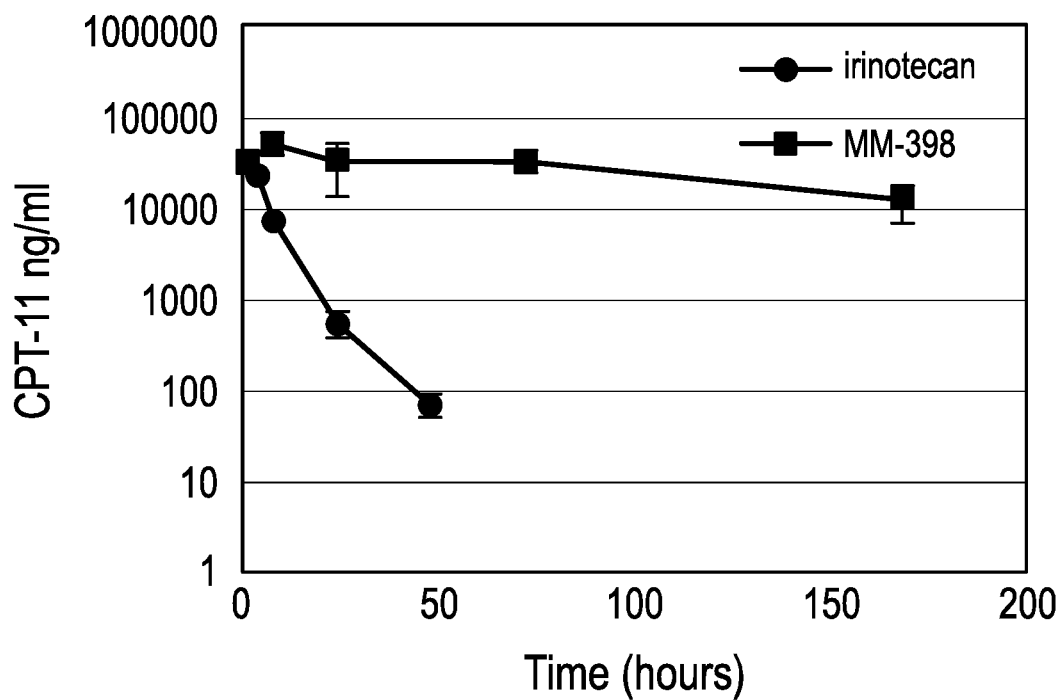
Figure 22D:
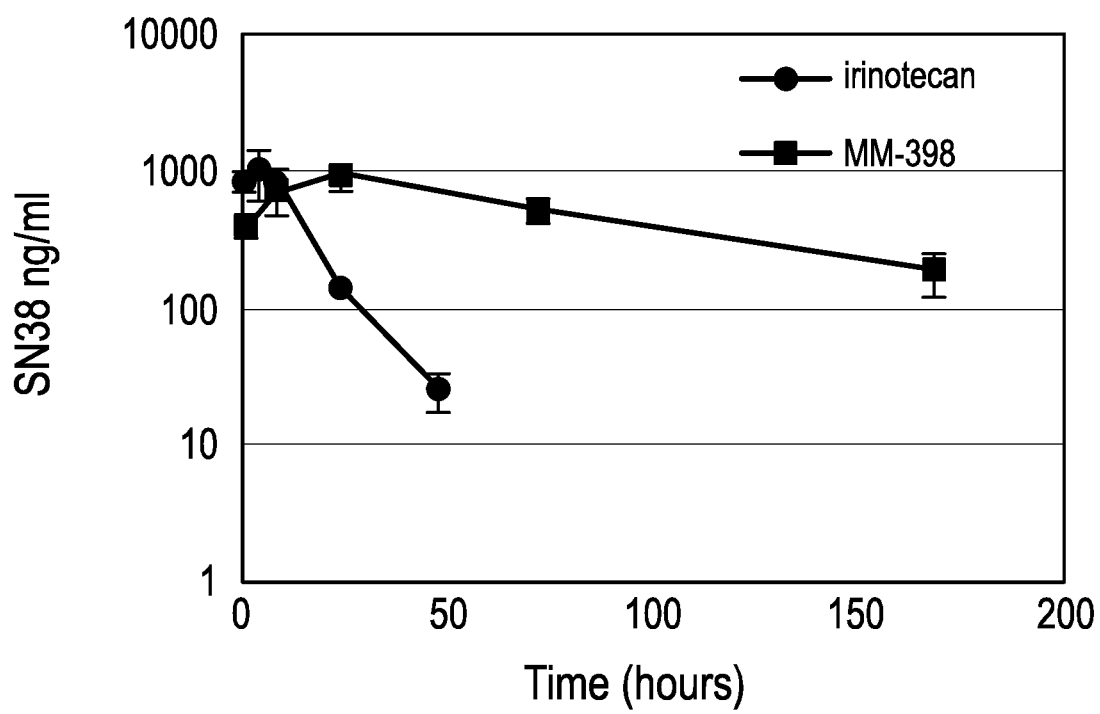
Figure 23A:
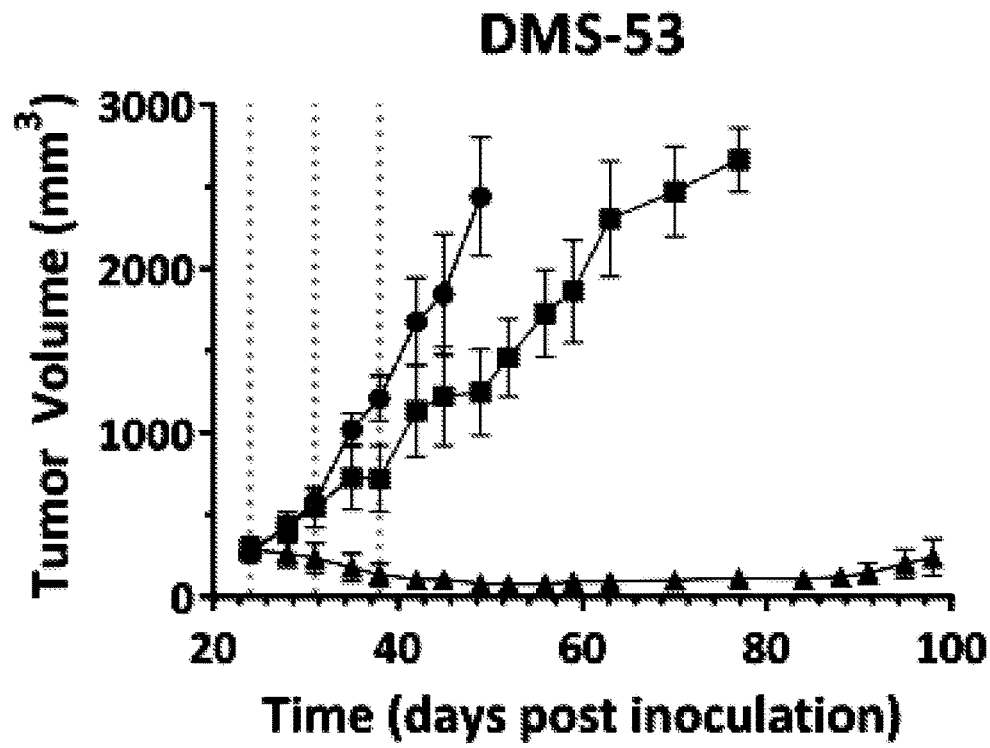
FIGS. 23A-23F are graphs showing Nal-IRI has greater anti-tumor activity than irinotecan and topotecan. NOD/SCID mice with subcutaneous (FIG. 23A) DMS-53, (FIG. 23B) DMS-114 or (FIG. 23C) NCI-H1048. SCLC xenograft tumors were treated with IV nal-IRI (16 mg/kg; triangles), IV irinotecan (33 mg/kg; diamonds), IP topotecan (0.83 mg/kg/wk days 1-2; squares) or vehicle control (circles). For DMS-114 and NCI-H1048 all groups have n=10; for DMS-53 n=4, 5 and 5 for control, topotecan and nal-IRI, respectively. Balb/c nude mice bearing subcutaneous patient-derived xenografts (FIG. 23D) LUN-182, (FIG. 23E) LUN-081 and (FIG. 24F) LUN-164 were treated with IV nal-IRI (16 mg/kg; triangles), IV irinotecan (33 mg/kg; diamonds), IP topotecan (0.83 mg/kg/wk days 1-2; squares) or vehicle control (circles). For all PDX models n=5 for all groups. Vertical dotted lines indicate start of weekly dosing and error bars indicate standard error of the mean.
Figure 23B:
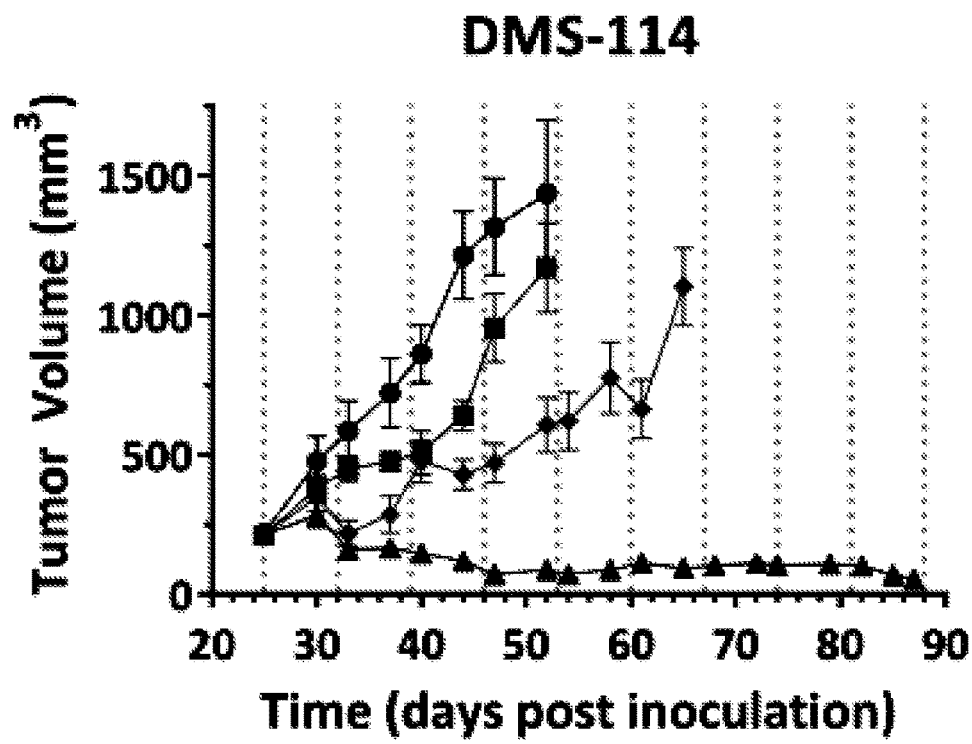
Figure 23C:
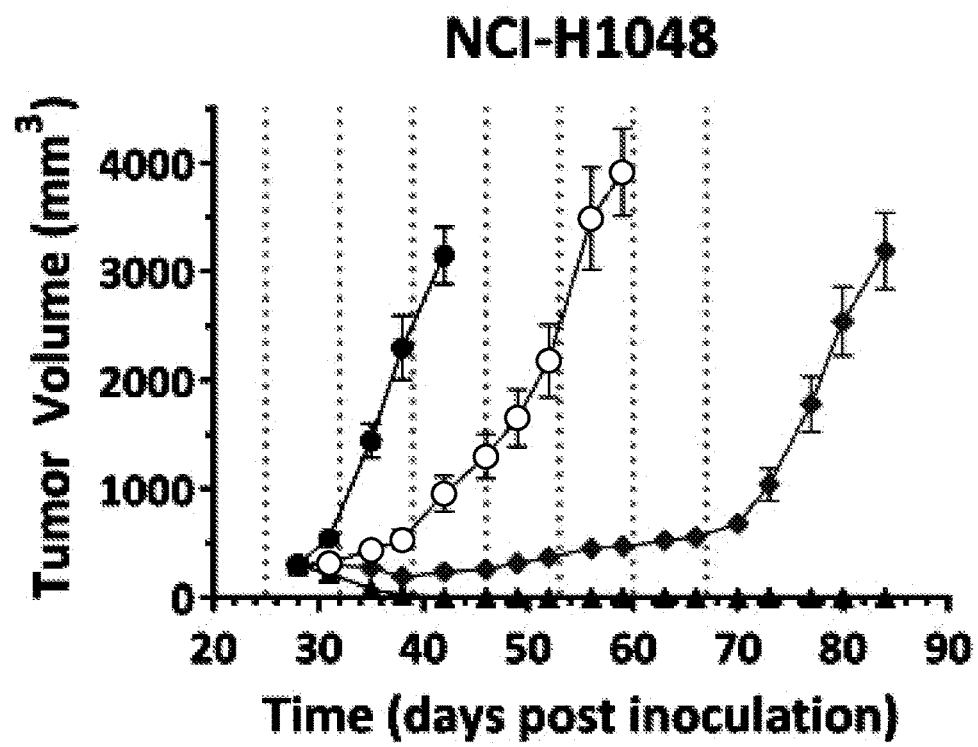
Figure 23D:
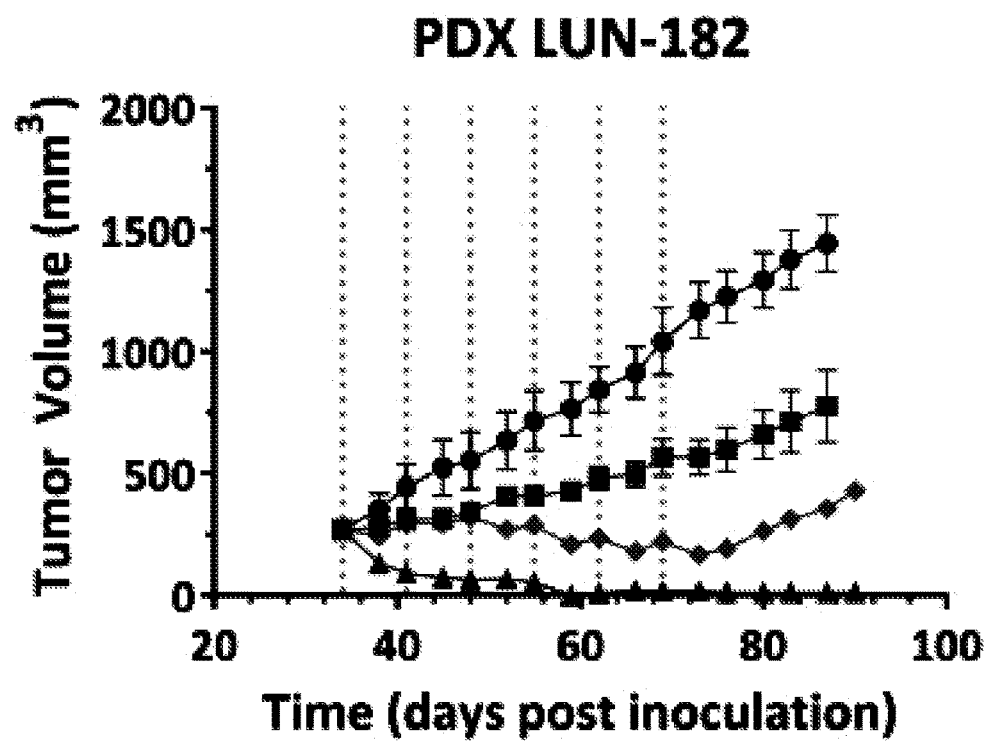
Figure 23E:
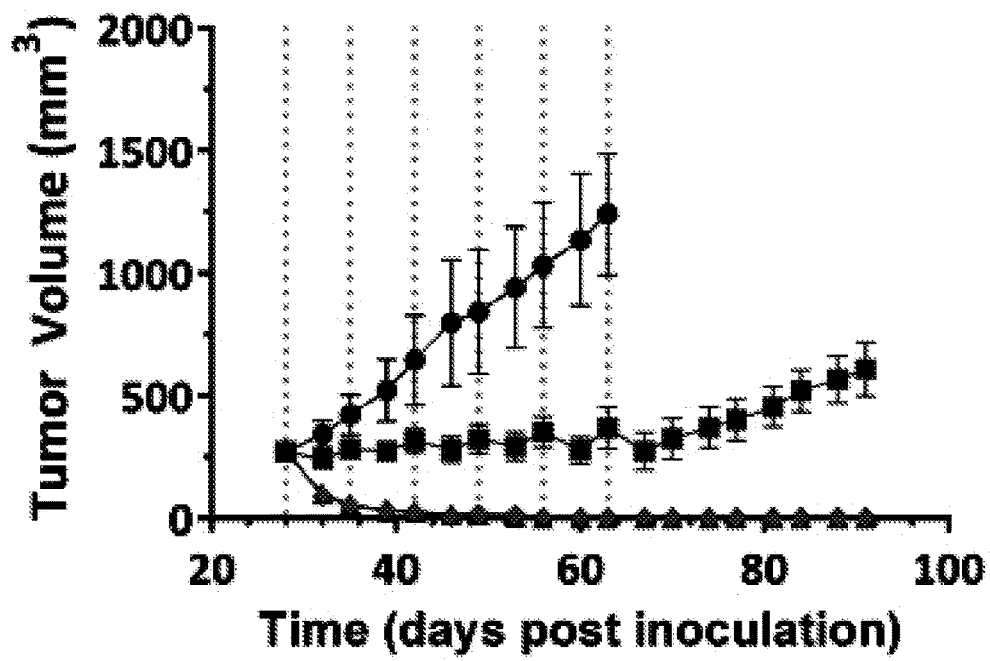
Figure 23F:
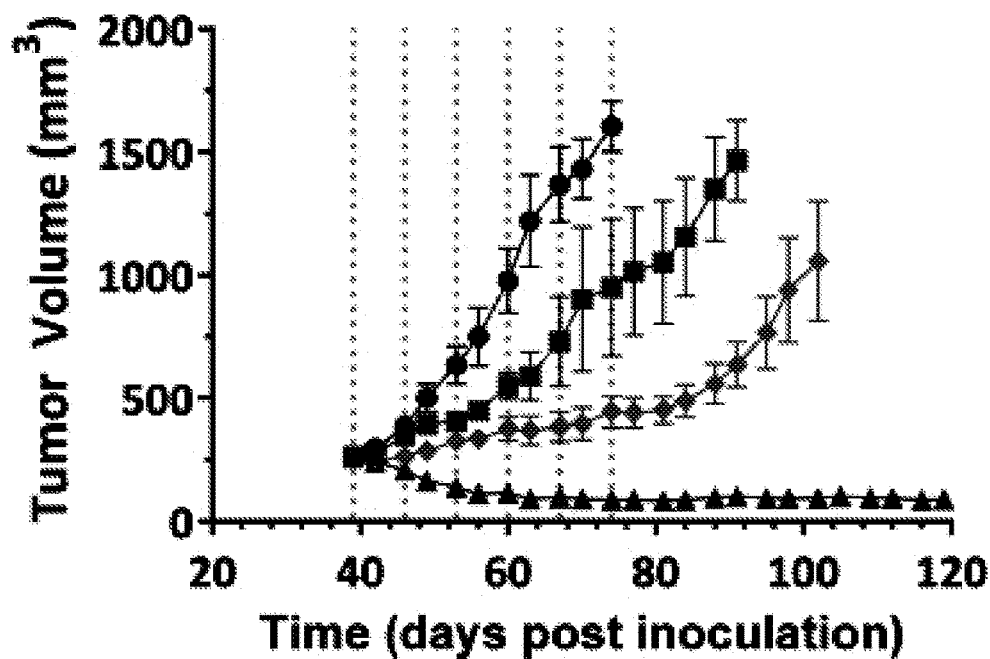

NOD/SCID mice with NCIH1048 SCLC xenograft tumors were treated weekly with the combination of 30 mg/kg carboplatin plus 25 mg/kg etoposide. When tumor reached approximately 1200 mm$^3$, mice were randomized to receive weekly treatment with topotecan (1.66 mg/kg/wk administered IP in equal fractions on days 1 and 2), non-liposomal irinotecan (33 mg/kg/wk administered IV on day 1) irinotecan liposome injection (16 mg/kg/wk administered IV on day 1), continue treatment with carboplatin plus etoposide or vehicle control. Vertical dotted lines indicate start of weekly dosing. Irinotecan liposome injection dose is shown on irinotecan HCl basis. After tumors progressed on first-line treatment with carboplatin plus etoposide, irinotecan liposome injection displayed significant anti-tumor activity compared to topotecan and irinotecan (p=0.0002 on day 70 and p=0.0002 on day 84 for topotecan and irinotecan, respectively). In carboplatin plus etoposide-treated SCLC tumors: Nal-IRI remains active and is trending towards complete response; non-liposomal irinotecan treatment is active but after 3rd cycle some tumors are trending regrowth; Topotecan (at 2× clinically relevant dose) seems to be active after 1-2 cycles but progress quickly after 3rd dose; carboplatin plus etoposide is not tolerable by the 5th cycle. As shown in FIG. 21A, irinotecan liposome injection had anti-tumor activity in the second line setting and, furthermore, had significantly greater anti-tumor activity than both non-liposomal irinotecan and topotecan. FIG. 21B is a survival graph for mice on each of the treatments.

Example 15: Irinotecan Liposome Injection has Improved Anti-Tumor Activity as Compared to Non-Liposomal Irinotecan HCl and Topotecan In Vivo The activity of irinotecan liposome injection, non-liposomal irinotecan and topotecan were directly compared at clinically relevant doses in two CDX models (DMS-114 and NCI-H1048) and the activity of irinotecan liposome injection and topotecan in one CDX model (DMS-53). Clinically relevant doses were calculated by using standard surface area to weight ratios conversion per NCI guidelines.

FIG. 23 presents tumor growth kinetics of mice bearing SCLC xenograft tumors that were treated weekly with irinotecan liposome injection, topotecan and non-liposomal irinotecan (two of the three). In the DMS-114 and NCI-H1048 models, irinotecan liposome injection displayed significantly greater anti-tumor activity than both non-liposomal irinotecan and topotecan. In the DMS-53 model, irinotecan liposome injection displayed significantly greater anti-tumor activity than did topotecan. Furthermore, 10 out of 10 mice treated in NCI-H1048 model treated with irinotecan liposome injection experienced complete regressions of their tumors as compared to 0 out of 10 mice treated with topotecan.

FIG. 23 shows the data obtained from NOD/SCID mice with subcutaneous (FIG. 23A) DMS-53, (FIG. 23B) DMS-114 or (FIG. 23C) NCI-H1048. SCLC xenograft tumors were treated with IV nal-IRI (16 mg/kg; triangles), IV irinotecan (33 mg/kg; diamonds), IP topotecan (0.83 mg/kg/wk days 1-2; squares) or vehicle control (circles). For DMS-114 and NCI-H1048 all groups have n=10; for DMS-53 n=4, 5 and 5 for control, topotecan and nal-IRI, respectively. Vertical dotted lines indicate start of weekly dosing and error bars indicate standard error of the mean. Irinotecan liposome injection dose is shown on irinotecan HCl basis. Following treatment, irinotecan liposome injection displayed significant anti-tumor activity compared to topotecan ($p<0.0001$ for DMS-114 on day 52 and $p<0.0001$ for NCI-H1048 on day 59; non-parametric t-test) and irinotecan ($p<0.0001$ for DMS-114 on day 65 and $p<0.0001$ for NCI-H1048 on day 84; non-parametric t-test).

In addition to the CDX models PDX models were also examined using subcutaneous patient-derived xenografts.

Balb/c nude mice bearing subcutaneous patient-derived xenografts (FIG. 23D) LUN-182, (FIG. 23E) LUN-081 and (FIG. 24F) LUN-164 were treated with IV nal-IRI (16 mg/kg; triangles), IV irinotecan (33 mg/kg; diamonds), IP topotecan (0.83 mg/kg/wk days 1-2; squares) or vehicle control (circles). For all PDX models n=5 for all groups. Vertical dotted lines indicate start of weekly dosing and error bars indicate standard error of the mean.

We claim:

1. A method of treating a human patient diagnosed with small cell lung cancer (SCLC) following disease progression on or after first-line platinum-based therapy for the SCLC, wherein the prior first-line platinum-based therapy has been discontinued, the method comprising administering to the human patient an antineoplastic therapy once every two weeks, the antineoplastic therapy consisting of liposomal irinotecan in a dose providing the equivalent of 70 mg/m² irinotecan free base.

2. The method of claim 1, wherein the platinum-based therapy comprises the prior, discontinued administration of cisplatin or carboplatin to treat the human patient diagnosed with SCLC.

3. The method of claim 1, wherein the human patient has a blood ANC greater than 1,500 cells/microliter without the use of hematopoietic growth factors, prior to the administration of the liposomal irinotecan.

4. The method of claim 1, wherein the human patient has a blood platelet count of greater than 100,000 cells per microliter, prior to the administration of the liposomal irinotecan.

5. The method of claim 1, wherein the human patient has a blood hemoglobin greater than 9 g/dL, prior to the administration of the liposomal irinotecan.

6. The method of claim 1, wherein the human patient has a serum creatinine of less than or equal to 1.5×ULN and a creatinine clearance of greater than or equal to 40 mL/min prior to the administration of the liposomal irinotecan.

7. The method of claim 1, wherein the human patient has not received a topoisomerase I inhibitor prior to administration of the liposomal irinotecan.

8. The method of claim 1, wherein the human patient has not received more than a single platinum-based therapy prior to administration of the liposomal irinotecan.

9. The method of claim 1, wherein the administration of the antineoplastic therapy comprises the steps of:
  (a) preparing a pharmaceutically acceptable injectable composition by diluting the liposomal irinotecan into 500 mL 5% Dextrose Injection (D5W) or 0.9% Sodium Chloride Injection to obtain the injectable composition; and
  (b) administering the injectable composition from step (a) to the patient in an infusion.

10. The method of claim 1, further comprising administering to the human patient a corticosteroid and an antiemetic prior to each administration of the antineoplastic therapy.

11. The method of claim 1, comprising administering to the human patient the antineoplastic therapy once every two weeks in a six-week cycle.

12. The method of claim 11, wherein the platinum-based therapy comprises the prior, discontinued administration of cisplatin or carboplatin to treat the human patient diagnosed with SCLC.

13. The method of claim 12, wherein the human patient has one or more of the following prior to the administration of the liposomal irinotecan:
  (a) a blood ANC greater than 1,500 cells/microliter without the use of hematopoietic growth factors;
  (b) a blood platelet count of greater than 100,000 cells per microliter;
  (c) a blood hemoglobin greater than 9 g/dL; and
  (d) a serum creatinine of less than or equal to 1.5×ULN and a creatinine clearance of greater than or equal to 40 mL/min.

14. The method of claim 13, wherein the human patient has not received a topoisomerase I inhibitor prior to administration of the liposomal irinotecan; and the human patient has not received more than a single platinum-based therapy prior to administration of the liposomal irinotecan.

15. The method of claim 13, wherein the method comprises administering the antineoplastic therapy for at least three six-week cycles.

16. The method of claim 11, wherein the administration of the antineoplastic therapy comprises the steps of:
(a) preparing a pharmaceutically acceptable injectable composition by diluting the liposomal irinotecan into 500 mL 5% Dextrose Injection (D5W) or 0.9% Sodium Chloride Injection to obtain the injectable composition; and
(b) administering the injectable composition from step (a) to the patient in an infusion.

17. The method of claim 16, further comprising administering to the human patient a corticosteroid and an antiemetic prior to each administration of the antineoplastic therapy.

18. The method of claim 1, comprising administering to the human patient the antineoplastic therapy once every two weeks for a total of at least three six-week cycles, wherein the human patient has the following prior to the administration of each antineoplastic therapy of liposomal irinotecan:
(a) a blood ANC greater than 1,500 cells/microliter without the use of hematopoietic growth factors;
(b) a blood platelet count of greater than 100,000 cells per microliter;
(c) a blood hemoglobin greater than 9 g/dL; and
(d) a serum creatinine of less than or equal to 1.5×ULN and a creatinine clearance of greater than or equal to 40 mL/min.

19. The method of claim 18, wherein:
(e) the human patient has not received a topoisomerase I inhibitor prior to administration of the liposomal irinotecan and has not received more than a single platinum-based therapy prior to administration of the liposomal irinotecan; and
(f) the method further comprises administering to the human patient a corticosteroid and an antiemetic prior to each administration of the antineoplastic therapy.

20. The method of claim 19, wherein the administration of the antineoplastic therapy comprises the steps of:
(i) preparing a pharmaceutically acceptable injectable composition by diluting the liposomal irinotecan into 500 mL 5% Dextrose Injection (D5W) or 0.9% Sodium Chloride Injection to obtain the injectable composition; and
(ii) administering the injectable composition from step (i) to the patient in an infusion.

21. The method of claim 9, comprising administering the injectable composition from step (a) to the patient in a 90-minute infusion.

22. The method of claim 16, comprising administering the injectable composition from step (a) to the patient in a 90-minute infusion.

23. The method of claim 20, comprising administering the injectable composition from step (i) to the patient in a 90-minute infusion.

24. The method of claim 1, wherein the liposomal irinotecan comprises unilamellar lipid bilayer vesicles, encapsulating an aqueous space containing irinotecan in a gelated or precipitated state as the sucrose octasulfate salt.

25. The method of claim 24, wherein the vesicles comprise phosphatidylcholine, cholesterol, and a polyethyleneglycol-derivatized phosphatidyl-ethanolamine.

26. The method of claim 25, wherein the polyethylene glycol in the polyethyleneglycol-derivatized phosphatidyl-ethanolamine is methoxy terminated and has a molecular weight of 2000, and the phosphatidyl-ethanolamine is distearoylphosphatidyl ethanolamine.

27. The method of claim 25, wherein the polyethyleneglycol-derivatized phosphatidyl-ethanolamine is in the amount of approximately one polyethyleneglycol-derivatized phosphatidyl-ethanolamine molecule for 200 phospholipid molecules in the irinotecan liposome.

28. The method of claim 26, wherein the sucrose octasulfate salt liposome injection comprises phosphatidylcholine, cholesterol, and methoxy-terminated polyethylene glycol-distearoylphosphatidyl ethanolamine in a molar ratio of 3:2:0.015.

29. The method of claim 24, wherein the vesicles comprise 1,2-distearoyl-sn-glycero-3-phosphocholine (DSPC), cholesterol, and methoxy-terminated polyethylene glycol (MW 2000)-distearoylphosphatidyl ethanolamine (MPEG-2000-DSPE).

30. The method of claim 29, wherein the vesicles comprise 1,2-distearoyl-sn-glycero-3-phosphocholine (DSPC), cholesterol, and methoxy-terminated polyethylene glycol (MW 2000)-distearoylphosphatidyl ethanolamine (MPEG-2000-DSPE) in a molar ratio of about 3:2:0.015.

* * * * *